United States Patent
Wagner et al.

(10) Patent No.: US 11,181,521 B2
(45) Date of Patent: Nov. 23, 2021

(54) INTRA-DROPLET SURFACE ENGINEERING TO CAPTURE A MOLECULAR TARGET

(71) Applicants: UNIVERSITE DE STRASBOURG, Strasbourg (FR); CENTRE NATIONAL DE LA RECHERCHE SCIENTIFIQUE, Paris (FR); CENTRE INTERNATIONAL DE RECHERCHE AUX FRONTIERES DE LA CHIMIE, Strasbourg (FR)

(72) Inventors: Alain Wagner, Strasbourg (FR); Sylvain Ursuegui, Strasbourg (FR); Michael Ryckelynck, Strasbourg (FR); Ketty Pernod, Gries (FR); Andrew David Griffiths, Paris (FR)

(73) Assignees: UNIVERSITE DE STRASBOURG, Strasbourg (FR); CENTRE NATIONAL DE LA RECHERCHE SCIENTIFIQUE, Paris (FR); CENTRE INTERNATIONAL DE RECHERCHE AUX FRONTIÈRES DE LA CHIMIE, Strasbourg (FR)

( * ) Notice: Subject to any disclaimer, the term of this patent is extended or adjusted under 35 U.S.C. 154(b) by 0 days.

(21) Appl. No.: 16/091,217

(22) PCT Filed: Apr. 4, 2017

(86) PCT No.: PCT/EP2017/058035
§ 371 (c)(1),
(2) Date: Oct. 4, 2018

(87) PCT Pub. No.: WO2017/174610
PCT Pub. Date: Oct. 12, 2017

(65) Prior Publication Data
US 2019/0113509 A1 Apr. 18, 2019

(30) Foreign Application Priority Data

Apr. 5, 2016 (EP) .................................... 16305394

(51) Int. Cl.
*G01N 33/543* (2006.01)
(52) U.S. Cl.
CPC ... *G01N 33/54346* (2013.01); *G01N 33/5432* (2013.01); *G01N 33/54353* (2013.01)
(58) Field of Classification Search
CPC ....... G01N 33/54346; G01N 33/54353; G01N 33/5432
See application file for complete search history.

(56) References Cited

U.S. PATENT DOCUMENTS 7,208,174 B2   4/2007   Huwyler et al.

FOREIGN PATENT DOCUMENTS

| EP | 2436673 | 4/2012 |
| EP | 3202424 | 8/2017 |

(Continued)

OTHER PUBLICATIONS

Kreutz et al. Laterally mobile, functionalized self-assebled monolayers at the fluorous-aqueous interface in a plug-based microfluidic system: characterizaiton and testing with membrane protein cryltallization. J. Am. Chem. Soc. 2009, pp. 6042-6043, vol. 131, supplementary pp. S1-S21 (Year: 2009).*

(Continued)

*Primary Examiner* — Shafiqul Haq
(74) *Attorney, Agent, or Firm* — Saliwanchik, Lloyd & Eisenschenk

(57) ABSTRACT

The present invention relates to a method for capturing a molecular target present in the aqueous phase of a water-in-oil emulsion, said method being based on the use of a binding system comprising (a) a surfactant bearing a func- (Continued)

tional moiety on its hydrophilic head group and (b) a chemoprobe that acts as a molecular staple between the functionalized surfactant and the molecular target and comprises at least two distinct domains namely (i) at least one capture moiety which is able to specifically bind the molecular target and (ii) at least one binding domain which is able to interact with the functional group of the surfactant through covalent or non-covalent interactions, directly or through a binding intermediary.

20 Claims, 22 Drawing Sheets

Specification includes a Sequence Listing.

(56) References Cited

FOREIGN PATENT DOCUMENTS

| WO | WO 2007/048121 | 4/2007 |
|---|---|---|
| WO | WO 2014/1608444 | 10/2014 |
| WO | WO 2016/145031 | 9/2016 |
| WO | WO 2016/172183 | 10/2016 |
| WO | WO 2017/123627 | 7/2017 |

OTHER PUBLICATIONS

Kreutz, J. E. et al. "Laterally Mobile, Functionalized Self-Assembled Monolayers at the Fluorous—Aqueous Interface in a Plug-Based Microfluidic System: Characterization and Testing with Membrane Protein Crystallization" *Journal of the American Chemical Society*, 2009, pp. 6042-6043, vol. 131.

Zelisko, P. M. et al. "Water-in-Silicone Oil Emulsion Stabilizing Surfactants Formed From Native Albumin and $\alpha,\omega$-Triethoxysilylpropyl-Polydimethylsiloxane" *Biomacromolecules*, 2008, pp. 2153-2161, vol. 9, No. 8.

Written Opinion in International Application No. PCT/EP2017/058035, dated Aug. 1, 2017, pp. 1-7.

Mourtas, S. et al. "Curcumin-decorated nanoliposomes with very high affinity for amyloid-$\beta$1-42 peptide" *Biomaterials*, 2011, pp. 1635-1645, vol. 32.

* cited by examiner

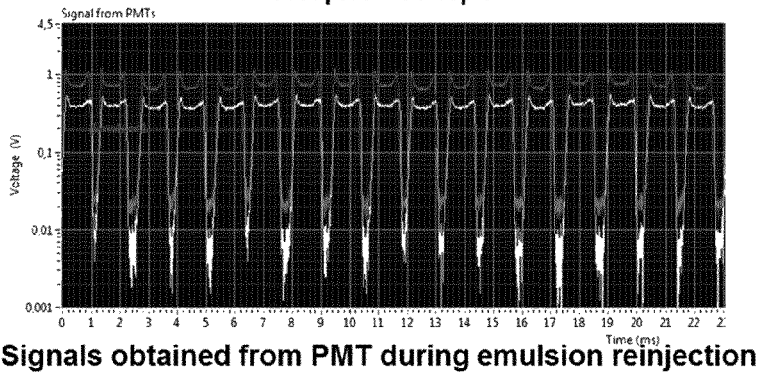
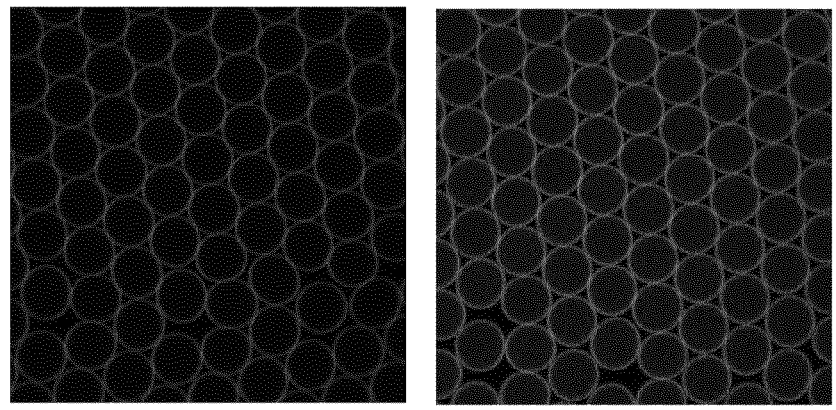
Figure 8
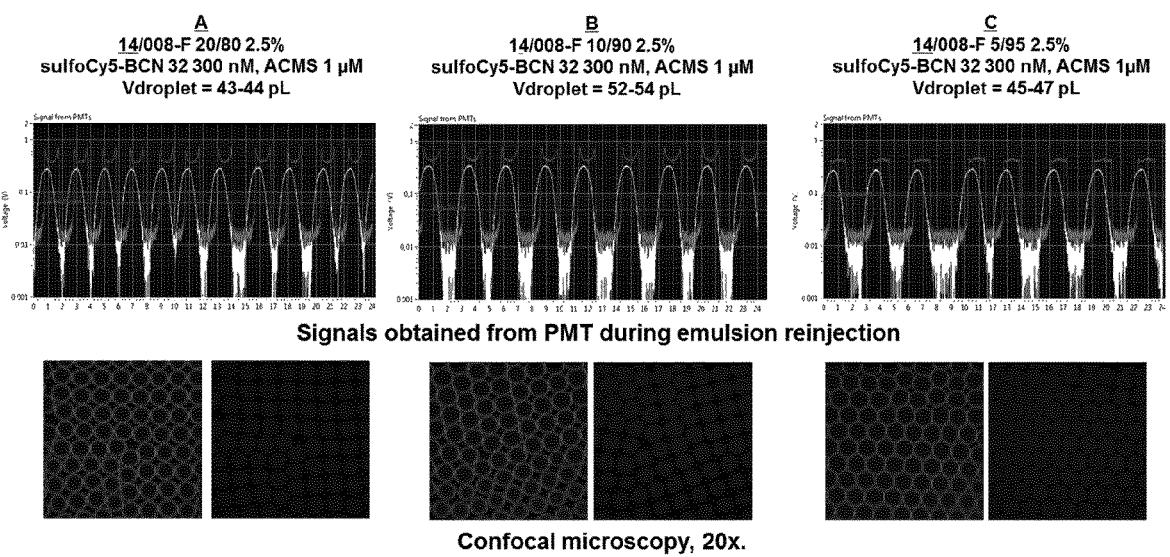
Figure 9

Double emulsion production

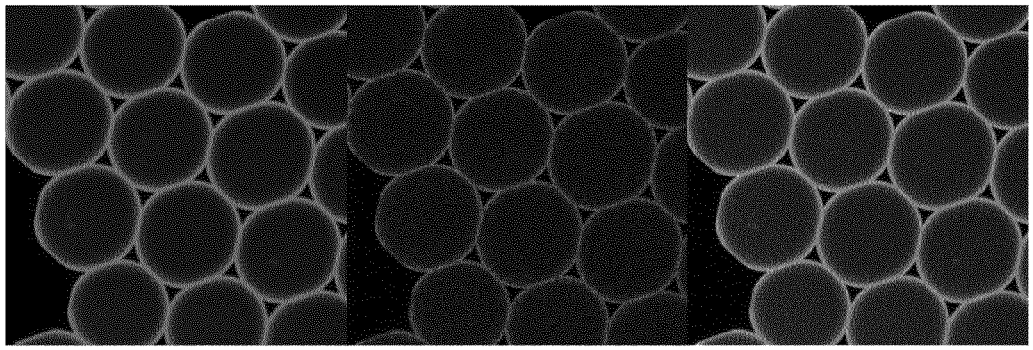

2.5 % (w/w) of Biotin-PEG-Krytox (GiLa) surfactant in HFE7500:
AlexaFluor532 streptavidin 1uM; [Biotin]Antibody FITC 100nM in PBS; merge image (right)

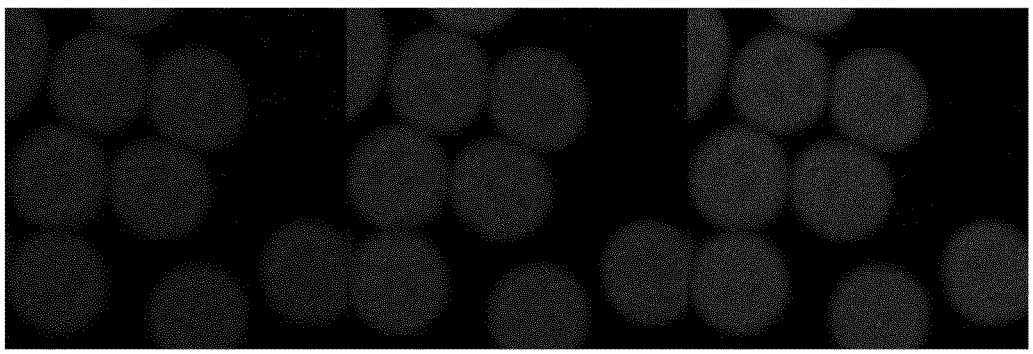

2.5 % (w/w) of PEG-di-Krytox surfactant in HFE7500:
AlexaFluor532 streptavidin 1uM; [Biotin]Antibody FITC 100nM in PBS; merge image (right)

Figure 25

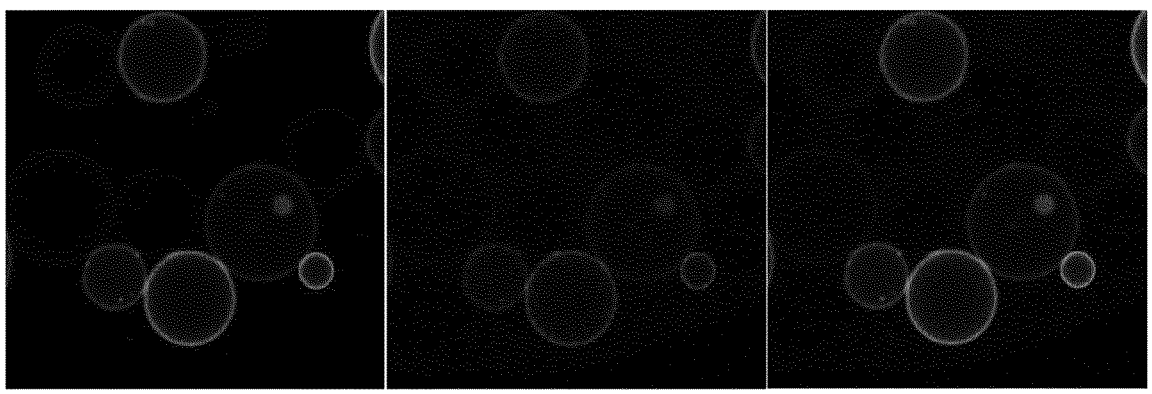

2.5 % (w/w) of Biotin-PEG-Krytox (GiLa) surfactant in HFE7500:
AlexaFluor532 streptavidin 1uM; [Biotin]Antibody FITC 100nM in PBS; merge image (right)

Figure 26

A.
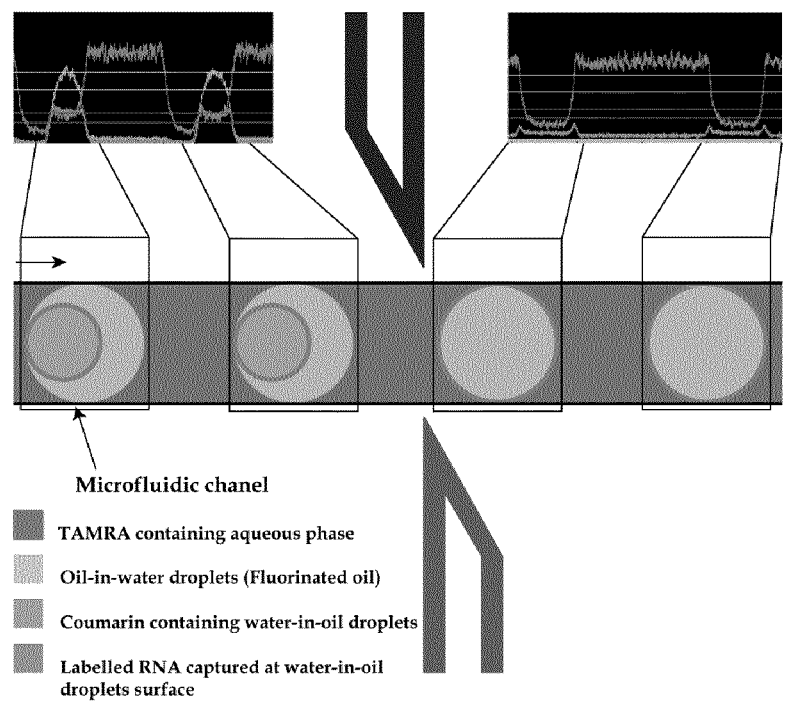
B.
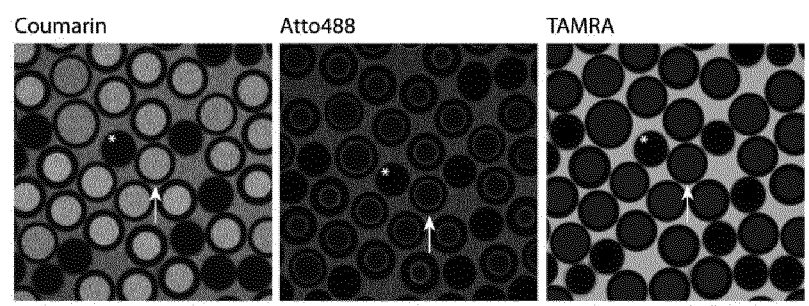
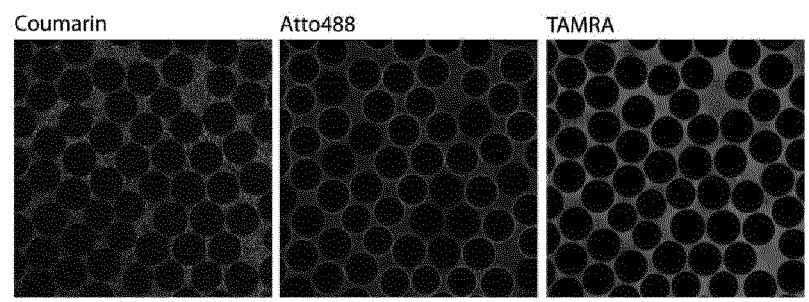
Figure 37

SEQUENCE LISTING

<160> NUMBER OF SEQ ID NOS: 13

<210> SEQ ID NO 1
<211> LENGTH: 35
<212> TYPE: DNA
<213> ORGANISM: Artificial Sequence
<220> FEATURE:
<223> OTHER INFORMATION: Amino-modified oligonucleotide
<220> FEATURE:
<221> NAME/KEY: misc_feature
<222> LOCATION: (1)..(1)
<223> OTHER INFORMATION: 5' Amino Modifier C12 and Internal Cy5TM

<400> SEQUENCE: 1
gatacgaatt cgggtgttct gctggtagtg gtcgg                              35

<210> SEQ ID NO 2
<211> LENGTH: 34
<212> TYPE: DNA
<213> ORGANISM: Artificial Sequence
<220> FEATURE:
<223> OTHER INFORMATION: Complementary oligonucleotide
<220> FEATURE:
<221> NAME/KEY: misc_feature
<222> LOCATION: (1)..(1)
<223> OTHER INFORMATION: 5'Atto(TM) 488 (NHS ester)
<220> FEATURE:
<221> NAME/KEY: misc_feature
<222> LOCATION: (1)..(1)
<223> OTHER INFORMATION: 5'Atto 488 (NHS ester)

<400> SEQUENCE: 2
ccactaccag cagaacaccc ccagaattcg tatc                               34

<210> SEQ ID NO 3
<211> LENGTH: 18
<212> TYPE: DNA
<213> ORGANISM: Artificial Sequence
<220> FEATURE:
<223> OTHER INFORMATION: amino-modified oligonucleotide
<220> FEATURE:
<221> NAME/KEY: misc_feature
<222> LOCATION: (1)..(1)
<223> OTHER INFORMATION: 5' Amino Modifier C12
<220> FEATURE:
<221> NAME/KEY: misc_feature
<222> LOCATION: (18)..(18)
<223> OTHER INFORMATION: 3' Cy5 introduced on supported resin

<400> SEQUENCE: 3
ttgctgtagc caaattcg                                                 18

<210> SEQ ID NO 4

```
<211> LENGTH: 18
<212> TYPE: DNA
<213> ORGANISM: Artificial Sequence
<220> FEATURE:
<223> OTHER INFORMATION: Complementary oligonucleotide
<220> FEATURE:
<221> NAME/KEY: misc_feature
<222> LOCATION: (18)..(18)
<223> OTHER INFORMATION: 3' Atto 488 (NHS ester)

<400> SEQUENCE: 4
cgaatttggc tacagcaa                                              18

<210> SEQ ID NO 5
<211> LENGTH: 18
<212> TYPE: DNA
<213> ORGANISM: Artificial Sequence
<220> FEATURE:
<223> OTHER INFORMATION: amino modified oligonucleotide
<220> FEATURE:
<221> NAME/KEY: misc_feature
<222> LOCATION: (1)..(1)
<223> OTHER INFORMATION: 5' Amino Modifier C12
<220> FEATURE:
<221> NAME/KEY: misc_feature
<222> LOCATION: (18)..(18)
<223> OTHER INFORMATION: 3' Cy5 introduced on supported resin

<400> SEQUENCE: 5
ttgctgtagc caaattcg                                              18

<210> SEQ ID NO 6
<211> LENGTH: 18
<212> TYPE: DNA
<213> ORGANISM: Artificial Sequence
<220> FEATURE:
<223> OTHER INFORMATION: Complementary oligonucleotide
<220> FEATURE:
<221> NAME/KEY: misc_feature
<222> LOCATION: (18)..(18)
<223> OTHER INFORMATION: 3' Atto 488 (NHS ester)

<400> SEQUENCE: 6
cgaatttggc tacagcaa                                              18

<210> SEQ ID NO 7
<211> LENGTH: 27
<212> TYPE: DNA
<213> ORGANISM: Artificial Sequence
<220> FEATURE:
<223> OTHER INFORMATION: Amino modified oligonucleotide
<220> FEATURE:
<221> NAME/KEY: misc_feature
<222> LOCATION: (1)..(1)
<223> OTHER INFORMATION: 5' Amino Modifier C12

<400> SEQUENCE: 7
ttgcagtttt tttttttttt tttttttt                                   27

<210> SEQ ID NO 8
<211> LENGTH: 27
<212> TYPE: DNA
<213> ORGANISM: Artificial Sequence
<220> FEATURE:
<223> OTHER INFORMATION: Complementary oligonucleotide
<220> FEATURE:
<221> NAME/KEY: misc_feature
<222> LOCATION: (1)..(1)
<223> OTHER INFORMATION: 5' Atto 488 (NHS ester)

<400> SEQUENCE: 8
```
ttgatccaaa aaaaaaaaaa aaaaaaa                                          27

<210> SEQ ID NO 9
<211> LENGTH: 987
<212> TYPE: DNA
<213> ORGANISM: Artificial Sequence
<220> FEATURE:
<223> OTHER INFORMATION: Template GAPDH DNA

<400> SEQUENCE: 9
taatacgact cactataggg atggggaagg tgaaggtcgg agtcaacgga tttggtcgta      60
ttgggcgcct ggtcaccagg gctgctttta actctggtaa agtggatatt gttgccatca     120
atgacccctt cattgacctc aactacatgg tttacatgtt ccaatatgat tccacccatg     180
gcaaattcca tggcaccgtc aaggctgaga cgggaagct tgtcatcaat ggaaatccca     240
tcaccatctt ccaggagcga gatccctcca aaatcaagtg gggcgatgct ggcgctgagt     300
acgtcgtgga gtccactggc gtcttcacca ccatggagaa ggctgggct catttgcagg     360
ggggagccaa aagggtcatc atctctgccc cctctgctga tgcccccatg ttcgtcatgg     420
gtgtgaacca tgagaagtat gacaacagcc tcaagatcat cagcaatgcc tcctgcacca     480
ccaactgctt agcaccectg gccaaggtca tccatgacaa ctttggtatc gtggaaggac     540
tcatgaccac agtccatgcc atcactgcca cccagaagac tgtggatggc cctccggga     600
aactgtggcg tgatggccgc ggggctctcc agaacatcat ccctgcctct actggcgctg     660
ccaaggctgt gggcaaggtc atccctgagc tgaacgggaa gctcactggc atggccttcc     720
gtgtccccac tgccaacgtg tcagtggtgg acctgacctg ccgtctagaa aaacctgcca     780
aatatgatga catcaagaag gtggtgaagc aggcgtcgga gggcccctc aagggcatcc     840
tgggctacac tgagcaccag gtggtctcct ctgacttcaa cagcgacacc cactcctcca     900
cctttgacgc tggggctggc attgccctca acgaccactt tgtcaagctc atttcctggt     960
atgacaacga atttggctac agcaaca                                         987

<210> SEQ ID NO 10
<211> LENGTH: 53
<212> TYPE: DNA
<213> ORGANISM: Artificial Sequence
<220> FEATURE:
<223> OTHER INFORMATION: GAPDH forward primer

<400> SEQUENCE: 10
ggaacttgaa ttctaatacg actcactata gggatgggga aggtgaaggt cgg            53

<210> SEQ ID NO 11
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 11
tgttgctgta gccaaattcg                                                  20

<210> SEQ ID NO 12
<211> LENGTH: 970
<212> TYPE: RNA
<213> ORGANISM: Artificial Sequence
<220> FEATURE:
<223> OTHER INFORMATION: GAPDH RNA fragment

```
<400> SEQUENCE: 12
gggaugggga aggugaaggu cggagucaac ggauuugguc guauugggcg ccuggucacc      60
agggcugcuu uuaacucugg uaaaguggau auuguugcca ucaaugaccc cuucauugac     120
cucaacuaca ugguuuacau guccaauau gauuccaccc auggcaaauu ccauggcacc      180
gucaaggcug agaacgggaa gcuugucauc aauggaaauc ccaucaccau cuuccaggag     240
cgagaucccu ccaaaaucaa guggggcgau gcuggcgcug aguacgucgu ggaguccacu     300
ggcgucuuca ccaccaugga gaaggcuggg gcucauuugc aggggggagc caaaaggguc     360
aucaucucug cccccucugc ugaugccccc auguucguca uggguguga ccaugagaag      420 uaugacaaca gccucaagau caucagcaau gccuccugca ccaccaacug cuuagcaccc     480
cuggccaagg ucauccauga caacuuuggu aucguggaag gacucaugac cacaguccau     540
gccaucacug ccacccagaa gacuguggau ggccccuccg ggaaacugug gcgugauggc     600 cgcgggcuc uccagaacau caucccugcc ucuacuggcg cugccaaggc uguggcaag      660 gucauccug agcugaacgg gaagcucacu ggcauggccu uccgucccc cacugccaac      720 gugucagugg uggaccugac cugccgucua gaaaaaccug ccaaauauga ugacaucaag     780 aagguggugua agcaggcguc ggagggcccc cucaagggca uccugggcua cacugagcac     840
cagguggucu ccucugacuu caacagcgac acccacuccu ccaccuuuga cgcuggggcu     900
ggcauugccc ucaacgacca cuuugucaag cucauuccu gguaugacaa cgaauuuggc      960
uacagcaaca                                                           970

<210> SEQ ID NO 13
<211> LENGTH: 18
<212> TYPE: DNA
<213> ORGANISM: Artificial Sequence
<220> FEATURE:
<223> OTHER INFORMATION: Capture DNA
<220> FEATURE:
<221> NAME/KEY: misc_feature
<222> LOCATION: (1)..(1)
<223> OTHER INFORMATION: 5'-NH2-C12

<400> SEQUENCE: 13
ttgctgtagc caaattcg                                                   18
```

INTRA-DROPLET SURFACE ENGINEERING TO CAPTURE A MOLECULAR TARGET

CROSS-REFERENCE TO RELATED APPLICATION

This application is the U.S. national stage application of International Patent Application No. PCT/EP2017/058035, filed Apr. 4, 2017.

The Sequence Listing for this application is labeled "Seq-List.txt" which was created on Sep. 27, 2018, and is 7 KB. The entire content of the sequence listing is incorporated herein by reference in its entirety.

FIELD OF THE INVENTION

The present invention relates to interface chemistry in droplet-based systems, preferably in microfluidic systems, and in particular to interfaces allowing specific interactions and capture of a molecule of interest.

BACKGROUND OF THE INVENTION

Microdroplets in microfluidics provide a compartment in which species or reaction can be isolated. Typically, microdroplets of one phase are generated in another, immiscible phase by exploiting capillary instabilities in a microfluidic two-phase flow. The addition of a surfactant to either or both of the phases stabilizes the microdroplets against coalescence and allows them to function as discrete microreactors.

A wide range of chemical and biological reactions can be performed inside aqueous microdroplets, including for example DNA/RNA amplification (Mazutis et al., A.D. Lab Chip, 2009, 9, 2665-2672; Mazutis et al., Anal. Chem., 2009, 81(12), 4813-4821), in vitro transcription/translation (Courtois et al., Chembiochem., 2008, 9(3), 439-446), enzymatic catalysis (Baret et al., Lab Chip, 2009, 9(13), 1850-1858), and cell-based assays (Clausell-Tormos et al., Chem. Biol., 2008, 15(8), 427-437; Brouzes et al., Proc. Natl. Acad. Sci. USA, 2009, 106(34), 14195-14200). The tiny size of the microdroplets—1 picoliter to 1 nanoliter in volume—facilitates extremely high throughputs ($10^4$ samples per second) and vastly reduced reagent consumption.

Recently, functionalized surfactants have been designed to concentrate molecules of interest at the droplet interface. His-tag binding chemistry has been implemented to design functionalized surfactant allowing specific adsorption of proteins at the inner interface of the droplet (Kreutz et al., 2009, J. Am. Chem. Soc. 131, 6042-6043). However, this process is restricted to the capture of recombinant proteins bearing a His-tag.

Furthermore, even after adsorption, characterisation of the reactions or species inside a droplet can be limited by the diversity of molecules present in the droplet and their potential interactions.

There is thus a need for new methods for capturing a molecular target of interest from complex medium and suitable for microfluidic technology.

SUMMARY OF THE INVENTION

The present invention provides a new method for capturing a molecular target present in the aqueous phase of a water-in-oil emulsion, based on the use of a binding system comprising (a) a surfactant bearing a functional moiety on its hydrophilic head group and (b) a chemoprobe.

In a first aspect, the present invention relates to a method for capturing a molecular target, said method comprising:

a) providing water-in-oil emulsion droplets comprising a functionalized surfactant at the interface of droplets, said functionalized surfactant comprising at least one lipophilic tail linked to a functionalized hydrophilic head, b) contacting said functionalized surfactant with a chemoprobe present or added in the aqueous phase of the droplets, said chemoprobe comprising at least (i) one capture moiety capable of specific binding to a molecular target and at least (ii) one binding domain capable of direct or indirect binding to the functionalized surfactant, and c) contacting said functionalized surfactant with the molecular target present or added in the aqueous phase of the droplets, thereby capturing the molecular target at the inner interface of the emulsion droplets, and wherein steps b) and c) are performed simultaneously or sequentially, in any order.

The molecular target is captured at the inner interface of the emulsion droplets through (i) the direct or indirect binding of the chemoprobe to the functionalized surfactant and (ii) the specific binding of the chemoprobe to the molecular target. The functionalized surfactant may comprise one or several functional moieties on a hydrophilic head group. The chemoprobe may directly or indirectly interact with one or several of the functional moieties present in a hydrophilic head of the functionalized surfactant.

Preferably, the method of the invention is implemented using a microfluidic system.

The method may further comprise inverting the phase of water-in-oil emulsion droplets thereby producing oil-in-water emulsion droplets and exposing the captured molecular target at the outer surface of the emulsion droplets.

The method may also further comprise a step of recovering, detecting, and/or quantifying the captured molecular target.

Preferably, the molecular target is a protein or a nucleic acid.

Preferably, the capture moiety of the chemoprobe is selected from the group consisting of an antibody, a spiegelmer, a peptide aptamer, an aptamer, a ligand or a substrate of the molecular target, a nucleic acid capable of hybridizing the molecular target, and a receptor fragment able to bind the molecular target.

In preferred embodiments, the functionalized surfactant is a diblock or triblock surfactant.

The chemoprobe may bind the functionalized surfactant through covalent or non-covalent interactions, preferably through covalent interactions.

The chemoprobe may directly bind the functionalized surfactant through covalent interactions. Preferably, the functionalized hydrophilic head of the surfactant and the binding domain of the chemoprobe each bear a reactive chemical moiety able to react together through a click reaction or a bioconjugation reaction.

Alternatively, the chemoprobe may bind the functionalized surfactant via a binding intermediate. Preferably, the functionalized hydrophilic head of the surfactant and the binding intermediate each bear a reactive chemical moiety able to react together through a click reaction or a bioconjugation reaction.

In particular, the click reaction may be selected from the group consisting of copper-catalyzed azide-alkyne dipolar cycloaddition (CuAAC), strain promoted alkyne-azide cycloaddition (SPAAC), Diels-Alder reactions with tetrazines and strained alkynes or alkenes, tetrazine-isonitrile cycloaddition thiol-alkene click reaction such as maleimide-cysteine cycloaddition, and a sydnone-alkyne cycloaddition, preferably is a strain promoted alkyne-azide cycloaddition (SPAAC).

The chemoprobe may bind the functionalized surfactant through non-covalent interactions, directly or via a binding intermediate. In particular, the non-covalent interaction between the chemoprobe and the functionalized surfactant may rely on an affinity system or protein tags.

In some embodiments, the molecular target is from a biological entity encapsulated within the droplets and the method optionally comprises lysing said entity to release said molecular target.

Preferably, each emulsion droplet comprises a single genetic element or biological entity.

In a second aspect, the present invention also relates to a kit to capture a molecular target according to the method of the invention, comprising
  a functionalized surfactant comprising at least one lipophilic tail linked to a functionalized hydrophilic head; and
  a chemoprobe comprising at least (i) one capture moiety capable of specific binding to a molecular target and at least (ii) one binding domain capable of direct or indirect binding to the functionalized surfactant.

The kit may further comprise a binding intermediate which is able to bind both the chemoprobe and the functionalized surfactant thereby acting as a bridge between said two entities.

The kit may also further comprise
  non-functionalized surfactant(s); and/or
  an aqueous phase; and/or
  an oil phase; and/or
  a microfluidic chip, preferably a microfluidic chip comprising a module for generating water-in-oil emulsion droplets or re-injecting water-in-oil emulsion, a module for creating double emulsion in fluid communication and downstream of the module for generating water-in-oil emulsion droplets or re-injecting water-in-oil emulsion, and a phase inversion module in fluid communication and downstream of the module for creating double emulsion; and/or
  a leaflet providing guidelines to use such a kit.

The present invention also relates to the use of a kit of the invention for capturing a molecular target according to the method of the invention.

In some embodiments of the method or the kit of the invention, the functionalized surfactant comprises or consists in a moiety of formula (Ib)

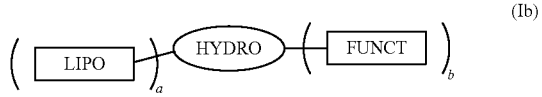

(Ib)

wherein:
  a and b are integers independently selected from 1 to 5,
  each LIPO is a lipophilic tail independently selected from the group consisting of a saturated or unsaturated hydrocarbon chain, optionally interrupted by one or several heteroatoms and optionally substituted by one or several groups selected from $C_1$-$C_3$ alkyl groups, halogens such as F, Cl or Br, —OH, —OMe, and —$CF_3$, a perfluoropolyether chain, a perfluorocarbon chain and combinations thereof, each HYDRO is a hydrophilic head comprising a moiety independently selected from a dimorpholinophosphate group, a polyether, a polyetheramine, a polyglycerol, and combinations thereof,
  each FUNCT is a functional moiety of the surfactant selected from an alkynyl group, an azido group, a biotin, a streptavidin and an avidin.

In some other embodiments of the method or the kit of the invention, the functionalized surfactant comprises
  one or two lipophilic tails comprising, or consisting of the moiety of formula ($L_1$):

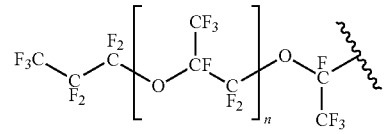

(L1)

wherein n is an integer from 25 to 45
  one hydrophilic head bearing at least one (e.g. 1 or 2) moiety of formula ($H_2$)

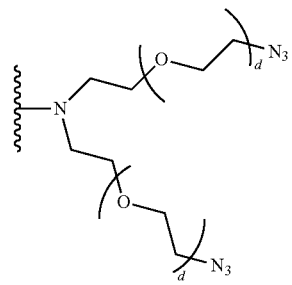

($H_2$)

wherein d is an integer from 1 to 12.

BRIEF DESCRIPTION OF THE DRAWINGS

FIG. 8: Double functionalization of microdroplet surface. Oil phase: 2.5% Krytox-peg$_{12}$-azide 14 in Novec 7500/ Aqueous phase: sulfoCy5-BCN 32 200 nM, TAMRA-peg$_6$-BCN 30 200 nM in Pluronic 0.01% (in PBS 1×).
FIG. 9: SPAAC reaction after dilution of diblock-azide 14 in non-functionalized commercial fluorosurfactant 008-F. Oil phase: 2.5% in Novec 7500 A=Krytox-peg$_{12}$-azide 14/008-F 80/20, B=Krytox-peg$_{12}$-azide 14/008-F 90/90, C=Krytox-peg$_{12}$-azide 14/008-F 95/5. Aqueous phase: A, B, C=sulfoCy5-BCN 32 300 nM, ACMS 1 µM in Pluronic 0.01% (in PBS 1×).

FIG. 25: Confocal images of AlexaFluor532 streptavidin and biotinylated antibody fluorescence before phase inversion.

FIG. 26: Confocal images of AlexaFluor532 streptavidin and biotinylated antibody fluorescence after phase inversion.

FIG. 37. Droplet imaging before and after the inversion procedure. A. Schematic of the inversion process with the fluorescence profile of the droplets recorded during the process. Electrodes are represented by the red and blue structures aside the channel. Droplets circulate from the left to the right. B. Top raw: w/o/w droplets before the inversion procedure. w/o/w droplets (white arrow) can easily be distinguished from the empty o/w droplets (white asterisk) since only the former displayed a coumarin signal (blue channel) inside the droplets. Moreover, the captured RNA is materialized by the formation of a green ring inside occupied w/o/w droplets. Bottom raw: w/o/w droplets converted into o/w droplets after the inversion procedure. While the green ring of captured RNA is still observed at the surface of the droplet (outer surface) the blue signal has been completely eliminated from inside the droplets. In both sets of pictures, the free green fluorescence observed outside the droplets was assigned to a cross-talk from the concentrated TAMRA that is slight excited by the blue laser and slightly emit in the green channel. Droplets were imaged by exciting the coumarin with a 408 nm laser and collecting the light emitted at 410-483 nm while the green fluorescence was visualized by exciting Atto 488 with a 488 nm laser and collecting the light emitted at 499-553 nm the and orange fluorescence was visualised by exciting TAMRA with a 561 nm laser and collecting the light emitted at 559-735 nm.

DETAILED DESCRIPTION OF THE INVENTION

Figure 1:
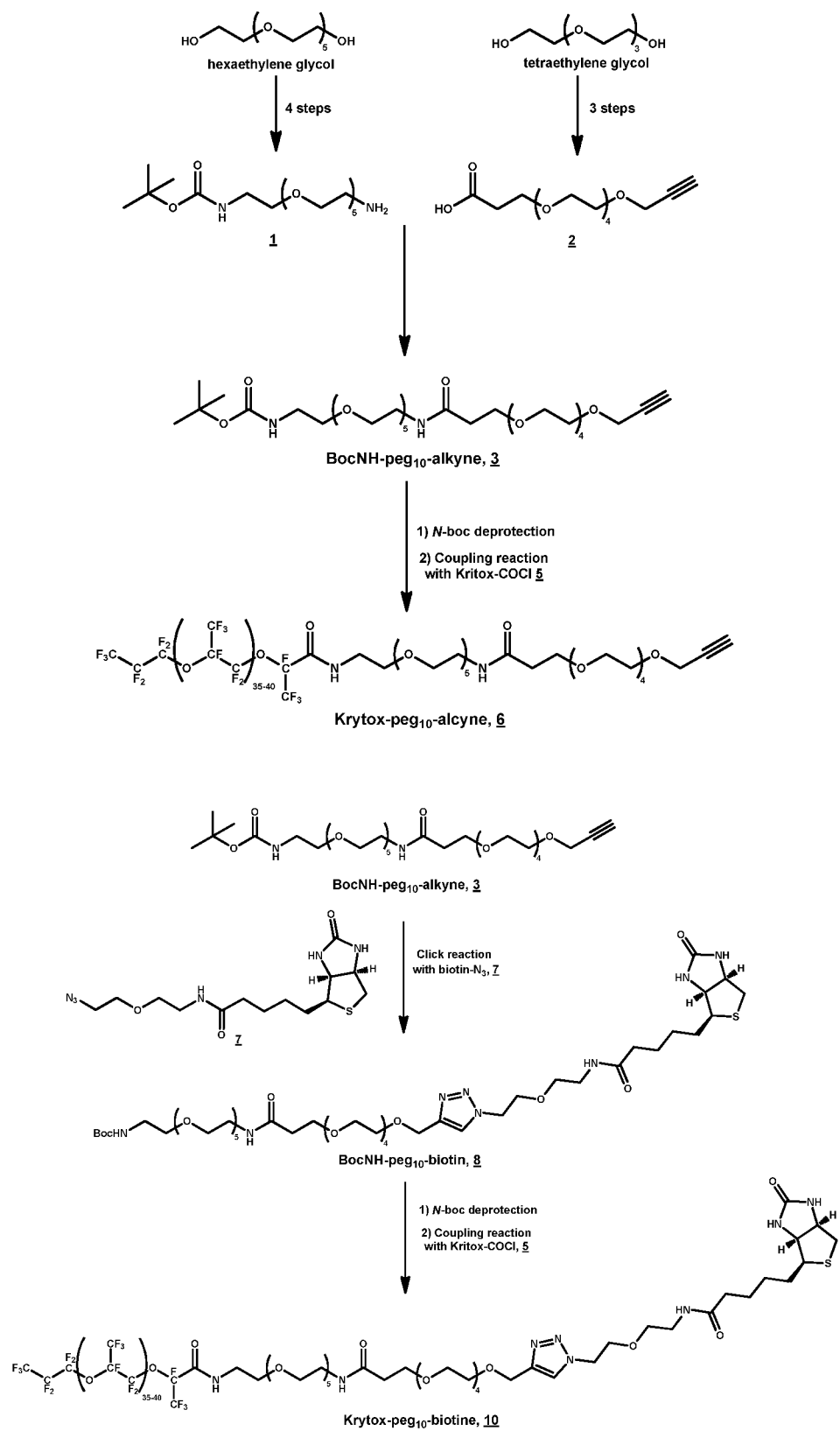
FIG. 1: Strategy synthesis of Krytox-peg$_{10}$-alkyne and Krytox-peg$_{10}$-biotin.

The inventors conceived a new method for capturing a molecular target present in the aqueous phase of a water-in-oil emulsion.

The method is based on the use of a binding system comprising (a) a surfactant bearing a functional moiety on its hydrophilic head group and (b) a chemoprobe.

The chemoprobe comprises at least two distinct domains namely (i) at least one capture moiety which is able to specifically bind the molecular target and (ii) at least one binding domain which is able to interact with the functional group of the surfactant through covalent or non-covalent interactions, directly or through a binding intermediary. The chemoprobe thus acts as a molecular staple between the functionalized surfactant and the molecular target, whereby the molecular target is captured at the inner surface of the emulsion droplets.

The capture of the molecular target at the inner surface of the emulsion droplets aims at promoting its recovery, detection and/or quantification.

The method for capturing a molecular target developed by the inventors can be used in various biotechnological fields, in particular in single cell proteomic analysis, and is particularly adapted to be implemented in microfluidic systems.

Noteworthy, the method of the invention is not limited to the capture of recombinant proteins bearing a specific tag such as a His-tag. It can be implemented for the capture of any molecular target of interest.

Accordingly, in a first aspect, the present invention relates to a method for capturing a molecular target, said method comprising:

a) providing water-in-oil emulsion droplets comprising a functionalized surfactant at the interface of droplets, said functionalized surfactant comprising at least one lipophilic tail linked to a functionalized hydrophilic head, b) contacting said functionalized surfactant with a chemoprobe present or added in the aqueous phase of the droplets, said chemoprobe comprising at least (i) one capture moiety capable of specific binding to a molecular target and at least (ii) one binding domain capable of direct or indirect binding to the functionalized surfactant, and c) contacting said functionalized surfactant with the molecular target present or added in the aqueous phase of the droplets, thereby capturing the molecular target at the inner interface of the emulsion droplets.

In the method of the invention, steps b) and c) may be performed simultaneously or sequentially, in any order.

In an embodiment, the aqueous phase of the droplets provided in step a) comprises a molecular target and a chemoprobe.

In another embodiment, the aqueous phase of the droplets provided in step a) comprises a molecular target and a chemoprobe is then added to the aqueous phase.

In a further embodiment, the aqueous phase of the droplets provided in step a) comprises a chemoprobe, and a molecular target is then added to the aqueous phase.

In another embodiment, the aqueous phase of the droplets provided in step a) does not comprise neither a molecular target nor a chemoprobe. In this embodiment, the molecular target and the chemoprobe are then added to the aqueous phase of the droplets, simultaneously or sequentially, in any order.

The addition of a chemoprobe or a molecular target in the aqueous phase of a droplet may be carried out by using any method well-known by the skilled person such as droplet fusion or pico-injection.

It should be noted that, as detailed below, each droplet may comprise one or several functionalized surfactants, one or several chemoprobes and one or several molecular targets.

Water-in-Oil Emulsion Droplets

In step (a) of the method, water-in-oil emulsion droplets are provided. These droplets are characterized as comprising a functionalized surfactant at their interface. In some embodiments, the aqueous phase of these droplets may comprise a molecular target and/or a chemoprobe.

As used herein, the term "droplet" or microdroplet" refers to an isolated portion of a first fluid that is surrounded by a second fluid. A droplet may be spherical or of other shapes depending on the external environment. Typically, the droplet has a volume of less than 1 µL, preferably of less than 1 nL, and more preferably of less than 500 pL. For instance, a droplet may have a volume ranging from 10 to 500 pL, preferably from 10 to 250 pL, more preferably from 10 to 200 pL and even more preferably of about 40 pL.

The terms "water-in-oil emulsion droplet", "water-in-oil droplet" and "w/o droplet" are used herein interchangeably and refer to an isolated portion of an aqueous phase that is completely surrounded by an oil phase. The term "water-in-oil emulsion" or "w/o emulsion" refers to an emulsion comprising an aqueous phase in the form of droplets dispersed in an oil phase. Preferably, the droplets have a homogenous distribution of diameters, i.e., the droplets may have a distribution of diameters such that no more than about 10%, about 5%, about 3%, about 1%, about 0.03%, or about 0.01% of the droplets have an average diameter greater than about 10%, about 5%, about 3%, about 1%, about 0.03%, or about 0.01% of the average diameter of the droplets. Preferably, the water-in-oil emulsion is a monodispersed emulsion, i.e. an emulsion comprising droplets of the same volume. Techniques for producing such a homogenous distribution of diameters are well-known by the skilled person (see for example WO 2004/091763). Typically, the w/o droplet has a volume of less than 1 nL, and more preferably of less than 500 pL. Preferably, a w/o droplet has a volume ranging from 10 to 500 pL, more preferably from 10 to 250 pL, even more preferably from 10 to 100 pL. In preferred embodiments, a w/o droplet has a volume ranging from 15 to 50 pL, preferably from 20 pL to 40 pL.

The aqueous phase is typically water or an aqueous buffer solution, such as Tris HCl buffer, Tris HCl/EDTA (TE) buffer, phosphate buffer saline (PBS) or acetate buffer. In some embodiments, the aqueous phase may contain a water-soluble organic solvent such as ethanol, methanol, acetonitrile, dimethylformamide, and dimethylsulfoxide. Preferably, the aqueous phase is water or an aqueous buffer solution.

The oil phase used to generate the w/o droplets may be selected from the group consisting of fluorinated oil such as FC40 oil (3M®), FC43 (3M®), FC77 oil (3M®), FC72 (3M®), FC84 (3M®), FC70 (3M®), HFE-7500 (3M®), HFE-7100 (3M®), perfluorohexane, perfluorooctane, perfluorodecane, Galden-HT135 oil (Solvay Solexis), Galden-HT170 oil (Solvay Solexis), Galden-HT110 oil (Solvay Solexis), Galden-HT90 oil (Solvay Solexis), Galden-HT70 oil (Solvay Solexis), Galden PFPE liquids, Galden® SV Fluids or H-Galden® ZV Fluids; and hydrocarbon oils such as Mineral oils, Light mineral oil, Adepsine oil, Albolene, Cable oil, Baby Oil, Drakeol, Electrical Insulating Oil, Heat-treating oil, Hydraulic oil, Lignite oil, Liquid paraffin, Mineral Seal Oil, Paraffin oil, Petroleum, Technical oil, White oil, Silicone oils or Vegetable oils. Preferably, the oil phase is fluorinated oil such as HFE-7500 (CAS number: 297730-93-9), FC40 oil (CAS Number: 51142-49-5), Galden-HT135 oil (CAS number: 69991-67-9) or FC77 oil (CAS Number: 86508-42-1), more preferably is HFE-7500 (also named Novec 7500). The skilled person may easily select suitable phase oil to implement the methods of the invention.

The water-in-oil emulsion can be prepared by any method known by the skilled artisan. In particular the water in oil emulsion can be prepared on a microfluidic system.

Molecular Targets

In the method of the invention, the functionalized surfactant is contacted with a molecular target present or added in the aqueous phase of the droplets.

The molecular target may be dissolved or suspended in the aqueous phase.

As used herein, the term "molecular target" refers to any kind of molecules to be recovered, detected and/or quantified which may be possibly present in the aqueous phase of the emulsion. The molecular target can be a biomolecule, i.e. a molecule that is present in living organisms, or a chemical compound that is not naturally found in living organism such as pharmaceutical drugs, toxicants, heavy metals, pollutants, etc. . . . . Preferably, the molecular target is a biomolecule. Examples of biomolecules include, but are not limited to, nucleic acids, e.g. DNA or RNA molecules, proteins such as antibodies, enzymes or growth factors, lipids such as fatty acids, glycolipids, sterols or glycerolipids, vitamins, hormones, neurotransmitters, and carbohydrates, e.g., mono-, oligo- and polysaccharides. The terms "polypeptide", "peptide" and "protein" are used interchangeably to refer to a polymer of amino acid residues, and are not limited to a minimum length. The protein may comprise any post-translational modification such as phosphorylation, acetylation, amidation, methylation, glycosylation or lipidation. As used herein, the term "nucleic acid" or "polynucleotide" refers to a polymeric form of nucleotides of any length, either ribonucleotides or deoxyribonucleotides. Preferably, the molecular target is a protein or a nucleic acid. More preferably, the molecular target is a protein.

The molecular target may be added to the aqueous phase before forming the emulsion or after. Preferably, the molecular target is present in a complex medium such as a cell lysate, a cell extract such as a DNA, protein, lipid extract, or in the form of a cell or genetic element, said complex medium being added to the aqueous phase.

In a particular embodiment, the molecular target is obtained from a genetic element encapsulated within the droplets. Preferably, each droplet contains only one genetic element. As used herein, a genetic element may be a molecule or molecular construct comprising a nucleic acid. The genetic element may comprise any nucleic acid (for example, DNA, RNA or any analogue, natural or artificial, thereof). The nucleic acid component of the genetic element may moreover be linked, covalently or non-covalently, to one or more molecules or structures, including proteins, chemical entities and groups, solid-phase supports such as magnetic beads, and the like.

In this embodiment, the droplets may further comprise an in vitro transcription and/or translation system or a nucleic acid amplification system.

Many suitable in vitro transcription and/or translation systems are commercially available. Such systems typically combine a prokaryotic phage RNA polymerase and promoter (e.g. T7, T3, or SP6) with eukaryotic (e.g. rabbit reticulocyte or wheat germ) or prokaryotic (e.g. E. coli) extracts, or cell-free translation systems reconstituted with purified components, to synthesize proteins from DNA templates. The appropriate system may vary depending on several parameters such as the nature of the molecular target, e.g. nucleic acid or protein, or the nature of the genetic element, e.g. organism of origin, nature of the promoter, etc . . . , as will be apparent to the skilled person.

Methods of amplifying genetic elements compartmentalized in emulsion droplets are well-know and widely practiced by the skilled person (see for example, Chang et al. Lab Chip. 2013 Apr. 7; 13(7):1225-42; Zanoli and Spoto, Biosensors 2013, 3, 18-43). In particular, the amplification may be performed by any known technique such as polymerase chain reaction (PCR), reverse transcription polymerase chain reaction (RT-PCR), nucleic acid sequence-based amplification (NASBA), loop-mediated isothermal amplification (LAMP), helicase-dependent amplification (HDA), rolling circle amplification (RCA), multiple displacement amplification (MDA) and recombinase polymerase amplification (RPA). The suitable method can be easily chosen by the skilled person depending on the nature of the encapsulated genetic element and the molecular target.

In another particular embodiment, the molecular target is from a biological entity encapsulated with the droplets. Preferably, each droplet contains only one biological entity.

The biological entity may be any organism of interest including, but not being limited to, prokaryotic cells, eukaryotic cells such as animal, plant, fungal or algae cells, protoplasts or viral particles such as animal, plant or bacterial viruses.

The molecular target may be secreted by the biological entity encapsulated in the droplet or exposed at the surface of the biological entity.

The molecular target may also be kept inside the biological entity, e.g. non-secreted protein. In this case, the method of the invention may further comprise lysing said biological entity to release the molecular target. This lysis may be performed using physical, chemical or biological means. In particular, the biological entity may be lysed using radiation (e.g. UV, X or γ-rays) or laser (see e.g. Rau et al. Appl. Phys. Lett. 2004. 84, 2940-2942). The lysis may also be induced by osmotic shock or by addition of a detergent or enzyme (see, e.g. Kintses et al. Chem. Biol. 2012. 19, 1001-1009; Novak et al. Angew. Chem. Int. Ed. 50, 390-395 (2011); Brown, R. B. & Audet, J. R. Soc. Interface 5, S131-S138 (2008)). In this case, a component altering the osmotic balance or the detergent or enzyme may be introduced inside the droplet by any known technique such as pico-injection or droplet fusion.

Surfactants

The water-in-oil emulsion comprises one or several surfactants. Said surfactant(s) can aid in controlling or optimizing droplet size, flow and uniformity and stabilizing aqueous emulsions. Suitable surfactants for preparing the water-in-oil emulsion of the invention are typically non-ionic and contain at least one hydrophilic head and one or several lipophilic tails, preferably one or two lipophilic tails. Said hydrophilic head(s) and the tail(s) may be directly linked, or linked via a spacer moiety. As used herein, a diblock surfactant refers to a surfactant comprising one hydrophilic head and one lipophilic chain. A triblock surfactant refers to a surfactant comprising one hydrophilic head and two lipophilic chains. Examples of suitable surfactants include, but are not limited to, sorbitan-based carboxylic acid esters such as sorbitan monolaurate (Span 20), sorbitan monopalmitate (Span 40), sorbitan monostearate (Span 60) and sorbitan monooleate (Span 80); block copolymers of polyethylene glycol and polypropylene glycol such as the tri-block copolymer EA-surfactant (RainDance Technologies) and DMP (dimorpholino phosphate)-surfactant (Baret, Kleinschmidt, et al., 2009); polymeric silicon-based surfactants such as Abil EM 90; triton X-100; and fluorinated surfactants such as PFPE-PEG and perfluorinated polyethers (e.g., Krytox-PEG, DuPont Krytox 157 FSL, FSM, and/or ESH). In the context of the invention, preferred surfactants are fluorinated surfactants, i.e. fluorosurfactants, and in particular fluorosurfactants comprising a perfluorinated polyether chain.

The total amount of surfactant (including non-functionalized and functionalized surfactants) in the carrier oil is preferably chosen in order to ensure stability of the emulsion and prevent spontaneous coalescence of droplets. Typically, the carrier oil used to generate droplets comprises from 0.5 to 10% (w/w), preferably from 1 to 8% (w/w), more preferably from 1 to 5% (w/w), and even more preferably from 2 to 5% (w/w) of surfactant. In some preferred embodiments, the carrier oil used to generate droplets comprises from 2 to 2.5% (w/w) of surfactant (including non-functionalized and functionalized surfactants).

Functionalized Surfactants

Water-in-oil emulsion droplets provided in step (a) comprise a functionalized surfactant at their interface. The interface of these droplets may comprise only functionalized surfactant(s) or a mix of functionalized and non-functionalized surfactants. The ratio between functionalized and non-functionalized surfactants may vary according to the specific use of the method of the invention and can be easily adapted by the skilled person. For example, functionalized surfactant may represent from 1 to 50% (w/w) of total surfactants, preferably from 2 to 30% (w/w), and more preferably from 5 to 20% (w/w).

As used herein, a "functionalized surfactant" refers to a surfactant which bears at least one functional moiety either on one of its hydrophilic head(s) or lipophilic tail(s). In the context of the invention, the functional moiety is preferably present on a hydrophilic head of the surfactant. In preferred embodiments, the term "functionalized surfactant" refers to a surfactant comprising one or two lipophilic tails, preferably two lipophilic tails (i.e. triblock surfactant), linked to a functionalized hydrophilic head.

The functionalized surfactant may comprise one or several (for instance, 2, 3, 4, 5, or 6) functionalized hydrophilic heads, whereby said surfactant can bind to one or several (for instance, 2, 3, 4, 5, or 6) chemoprobes (or binding intermediates). In embodiments wherein the surfactant comprises several functionalized hydrophilic heads, these heads may be identical or different and may bind to identical or different chemoprobes (or binding intermediates).

The one or more hydrophilic heads of the functionalized surfactant may each comprise one or several (e.g. 2, 3, 4 or 5) functional moieties.

As used herein, a "functional moiety" is virtually any chemical or biological entity which provides the surfactant with a function of interest. For instance, the functional moiety can enable to create a covalent interaction between the surfactant and an entity of interest. In other words, the functional moiety may comprise a chemical reactive group which can promote the formation of a covalent bond with the entity of interest. For instance, the functional moiety may comprise a chemical reactive group suitable to create a covalent bond by click-chemistry or by bioconjugation reaction. Bioconjugation reactions encompass reactions between amino acids such as lysine, cysteine or tyrosine with reactive groups as detailed in Koniev, O., Wagner, A, Chem. Soc. Rev., 44, 5495 (2015). For instance, the functional moiety may comprise a maleimide group or a squarane moiety, which can react with cysteine or tyrosine residues, respectively. Bioconjugation reactions are for instance depicted in the below table:

a) Amine conjugation

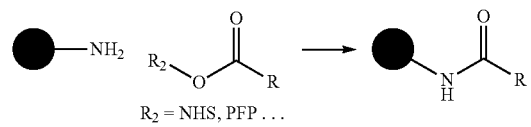

amine/activated ester

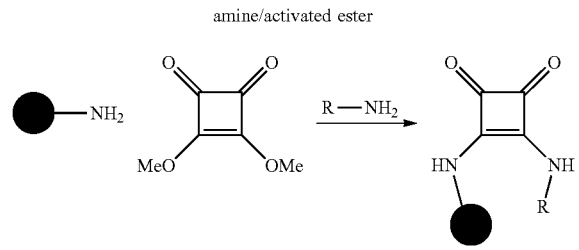

amine/squarate b) Bioconjugation via carbon-nitrogen double bonds.

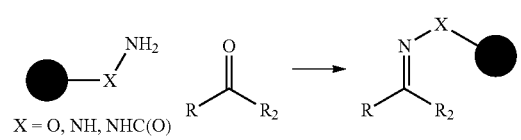

c) Thiol conjugation

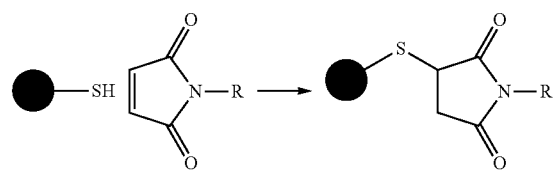

thiol/maleimide

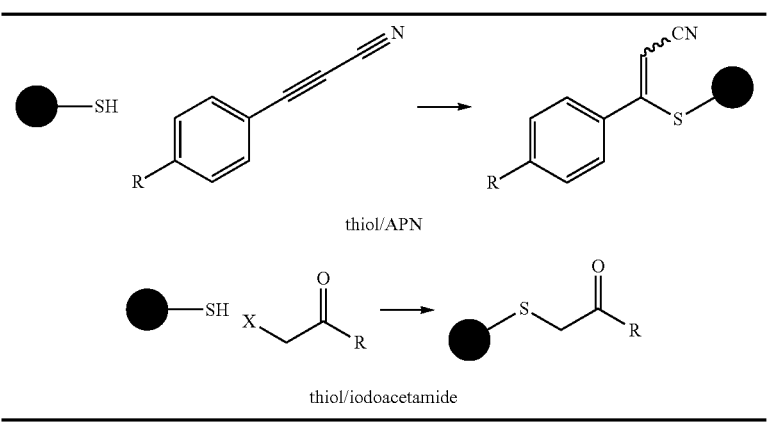

thiol/APN thiol/iodoacetamide

Alternatively, the functional moiety can enable to bind selectively and non-covalently an entity of interest.

In the present invention and as explained below, the functionalized surfactant is involved in the capture of the molecular target which is present in the aqueous phase of the emulsion, through interaction with the chemoprobe. Indeed, the functionalized surfactant enables to immobilize the chemoprobe on the inner interface of the droplets through its functional moiety, and thus to capture the molecular target. The functionalized surfactant has thus to be able to bind, directly or indirectly (i.e. via a binding intermediate), the chemoprobe. The functional moiety is thus selected with respect to the couple(s) chemoprobe(s)/functionalized surfactant(s) or in view of the combination chemoprobe(s)/binding intermediate(s)/functionalized surfactant(s). It goes without saying that, in the context of the invention, the functional moiety is selected so as to enable a specific binding with the chemoprobe, even in the presence of a complex medium.

The skilled person may easily select the functional moiety in view of the entity of interest to bind and the type of interactions (covalent or non-covalent interactions) to create between the surfactant and the entity of interest, in the present case the chemoprobe or a binding intermediate.

Each droplet of the emulsion may comprise one or several functionalized surfactant specific of one or several chemoprobes or binding intermediates.

In some embodiments, the functionalized surfactant may comprise a detection mean, such as a fluorophore or a MS-tag, which may be present on one of its tail and/or head.

In some other or additional embodiments, the functionalized surfactant may comprise one or more functionalized hydrophilic heads, each hydrophilic head being optionally linked to at least one tail and each hydrophilic head optionally bearing at least one functional moiety. In other words, the functionalized surfactant of the invention may be a multiblock and/or a multifunctionalized surfactant. Each hydrophilic head, tail and functional moiety of a surfactant may be identical or different.

For instance, the functionalized surfactant of the invention comprises, or consists in, a moiety of formula (Ia):

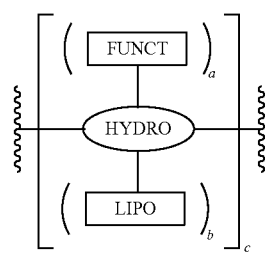

(Ia)

wherein
FUNCT stands for a functional moiety,
HYDRO stands for a hydrophilic head,
LIPO stands for a lipophilic tail,
each a and b are integers which are independently selected from 0 to 20, preferably from 0 to 5, such as 0, 1, 2, 3, 4 or 5, and
c is an integer from 1 to 20, preferably from 1 to 10, such as 1, 2, 3, 4, 5, 6, 7, 8, 9 or 10. With the proviso that said functionalized surfactant comprises at least one LIPO group linked to a HYDRO moiety bearing at least one FUNCT.

The Inventors show that the weight ratio between the hydrophilic part (namely the HYDRO head(s)) and the lipophilic part (namely the LIPO chain(s)) of the functionalized surfactant may have some impact on the capacity of the functionalized surfactant to stabilize the emulsion. In some embodiments, the weight ratio of "the lipophilic part" to "the hydrophilic part" in the functionalized surfactant is from 2.5 to 15, for instance from 2.5 to 7.5, from 3.0 to 7.0, from 6 to 15 or from 5.5 to 14.

A weight ratio from 2.5 to 15 encompass a weight ratio from 2.5 to 5.0, from 5.0 to 6.0, from 6.0 to 7.0, from 7.0 to 10, from 10 to 12, from 12 to 13, from 13 to 14.

In some embodiments, each HYDRO head has a molecular weight ranging from 500 to 2500 g·mol$^{-1}$, for instance from 500 to 1500 g·mol$^{-1}$, from 600 to 1500 g·mol$^{-1}$, from 600 to 1000 g·mol$^{-1}$ or from 1000 to 1500 g·mol$^{-1}$. In some other or additional embodiments, each LIPO chain has a molecular weight from 4000 to 8500 g·mol$^{-1}$, for instance from 6000 to 7000 g·mol$^{-1}$, such as about 6 500 g·mol$^{-1}$.

In some embodiments, the functionalized surfactant comprises, or consists in, a moiety of formula (Ia) which comprises at least two HYDRO moieties (i.e. c is at least 2), each HYDRO bearing at least one FUNCT moiety (i.e. each a is at least 1) and wherein b is 0 except for one HYDRO moiety in which b is at least 1, preferably 2 or 3.

In some embodiments, the functionalized surfactant comprises or consists in a moiety of formula (Ib)

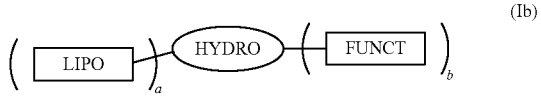

Wherein: a, b, LIPO, HYDRO and FUNCT are as defined in formula (Ia).

In some embodiments, the functionalized surfactant is of formula (Ib), wherein a is 1 or 2 and b is selected from 1, 2, 3 and 4.

In some other embodiments, the functionalized surfactant is of formula (Ib) wherein a is an integer from 1 to 6, more preferably 1, 2, or 3, and b is an integer from 1 to 3, more preferably 1 or 2.

In another embodiment, the functionalized surfactant comprises or consists in a moiety of formula (Ic)

wherein a, HYDRO and FUNCT are as defined in formula (Ib) or (Ia). Preferably, a is 1, 2 or 3.

In some preferred embodiments, the LIPO, HYDRO and FUNCT moieties present in the functionalized surfactant, in particular as depicted in any one of formula (Ia), (Ib) or (Ic) are as follows:
- each LIPO is a lipophilic tail independently selected from the group consisting of a saturated or unsaturated alkyl chain, optionally interrupted by one or several heteroatoms and optionally substituted by one or several groups selected from $C_1$-$C_3$ alkyl groups, halogens such as F, Cl or Br, —OH, —OMe, and —$CF_3$, a perfluoropolyether chain, a perfluorocarbon chain and combinations thereof,
- each HYDRO is a hydrophilic head comprising a moiety independently selected from a dimorpholinophosphate group, a polyether, a polyetheramine, a polyglycerol, and combinations thereof,
- each FUNCT is the functional moiety of the surfactant and is able to interact with the chemoprobe or the binding intermediate through covalent or non-covalent interactions.

When the surfactant comprises several LIPO groups, said LIPO may be the same or different.

When the surfactant comprises several HYDRO groups, said HYDRO groups may be the same or different.

When the surfactant comprises several FUNCT moieties, said FUNCT groups may be the same or different. In some embodiments, the surfactant comprises at least two distinct FUNCT. The presence of distinct FUNCT moieties in the functionalized surfactants may be useful to selectively capture distinct molecular targets.

LIPO and HYDRO on one hand and HYDRO and FUNCT on the other hand may be directly linked, or linked via a connector group or a linker. A connector group refers to moiety comprising a heteroatom and able to connect two chemical groups. Preferably the connector group is selected from —O—, C(=O)—OC(O)—, —C(O)O—, —OC(O)O—, —S—, —SS—, —SC(O)—, —OC(S)—, —$NR^1$—, —$NR^1$C(O)—, —C(O)$NR^1$—, —$NR^1$C(S)—, —C(S)$NR^1$—, —OC(O)S—, —OC(S)O—, —SC(O)O—, —OC(S)S—, —SC(O)S—, —SC(S)O—, —SC(S)S—, —OC(O)$NR^1$—, —OC(S)$NR^1$—, —$NR^1$C(S)O—, —$NR^1$C(O)S—, —$NR^1$C(O)$NR^2$—, —$NR^1$C(S)$NR^2$—, —SC(O)S—, —SC(S)O—, —S(O)—, —S(O)_2—, —O($CR^1R^2$)O—, —C(O)O($CR^1R^2$)O—, —OC(O)O($CR^1R^2$)O—, —P(O)($R^1$)—, —P(O)(O$R^1$)—, —P(O)($R^1$)O—, —OP(O)(O$R^1$)—, —OP(O)($R^1$)O—, —$NR^1$P(O)($R^2$)—, —$NR^1$P(O)(O$R^2$)—, —$NR^1$P(O)($R^2$)O—, —OP(O)(O$R^1$)— and —OP(O)($R^1$)O— wherein $R^1$ and $R^2$ are independently H or $CH_3$, preferably H or via a linker.

As used herein, a "linker" refers to any chemical group comprising from 2 to 40, preferably from 2 to 30 carbon atoms and at least one connector group as described above. Examples of linkers are for instance described in table 4 of US patent application 2010/0240883. Another example of an appropriate linker is iminodiacetic acid moiety.

In some embodiments, the linker comprises at least one cyclic moiety. The cyclic moiety typically has 5 to 14 ring atoms and may comprise one or several heteroatoms such as O, N, or S. The cyclic moiety may be aliphatic or aromatic. The cyclic moiety may comprise 2 or 3 rings which are fused together. Preferred cyclic moieties are 5-atom or 6-atom rings.

Cyclic moieties of interest encompass, without being limited to, pyrrole, furan, thiophene, pyrazole, imidazole, oxazole, triazole, phenyl, naphthalene, pyridine, piperidine, pyridazine, pyrimidine, pyrazine, oxazine, dioxine, triazine, piperazine, morpholine, and thiazine.

In some other embodiments, the linker is a saturated or unsaturated hydrocarbon chain, optionally interrupted by one or several heteroatoms or by one or several cycles or heterocycles; and optionally substituted by one or several groups selected from $C_1$-$C_3$ alkyl groups, halogens such as F, Cl or Br, —OH, —OMe, and —$CF_3$; said linker having a connector group at least one of its extremity. In some embodiments, the linker may be of formula:

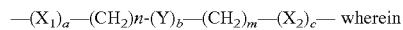 wherein a, b and c are independently 1 or 0,
n et m are independently an integer from 0 to 30, preferably from 0 to 10 such as 1, 2, 3, 4 or 5,
$X_1$ and $X_2$ are independently selected from connectors groups as described above, in particular —O—, —$NH_2$, —C(=O)—, OC(=O), (C=O)O, NHC(=O), C(=O)NH, NHC(=O)NH, NHC(=O)O, and OC(=O)NH,
Y is selected from O, NH, and three to eight, preferably five to six-membered aliphatic or aromatic rings. In some embodiments, Y is a heterocycle, preferably a five-membered heterocycle such as triazole, pyrrole, thiophene, or imidazole.

In some alternate or additional embodiments, the functionalized surfactant comprises at least one cleavable linker. The at least one cleavable linker preferably links together a LIPO moiety and a HYDRO moiety. The cleavable linkers can be selected among the group consisting of enzymatically cleavable linkers, nucleophile/base sensitive linkers, reduction sensitive linkers, photocleavable linkers, electrophile/acid sensitive linkers, and oxidation sensitive linkers, for instance as illustrated in Leriche, et al. Bioorg. Med. Chem. 20, 571 (2012). Other examples of cleavable linkers can be found in West et al. Current Drug Discovery Technologies, 2, 123 (2005).

Preferably, the surfactants comprise one or two LIPO chains, which can be identical or different. In some embodiments, the surfactants comprise two identical LIPO chains.

In some embodiments, each LIPO present in the surfactant is independently selected from perfluoropolyether chains and perfluorocarbon chains. Preferably, each LIPO is a perfluoropolyether chain comprising from 10 to 50 monomers, preferably from 25 to 45 monomers.

Examples of perfluoropolyethers chain encompass, without being limited to, poly((per)fluoromethylene oxide), poly((per)fluoroethylene oxide), poly((per)fluoropropylene oxide) (also called polyhexafluoropropylene oxide) and poly((per)fluorobutylene oxide).

In some embodiments, each LIPO is a polyhexafluoropropylene oxide chain comprising from 10 to 50 monomers. For instance, each LIPO may comprise the following moiety ($L_1$):

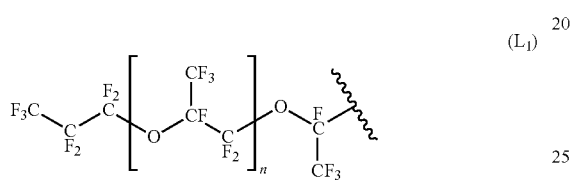

wherein n is an integer from 25 to 45, preferably from 35 to 40.

In some embodiments, each HYDRO comprises at least one polyether chain comprising from 2 to 50 monomers, preferably from 2 to 30 monomers, more preferably from 2 to 10 monomers, such as 2, 3, 4, 5, 6, 7, 8, 9 and 10 monomers. HYDRO may comprise several polyether chains, for instance 2, 3, 4, 5, 6, or 7 polyether chains, each polyether chain comprising from 2 to 50 monomers. The polyether chains are preferably linearly connected. The connection between two consecutive polyether chains may be of any type, and can be for instance performed via a connector group or a linker as described above. Each polyether chain may bear one or several FUNCT moieties, which can be the same or different.

Examples of suitable polyether chains encompass polyethylene glycol, polypropylene glycol, poly(ethylene glycol) diamine and poly(propylene glycol) diamine.

For instance, HYDRO may comprise one or several polyethylene glycol chains comprising from 2 to 30, preferably from 2 to 10 monomers, said polyethylene glycol chains being linearly connected.

As further detailed below, each functional moiety FUNCT may be of any type, with the proviso that FUNCT comprises a moiety enabling to create covalent or non-covalent interactions with the chemoprobe or the binding intermediate of interest.

Each FUNCT is thus selected depending on the interaction to achieve with said chemoprobe or binding intermediate. Examples of FUNCT are further detailed below in the section entitled "*Interactions between the functional surfactant and the chemoprobe*".

The FUNCT moieties present in the surfactant may be the same or may be different. In some embodiments, the functionalized surfactant comprises from 1 to 4 FUNCT moieties, preferably one or two FUNCT moieties.

In some embodiments, each FUNCT moiety has a molecular weight lower than 2000 g·mol$^{-1}$, preferably lower than 1000 g·mol$^{-1}$.

In some further embodiments, each FUNCT comprises a reactive chemical group suitable to perform a click reaction, such as an azide-alkyne dipolar addition and iminosydnone or sydnone derivatives-strained alkyne cycloadditions as described in PCT/EP2015/060805 and PCT/EP2015/063750, the disclosure of which being incorporated herein by reference.

For instance, each FUNCT may comprise an azido group or an alkyne group, such as a strained alkynyl group. Strained alkynyl groups encompass, without being limited to, cyclooctyne scaffolds (a)-(f):

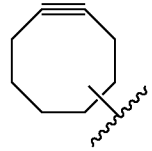

(a)

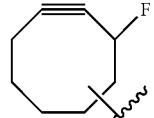

(b)

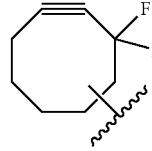

(b)

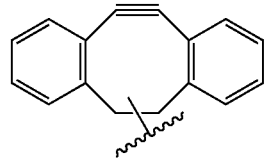

(c)

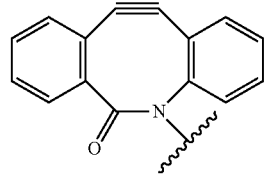

(d)

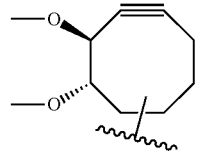

(e)

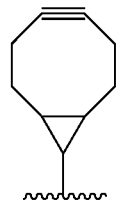

(f)

In some other embodiments, each FUNCT enables to promote direct or indirect non-covalent interactions with the chemoprobe. Each FUNC may be selected in the group consisting of biotin, avidin and streptavidin, preferably biotin.

In some embodiments, the functionalized surfactant is of formula (Ic). In some more specific embodiments, the functionalized surfactant of the invention is a diblock surfactant of formula (II):

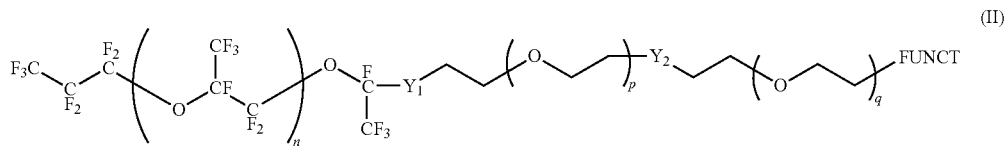

(II)

wherein
n is an integer from 25 to 45, preferably from 35 to 40,
p and q are integers independently selected from 1 to 10, preferably from 2 to 8,
$Y_1$ and $Y_2$ are independently selected among connectors and linkers as described above, in particular $Y_1$ and $Y_2$ are selected from the group consisting of —O—, —NH$_2$, —C(=O)—, OC(=O), (C=O)O, NHC(=O), C(=O)NH, NHC(=O)NH, NHC(=O)O, and OC(=O)NH, and
FUNCT being as further defined below and referring to the functional moiety of the functional surfactant. For instance, FUNCT comprises a moiety selected from a biotin, an azido group, an alkynyl group, in particular a strained alkynyl group as described below.

Examples of functional surfactants of formula (II) are for instance:

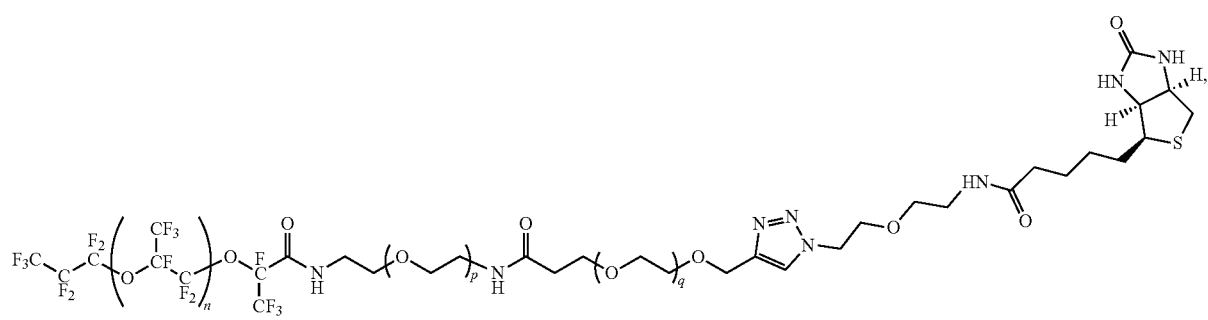

(i)

with n = 35-40, p = 5 and q = 4

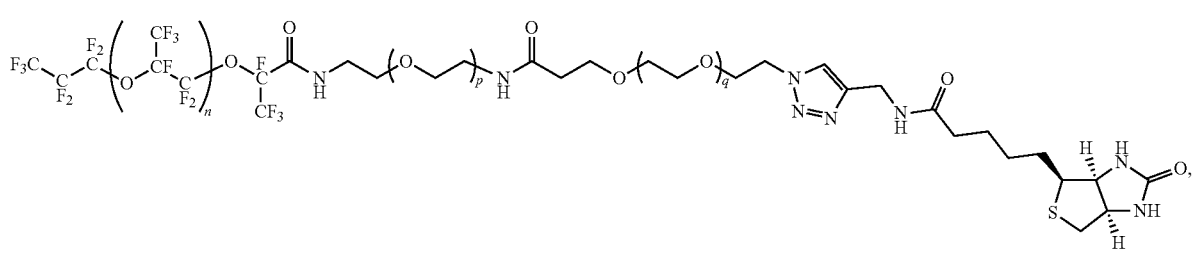

(ii)

with n = 35-40, p = q = 5

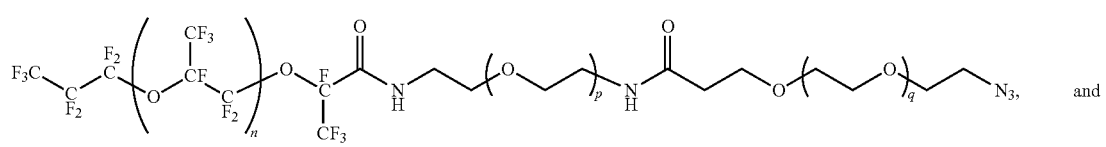

(iii)

and with n = 35-40, p = q = 5

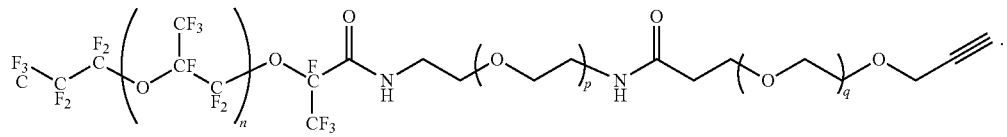

(iv)

with n = 35-40, p = 5, q = 4

In some other embodiments, the functionalized surfactant of the invention is a triblock surfactant of formula (IIIa):

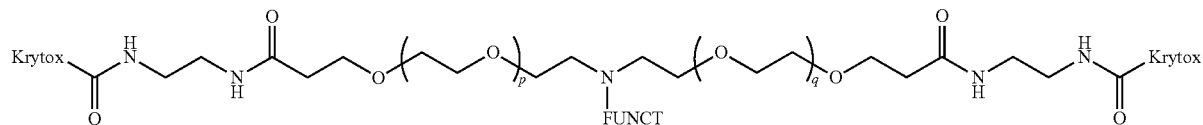

(IIIa)

wherein:
p and q are integers independently selected from 1 to 10, preferably from 2 to 8,
Krytox is

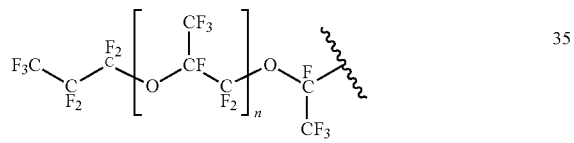

with n is from 25 to 45, preferably n=35-40,
FUNCT as further defined below and refers to the functional moiety of the functional surfactant. For instance, FUNCT comprises a moiety selected from a biotin, an azido group, an alkynyl group, in particular a strained alkynyl group as described below.

Examples of functionalized surfactants of formula (IIIa) are for instance:

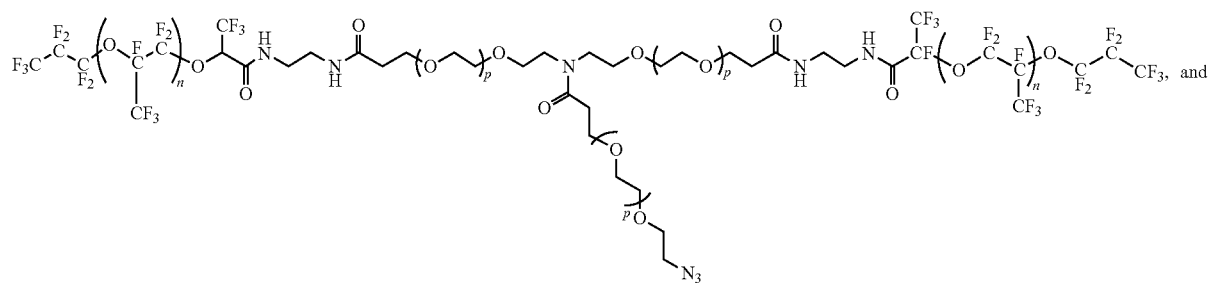

(i)

with n = 35-40 and p = 6, 5, or, 4

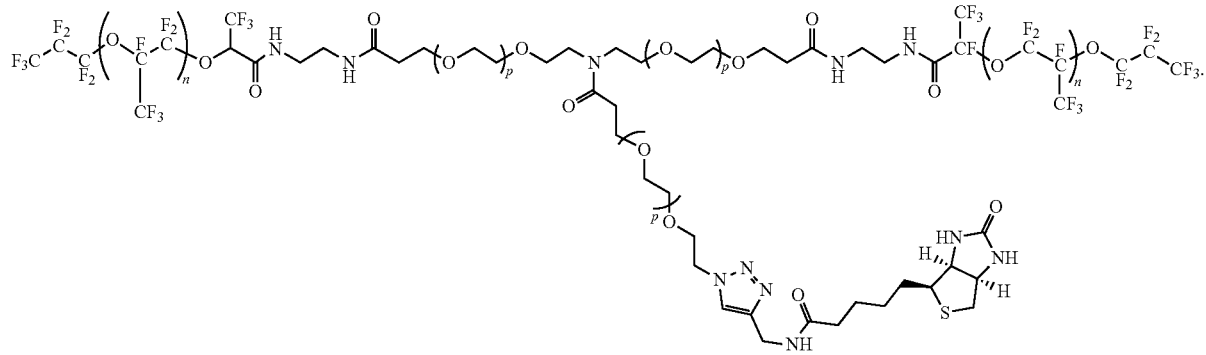

with n = 35-40 and p = 6, 5, or, 4

In a particular aspect, the invention relates to a functionalized surfactant comprising:
one or two lipophilic tails (LIPO), linked to
a hydrophilic head (HEAD), said hydrophilic head bearing at least one, for instance 1, 2, 3 or 4 moieties, of formula ($H_1$):

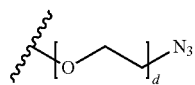

(H₁)

wherein d is an integer from 1 to 12, for instance from 2 to 6.

The LIPO is as defined above. In a preferred embodiment, LIPO is selected from perfluoropolyether chains and perfluorocarbon chain comprising from 10 to 50 monomers, preferably from 25 to 45 monomers. Examples of perfluoropolyethers chain encompass, without being limited to, poly((per)fluoromethylene oxide), poly((per)fluoroethylene oxide), poly((per)fluoropropylene oxide) (also called polyhexafluoropropylene oxide) and poly((per)fluorobutylene oxide). For instance, each LIPO present in the functionalized surfactant may comprise, or consist in, the following moiety ($L_1$):

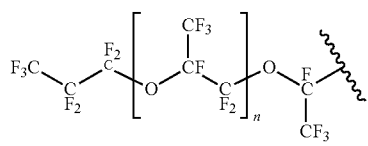

(L₁)

wherein n is an integer from 25 to 45, preferably from 35 to 40.

In some embodiments, the weight ratio of the lipophilic part (namely the LIPO chain(s)) to the hydrophilic part (namely the hydrophilic head (HEAD)) in the functionalized surfactant is from 2.5 to 15, for instance from 6 to 15 or from 6.5 to 14.

In some additional or alternate embodiments, the molecular weight of the functionalized surfactant is from 6000 to 20 000 g·mol$^{-1}$, for instance from 6 500 to 16 000 g·mol$^{-1}$ or from 7 000 to 15 000 g·mol$^{-1}$.

In some embodiments, the functionalized surfactant of the invention comprises:
one or two lipophilic tails (LIPO) comprising, or consisting in, the moiety of formula (L1):

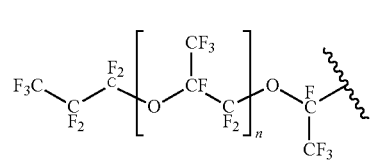

wherein n is an integer from 25 to 45, preferably from 35 to 40, linked to
A hydrophilic head (HEAD), said hydrophilic head bearing at least one, for instance 1, 2, 3 or 4 moieties of the following formula ($H_1$):

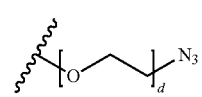

(H₁)

wherein d is an integer from 1 to 12, for instance from 2 to 6.

Preferably, the weight ratio of the lipophilic part to the hydrophilic part in said functionalized surfactant is from 2.5 to 15, preferably from 2.5 to 7.5.

In some embodiments, the hydrophilic head of the functionalized surfactant may comprise at least two moieties of the following formula ($H_1$):

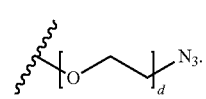

(H₁)

For instance, the hydrophilic head of the functionalized surfactant may comprise at least one moiety of formula ($H_2$):

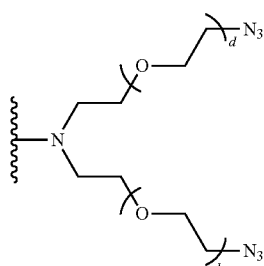

(H₂)

wherein d is an integer from 1 to 12, for instance from 2 to 6, such as 3, 4 or 5.

In a particular embodiment, the functionalized surfactant of the invention comprises:
- one or two lipophilic tails (LIPO) comprising, or consisting of, a moiety of formula ($L_1$), said one or two LIPO being linked to
- a hydrophilic head (HEAD), said hydrophilic head comprising one or two moieties of formula ($H_2$) as defined above.

For instance, the functionalized surfactant may comprise one $H_2$ moiety and one $L_1$ moiety. Alternatively, the functionalized surfactant may comprise two $H_2$ moieties and one $L_1$ moieties. As another example, the functionalized surfactant may comprise two $H_2$ moiety and two $L_1$ moieties.

The molecular weight of the functionalized surfactant is from 6 000 to 20 000 g·mol⁻¹, for instance from 6 500 to 16 000 g·mol⁻¹ or from 7 000 to 15 000 g·mol⁻¹.

The hydrophilic head (HEAD) typically comprises a Central moiety (CENTRAL). The central moiety is a $C_2$-$C_{40}$, preferably a $C_2$-$C_{30}$ group which may comprise one or several heteroatoms such as N, O or S. The central moiety bears the $H_1$ or $H_2$ moieties and is linked to the at least one LIPO group. The Central moiety is typically a linker which may optionally comprise one or several polyether chains, for instance 1 to 4 polyether chains. The polyethers chains typically comprise from 2 to 12 monomers, such as 2 to 6 monomers. A preferred polyether chain is polyethylene glycol and derivatives thereof. The linker present in the Central moiety may be any linker as defined above.

For instance, the linker may comprise at least one cyclic moiety having from 5 to 14 ring atoms. The ring atoms may comprise one or several heteroatoms such as O, N, or S. The cyclic moiety may be aliphatic or aromatic. The cyclic moiety may comprise 2 or 3 rings which are fused together. Preferred cyclic moieties are 5-atom or 6-atom rings. Cyclic moieties of interest encompass, without being limited to, pyrrole, furan, thiophene, pyrazole, imidazole, oxazole, triazole, triazine, phenyl, naphthalene, pyridine, piperidine, pyridazine, pyrimidine, pyrazine, oxazine, dioxine, piperazine, morpholine, and thiazine.

The $L_1$ and/or $H_2$ moieties can be connected to said cyclic moiety directly or by the mean of a connector and/or a polyether chain.

As another example, the linker may be a saturated or unsaturated hydrocarbon chain having a connector group at least one of its extremity. Said hydrocarbon chain is optionally interrupted by one or several heteroatoms, or by one or several carbon cycles or heterocycles. Said hydrocarbon chain may be further substituted by one or several groups selected from $C_1$-$C_3$ alkyl groups, halogens such as F, Cl or Br, —OH, —OMe, and —CF₃.

For instance, the Central moiety may be of one of the following formula:

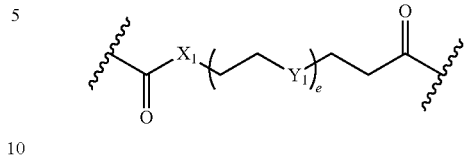

wherein e is an integer from 1 to 12, preferably from 2 to 6 such as 3, 4 or 5, $X_1$ and $Y_1$ are independently selected from NH, CH₂ and O,

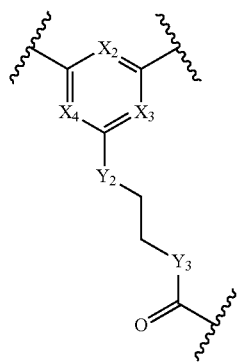

wherein $Y_2$ and $Y_3$ are independently selected from NH, CH₂ or O and $X_2$, $X_3$ and $X_4$ are independently selected from CH and N, and

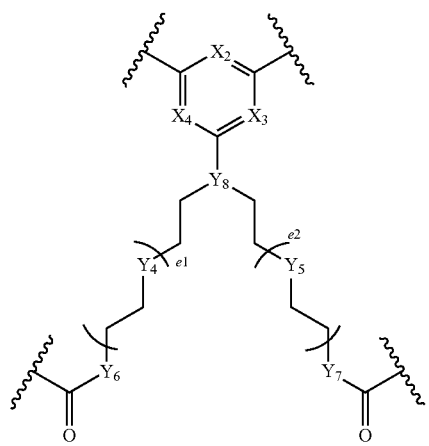

wherein
- $X_2$, $X_3$ and $X_4$ are independently selected from CH and N,
- $Y_8$ is CH or N,
- $Y_4$, $Y_5$, $Y_6$ and $Y_7$ are independently selected from NH, O and CH₂ and,
- e1 and e2 are integers independently selected from 1 to 12, preferably from 2 to 6 such as 2, 3, 4, 5 or 6.

Functionalized surfactants comprising such a central moiety are for instance:
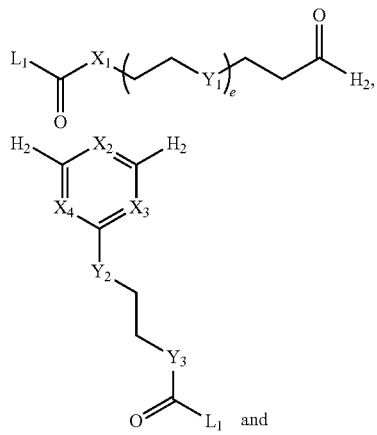
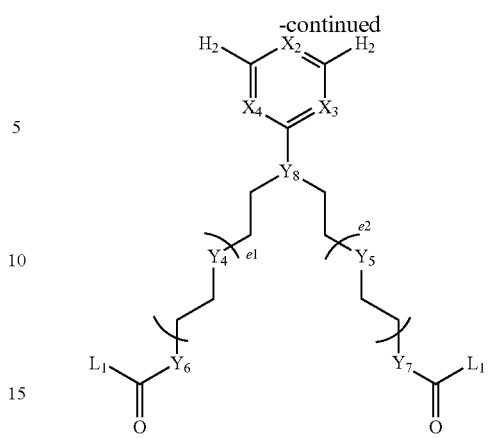
wherein $L_1$ and $H_2$ are as defined above.
For illustration, the functionalized surfactant of the invention may be selected among:
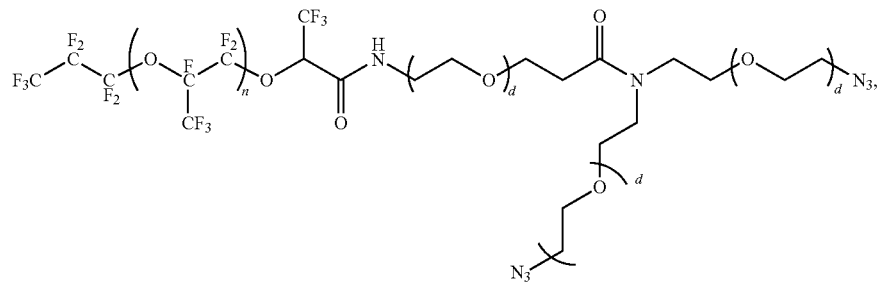
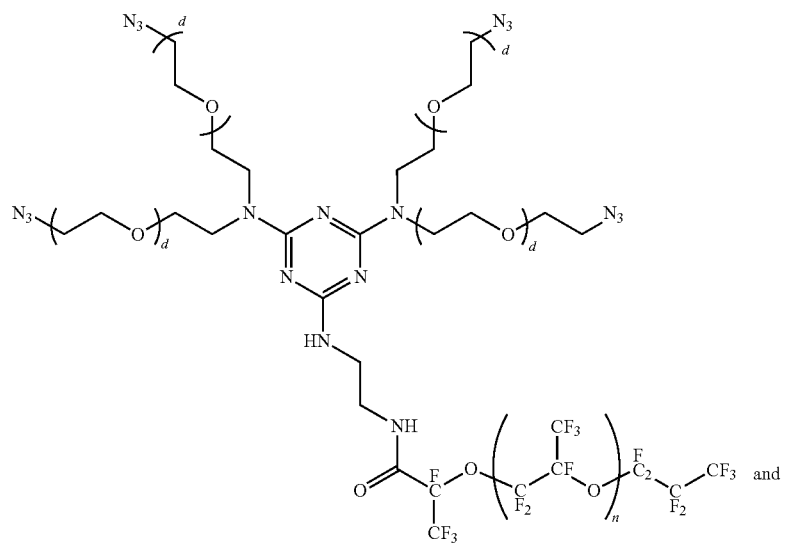
and -continued

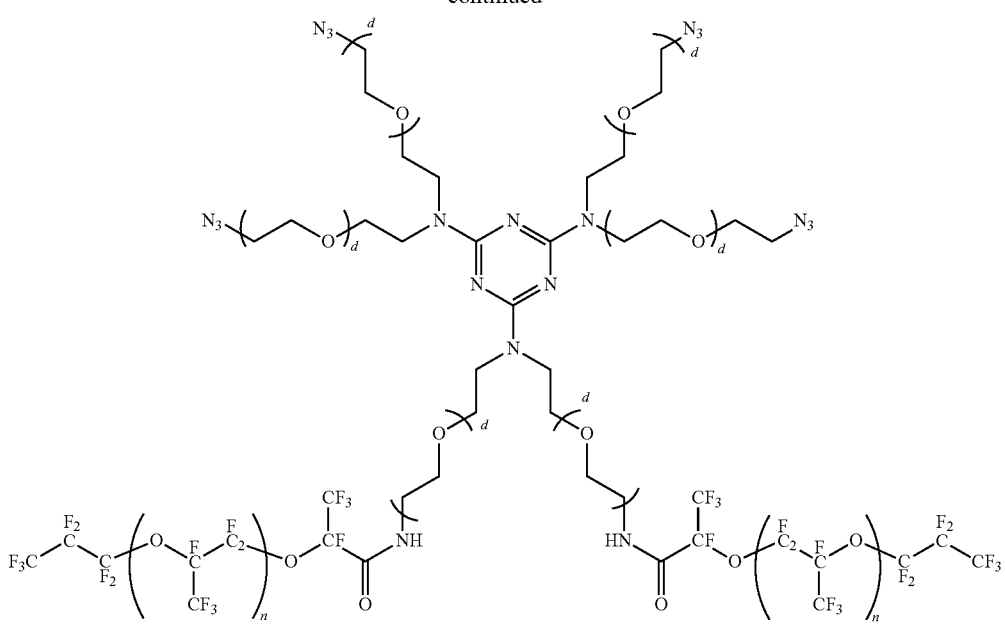

Wherein n is an integer from 25 to 45, preferably from 35 to 40 and d is an integer from 1 to 12, preferably from 2 to 6.

Preferred surfactants are those wherein n is an integer from 35 to 45 and d is 3.

The functionalized surfactants may be prepared by chemical synthesis. For instance, diblock surfactants of formula (II) may be prepared by pseudo-peptidic coupling reactions between a peg-based hydrophilic chain bearing a free amine and the perfluoropolyether acidic chain prealably activated as its acyl chloride form. The hydrophilic chain can be obtained by coupling two oligoethylene glycol derivatives conveniently functionalized, for instance with biotin or alkyne group.

Functionalized triblock surfactants of formula (IIIa) can be prepared from a trifunctional peg derivative by pseudo-peptidic coupling reaction with Krytox-COCl. The trifunctional peg derivative can be prepared by reductive azide dimerization of an oligoethylene glycol derivative bearing an azide and an N-protected amino moiety followed by the pseudo-peptidic coupling of an acid peg chain with the central secondary amine.

The synthesis of some diblock and triblock surfactants is described further below in the section "Examples".

It goes without saying that the invention also relates to functionalized surfactants per se described herein, in particular those of formula (Ia), (Ib), (Ic), (II) and (Ma) or those comprising $H_1$ or $H_2$ moieties as described above.

Interactions Between the Functional Surfactant and the Chemoprobe

As mentioned above, the functional moiety of the functionalized surfactant may promote either covalent or non-covalent interactions with the chemoprobe. This interaction may be direct or indirect, i.e. through a binding intermediate.

In an embodiment, the functional moiety promotes covalent interactions with the chemoprobe or a binding intermediate, preferably specific covalent interactions with the chemoprobe or a binding intermediate.

As used herein, a "covalent interaction" between the functionalized surfactant and the chemoprobe or binding intermediate, refers to the creation of a covalent bond (i.e. at least one covalent bond) between the hydrophilic head of the functionalized surfactant and the binding domain of the chemoprobe or binding intermediate. The covalent bond(s) can be formed by reaction of a chemical reactive group present on the binding domain of the chemoprobe or binding intermediate with another chemical reactive group present in the functional moiety of the functionalized surfactant. In a preferred embodiment, the reactive group present on the chemoprobe or binding intermediate and that present on the functionalized surfactant are selected so as to react together through a click-reaction and/or a bioconjugation reaction, in particular as described above. In some particular embodiments, the reactive group present on the chemoprobe or binding intermediate and that present on the functionalized surfactant are selected so as to react together through a click-reaction. The term "specific covalent interactions" is used herein to indicate that the functional moiety of the surfactant has the capacity to create a covalent bond (i.e. at least one covalent bond) with the binding domain of the chemoprobe or the binding intermediate, while having relatively little detectable reactivity with other structures present in the aqueous phase. Preferably, the specific covalent interaction is a biorthogonal or biocompatible reaction between the functional moiety of the surfactant and a specific reactive group present in the binding domain of the chemoprobe or the binding intermediate.

"Click-reaction" or "Click-chemistry" is a concept introduced by Sharpless in 2001. "Click chemistry" generally refers to chemical reactions characterized by high yields, high chemoselectivity, which are simple to conduct and which generate inoffensive by-products. "Click reactions" can be typically conducted in complex media with high efficiency. Click reactions are typically used to create covalent heteroatom links (C—X—C) between two entities of interest. For review about click chemistry, one can refer to Kolb et al., Angew. Chem. Int. Ed. 2001, 40, 2004-2021) and to Rudolf et al., Current opinion in Chemical Biology, 2013, 17:110-117.

Examples of click reactions encompass, without being limited to, copper-catalyzed azide-alkyne dipolar cycloadditions (CuAAC), strain-promoted alkyne-azide cycloaddition (SPAAC), Diels-Alder reactions with tetrazines and strained alkynes or alkenes, tetrazine-isonitrile cycloadditions, thiol-alkene click reactions such as maleimide-cysteine cycloadditions, Staudinger azide-triarylphosphine conjugation, and sydnone-alkyne cycloadditions.

In the context of the invention, the click reactions can be conducted in aqueous media.

As mentioned above, in some aspects, the click reaction may be "bioorthogonal" or "biocompatible", this means that the reagents involved in the click reaction may react selectively and rapidly with each other in the presence of a plurality of biological entities. In some embodiments, the click reaction may be conducted in media comprising living cells, without interfering with cellular process.

For instance, biocompatible or biorthogonal click reactions encompass metal-free click-reactions (i.e. which do not require metal catalysts). Examples of metal-free click reactions are depicted hereunder:

Approach 1: Azide/cycloalkyne reaction

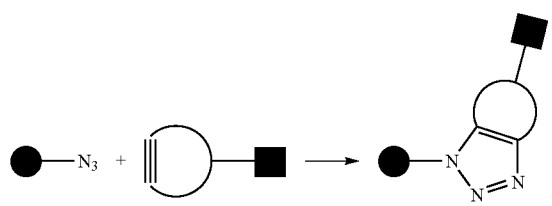

Approach 2: Tetrazine/Cyclooctene reaction

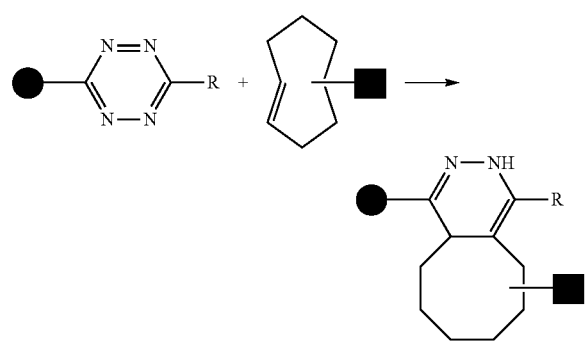

Approach 3: Tetrazole/Alkene reaction

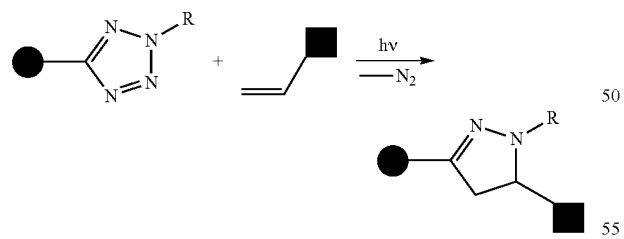

Approach 4: Chloro-oxime/Norbornene reaction

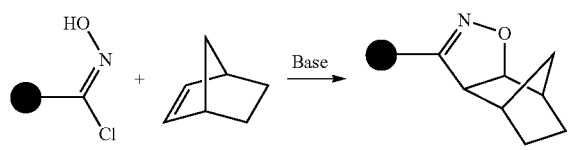

Approach 5: Thiol/alkene or Thiol/maleimide reaction

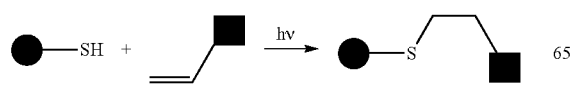

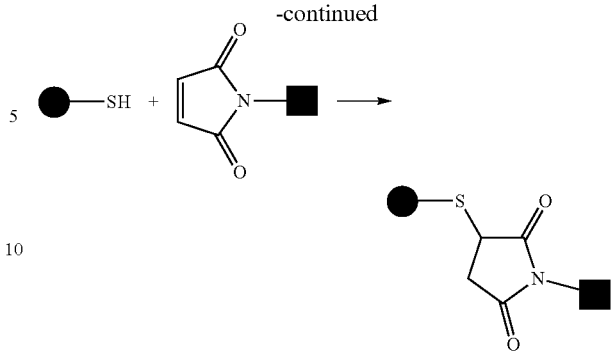

Other metal-free click-reactions of interest are for instance iminosydnone or sydnone derivatives-strained alkyne cycloadditions as described in PCT/EP2015/060805 and PCT/EP2015/063750, the disclosure of which being incorporated herein by reference.

For a review concerning biorthogonal chemistry, including click-chemistry, one can refer to Sletten and Bertozzi, Angew. Chem. Int. Ed. Engl. 2009, 48(38):6974-6998, the disclosure of which being incorporated herein by reference.

Preferred click-reactions are free-metal reaction, i.e. click-reactions which do not require the presence of a metal catalyzer such as copper salt.

In the context of the present invention, a preferred free-metal click reaction is strain-promoted alkyne-azide 1,3-dipolar cycloaddition (SPAAC) which refers to the reaction between an azido group and a strained alkyne moiety which leads to the formation of a triazole moiety. Typically, such a click reaction does not need the presence of a catalyst to occur.

Preferred strained alkynes are $C_6$-$C_{30}$ alkynes wherein the triple bond is sterically strained, in particular in a cyclooctyne scaffold. The strained alkyne may comprise a cyclooctyne scaffold which may be optionally substituted by one or several substituents such as halogens and/or fused to one or several cycles, including heterocycles. For instance, the strained alkyne may comprise one of the following cyclooctyne scaffolds (a)-(f):

(a)

(b)

(b)

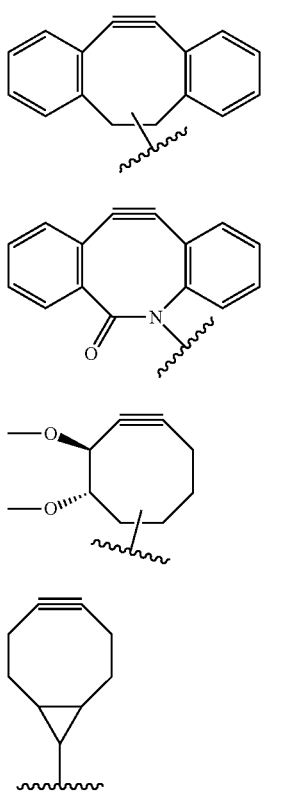

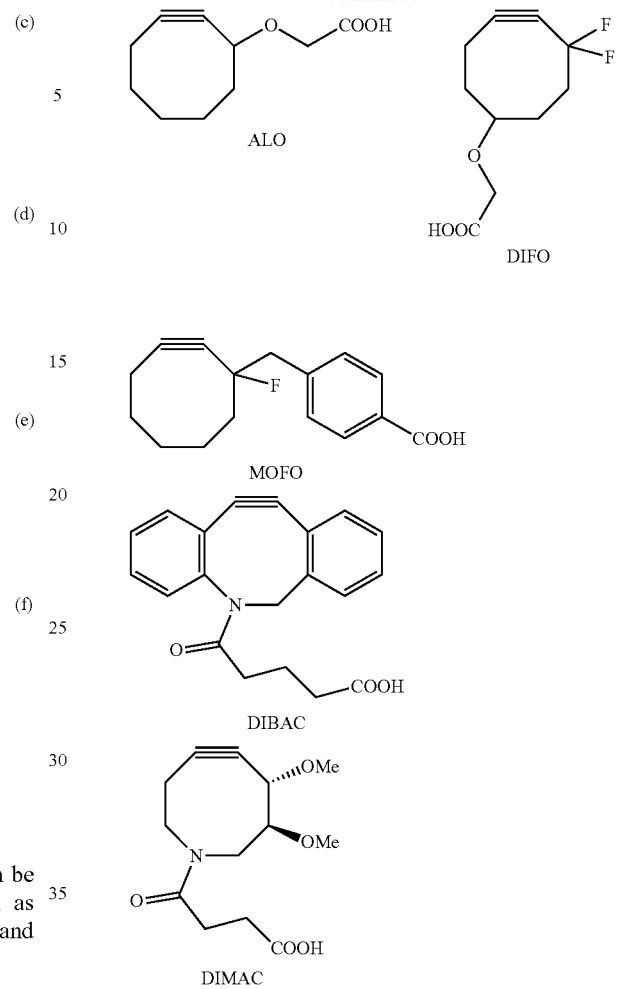

Strained alkynes containing one of said scaffolds can be prepared from commercially available reagents such as OCT, DIBO, BARAC, ALO, DIFO, MOFO, DIBAC and DIMAC:

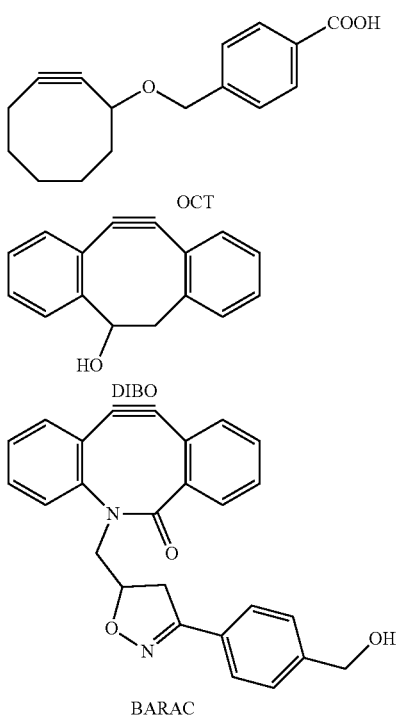

Accordingly, the functional moiety of the surfactant (i.e. FUNCT) can bear an azido group while the binding domain of the chemoprobe or binding intermediate can bear a strained alkyne scaffold, and vice versa. Preferably, the strained alkynyl group is selected from cyclooctyne scaffolds (a)-(f) as shown above, and more preferably is cyclooctyne scaffold (f).

In some embodiments, the chemoprobe or binding intermediate may bear several chemical reactive groups, e.g. 2, 3, 4, 5 or 6 chemical reactive groups. Said chemical groups may enable the chemoprobe or binding intermediate to interact with several functionalized surfactants. Alternatively, said chemical groups may enable the chemoprobe or binding intermediate to create several covalent bonds with one single functionalized surfactant bearing several functional moieties, such as 2, 3, or 4 functional moieties.

As mentioned above, the chemical reactive group(s) present in the binding domain of the chemoprobe or binding intermediate are preferably selected from strained alkynes and azido group. Preferably, the chemoprobe or binding intermediate bears one single type of chemical reactive groups. The chemical reactive group(s) can be introduced by bioconjugation reaction. For illustration only, the binding domain of the chemoprobe or binding intermediate may bear one of the following moieties:

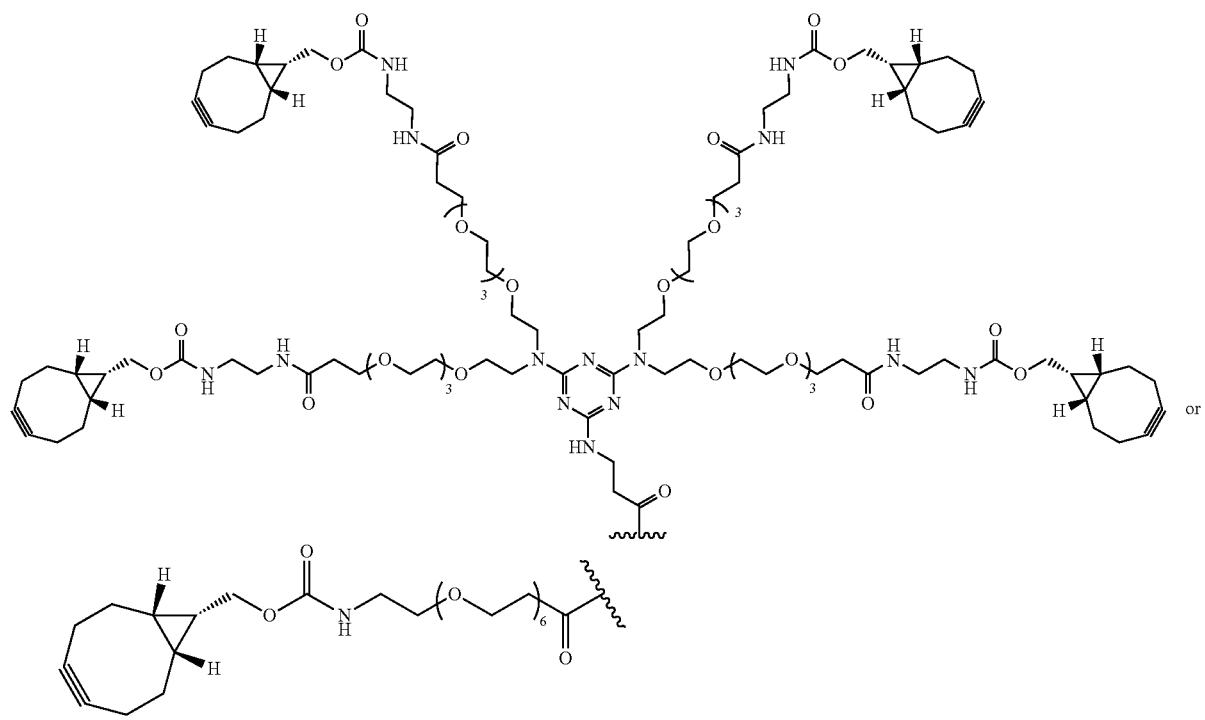

In another embodiment, the functional moiety promotes non-covalent interactions with the chemoprobe or a binding intermediate.

As used herein, a non-covalent interaction between the functionalized surfactant and the chemoprobe or binding intermediate, refers to the formation of a complex involving the functional moiety of the surfactant and a binding domain of the chemoprobe or the binding intermediate. Preferably, the functional moiety specifically binds to the binding domain of the chemoprobe or binding intermediate.

The term "specifically binding" is used herein to indicate that the functional moiety of the surfactant has the capacity to recognize and interact specifically with the binding domain of the chemoprobe or the binding intermediate, while having relatively little detectable reactivity with other structures present in the aqueous phase. There is commonly a low degree of affinity between any two molecules due to non-covalent forces such as electrostatic forces, hydrogen bonds, Van der Waals forces and hydrophobic forces, which is not restricted to a particular site on the molecules, and is largely independent of the identity of the molecules. This low degree of affinity can result in non-specific binding. By contrast when two molecules bind specifically, the degree of affinity is much greater than such non-specific binding interactions. In specific binding a particular site on each molecule interacts, the particular sites being structurally complementary, with the result that the capacity to form non-covalent bonds is increased. Specificity can be relatively determined by binding or competitive assays, using e.g., Biacore instruments. The affinity of a molecule X for its partner Y can generally be represented by the dissociation constant (Kd). In preferred embodiments, the Kd representing the affinity of the functional moiety of the surfactant and the binding domain of the chemoprobe or binding intermediate is from $1.10^{-6}$ M or lower, preferably from $1.10^{-7}$ M or lower, and even more preferably from $1.10^{-8}$ M or lower.

According to the type of interaction between the functional moiety of the surfactant and the binding domain of the chemoprobe or binding intermediate, the functional moiety may comprise, for example, an antibody, or a fragment or derivative thereof such as Fab', Fab', $F(ab)_2$, $F(ab')_2$, $F(ab)_3$, Fv, single-chain Fv (ScFv), diabodies or VHH, a ligand, a peptide or protein, an aptamer, a polysaccharide, a small organic molecule, a protein tag, or a cation binding group, while the binding domain of the chemoprobe or the binding intermediate comprises a group which specifically binds said functional moiety, or vice versa.

The interaction between the functionalized surfactant and the chemoprobe or the binding intermediate, may rely on various interaction systems such as affinity systems, ligand/anti-ligand couples or protein tags.

For example, the interaction between the functionalized surfactant and the chemoprobe or the binding intermediate may rely on cation binding groups (e.g. nitrilotriacetate (NTA, for binding to His tags), iminediacetate or triazacyclononane), protein binding tags or ligand/anti-ligand couples (e.g. antibody/antigen such as biotin/anti-biotin antibody and digoxygenine/anti-digoxigenin antibody, or ligand/receptor).

In a preferred embodiment, the functional moiety of the surfactant comprises a protein binding tag while the chemoprobe or the binding intermediate comprises a protein, a peptide or a fragment thereof which specifically binds said tag, or vice versa. A multitude of protein tags are well-known by the skilled person (see for example Young et al. Biotechnol. J. 2012, 7, 620-634) and include, for example, biotin (for binding to streptavidin or avidin derivatives), glutathione (for binding to proteins or other substances linked to glutathione-S-transferase), maltose (for binding to proteins or other substances linked to maltose binding protein), lectins (for binding to sugar moieties), c-myc tag, hemaglutinin antigen (HA) tag, thioredoxin tag, FLAG tag, polyArg tag, polyHis tag, Strep-tag, OmpA signal sequence tag, calmodulin-binding peptide, chitin-binding domain, cellulose-binding domain, S-tag, and Softag3, and the like.

In some embodiments, the chemoprobe and the functionalized surfactant directly interact together. For instance, the functional moiety of the surfactant may comprise a protein tag, e.g. biotin, while the binding domain of the chemoprobe comprises a group specifically interacting with said tag e.g. streptavidin or avidin, or vice versa. Alternatively, the functional moiety of the surfactant may comprise an aptamer or an antibody, while the chemoprobe comprises the ligand of said aptamer or said antibody, and vice versa.

In some other embodiments, the chemoprobe and the functionalized surfactant interact through a binding intermediate. In such a case, the binding intermediate is able to bind both the chemoprobe and the surfactant and thus acts as a bridge between said two entities. The binding intermediate thus contains a first binding domain able to bind to the chemoprobe and a second binding domain able to bind the functionalized surfactant. The binding domains of the intermediate can be of any type and are selected depending on the functional moiety of the surfactant and the binding domain of the chemoprobe.

For instance, the binding intermediate may be a streptavidin while the functional moiety of the surfactant and the binding domain of the chemoprobe both comprise a biotin. In such an embodiment, the chemoprobe may be a biotinylated aptamer or a biotinylated antibody specific to the molecular target.

The chemoprobe may comprise one or several (for instance, 2, 3, or 4) binding domains, whereby said chemoprobe can bind to one or several (for instance, 2, 3, or 4) functionalized surfactants or binding intermediates. In these embodiments, binding domains of the chemoprobe may be identical or different and may bind to identical or different functionalized surfactants or binding intermediates.

Contact of the Molecular Target with the Chemoprobe

In the method of the invention, the molecular target present in the aqueous phase is contacted with a chemoprobe comprising (i) at least one capture moiety capable of specific binding to the molecular target and (ii) at least one binding domain capable of directly or indirectly binding to the functionalized surfactant.

The chemoprobe may comprise one or several (for instance, 2, 3, or 4) capture moieties, whereby said chemoprobe can bind one or several (for instance, 2, 3, or 4) molecular targets. In embodiments wherein the chemoprobe comprises several capture moieties, these moieties may be identical or different and may target identical or different molecular targets.

The capture moiety of the chemoprobe may be any group which can specifically bind the molecular target. Examples of such groups include, but are not limited to an antibody, a fragment or derivative of an antibody, an aptamer, a spiegelmer, a peptide aptamer, a ligand or a substrate of the molecular target, a nucleic acid capable of hybridizing the molecular target, and a receptor or receptor fragment able to bind the molecular target.

In some preferred embodiments, the capture moiety of the chemoprobe is an antibody directed against the molecular target, a fragment or derivative of such antibody which is able to bind to the molecular target.

The binding domain of the chemoprobe, i.e. the domain which binds the functionalized surfactant or the binding intermediate, may be of any type, with the proviso that it comprises a moiety enabling to create covalent or non-covalent interactions with the functionalized surfactant or the binding intermediate, as explained and detailed above.

The binding domain of the chemoprobe may be easily chosen by the skilled person depending on the nature of the functionalized moiety of the surfactant or, when a binding intermediate is used, the nature of the domain of the binding intermediate interacting with the chemoprobe.

In preferred embodiments, the binding domain of the chemoprobe comprises a group selected from reactive chemical groups for click-reaction and protein tags. In particular, the binding domain of the chemoprobe may comprise a moiety selected from an azido group, an alkynyl group, a strained cycloalkynyl group and a protein tag such as biotin.

In some embodiments, the chemoprobe is an antibody directed against the molecular target and functionalized with a protein tag, preferably biotin, or with a chemical reactive group for click reaction such as a strained cycloalkynyl group, an azido group or an iminosydnone or sydnone derivative.

In a particular embodiment, the functional moiety of the surfactant comprises an azido group and the binding domain of the chemoprobe comprises a strained cycloalkynyl group, or vice-versa.

In another particular embodiment, the functional moiety of the surfactant is biotin and the binding domain of the chemoprobe is streptavidin, or vice-versa.

In a further particular embodiment, the functional moiety of the surfactant is a biotin, the binding intermediate is streptavidin and the binding domain of the chemoprobe is biotin.

In some embodiment, the chemoprobe and/or the binding intermediate may comprise at least one cleavable linker. Said cleavable linkers may be as defined above for the surfactants.

The chemoprobe may be encapsulated within the droplets, optionally with the molecular target, during the generation of droplets or may be added to the droplets by any methods known by the skilled person such as pico-injection or droplet fusion.

In embodiments wherein the chemoprobe is able to directly interact with the functionalized surfactant, the chemoprobe binds the molecular target and captures it at the inner interface of the droplets by interacting with the functional moiety of the surfactant.

In embodiments wherein the chemoprobe interacts with the functionalized surfactant through a binding intermediate, the chemoprobe binds the molecular target and the binding intermediate, and captures the molecular target at the inner interface of the droplets through the binding of the binding intermediate with the functional moiety of the surfactant.

In the method of the invention, the bindings between the chemoprobe, the functionalized surfactant, the molecular target, and optionally the binding intermediate, can take place in any order. In an embodiment, the chemoprobe simultaneously binds to the molecular target and the functionalized surfactant, optionally via a binding intermediate. In another embodiment, the chemoprobe firstly interacts with the molecular target, whereby a complex is formed between the molecular target and the chemoprobe. Then, said complex binds to the functionalized surfactant via the chemoprobe entity, and optionally via a binding intermediate. In a further embodiment, the chemoprobe firstly binds to the surfactant, optionally via a binding intermediate, and then binds to the molecular target.

Each droplet of the emulsion may comprise one or several chemoprobes specific of one or several molecular targets. In embodiments wherein each droplet comprises several chemoprobes, these chemoprobes may bind to identical or different functionalized surfactants.

Preferably, in embodiments wherein the functional moiety of the surfactant or the binding domain of the chemoprobe or the binding intermediate, comprises a strained cycloalkynyl group, the aqueous phase further comprise a poloxamer, e.g. Pluronics such as Pluronic® F-127 (Sigma), a poloxamer (triblock copolymer) of polypropylene glycol which is hydrophobic and sticks to the hydrophobic surface, to prevent adsorption of strained cycloalkynyl groups on microfluidic chip matrices, in particular PDMS chips.

Microfluidic Systems

In preferred embodiments, the method of the invention is implemented using a microfluidic system.

As used herein, the term "microfluidic device", "microfluidic chip" or "microfluidic system" refers to a device, apparatus or system including at least one microfluidic channel.

The microfluidic system may be or comprise silicon-based chips and may be fabricated using a variety of techniques, including, but not limited to, hot embossing, molding of elastomers, injection molding, LIGA, soft lithography, silicon fabrication and related thin film processing techniques. Suitable materials for fabricating a microfluidic device include, but are not limited to, cyclic olefin copolymer (COC), polycarbonate, poly(dimethylsiloxane) (PDMS), poly(methyl methacrylate) (PMMA), and glass. Preferably, microfluidic devices are prepared by standard soft lithography techniques in PDMS and subsequent bonding to glass microscope slides. Due to the hydrophilic or hydrophobic nature of some materials, such as glass, which adsorbs some proteins and may inhibit certain biological processes, a passivating agent may be necessary. Suitable passivating agents are known in the art and include, but are not limited to silanes, fluorosilanes, parylene, n-dodecyl-β-D-maltoside (DDM), poloxamers such as Pluronics.

As used herein, the term "channel" refers to a feature on or in an article (e.g., a substrate) that at least partially directs the flow of a fluid. The term "microfluidic channel" refers to a channel having a cross-sectional dimension of less than 1 mm, typically less than 500 m, 200 m, 150 m, 100 m or 50 am, and a ratio of length to largest cross-sectional dimension of at least 2:1, more typically at least 3:1, 5:1, 10:1 or more. It should be noted that the terms "microfluidic channel", microchannel" and "channel" are used interchangeably in this description. The channel can have any cross-sectional shape (circular, oval, triangular, irregular, square or rectangular, or the like). Preferably, the channel has a square or rectangular cross-sectional shape. The channel can be, partially or entirely, covered or uncovered.

As used herein, the term "cross-sectional dimension" of a channel is measured perpendicular to the direction of fluid flow.

Water-in-oil emulsion droplets can be generated on the device used to implement the method of the invention ("on-chip") or on another system ("off-chip").

In an embodiment, w/o droplets production is carried out in an on-chip droplet generation module. Droplets may be produced by any technique known by the skilled person to generated droplets on microfluidic devices such as drop-breakoff in co-flowing streams, cross-flowing streams in a T-shaped junction, and hydrodynamic flow-focusing (reviewed by Christopher and Anna, 2007, J. Phys. D: Appl. Phys. 40, R319-R336).

In another embodiment, w/o droplets are generated on another system before to be re-injected on the chip. In a particular embodiment, the droplets are generated on a droplet generation module on another system and are then re-injected on the system used to implement the method of the invention through an emulsion re-injection module. Typically, droplets may be re-injected through an emulsion re-injection module comprising a ψ-shaped structure where injected droplets are spaced by carrier oil supplying by at least one, preferably two side channels connected with the re-injection channel.

In a preferred embodiment, the w/o droplets have a cross-sectional dimension that is substantially equal to the largest dimension of the channel perpendicular to fluid flow in which the droplets are located.

In an embodiment, the w/o droplets are provided (generated or re-injected) to the fluidic system at a frequency ranging from 0.01 Hz to 10 kHz, preferably from 0.1 kHz to 5 kHz, more preferably from 0.5 kHz to 2.5 kHz. A frequency of 1 kHz means that droplets are provided at a rate of 1000 droplets per second. This frequency may be easily chosen and adjusted by the skilled person.

In a particular embodiment, the microfluidic chip used in the method of the invention, comprises droplet generation module or an emulsion re-injection module in fluid communication with a mixing module. This mixing module may insure homogeneous mixing of the contents of the droplets and thus optimize the capture of molecular targets at the interface. Exemplary mixing modules include, but are not limited to, chaotic mixers (Stroock et al. Science, vol. 295, pp. 647-651, 2002) or serpentine mixing modules (Liu et al. J. Microelectromech. Syst, 9, pp. 190-197, 2000).

Alternatively, or in addition, the microfluidic chip used in the method of the invention may comprise a delay line, in particular a delay line allowing reliable incubation time such as disclosed in the patent application WO 2010/042744.

Phase Inversion

The inventors have developed and herein provide systems and methods for reliable phase inversion of water-in-oil emulsion droplets, in particular in microfluidic systems. They demonstrated that water-in-oil emulsions can be efficiently inverted by creating double emulsion and destabilising said emulsion thereby producing oil-in-water emulsion.

Furthermore, they showed that molecules captured on the inner interface of the water-in-oil droplets through interaction with the functionalized surfactant, remain attached after phase inversion. These molecules are thus exposed on the outer surface of the droplets and are accessible to further characterization or assays.

The method of inverting the phase of water-in-oil emulsion droplets thus comprises (i) forming double emulsion droplets from said water-in-oil emulsion droplets; and (ii) destabilising said emulsion in order to produce oil-in-water emulsion.

As used herein, the term "double emulsion droplet" refers to water-in-oil-in-water droplet (also named w/o/w droplet) and consists of an aqueous droplet inside an oil droplet, i.e. an aqueous core and an oil shell, surrounded by an aqueous carrier fluid. Preferably, the double emulsion droplets have a homogenous distribution of diameters, i.e., the droplets may have a distribution of diameters such that no more than about 10%, about 5%, about 3%, about 1%, about 0.03%, or about 0.01% of the droplets have an average diameter greater than about 10%, about 5%, about 3%, about 1%, about 0.03%, or about 0.01% of the average diameter of the droplets. Preferably, the double emulsion is a monodispersed emulsion, i.e. an emulsion comprising droplets of the same volume. Typically, the w/o/w droplet has a volume of less than 2000 pL, preferably of less than 1500 pL. Preferably, a w/o/w droplet has a volume ranging from 40 pL to 1500 pL, more preferably from 40 pL to 500 pL, even more preferably from 40 pL to 200 pL, and in particular from 40 pL to 150 pL. In preferred embodiments, the ratio of oil shell over aqueous core is between 1 and 10 (v/v), preferably between 1.5 and 5 (v/v).

The aqueous carrier fluid is typically water or an aqueous buffer solution, such as Tris HCl buffer, Tris HCl/EDTA (TE) buffer, phosphate buffer saline (PBS) or acetate buffer. In some embodiments, the aqueous phase may also be chosen from organic solutions such as ethanol, methanol, acetonitrile, dimethylformamide, and dimethylsulfoxide. In a preferred embodiment, the aqueous carrier fluid is water. Even more preferably, the aqueous carrier fluid is a buffered medium of low salinity such as buffers comprising Tris or HEPES, preferably at a concentration of 100 mM or less, more preferably at a concentration of 10 mM or less.

The aqueous carrier fluid may comprise one or several water-soluble surfactants such as Tween 20, Tween 80, SDS, Triton X-100, Pluronics, perfluorooctanol, NP40 or CHAPS. Preferably, the aqueous carrier fluid comprises Triton X-100 and/or Tween 20. Preferably, said water-soluble surfactant(s) are present in the aqueous carrier fluid at a concentration ranging from 0.05% to 2%, preferably from 0.1 to 1% (w/w).

Methods for producing double emulsions, and in particular monodispersed double emulsions, in microfluidic systems are well known by the skilled person. In particular, double emulsion droplets may be produced using a flow-focusing junction (see for example Yan et al., 2013, Micromachines, 4, 402-413 and the patent application WO 2011/028764) or a T-shaped junction (see for example Okushima et al., 2004, Langmuir, 20, 9905-9908). In a preferred embodiment, double emulsion droplets are formed using a flow-focusing junction.

Double emulsions may be prepared by controlling the hydrophilicity and/or hydrophobicity of the channels used to form such emulsion. In particular, double emulsions may be produced using partially hydrophilic and partially hydrophobic microfluidic devices.

As demonstrated by the inventors in the experimental section, oil-in-water emulsion may be obtained from double emulsion droplets through electrical destabilisation, electroporation or spontaneous destabilisation.

In a first embodiment, double emulsion droplets are destabilised by applying an electric field. In this embodiment, the method of inverting the phase of water-in-oil emulsion droplets comprises:
  (i) forming double emulsion droplets from said water-in-oil emulsion droplets, and
  (ii) causing said double emulsion droplets to move within a hydrophilic channel of a fluidic system, preferably a microfluidic system, the cross section of said hydrophilic channel being substantially similar to the cross section of double emulsion droplets, and
  (iii) applying an electric field to said double emulsion droplets such that the inner aqueous phase coalesces with external aqueous phase thereby producing oil-in-water emulsion droplets.

The electric field is used to destabilize and break the oil capsule of w/o/w droplets in order to obtain oil-in-water emulsion droplets. The main difficulty is to preserve the integrity of the interface between the oil capsule and the aqueous core. In particular, it is important that captured molecular targets remain attached on the outer surface of the inversed droplets for further characterization or assays.

The inventors observed that if the cross-section of the w/o/w droplets is substantially greater than the cross-section of the channel, droplets are too tight and this geometry results in the formation of two thin films near the channel walls and two oil-in-water droplets instead of one. Conversely, if the cross-section of the w/o/w droplets is substantially smaller than the cross-section of the channel, droplets rotate on themselves under the effect of the flow of the continuous phase. This geometry results in the formation of several thin films near the channel walls and several oil-in-water droplets instead of one. When the droplet cross-section is adjusted to the cross-section of the channel, the rupture of the phase interface occurs at only one point and results in only one oil-in-water droplet. Thus, in the present invention, the electric field is applied to the double emulsion flowing in a hydrophilic channel having a cross section substantially similar to the cross section of double emulsion droplets.

The term "substantially similar", as used herein, denotes a sufficiently high degree of similarity between two numeric values, such that one of skill in the art would consider the difference between the two values to be of little or no statistical significance within the context of the characteristic measured by said values (e.g., sizes of the cross-sections). The difference between said two values is, for example, less than about 30%, 20%, 10% or 5%. Preferably, the cross section of the hydrophilic channel is about 30% smaller than the cross section of double emulsion droplets.

The electric field applied to a double emulsion droplet induces coalescence of the inner aqueous phase (i.e. aqueous core) with the external aqueous phase (i.e. aqueous carrier fluid) thereby producing oil-in-water emulsion droplet.

The electric field may be generated from an electric field generator, i.e., a device or system able to create an electric field. The electric field generator may produce an AC field (i.e., one that varies periodically with respect to time, for example, sinusoidally, sawtooth, square, etc.), a DC field (i.e., one that is constant with respect to time), a pulsed field, etc.

Techniques for producing a suitable electric field (which may be AC, DC, etc.) are well known to those of ordinary skill in the art. In particular, an electric field may be produced by applying voltage across a pair of electrodes, which may be positioned on or embedded within the fluidic system (for example, within a substrate defining the channel or under the channel using gold or ITO vapour deposition), and/or positioned proximate to the channel such that at least a portion of the electric field interacts with the double emulsion (for example, electrodes may consist in microchannels aside the fluidic channels and filled with a solder or a salt solution to which the electrical field is applied). Preferably, the electric field generator applies a sinusoidal or squared-shape current.

The electric field generator may apply a voltage with a frequency between 1 kHz and 1 GHz, preferably between 1 kHz and 50 kHz, more preferably of a frequency between 10 kHz and 30 kHz and even more preferably a frequency between 20 kHz and 30 kHz, and an amplitude between 100 V and 10 000 V, preferably from 1 500 V to 3000 V, and more preferably from 2000 V to 3000 V.

In a particular embodiment, the electric field generator applies a sinusoidal voltage with a frequency of about 10 kHz and an amplitude of about 300 V.

In a preferred embodiment, the electric field generator applies an AC field, preferably a squared-shape current.

Preferably, the frequency is from 20 kHz to 30 kHz and the amplitude is from 2,000 V to 3,000 V.

In preferred embodiments, and in order to provide optimal droplet inversion, w/o/w droplets pass the electrodes at a frequency from 10 to 1000 droplets per second, preferably at a frequency from 100 to 500 droplets per second and more preferably at a frequency from 250 to 350 droplets per second. The frequency of the droplets may be adjusted by injection oil spacer, preferably surfactant-free oil, e.g. using a ψ-shaped structure.

Preferably, in order to avoid undesirable coalescence upstream of this phase inversion module, an electrical shielding is provided, typically using one or several shielding electrodes. These shielding electrodes are grounded and therefore impose a zero voltage boundary condition for the rest of the chip, in particular for upstream modules such as the re-injection or droplet generation module and the module for creating double emulsion, or downstream modules such as an emulsion collection module. These shielding electrodes are commonly used by the skilled person.

Preferably, the section of the hydrophilic channel between the module for creating double emulsion, e.g. the nozzle or the T-shaped junction, and the phase inversion module applying the electric field is of more than 4 mm, preferably more than 4.1, 4.2, 4.5, or 5 mm, i.e. double emulsion droplets have thus to flow more than 4 mm before to go through the electric field.

In a second embodiment, double emulsion droplets are destabilised by electroporation. In this embodiment, the method of inverting the phase of water-in-oil emulsion droplets comprises (i) forming double emulsion droplets from said water-in-oil emulsion droplets; and (ii) applying a voltage to said double emulsion droplets sufficient to break the oil capsule of double emulsion droplets thereby producing oil-in-water emulsion droplets.

Preferably, in this embodiment, the double emulsion is generated in a microfluidic chip before to be placed in an electroporation cuvette wherein the voltage is applied using an electroporator.

The applied voltage is from 20V to 500V during 10 ms to 1000 ms. In a preferred embodiment, the applied voltage is about 50V during about 100 ms.

In a third embodiment, double emulsion droplets are spontaneously destabilised. In this embodiment, the method of inverting the phase of water-in-oil emulsion droplets comprises (i) forming double emulsion droplets from said water-in-oil emulsion droplets; and (ii) incubating these droplets until the oil capsules break by itself.

Preferably, double emulsion droplets are incubated in a microfluidic chip using a delay-line. Such delay-lines are well-known and commonly used by the skilled person (see for example, the European patent application EP 2 340 435).

Preferably, double emulsion droplets are incubated are incubated for at least 2 min, more preferably for at least 5 min, and even more preferably for at least 10 min.

Optionally, non-inverted droplets may be further eliminated based on their size that was bigger than the inverted one.

Optionally, after phase inversion, oil-in-water emulsion droplets may be stabilized by adding surfactant to the aqueous carrier fluid. Surfactant can be provided by inlets downstream of the phase inversion module.

Oil-in-water emulsion droplets may be collected, in particular to be submitted to further analysis. Preferably, before collection, o/w droplets are stabilized by surfactant in order to prevent any coalescence during the storage.

The microfluidic system used in the present invention, in particular for the phase inversion, may combine the production of a double emulsion (i.e. w/o/w emulsion) and its inversion. The system may thus comprise:

a module for generating water-in-oil emulsion droplets (i.e. a module that produces droplets using any known techniques such as breakup in co-flowing streams, breakup in cross-flowing streams, for example at T-shaped junctions, breakup in elongational or stretching dominated flows, as for example in hydrodynamic flow-focusing), or re-injecting water-in-oil emulsion (e.g. an emulsion re-injection module comprising a ψ-shaped structure), a module for creating double emulsion (e.g. using flow-focusing junction or a T-shaped junction) in fluid communication and downstream of the module for generating water-in-oil emulsion droplets or re-injecting water-in-oil emulsion, and a phase inversion module in fluid communication and downstream of the module for creating double emulsion.

Figure 29:
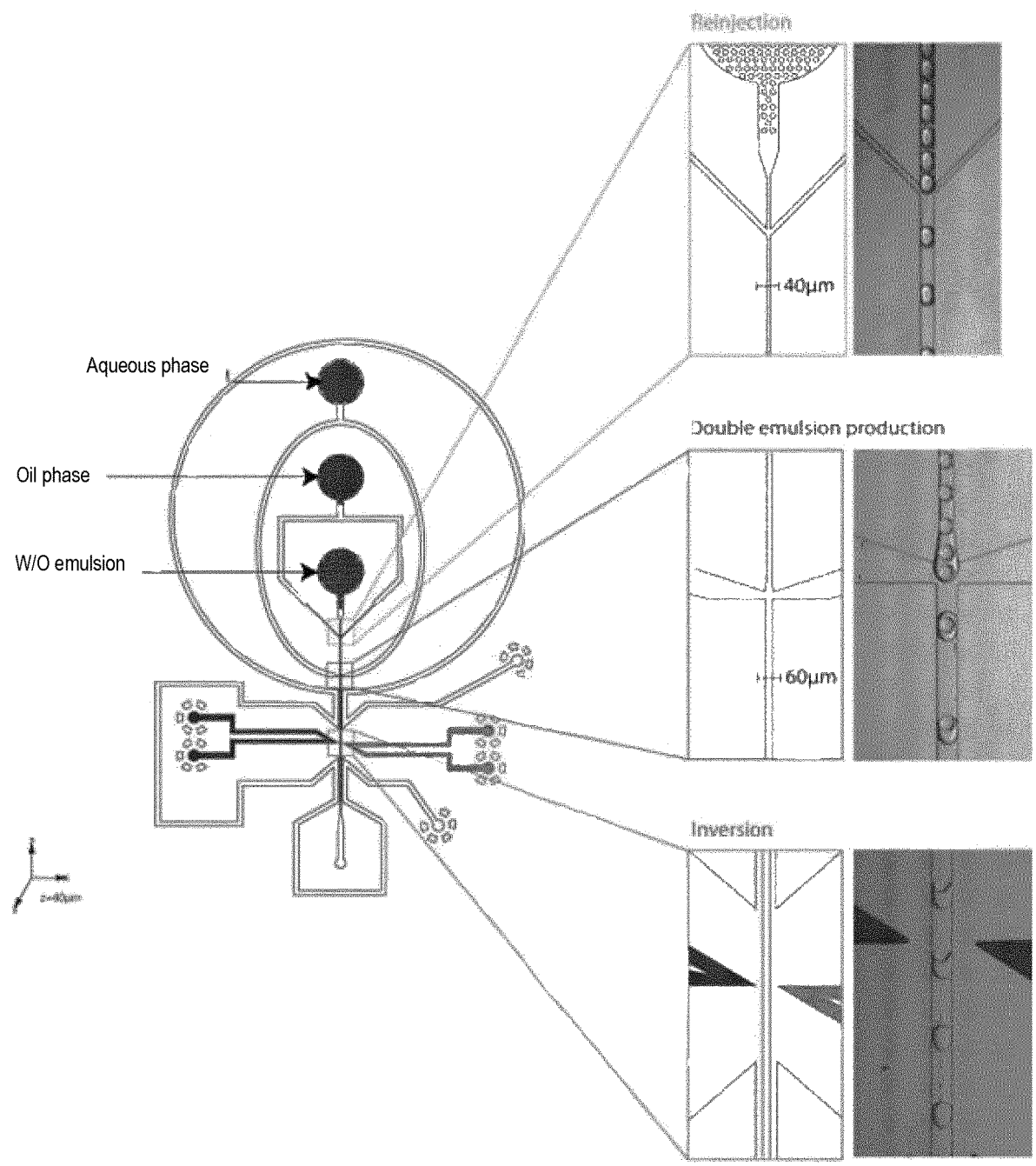
FIG. 29: Microfluidic system comprising a module for re-injecting water-in-oil emulsion comprising a ψ-shaped structure, a module for creating double emulsion using a T-shaped junction and a phase inversion module.

An illustrative example of such system is presented in FIG. 29.

Alternatively, the production of double emulsion and the inversion process may be decoupled and performed on different microfluidic chips. In this case, the double emulsion is produced on a first microfluidic system comprising a module for generating water-in-oil emulsion droplets or re-injecting water-in-oil emulsion as defined above, a module for creating double emulsion as defined above and in fluid communication and downstream of the module for generating water-in-oil emulsion droplets or re-injecting water-in-oil emulsion, and an emulsion collection module (i.e. a module to collect double emulsion droplets) in fluid communication and downstream of the module for creating double emulsion.

The double emulsion is then re-injected into a second microfluidic system comprising a module for re-injecting double emulsion (e.g. an emulsion re-injection module comprising a ψ-shaped structure), and a phase inversion module in fluid communication and downstream of the module for re-injecting double emulsion.

Preferably, the phase inversion module comprises one or more electrodes that generate an electric field directed to a hydrophilic channel. As specified above, the electrodes may be positioned on or embedded within the fluidic system, or positioned proximate to the channel such that at least a portion of the electric field interacts with the double emulsion.

As used herein, the term "upstream" refers to components or modules in the direction opposite to the flow of fluids from a given reference point in a microfluidic system.

As used herein, the term "downstream" refers to components or modules in the direction of the flow of fluids from a given reference point in a microfluidic system.

In embodiments wherein double emulsion is produced on the microfluidic system used for phase inversion, the channels of said system are partially hydrophilic and partially hydrophobic. The region downstream of the module for generating or re-injecting water-in-oil emulsion droplets and upstream of the module for creating double emulsion droplets is hydrophobic. On the contrary, the region downstream of the module for creating double emulsion droplets is hydrophilic.

A localized hydrophilic region may be created in a hydrophobic microfluidic channel by various methods known and appreciated by one of skill in the art, including, but not limited to, applying various treatments such as oxygen plasma, applying a hydrophilic coating such as poly(ethylene glycol) or a fluorinated activated silane, chemically grafting small molecules or polymers onto the dielectric layer to increase the hydrophilicity of the surface, and/or constructing the microfluidic channel with a material having surface chemistry that may be initiated with ultraviolet (UV) light, such that shining UV light to the localized region will induce said surface chemistry resulting in a change in the material surface property of the region from relatively hydrophobic to relatively hydrophilic. All these techniques to control the wetting properties of microfluidic devices are well-known by the skilled person and described for example in the patent applications WO 2011/028764 and WO 2009/120254.

On the contrary, a localized region of a channel may be rendered more hydrophobic by various well-known methods including, but not limited to, applying coating materials such as a polysilicon and/or hydrophobic coating materials such as a polydimethylsiloxane composition or a polytetrafluoroethylene composition (e.g. TEFLON-AF).

In embodiments wherein double emulsion is produced on a different system than the microfluidic system used for phase inversion, the channels of the first system (i.e. producing the double emulsion) are hydrophobic and the channels of the second system (i.e. phase invention system) are hydrophilic.

In some embodiments, the phase inversion module is the region of the microfluidic system wherein an electric field is applied on double emulsion droplets in order to obtain oil-in-water emulsion. This module is in fluid communication and downstream of the module for creating double emulsion and comprises an hydrophilic channel and one or more electrodes that generate an electric field directed to said hydrophilic channel in which double emulsion droplets flow.

Typically, the electric field is produced by applying voltage across a pair of electrodes. These electrodes may be positioned on or embedded within the fluidic system (for example, within a substrate defining the channel), and/or positioned proximate the channel (e.g. at about 50 μm) such that at least a portion of the electric field interacts with the double emulsion. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide, etc., as well as combinations thereof. The electrodes may be formed of the same material, or different materials. The electrodes may also be liquid electrodes made of salt solution (e.g. NaCl) molded around the hydrophilic channel in which droplets flow.

The electric field generator may be integral to or separate from the fluidic system containing the hydrophilic channel. As used herein, "integral" means that portions of the components integral to each other are joined in such a way that the components cannot be manually separated from each other without cutting or breaking at least one of the components.

Preferably, one or several shielding electrodes are provided to prevent the electric field to spread everywhere. These electrodes are grounded and therefore impose a zero voltage boundary condition for upstream and/or downstream regions, in particular for the re-injection or droplet generation module and the module for generating double emulsion.

Preferably, even if shielding electrodes are provided, the distance between the phase inversion module and the module for generating double emulsion is of more than 4 mm, preferably more than 4.1, 4.2, 4.5, or 5 mm.

The microfluidic system may further comprise a spacing module in fluid communication and downstream of the module for generating or re-injecting water-in-oil emulsion droplets, for the purpose of changing the spacing between droplets before creating double emulsion. This spacing module comprises one or more inlet channels to inject or remove fluid, preferably oil phase, between droplets in a fluidic stream.

The microfluidic system may further comprise a spacing module in fluid communication and downstream of the module for creating double emulsion droplets, for the purpose of changing the spacing between droplets before the phase inversion module. This spacing module comprises one or more inlet channels to inject or remove fluid, preferably aqueous phase, between droplets in a fluidic stream.

The microfluidic system may further comprise a detection module (e.g. a module to detect a signal such as a fluorescent signal), a stabilization module (e.g. a module wherein a surfactant is added to the aqueous carrier phase in order to stabilize the inversed emulsion), a droplet sorting module (e.g. a module to sort droplets based on any detectable signal such as a fluorescent signal) and/or a droplet collection module (a module to collect droplet, for example to carry out further off-chip analysis).

Detection, Recovering and/or Quantification of Captured Molecular Targets

After capture of the molecular target at the inner interface of the droplets thanks to the interactions between i) the molecular target and the chemoprobe, and ii) the chemoprobe and the functionalized surfactant (optionally through interaction with a binding intermediate), the captured molecular target may be detected, recovered and/or quantified.

The method of the invention may thus further comprise a step of detecting, recovering and/or quantifying the captured molecular target.

This step may be carried out directly in the w/o droplets or after inverting the phase of droplets to produce oil-in water emulsion droplets and to expose captured targets at the outer surface of droplets as described above.

The choice of the method used to detect, recover or quantify the molecular target depends on several parameters such as the nature of the functionalized surfactant, the chemoprobe or the molecular target, and the presence or absence of a step of inverting the emulsion phase.

In an embodiment, captured molecular targets are detected, recovered and/or quantified after phase inversion. Optionally, the method may further comprise, before detecting, recovering or quantifying, washing o/w droplets in order to eliminate non-captured molecules.

In this embodiment, captured molecular targets may be recovered from the interface of the droplets by any methods known by the skilled person, for example by disrupting the interaction between the chemoprobe and the molecular target or by disrupting the interaction between the chemoprobe and the functionalized surfactant and or the binding intermediate.

Alternatively, in embodiments wherein the functionalized surfactant, the chemoprobe and/or the binding intermediate comprises a cleavable linker, this linker may be cleaved to allow the release and recovering of the captured molecular targets.

After phase inversion, captured molecular targets are exposed at the outer surface of droplets and can thus be easily detected using any methods known by the skilled person, for example using an antibody or another ligand which is specific to the molecular target and comprises a mean for detection.

As used herein, "a mean of detection" refers to any entity which may be useful for detection purpose, in terms of detection or calibration. For instance the mean of detection may be a MS-tag or a fluorophore.

In a particular embodiment, captured molecular targets are detected/quantified using one or several antibodies directed against said targets and comprising a MS-tag. Different MS-tag may be used to detect/quantify simultaneously different targets. Preferably, in this case, the w/o emulsion comprises a surfactant comprising a hydrophilic head linked to a MS-tag. Detection or quantification of targets may be performed by mass spectrometry analysis after cleavage of MS-tags. The tag of the surfactant may be used as a calibrator for mass spectrometry analysis.

In another embodiment, captured molecular targets are detected, recovered and/or quantified directly in the w/o droplets.

To recover molecular target captured at the inner surface of the droplets, the emulsion may be broken by any methods known by the skilled person such as methods described in Mazutis et al. Nat. Protoc., 2013, 8, 870 or Chokkalingam et al. Lab Chip, 2014, 14, 2398.

After emulsion breaking, the captured molecular targets may be recovered by any methods known by the skilled person, for example by disrupting the interaction between the chemoprobe and the molecular target or by disrupting the interaction between the chemoprobe and the functionalized surfactant and/or the binding intermediate. When the functionalized surfactant, the chemoprobe and/or the binding intermediate comprises a cleavable linker, this linker may be cleaved to allow the release and recovering of the captured molecular targets.

The detection or quantification of captured molecular target may be carried out directly in the w/o droplets using an antibody or another ligand which is specific to the molecular target and comprises a mean of detection.

In a particular embodiment, the detection or quantification of captured molecular target is carried out directly in the w/o droplets using microfluidic laser/PMT detection thank to a ligand specific to the molecular target and detectable by laser/PMT, e.g. an antibody conjugated to a fluorophore.

In another particular embodiment, the detection or quantification of captured molecular target is carried out directly in the w/o droplets using proximity ligation assay (PLA, Gullberg et al., Proc. Natl. Acad. Sci. U.S.A., 2004; Soderberg et al., Nature Methods, 2006). By converting the detection of specific proteins to the detection of DNA sequences this technic enables highly sensitive protein analysis. Briefly, this method requires an antibody directed against the molecular target and an antibody directed against the chemoprobe, each antibody containing oligonucleotides extension as probes. When the molecular target is captured by the chemoprobe, the proximity of these probes bearing oligonucleotide sequences leads to a ligation reaction resulting in the formation of an amplifiable target. Amplification may be performed by any methods known by the skilled person such as rolling circle amplification, using detectable probes such as fluorescent probes. Using calibration curve, the signal intensity at the inner interface of the droplets, allows the detection and quantification of the molecular target. PLA analysis may be performed simultaneously in the same droplets for several targets using different detectable probes.

In a further particular embodiment, the captured molecular target is a nucleic acid and the detection or quantification of said target is carried out directly in the w/o droplets using in vitro transcription and/or translation system and/or a nucleic acid amplification system. Detection and/or quantification are then performed by detecting or quantifying the product of the transcription and/or translation system or of the nucleic acid amplification system. Methods to carry out in vitro transcription and/or translation or nucleic acid amplification in droplets are well known by the skilled person.

The method of the invention may further comprise sorting w/o droplets comprising the desired captured molecular target. The skilled person may use any methods known in the art, such as methods reviewed in the article of Wyatt Shields et al (Lab Chip. 2015 Feb. 16; 15(5): 1230-1249).

Uses of the Method of the Invention

Thanks to the great variety of molecular targets that can be captured at the interface of the droplets through binding to the functionalized surfactant, the method of the invention may be used in various applications. As illustration, the method may be used in genomics, epigenomics, transcriptomics, proteomics, metabolomics, lipidomics, interactomics, secretomics approaches, and in particular in single cell "omics" to apprehend cellular diversity and heterogeneity. An application among others may be to define the normal cell-to-cell variation, to correlate the variation with changes in biological function and disease processes and finally to identify personalized therapy.

The method of the invention may also be used to detect, recover and/or quantify one or several molecular targets of interest, in particular of diagnostic/prognostic/theranostic importance.

The method of the invention may further comprise providing a sample from a subject, said sample comprising a molecular target of interest to be captured at the interface of droplets according to the method of the invention.

The term "sample", as used herein, means any sample containing cells derived from a subject, preferably a sample which contains nucleic acids. Examples of such samples include fluids such as blood, plasma, saliva, urine, cerebrospinal fluid and seminal fluid samples as well as biopsies, organs, tissues or cell samples. It may be fresh, frozen or fixed (e.g. formaldehyde or paraffin fixed) sample. In some particular embodiments, the sample may be a disease sample, preferably a cancer sample, i.e. a sample containing tumoral cells derived from a patient.

As used herein, the term "subject" or "patient" refers to an animal, preferably to a mammal, even more preferably to a human, including adult, child and human at the prenatal stage.

Said sample may be treated prior to be used in the method of the invention, e.g. to extract nucleic acid, proteins, lipids, etc . . . , to wash cells, to isolate cells from tissues or organs, etc. . . .

In a preferred embodiment, each w/o droplet used in the method of the invention comprises a single cell obtained from a patient sample and one or several molecular targets of diagnostic/prognostic/theranostic importance may be captured/detected and/or quantified using the method of the invention.

Kits and Uses Thereof

In another aspect, the present invention also relates to a kit for capturing a molecular target, comprising a functionalized surfactant comprising at least one lipophilic tail linked to a functionalized hydrophilic head; and a chemoprobe comprising at least (i) one capture moiety capable of specific binding to a molecular target and at least (ii) one binding domain capable of direct or indirect binding to the functionalized surfactant.

In particular, the kit may comprise:

any one of functionalized surfactants as defined above; in particular as depicted in any one of formula (Ia), (Ib), (Ic), (II) and (Ma) or those comprising H1 or H2 moieties as described above;

a chemoprobe as defined above, i.e. comprising (i) a capture moiety capable of specific binding to said molecular target and (ii) a binding domain capable of direct or indirect binding to said functionalized surfactant, i.e. to the FUNCT group of said surfactant; and optionally a binding intermediate as defined above, i.e. which is able to bind both the chemoprobe and the functionalized surfactant thereby acting as a bridge between said two entities.

All embodiments described above for the method of the invention are also encompassed in this aspect.

In an embodiment, the functionalized surfactant and the binding domain of the chemoprobe comprise a functional moiety with a chemical reactive group suitable to create a covalent bond by click-chemistry. Preferably, the chemical reactive group suitable to create a covalent bond by click-chemistry is selected from the group consisting of azido group, and an alkynyl group such as a strained cycloalkynyl group.

In a particular embodiment, the functional moiety of the surfactant is an azido group and the binding domain of the chemoprobe is a strained cycloalkynyl group, or vice-versa.

In another embodiment, the kit comprises a functionalized surfactant with a functional moiety comprising protein tag, preferably a biotin, and a chemoprobe with a binding domain comprising a group that can specifically interact with the protein tag of the surfactant, preferably a streptavidin or avidin, or vice-versa.

In a particular embodiment, the kit comprises:
a functionalized surfactant with a functional moiety comprising a biotin,
a chemoprobe with a binding domain comprising a biotin, and
a binding intermediate which is streptavidin.

Preferably, the chemoprobe is a biotinylated aptamer or a biotinylated antibody specific to the molecular target.

Optionally, the kit may further comprise
non-functionalized surfactant(s);
an aqueous phase and/or an oil phase;
a microfluidic chip as described above, in particular a microfluidic chip comprising a phase inversion module; and/or
a leaflet providing guidelines to use such a kit.

The present invention also relates to the use of the kit of the invention for capturing a molecular target according to the method of the invention.

As used herein, the verb "to comprise" is used in its non-limiting sense to mean that items following the word are included, but items not specifically mentioned are not excluded.

In addition, reference to an element by the indefinite article "a" or "an" does not exclude the possibility that more than one of the element is present, unless the context clearly requires that there be one and only one of the elements. The indefinite article "a" or "an" thus usually means "at least one".

As used herein, the term "about" refers to a range of values ±10% of the specified value. For example, "about 20" includes ±10% of 20, or from 18 to 22. Preferably, the term "about" refers to a range of values ±5% of the specified value.

All patent and literature references cited in the present specification are hereby incorporated by reference in their entirety.

EXAMPLES

Abbreviations
ACMS: 7-aminocoumarin-4-methanesulfonic acid
ACN: acetonitrile
BCN: (1R,8S,9s)-bicyclo[6.1.0]non-4-yn-9-ylmethyl)
DCM: dichloromethane
DIEA: diisopropylethylamine
DMF: dimethyl formamide
EDC: 1-ethyl-3-(3-dimethylaminopropyl)carbodiimides
HBTU: N,N,N',N'-tetramethyl-O-(1H-benzotriazol-1-yl) uronium hexafluorophosphate
HOBt: hydroxybenzotriazole
HPLC: high performance liquid chromatography
NHS: N-hydroxysuccinimide
NMR: nuclear magnetic resonance
PDMS: polydimethylsiloxane
PMA: phosphomolybdic acid
PMT: photomultiplier tube
RP: reverse phase
SPAAC: strain-promoted alkyne-azide cycloaddition
TAMRA: tetramethylrhodamine
TEA: triethylamine
TFA: trifluoroacetic acid
THF: tetrahydrofuran
TLC: thin layer chromatography Example 1: Chemical Synthesis 1. Material and methods Experimental Procedures Unless otherwise indicated, reactions were carried out under an argon atmosphere in flame-dried glassware with magnetic stirring. Air and/or moisture-sensitive liquids were transferred via syringe. When required solutions were degassed by argon bubbling through a needle. Organic solutions were concentrated by rotary evaporation at 25-80° C. at 15-30 torr. Analytical thin layer chromatography (TLC) was performed using plates cut from aluminium sheets (ALUGRAM Xtra SIL G/UV$_{254}$ from Macherey-Nagel). Visualization was achieved under a 254 or 365 nm UV light and by immersion in an appropriate revelation solution.

Materials

All reagents were obtained from commercial sources and used without any further purifications. Anhydrous solvents used in experiments were obtained from Sigma-Aldrich or Alfa Aesar. Fluorinated solvents (Novec 7100, Novec 7500 and FC 3283) were purchased from 3M. All reagents used in the experiments were purchased from Aldrich, Alfa Aesar, Acros or TCI and were used without any further purification. Krytox157FS(H) was purchased from Dupond. Silica gel for column chromatography was purchased from Merck (Geduran® Si 60, 40-63 µm). Column flash chromatography was carried out using silica gel G-25 (40-63 µm) from Macherey-Nagel.

Instrumentation

NMR spectroscopy, $^1$H and $^{13}$C NMR spectra were recorded at 23° C. on Bruker 400 spectrometer. Recorded shifts are reported in parts per million (δ) and calibrated using residual non-deuterated solvent. Data are represented as follows: chemical shift, multiplicity (s=singlet, d=doublet, t=triplet, q=quartet, quint=quintet, m=multiplet, br=broad), coupling constant (J, Hz) and integration.

High resolution mass spectra (HRMS) were obtained using a Agilent Q-TOF (time of flight) 6520 and low resolution mass spectra using a Agilent MSD 1200 SL (ESI/APCI) with a Agilent HPLC1200 SL.

Low resolution mass spectra were obtained using a Agilent MSD 1200 SL (ESI/APCI) with a Agilent HPLC1200 SL and a Waters Acquity QDa (ESI) with a Waters Alliance 2695 HPLC.

Preparative HPLC procedures were performed on semi-preparative HPLC Shimadzu Auto-injector SIL-10A (pump: Shimadzu LC-8A, UV-Vis detector: Shimadzu SPD-10A, collector: Shimadzu fraction collector FRC-10A) using a Sunfire C18 (150 mm×19 mm i.d., 5 µm, Waters) at a flow of 17 mL/min. Per sample 1 mL was injected and water/ACN containing 0.05% TFA was used as eluent system. The gradient applied was 5% to 95% ACN in 40 minutes and 10 minutes of re-equilibration. Detection was done at 550 nm for TAMRA derivatives.

2. Functionalized Diblock Surfactants Synthesis

Four functionalized diblock surfactants were synthesized to perform capture at the inner surface of the microdroplet by two different strategies. An alkyne diblock surfactant (Krytox-peg$_{10}$-alkyne, 6) and an azide diblock surfactant (Krytox-peg$_{12}$-azide, 14) were synthesized to develop capture by click chemistry and two biotinylated diblock surfactants (Krytox-peg$_{10}$-biotin 10 and Krytox-peg$_{12}$-biotin 18) were prepared to perform capture by immuno-sandwich. Diblock surfactants were obtained by pseudo-peptidic coupling reactions between a peg-based hydrophilic chain bearing a free amine and the perfluoropolyether acidic chain activated as its acyl chloride form (Krytox157-COCl, 5). The hydrophilic chain was obtained by coupling two oligo-ethylene glycol derivatives conveniently functionalized (FIG. 1).

Firstly a peg$_{10}$ derivative 3 bearing an N-boc protected amino group and an alkyne was synthesized by a pseudo-peptidic coupling reaction between building blocks 1 and 2 beforehand obtained respectively from hexaethyleneglycol and tetraethyleneglycol. This intermediate led to the synthesis of the alkyne diblock surfactant 6 after N-boc cleavage and coupling with Krytox-COCl 5. Starting from intermediate 3 a biotinylated diblock surfactant 10 was obtained after click reaction with Biotin-N$_3$ 7, N-boc deprotection and coupling with Krytox-COCl 5.

Figure 2:
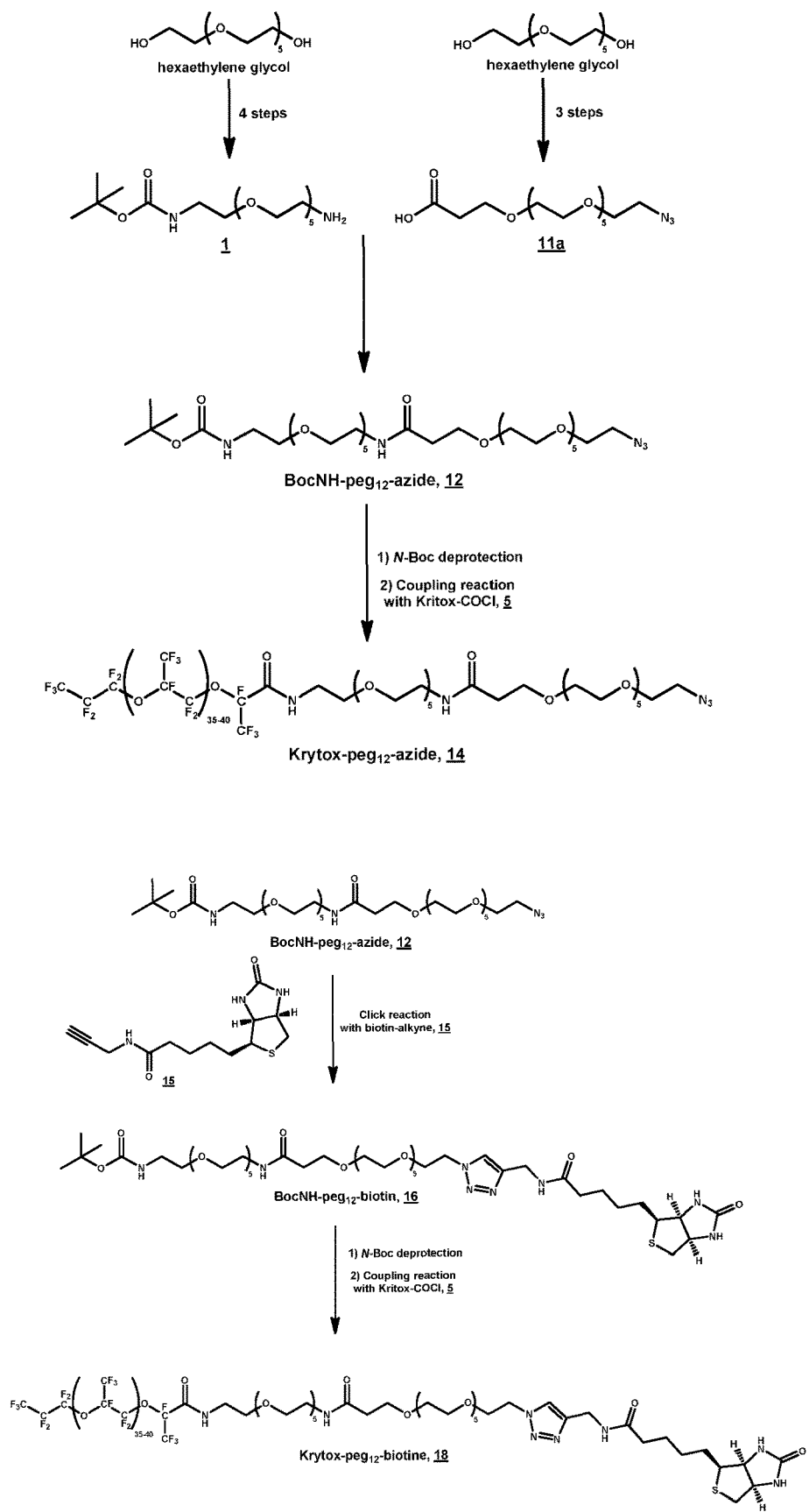
FIG. 2: Strategy synthesis of Krytox-peg$_{12}$-alkyne and Krytox-peg$_{12}$-biotin.

Secondly a peg$_{12}$ derivative containing an azide and an N-boc amino moieties was prepared by coupling the oligo-ethylene derivatives 1 and 12 both obtained from hexaethylene glycol (FIG. 2). The azide diblock surfactant 14 was obtained after N-boc deprotection and coupling with the fluorinated chain. A second biotinylated surfactant 18 was also synthesized after click reaction with biotin-alkyne 15, N-boc cleavage and coupling with Krytox-COCl 5.

tert-Butyl N-(17-amino-3,6,9,12,15-pentaoxaheptadecan-1-yl)carbamate 1 (Walton, J. G. A.; Patterson, S.; Liu, G.; Haraldsen, J. D.; Hollick, J. J.; Slawin, A. M. Z.; Ward, G. E.; Westwood, N.J. Org. Biomol. Chem., 2009, 7, 3049-3060), 4,7,10,13,16-pentaoxanonadec-18-ynoic acid 2 (Kumar, A.; Erasquin, U. J.; Qin, G.; Li, K.; Cai, C. Chem. Commun., 2010, 46, 5746-5748), (3aS,4S,6aR)-4-(7-(2-azidoethoxy)-5-oxoheptyl)tetrahydro-1H-thieno[3,4-d]imidazol-2(3H)-one (biotin-N$_3$) 7 (Azagarsamy, M. A.; Yesilyurt, V.; Thayumanavan, S. J. Am. Chem. Soc., 2010, 132, 4550-4551), N-(17-amino-3,6,9,12,15-pentaoxaheptadecan-1-yl)carbamate 11a (Tamura, S.; Inomata, S.; Ebine, M.; Genji, T.; Iwakura, I.; Mukai, M.; Shoji, M.; Sugai, T.; Ueda, M. Bioorg. Med. Chem. Lett., 2013, 23, 188-193) and 5-((3aS,4S,6aR)-2-oxohexahydro-1H-thieno[3,4-d]imidazol-4-yl)-N-(prop-2-yn-1-yl)pentanamide (biotin-alkyne) 15 (Decuypere, E.; Specklin, S.; Gabillet, S.; Audisio, D.; Liu, H.; Plougastel, L.; Kolodych, S.; Taran, F. Org. Lett., 2015, 17, 362-365) were synthesized according to procedures described in the literature.

BocNH-peg$_{10}$-alkyne, 3

(tert-Butyl N-[17-(4,7,10,13,16-pentaoxanonadec-18-ynamido)-3,6,9,12,15-pentaoxaheptadecan-1-yl] carbamate)

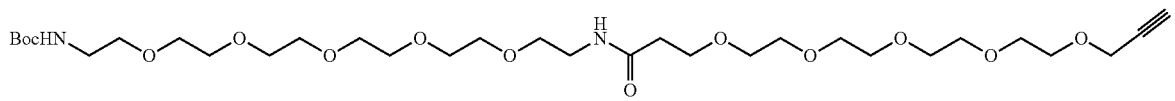 [SMILES: C#CCOCCOCCOCCOCCOCCC(=O)NCCOCCOCCOCCOCCOCCNC(=O)OC(C)(C)C]

$C_{31}H_{58}N_2O_{13}$ MW=666.80 g/mol

To a solution of 4,7,10,13,16-pentaoxanonadec-18-ynoic acid 2 (1.2 eq., 0.77 g, 2.54 mmol) in DCM (7 mL) under argon were added 1-(3-dimethylaminopropyl)-3-ethyl carbodiimide hydrochloride (1.5 eq., 0.61 g, 3.17 mmol) and HOBt (1.5 eq., 0.43 g, 3.17 mmol). The resulting mixture was stirred at room temperature for 20 minutes. A solution of tert-butyl N-(17-amino-3,6,9,12,15-pentaoxaheptadecan-1-yl)carbamate 1 (1 eq., 0.81 g, 2.12 mmol) and DIEA (2.5 eq., 0.87 mL, 5.29 mmol) in DCM (7 mL) was added and the reaction was stirred at room temperature for 12 hours. The resulting solution was diluted with water (50 mL) and extracted with DCM (2×50 mL). The combined organic layers were dried over MgSO$_4$ and concentrated under reduced pressure. The crude material was purified by silica gel flash chromatography (DCM to DCM/MeOH 9/1 in 30 minutes) to afford BocNH-peg$_{10}$-alkyne 3 (0.905 g, 1.36 mmol, 64%) as a yellow oil.

$^1$H NMR (CDCl$_3$, 400 MHz) δ 6.69 (brs, 1H), 5.07 (brs, 1H), 4.01 (d, J=2.0 Hz, 2H), 3.57-3.34 (m, 38H), 3.27-3.22 (m, 2H), 3.14-3.08 (m, 2H), 2.34 (t, J=2.4 Hz, 1H), 2.28 (t, J=6.2 Hz, 2H), 1.25 (s, 9H).

$^{13}$C NMR (CDCl$_3$, 100 MHz) δ 171.8, 156.4, 79.9, 75.0, 70.6-69.6, 69.1, 67.5, 66.4, 58.3, 53.1, 40.2, 39.0, 36.1, 28.7 (3C).

MS (ESI) m/z: 667.5 [M+H]$^+$.

NH$_2$-peg$_{10}$-alkyne (hydrochloride Salt), 4

19-Oxo-3,6,9,12,15,22,25,28,31,34-decaoxa-18-azaheptatriacont-36-yn-1-aminium Chloride

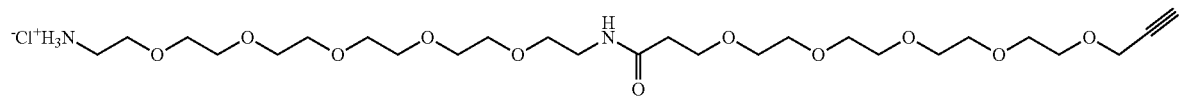

C$_{26}$H$_{51}$ClN$_2$O$_{11}$ MW=603.14 g/mol

To a solution of BocNH-peg$_{10}$-alkyne 3 (0.37 g, 0.55 mmol) in DCM (6 mL) was added a 4M HCl solution in dioxane (6 eq., 0.83 mL, 3.33 mmol). The reaction mixture was stirred at room temperature for 12 hours. Evaporation of the solvent under reduced pressure afforded NH$_2$-peg$_{10}$-alkyne 4 as a yellow oil (0.31 g, 0.55 mmol, quantitative).

$^1$H NMR (CDCl$_3$, 400 MHz) δ 7.92 (brs, 3H), 4.16 (d, J=2.4 Hz, 2H), 3.86-3.92 (m, 2H), 3.77-3.57 (m, 36H), 3.46-3.40 (m, 2H), 3.14-3.05 (m, 2H), 2.65 (t, J=5.6 Hz, 2H), 2.41 (t, J=2.2 Hz, 1H).

$^{13}$C NMR (CDCl$_3$, 100 MHz) δ 172.0, 79.7, 74.8, 70.5-70.0, 69.8, 69.6, 69.1, 67.4, 66.9, 58.4, 53.6, 40.3, 39.0, 36.7.

HRMS (ESI) m/z: calcd. for C$_{26}$H$_{52}$N$_2$O$_{11}$ [M+H]$^+$ 567.3487, found 567.3493.

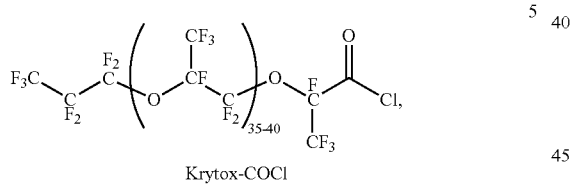

Krytox-COCl

To a solution of Krytox-157FSH-CO$_2$H (5 g) in Novec 7100 (40 mL) was added oxalyl chloride (3.4 mL) and the reaction mixture was stirred at 65° C. for 24 hours. After cooling to room temperature the solution was concentrated under reduced pressure to remove the solvent and excess of oxalyl chloride. The obtained crude Krytox acyl chloride 5 was used without any further purification step.

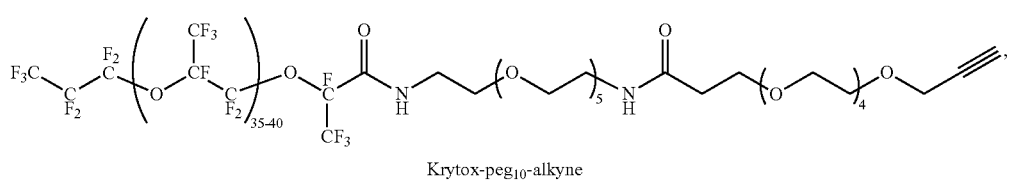

Krytox-peg$_{10}$-alkyne

To a solution of Krytox-COCl 5 (1.23 g) in Novec 7100 (25 mL) was added a solution of $NH_2$-$peg_{10}$-alkyne 4 (0.15 g) and TEA (92 μL) in THF (15 mL). The resulting mixture was vigorously stirred at room temperature for 24 hours. The crude product obtained after evaporation of the solvent was dissolved in FC 3283 (80 mL). The resulting solution was transferred in a separatory funnel and DCM (60 mL) was added forming an emulsion. After separation of the layers the desired compound was extracted in the FC 3283 layer. The latter was concentrated under reduced pressure to afford Krytox-$peg_{10}$-alkyne 6 as a sticky white oil.

BocNH-$peg_{10}$-biotin, 8

(tert-Butyl (17-oxo-1-(1-(2-(2-(5-((3aS,4S,6aR)-2-oxohexahydro-1H-thieno[3,4-d]imidazol-4-yl)pentanamido)ethoxy)ethyl)-1H-1,2,3-triazol-4-yl)-2,5,8,11,14,21,24,27,30,33-decaoxa-18-azapentatriacontan-35-yl)carbamate)

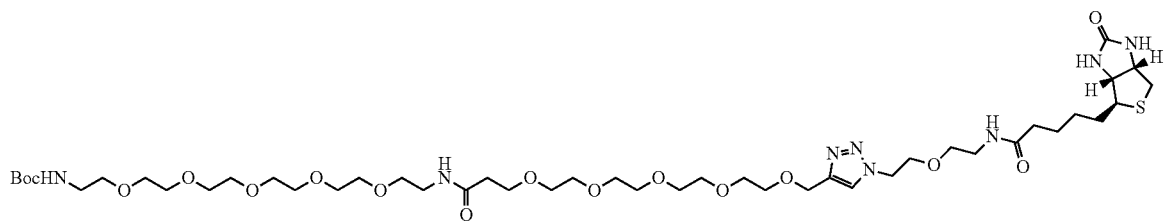 [SMILES: CC(C)(C)OC(=O)NCCOCCOCCOCCOCCOCCNC(=O)CCOCCOCCOCCOCCOCc1cn(CCOCCNC(=O)CCCC[C@@H]2SC[C@H]3NC(=O)N[C@@H]23)nn1]

$C_{45}H_{82}N_8O_{16}S$ MW=1023.24 g/mol

To a solution of BocNH-$peg_{10}$-alkyne 3 (300 mg, 0.45 mmol) in THF/$H_2O$ (10 mL, 1:1) were subsequently added (D)-biotin-$N_3$ 7 (1.5 eq., 240 mg, 0.67 mmol), sodium ascorbate (0.8 eq., 71 mg, 0.36 mmol) and copper(II) sulfate (0.3 eq., 21 mg, 0.13 mmol). The reaction mixture was stirred at room temperature for 48 hours. The resulting solution was diluted with water (50 mL), extracted with DCM (4×50 mL), dried over $MgSO_4$ and concentrated under reduced pressure. The crude material was purified by silica gel flash chromatography (DCM to DCM/MeOH 90/10 in 30 min) to afford BocNH-$peg_{10}$-biotin 8 as a colorless oil (327 mg, 0.32 mmol, 71% yield).

$^1$H NMR (CDCl$_3$, 400 MHz) 37.71 (s, 1H), 6.89 (brs, 1H), 6.64 (brs, 1H), 6.18 (brs, 1H), 5.45 (brs, 1H), 5.15 (brs, 1H), 4.64 (s, 2H), 4.49 (t, J=5.0 Hz, 2H), 4.45 (dd, J=4.8 and 7.6 Hz, 1H), 4.26 (dd, J=4.4 and 7.6 Hz, 1H), 3.81 (t, J=5.2 Hz, 2H), 3.70-3.55 (m, 34H), 3.51-3.46 (m, 6H), 3.41-3.31 (m, 4H), 3.28-3.23 (m, 2H), 3.12-3.06 (m, 1H), 2.85 (dd, J=4.8 and 12.8 Hz, 1H), 2.68 (d, J=12.8 Hz, 1H), 2.42 (t, J=6.0 Hz, 2H), 2.16 (t, J=7.2 Hz, 2H), 1.74-1.54 (m, 4H), 1.43-1.34 (m, 2H), 1.39 (s, 9H).

$^{13}$C NMR (CDCl$_3$, 100 MHz) δ 173.8, 171.6, 163.9, 156.2, 145.0, 124.2, 70.7-70.0, 69.0, 67.5, 64.7, 62.1, 60.4, 55.8, 50.4, 40.7, 40.6, 39.4, 39.2, 37.0, 35.7, 28.6, 28.2 (3C), 28.2, 25.7.

MS (ESI) m/z: 1023.4 [M+H]$^+$, 1045.3 [M+Na]$^+$.

$NH_2$-$peg_{10}$-biotin (hydrochloride Salt), 9

(17-Oxo-1-(1-(2-(2-(5-((3aS,4S,6aR)-2-oxohexahydro-1H-thieno[3,4-d]imidazol-4-yl)pentanamido)ethoxy)ethyl)-1H-1,2,3-triazol-4-yl)-2,5,8,11,14,21,24,27,30,33-decaoxa-18-azapentatriacontan-35-aminium chloride)

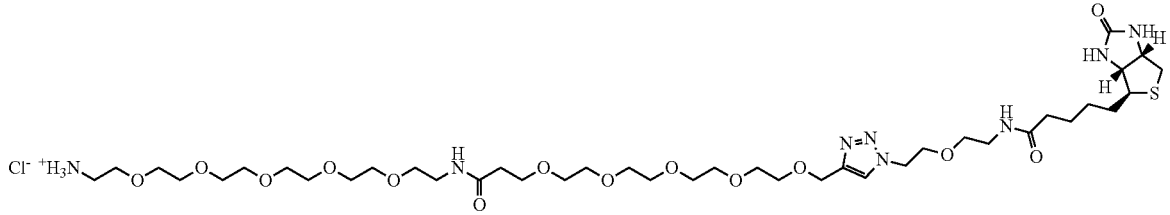 [SMILES: [Cl-] ; [NH3+]CCOCCOCCOCCOCCOCCNC(=O)CCOCCOCCOCCOCCOCc1cn(CCOCCNC(=O)CCCC[C@@H]2SC[C@H]3NC(=O)N[C@@H]23)nn1]

C<sub>40</sub>H<sub>75</sub>ClN<sub>5</sub>O<sub>14</sub>S MW=959.59 g/mol

To a solution of BocNH-peg$_{10}$-biotin 8 (0.23 g, 0.22 mmol) in DCM (6 mL) was added a 4M HCl solution in dioxane (15 eq., 0.84 mL, 3.37 mmol). The reaction mixture was stirred at room temperature for 5 hours. Evaporation of the solvent under reduced pressure afforded NH$_2$-peg$_{10}$-biotin 9 as a colorless oil (0.21 g, 0.22 mmol, quantitative yield).

$^1$H NMR (CD$_3$OD, 400 MHz) δ 8.72 (s, 1H), 4.91-4.85 (m, 4H), 4.76 (dd, J=4.8 and 8.0 Hz, 1H), 4.57 (dd, J=4.4 and 8.0 Hz, 1H), 3.99 (t, J=4.8 Hz, 2H), 3.80-3.58 (m, 40H), 3.46-3.41 (m, 4H), 3.32-3.38 (m, 1H), 3.13-3.18 (m, 2H), 3.04 (dd, J=4.8 and 13.2 Hz, 1H), 2.85 (d, J=13.2 Hz, 1H), 2.59 (t, J=6.0 Hz, 2H), 2.39 (t, J=7.2 Hz, 2H), 1.85-1.44 (m, 6H). NH$_2$ and NH signals are missing.

$^{13}$C NMR (CD$_3$OD, 100 MHz) δ 176.3, 174.3, 164.1, 145.3, 126.6, 71.8-70.7), 70.0, 68.4, 68.1, 64.6, 63.7, 62.0, 57.1, 52.2, 41.13, 40.8, 40.5, 40.3, 37.7, 36.8, 29.9, 29.6, 27.0.

HRMS (ESI) m/z: calcd. for C$_{40}$H$_{76}$N$_8$O$_{14}$S [M+2H]$^{2+}$ 462.2595, found 462.2597.

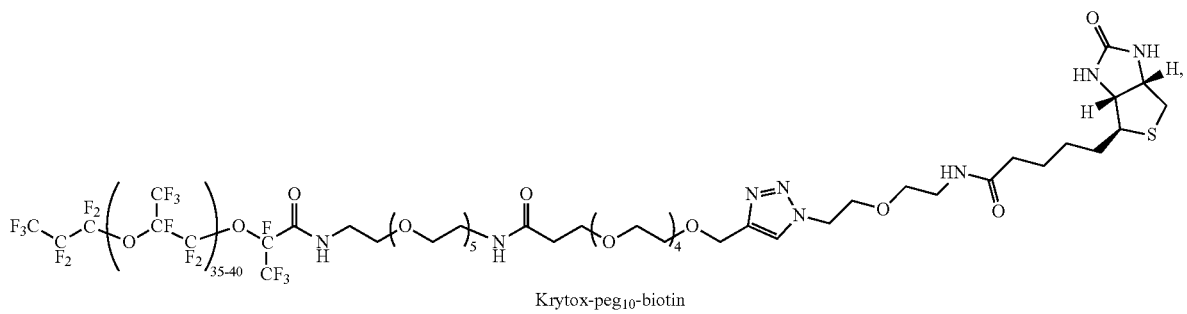

Krytox-peg$_{10}$-biotin

To a solution of Krytox-COCl 5 (1.00 g) in Novec 7100 (25 mL) was added a solution of NH$_2$-peg$_{10}$-biotin 9 (0.20 g) and TEA (75 µL) in THF (15 mL). The resulting mixture was vigorously stirred at room temperature for 48 h. The crude material obtained after evaporation of the solvent was dissolved in FC 3283 (80 mL). The resulting solution was transferred in a separatory funnel and DCM (60 mL) was added forming an emulsion. After separation of the layers the desired compound was extracted in the FC 3283 layer. The latter was concentrated under reduced pressure to afford Krytox-peg$_{10}$-biotin 10 as a sticky white oil.

BocNH-peg$_{12}$-azide, 12

(tert-Butyl (39-azido-19-oxo-3,6,9,12,15,22,25,28,31,34,37-undecaoxa-18-azanonatriacontyl)carbamate)

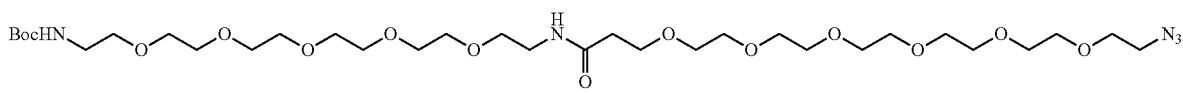 [SMILES: CC(C)(C)OC(=O)NCCOCCOCCOCCOCCOCCNC(=O)CCOCCOCCOCCOCCOCCOCCN=[N+]=[N-]]

$C_{32}H_{63}N_5O_{14}$ MW=741.87 g/mol

To a solution of 1-azido-3,6,9,12,15,18-hexaoxahenicosan-21-oic acid 11a (1 eq., 1.00 g, 2.64 mmol) in CHCl$_3$ (15 mL) were added 1-(3-dimethylaminopropyl)-3-ethyl carbodiimide hydrochloride (1.5 eq., 0.76 g, 3.95 mmol) and HOBt (1.5 eq., 0.53 g, 3.95 mmol). The resulting mixture was stirred at room temperature for 20 minutes. A solution of tert-butyl N-(17-amino-3,6,9,12,15-pentaoxaheptadecan-1-yl)carbamate 1 (1.2 eq., 1.20 g, 3.16 mmol) and DIEA (2.5 eq., 1.09 mL, 6.59 mmol) in CHCl$_3$ (10 mL) was added and the reaction was stirred at room temperature for 14 hours. The resulting solution was diluted with water (50 mL) and extracted with DCM (3×50 mL). The combined organic layers were dried over MgSO$_4$ and concentrated under reduced pressure. Purification by silica gel flash chromatography (DCM to DCM/MeOH 95/5 in 30 minutes) afforded BocNH-peg$_{12}$-azide 12 (1.62 g, 2.19 mmol, 83%) as a yellow oil.

$^1$H NMR (400 MHz, CDCl$_3$) δ 6.62 (brs, 1H), 5.05 (brs, 1H), 3.74 (t, J=6.0 Hz, 2H), 3.70-3.58 (m, 38H), 3.54 (q, J=5.4 Hz, 4H), 3.44 (dd, J=5.4 and 10.8 Hz, 2H), 3.39 (d, J=5.0 Hz, 2H), 3.31 (dd, J=5.0 and 10.0 Hz, 2H), 2.47 (t, J=6.0 Hz, 2H), 1.44 (s, 9H).

$^{13}$C NMR (100 MHz, CDCl$_3$) δ 171.2, 155.8, 78.7, 70.5-69.7, 67.1, 50.5, 40.2, 39.0, 36.8, 28.3 (3C).

MS (ESI) m/z: 764.2 [M+Na]$^+$.

NH$_2$-peg$_{12}$-azide, 13

(N-(17-Amino-3,6,9,12,15-pentaoxaheptadecyl)-1-azido-3,6,9,12,15,18-hexaoxahenicosan-21-amide)

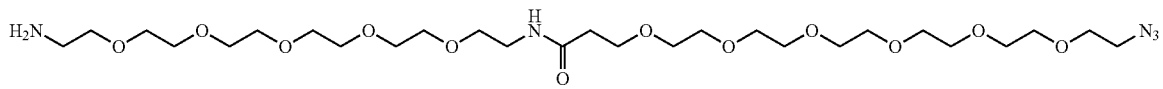 [SMILES: [N-]=[N+]=NCCOCCOCCOCCOCCOCCOCCC(=O)NCCOCCOCCOCCOCCOCCN]

$C_{27}H_{55}N_5O_{12}$ MW=641.75 g/mol

To a solution of BocNH-peg$_{12}$-azide 12 (1 eq., 0.40 g, 0.54 mmol) in DCM (15 mL) was added a 4M solution of HCl in dioxane (15 eq., 2.02 mL, 8.09 mmol) and the reaction mixture was stirred at room temperature for 4 hours. After evaporation the crude product was purified by silica gel flash chromatography (DCM to DCM/MeOH/NH$_4$OH 9/1.8/0.2) to afford NH$_2$-peg$_{12}$-azide 13 (0.34 g, 0.53 mmol, 98%) as a yellow oil.

$^1$H NMR (400 MHz, CDCl$_3$) δ 7.55 (brs, 1H), 3.82-3.56 (m, 46H), 3.44 (dd, J=5.3 and 10.5 Hz, 2H), 3.38 (t, J=5.0 Hz, 2H), 3.01 (t, J=5.0 Hz, 2H), 2.55 (t, J=6.2 Hz, 2H).

$^{13}$C NMR (100 MHz, CDCl$_3$) δ 171.4, 70.4-70.0, 69.7, 69.6, 69.5, 69.0, 67.1, 50.4, 40.4, 38.8, 36.5.

MS (ESI) m/z: 664.3 [M+Na]$^+$.

14

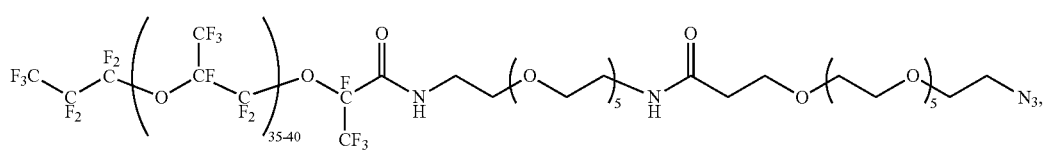

Krytox-peg$_{12}$-azide

To a solution of Krytox157FSH-COCl 5 (2.30 g) in Novec 7100 (45 mL) was added dropwise a solution of NH$_2$-peg$_{12}$-azide (0.25 g) and TEA (148 µL) in DCM (25 mL). The resulting mixture was vigorously stirred at room temperature for 36 hours. The crude material obtained after evaporation of the solvent was dissolved in FC 3283 (150 mL). The resulting solution was transferred in a separatory funnel and DCM (100 mL) was added forming an emulsion. After the separation of the layers the desired compound was extracted in the FC 3283 layer. The latter was concentrated under reduced pressure to afford Krytox-peg$_{12}$-azide 14 as a sticky yellow oil.

BocNH-peg$_{12}$-biotin, 16

(tert-Butyl (19-oxo-39-(4-((5-(((3aS,4S,6aR)-2-oxo-hexahydro-1H-thieno[3,4-d]imidazol-4-yl)pentanamido)methyl)-1H-1,2,3-triazol-1-yl)-3,6,9,12,15,22,25,28,31,34,37-undecaoxa-18-azanonatriacontyl) carbamate)

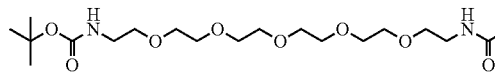

$C_{45}H_{82}N_8O_{16}S$ MW=1023.24 g/mol

In a round bottom flask were added BocNH-peg$_{12}$-azide 12 (1 eq., 350 mg, 0.47 mmol), 5-(((3aS,4S,6aR)-2-oxohexahydro-1H-thieno[3,4-d]imidazol-4-yl)-N-(prop-2-yn-1-yl) pentanamide 15 (1.3 eq., 172 mg, 0.61 mmol), THF (6 mL) and water (6 mL). The flask was evacuated and back flushed with argon. The process of evacuation and flushing was repeated three times. CuSO$_4$.5H$_2$O (0.3 eq., 35 mg, 0.14 mmol) and sodium ascorbate (0.8 eq., 75 mg, 0.38 mmol) were added to the mixture and the flask was evacuated and back flushed with argon. The resulting mixture was stirred at room temperature for 4 hours. The resulting solution was diluted with water (50 mL), extracted with DCM (4×50 mL), dried over MgSO$_4$ and concentrated under reduced pressure. Purification by silica gel flash chromatography (DCM to DCM/MeOH 8/2 in 30 minutes) afforded BocNH-peg$_{12}$-biotin 16 (405 mg, 0.40 mmol, 84%) as a yellowish oil.

$^1$H NMR (400 MHz, CDCl$_3$) 7.74 (s, 1H), 7.40 (brs, 1H), 6.76 (brs, 1H), 6.49 (brs, 1H), 5.87 (brs, 1H), 5.08 (brs, 1H), 4.62-4.47 (m, 4H), 4.41 (dd, J=5.5 and 15.0 Hz, 1H), 4.38-4.32 (m, 1H), 3.86 (t, J=5.1 Hz, 2H), 3.73 (t, J=6.1 Hz, 2H), 3.68-3.57 (m, 36H), 3.54 (dd, J=5.6 and 11.2 Hz, 4H), 3.43 (dd, J=5.4 and 10.8 Hz, 2H), 3.35-3.26 (m, J=4.9 Hz, 2H), 3.14 (dd, J=7.2 and 11.9 Hz, 1H), 2.93 (dd, J=5.0 and 12.8 Hz, 1H), 2.77 (d, J=12.6 Hz, 1H), 2.47 (t, J=6.1 Hz, 2H), 2.32-2.15 (m, 2H), 1.85-1.57 (m, 4H), 1.44 (s, 9H), 1.41-1.18 (m, 2H).

$^{13}$C NMR (101 MHz, CDCl$_3$) δ 173.2, 171.3, 164.4, 155.9, 144.9, 123.3, 78.8, 71.1-68.9, 69.7, 69.2, 67.2, 61.7, 60.2, 55.8, 50.1, 40.4, 40.2, 39.0, 36.7, 35.6, 34.4, 28.3 (3C), 28.2, 28.0, 25.4.

MS (ESI) m/z: 1023.4 [M+H]$^+$.

NH$_2$-peg$_{12}$-biotin, 17

(N-(17-Amino-3,6,9,12,15-pentaoxaheptadecyl)-1-(4-((5-(((3aS,4S,6aR)-2-oxohexahydro-1H-thieno[3,4-d]imidazol-4-yl)pentanamido)methyl)-1H-1,2,3-triazol-1-yl)-3,6,9,12,15,18-hexaoxahenicosan-21-amide)

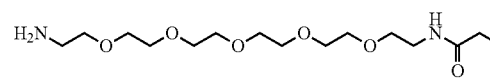

$C_{40}H_{74}N_8O_{14}S$ MW=923.12 g/mol

To a solution of BocNH-peg$_{12}$-biotin 16 (1 eq., 370 mg, 0.36 mmol) in DCM (5 mL) was added a 4M solution of HCl in dioxane (15 eq., 1.36 mL, 5.42 mmol) and the reaction was stirred at room temperature for 3 hours. After concentration the crude was purified by silica gel flash chromatography (DCM to DCM/MeOH/NH$_4$OH 8/1.8/0.2) to afford NH$_2$-peg$_{12}$-biotin 17 (295 mg, 0.32 mmol, 88%) as a yellowish oil.

$^1$H NMR (400 MHz, CDCl$_3$) δ 7.77 (brt, J=5.7 Hz, 1H), 7.72 (s, 1H), 7.03 (brs, 1H), 6.89 (brs, 1H), 6.46 (brs, 1H), 4.61-4.44 (m, 4H), 4.42-4.27 (m, 2H), 3.84 (t, J=5.2 Hz, 2H), 3.72 (t, J=6.1 Hz, 2H), 3.67-3.48 (m, 40H), 3.42 (dd, J=5.3 and 10.7 Hz, 2H), 3.12 (dd, J=7.2 and 11.7 Hz, 1H), 2.91 (dd, J=4.9 and 12.8 Hz, 1H), 2.86 (t, J=5.2 Hz, 2H), 2.77 (d, J=12.7 Hz, 1H), 2.46 (t, J=6.1 Hz, 2H), 2.29-2.13 (m, 2H), 2.05 (s, 2H), 1.85-1.58 (m, 4H), 1.54-1.31 (m, 2H).

$^{13}$C NMR (100 MHz, CDCl$_3$) δ 173.1, 171.2, 164.2, 144.9, 123.2, 72.6, 70.5-69.7, 69.5, 69.1, 67.1, 61.6, 60.0, 55.6, 49.8, 41.3, 40.3, 38.9, 36.6, 35.4, 34.4, 28.2, 27.9, 25.3.

MS (ESI) m/z: 923.5 [M+H]$^+$.

18

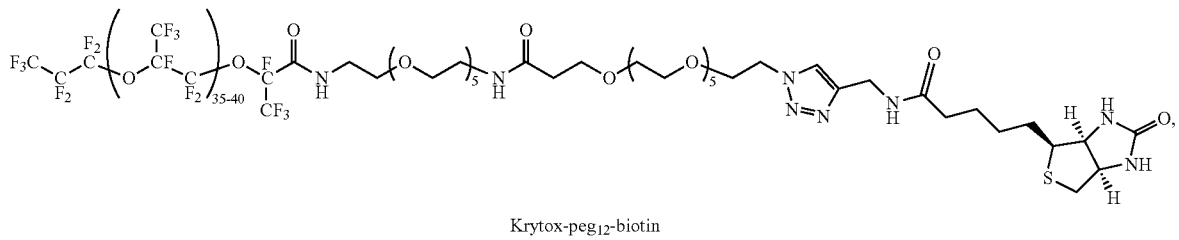

Krytox-peg$_{12}$-biotin

To a solution of Krytox157FSH-COCl 5 (1.670 g) in Novec 7100 (40 mL) was added a solution of H$_2$N-peg$_{12}$-biotin 17 (0.285 g) and TEA (107 μL) in DCM (20 mL). The crude product obtained after evaporation of the solvent was dissolved in FC 3283 (100 mL). The resulting solution was transferred in a separatory funnel and DCM (100 mL) was added forming an emulsion. After the separation of the two layers the desired compound was extracted in the FC 3283 layer. The latter was concentrated under reduced pressure to afford Krytox-peg$_{12}$-biotin 18 as a sticky white oil.

3. Functionalized Triblock Surfactants Synthesis

Figure 3:
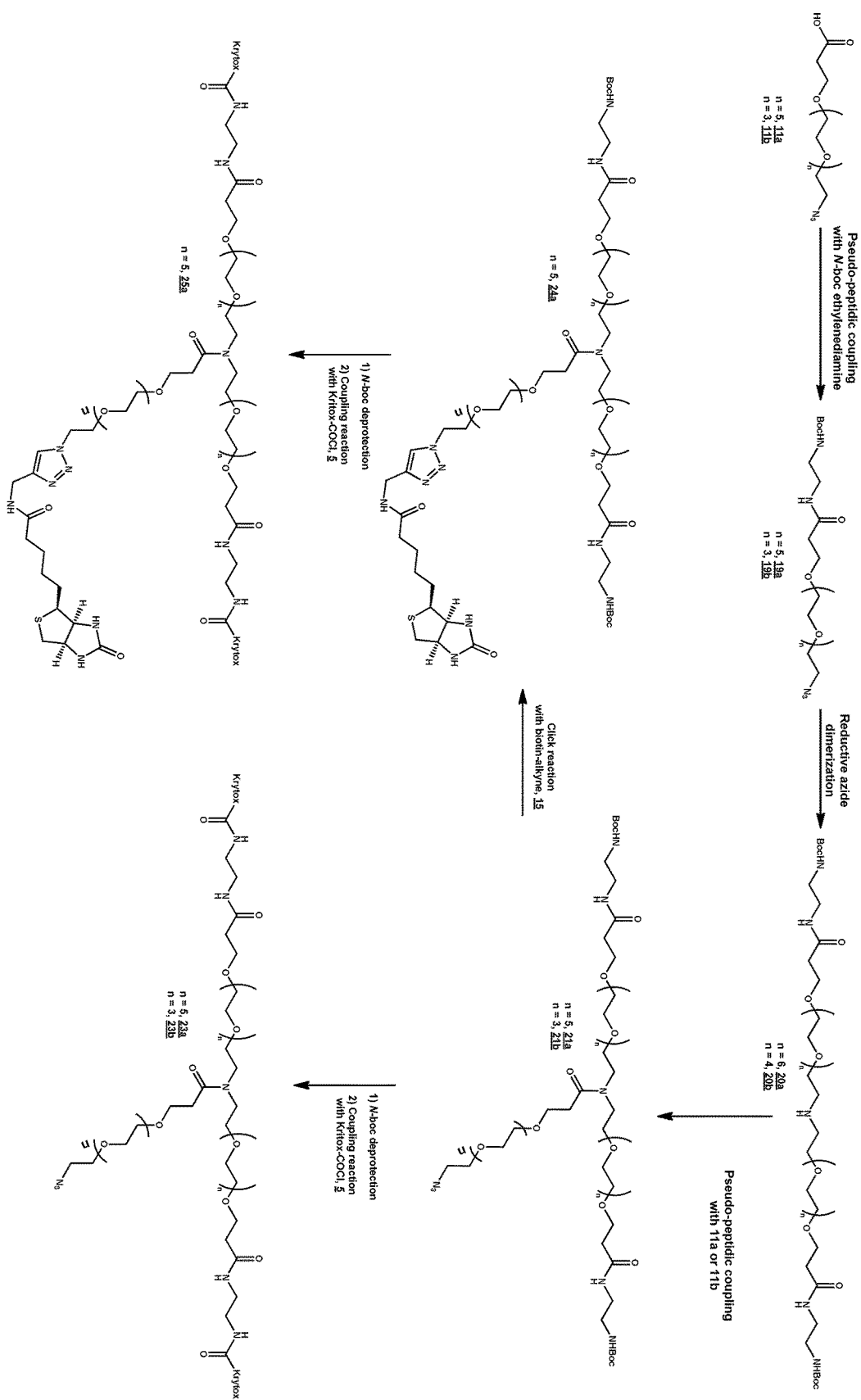
FIG. 3: Strategy synthesis of diKrytox-azide and diKrytox-biotin derivatives.

Functionalized triblock surfactants bearing an azide and a biotin moieties were synthesized according to the strategy synthesis reported in FIG. 3. The key step of this synthesis consisted in the preparation of a trifunctional peg derivative via reductive azide dimerization (Lange, M., Pettersen, A. L., Undheim, K. Tetrahedron, 1998, 54, 5745-5752; An, I.-H., Seong, H.-R., Ahn, K. H. Bull. Korean Chem. Soc., 2003, 25, 420-422). The substrates of this reaction were first obtained by coupling acidic oligoethylene azide derivatives (19a and 19b) with N-boc ethylenediamine. These resulting compounds were submitted to the reductive azide dimerization under hydrogenation condition to obtain trifunctional peg linkers 20a and 20b. Starting from these trifunctional linkers a third acidic peg azide chain was coupled to the central secondary amine afforded tri-peg derivatives bearing an azide moiety 21a and 21b. These intermediates led to the synthesis of the azide triblock surfactants 23a and 23b after N-boc cleavage followed by pseudo-peptidic coupling reaction with Krytox-COCl 5. A biotinylated triblock surfactant was also obtained starting from tripeg$_6$ azide intermediate 21a after click reaction with Biotin-alkyne 15, N-boc moieties deprotection and coupling with Krytox-COCl 5.

n = 5, 19a
n = 3, 19b 19a, tert-Butyl (1-azido-21-oxo-3,6,9,12,15,18-hexaoxa-22-azatetracosan-24-yl)carbamate, $C_{22}H_{43}N_5O_9$, MW=521.6 g/mol 19b, tert-Butyl (1-azido-15-oxo-3,6,9,12-tetraoxa-16-azaoctadecan-18-yl)carbamate, $C_{18}H_{35}N_5O_7$, MW=433.5 g/mol General procedure: To a solution of acid oligoethylene derivative (11a or 11b) in DCM (0.5 mmol/mL) were added HOBt (1.3 eq.) and EDC (1.3 eq.). The solution was stirred 15 minutes at room temperature. A solution of N-boc ethylene diamine (1.1 eq.) and TEA (3 eq.) in DCM (0.5 mmol/mL of N-boc ethylene diamine) was added and the reaction was stirred at room temperature for 12 hours. Completion of the reaction was monitored by TLC (DCM/MeOH/HCO$_2$H 9/1/0.1, PMA revelator). After concentration water was added and the solution was extracted with DCM. The crude material was purified by silica gel flash chromatography.

19a, gradient eluent for flash chromatography: EtOAc to EtOAc/MeOH 9/1 in 30 minutes. $^1$H NMR (400 MHz, CDCl$_3$) δ 6.87 (s, 1H), 5.24 (s, 1H), 3.75-3.62 (m, 24H), 3.40 (s, 4H), 3.29-3.20 (m, 2H), 2.46 (t, J=5.7 Hz, 2H), 1.44 (s, 9H). $^{13}$C NMR (101 MHz, CDCl$_3$) δ 172.2, 156.4, 79.2, 70.8-70.5, 70.4, 70.3, 70.0, 67.3, 50.7, 40.7, 39.7, 37.0, 28.5. MS (ESI) m/z: 434.2 [M+H]$^+$.

19b, gradient eluent for flash chromatography: DCM to DCM/MeOH 9/1 in 30 minutes. $^1$H NMR (400 MHz, CDCl$_3$) δ 6.92 (brs, 1H), 5.19 (brs, 1H), 3.84-3.58 (m, 16H), 3.45-3.30 (m, 4H), 3.29-3.18 (m, 2H), 2.46 (t, J=5.4 Hz, 2H), 1.46 (s, 9H). $^{13}$C NMR (100 MHz, CDCl$_3$) δ 172.1, 156.4, 79.1, 77.4, 77.1, 76.8, 70.6, 70.6, 70.5, 70.5, 70.3, 70.2, 79.0, 67.2, 50.7, 40.5, 39.1, 37.0, 28.4, 28.3. MS (ESI) m/z: 522.1 [M+H]$^+$.

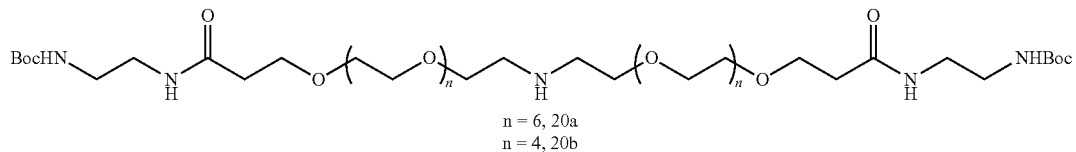

n = 6, 20a
n = 4, 20b 20a, di-tert-Butyl (4,46-dioxo-7,10,13,16,19,22,28,31,34,37,40,43-dodecaoxa-3,25,47-triazanonatetracontane-1,49-diyl)dicarbamate, $C_{44}H_{87}N_5O_8$, MW=974.2 g/mol 20b, di-tert-Butyl (4,34-dioxo-7,10,13,16,22,25,28,31-octaoxa-3,19,35-triazaheptatriacontane-1,37-diyl)dicarbamate, $C_{36}H_{71}N_5O_{14}$, MW=798.0 g/mol General Procedure:

To a solution of azide derivative (19a or 19b) in degassed dioxane (0.5 mmol/mL) was added Pd/C (0.05 eq.). The solution was stirred 4 hours at 60° C. under an hydrogen atmosphere. After cooling at room temperature the mixture was diluted in DCM and filtered through a pad of Celite®. After concentration the crude material was purified by flash chromatography (SiOH prealably desactivated with a solution of DCM/MeOH/NH$_4$OH 9/0.9/0.1, DCM to DCM/MeOH/NH$_4$OH 9/0.9/0.1 in 30 minutes).

20a, $^1$H NMR (400 MHz, CDCl$_3$) δ 6.93 (s, 2H), 5.30 (s, 2H), 3.72 (t, J=5.7 Hz, 4H), 3.68-3.54 (m, 44H), 3.38-3.30 (m, 4H), 3.28-3.18 (m, 4H), 2.81 (t, J=5.2 Hz, 4H), 2.46 (t, J=5.7 Hz, 4H), 1.43 (s, 18H). NH signal is missing. $^{13}$C NMR (100 MHz, CDCl$_3$) δ 171.7 (2C), 156.2 (2C), 78.5 (2C), 77.8 (2C), 77.5 (2C), 77.2 (2C), 70.3-70.0, 67.0 (2C), 48.9 (2C), 40.2 (2C), 39.5 (2C), 36.7 (2C), 28.3 (6C). MS (ESI) m/z: 798.4 [M+H]f.

20b, $^1$H NMR (400 MHz, CDCl$_3$) δ 6.95 (s, 2H), 5.31 (d, J=12.5 Hz, 2H), 3.74-3.55 (m, 32H), 3.38-3.32 (m, 4H), 3.27-3.19 (m, J=5.3 Hz, 4H), 2.80 (t, J=5.3 Hz, 4H), 2.46 (t, J=5.8 Hz, 4H), 1.43 (s, 18H). NH signal is missing. $^{13}$C NMR (100 MHz, CDCl$_3$) δ 172.2 (2C), 156.4 (2C), 79.2 (2C), 77.4 (2C), 77.2 (2C), 77.0 (2C), 76.7 (2C), 70.6-70.2 (6C), 67.3 (2C), 49.2 (2C), 40.6 (2C), 39.7 (2C), 37.0 (2C), 28.5 (6C). MS (ESI) m/z: 974.4 [M+H]$^+$.

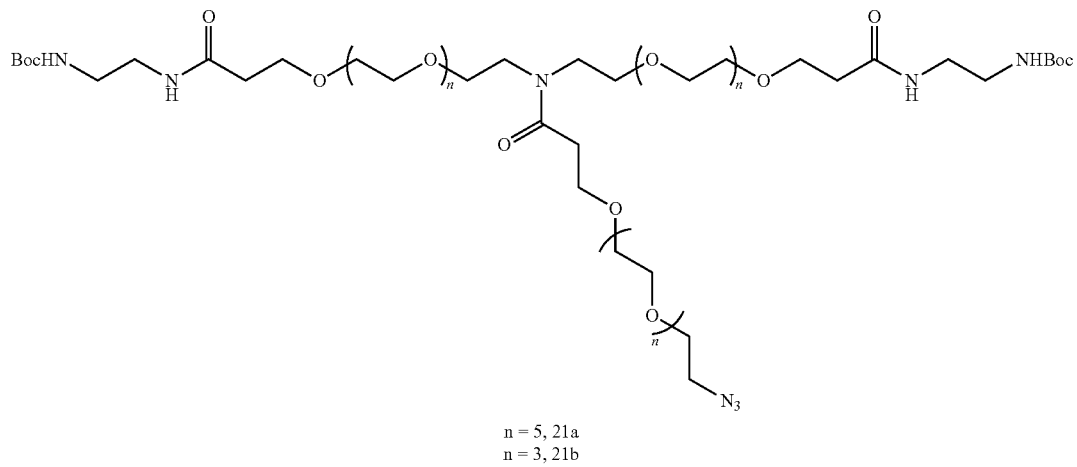

n = 5, 21a
n = 3, 21b 21a, di-tert-Butyl (25-(1-azido-3,6,9,12,15,18-hexaoxahenicosan-21-oyl)-4,46-dioxo-7,10,13,16,19,22,28,31,34,37,40,43-dodecaoxa-3,25,47-triazanonatetracontane-1,49-diyl)dicarbamate, $C_{59}H_{114}N_8O_{25}$, MW=1335.6 g/mol 21b, di-tert-Butyl (19-(1-azido-3,6,9,12-tetraoxapentadecan-15-oyl)-4,34-dioxo-7,10,13,16,22,25,28,31-octaoxa-3,19,35-triazaheptatriacontane-1,37-diyl)dicarbamate, $C_{47}H_{90}N_8O_{19}$, MW=1071.3 g/mol General Procedure:

To a solution of acid derivative (11a or 11b, 1.05 eq.) in DCM (0.5 mmol/mL) were added HOBt (1.3 eq.) and EDC (1.3 eq). The solution was stirred 15 minutes at room temperature. A solution of dialkylamine derivative (20a or 20b, 1.0 eq.) and TEA (3 eq.) in DCM (0.5 mmol/mL of dialkylamine) was added and the reaction was stirred at room temperature for 12 hours. Completion of the reaction was monitored by TLC (DCM/MeOH/HCO$_2$H 9/1/0.1, PMA revelator). After concentration the crude material was purified by silica gel flash chromatography (DCM to DCM/MeOH 85/15 in 30 minutes).

21a, $^1$H NMR (400 MHz, CDCl$_3$) δ 6.89 (s, 2H), 5.27 (s, 2H), 3.79-3.53 (m, 76H), 3.41-3.32 (m, 6H), 3.24 (d, J=5.3 Hz, 4H), 2.68 (t, J=7.0 Hz, 2H), 2.46 (t, J=5.7 Hz, 4H), 1.43 (s, 18H). $^{13}$C NMR (100 MHz, CDCl$_3$) δ 172.0, 171.2, 156.3, 78.9, 77.6, 77.3, 77.0, 70.6-70.2, 70.1, 69.9, 69.3, 69.2, 67.4, 67.2, 50.6, 48.7, 46.1, 40.4, 39.6, 36.8, 33.4, 28.4. MS (ESI) m/z: 1071.4 [M+H]$^+$.

21b, $^1$H NMR (400 MHz, CDCl$_3$) δ 6.91 (s, 2H), 5.27 (s, 2H), 3.81-3.52 (m, 52H), 3.41-3.30 (m, 6H), 3.24 (s, 4H), 2.68 (t, J=6.4 Hz, 2H), 2.45 (t, J=5.2 Hz, 4H), 1.43 (s, 18H). $^{13}$C NMR (100 MHz, CDCl$_3$) δ 171.1, 171.7, 171.1, 156.1, 78.7, 70.4-69.9, 69.7, 69.0, 67.2, 67.0, 53.3, 50.4, 48.5, 46.0, 40.2, 39.5, 36.6, 33.3, 28.2. MS (ESI) m/z: 668.6 [(M+2H)/2]$^{2+}$.

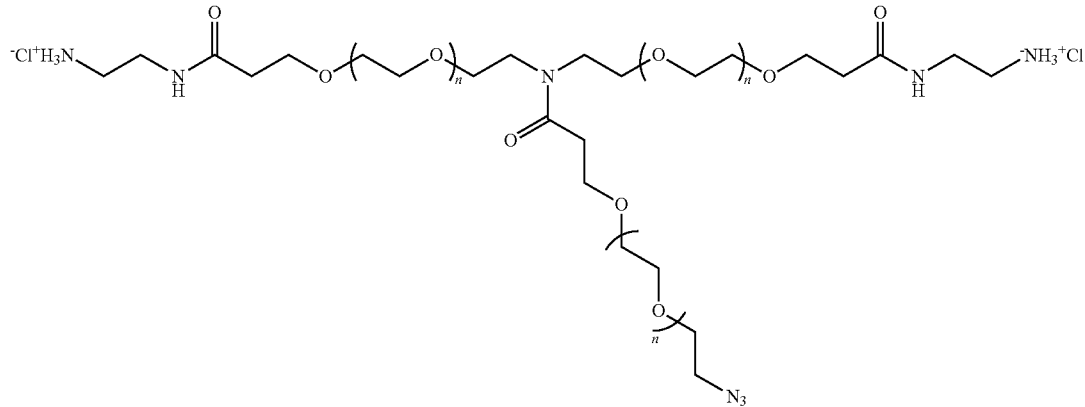

n = 5, 22a
n = 3, 22b 22a, 25-(1-Azido-3,6,9,12,15,18-hexaoxahenicosan-21-oyl)-4,46-dioxo-7,10,13,16,19,22,28,31,34,37,40,43-dodecaoxa-3,25,47-triazanonatetracontane-1,49-diaminium Chloride, $C_{49}H_{100}Cl_2N_8O_{21}$, MW=1208.3 g/mol 22b, 19-(1-Azido-3,6,9,12-tetraoxapentadecan-15-oyl)-4,34-dioxo-7,10,13,16,22,25,28,31-octaoxa-3,19,35-triazaheptatriacontane-1,37-diaminium chloride, $C_{37}H_{76}Cl_2N_8O_{15}$, MW=943.9 g/mol General Procedure:
To a solution of tripeg$_6$-azide (21a or 21b, 1.0 eq.) in DCM (0.05 mmol/mL) was added a 4M HCl solution in dioxane (20 eq.). The solution was stirred 3 hours at room temperature and concentrated under reduced pressure. The crude material was used in the next step without any further purification. Completion of the reaction was checked by TLC (DCM/MeOH 9/1, PMA or nihydrine revelator) and $^1$H NMR.

22a, $^1$H NMR (400 MHz, CD$_3$OD) 3 3.87-3.45 (m, 80H), 3.39 (s, 2H), 3.12 (s, 4H), 2.76 (s, 2H), 2.50 (s, 4H). NH$_2$ and NH signals are missing.

22b, $^1$H NMR (400 MHz, CD$_3$OD) 3 3.81-3.59 (m, 52H), 3.50 (dd, J=6.3 and 12.5 Hz, 4H), 3.43-3.37 (m, 2H), 3.09 (d, J=5.3 Hz, 4H), 2.76 (t, J=6.2 Hz, 2H), 2.51 (t, J=5.9 Hz, 4H). NH$_2$ and NH signals are missing.

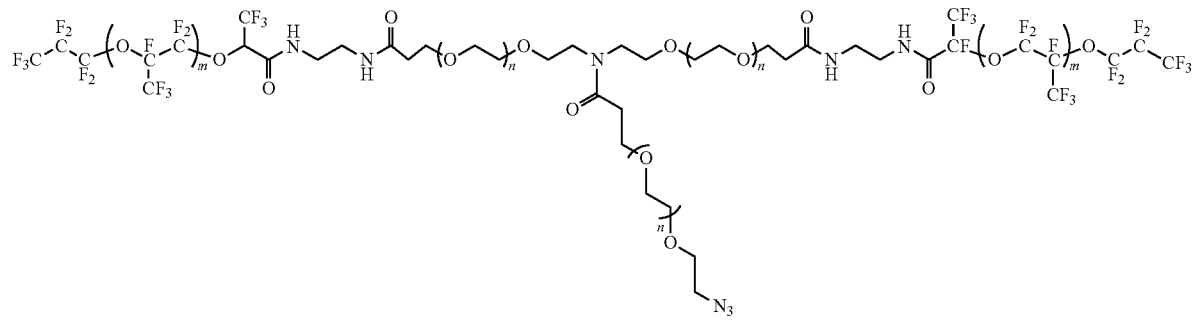

23a, diKrytox-peg$_{18}$-azide
23b, diKrytox-peg$_{12}$-azide n = 6, m = 35-40, 26a
n = 4, m = 35-40, 26b General Procedure:
To a solution of Krytox157FSH-COCl 5 (2 eq.) in Novec 7100 (0.1 g/mL) was added a solution of amine derivative (22a or 22b, 1 eq.) and TEA (3 eq.) in DCM (20 mL). The crude product obtained after evaporation of the solvent was dissolved in a mixture of Novec 7500/FC 3283 (1/1). The fluorous layer was washed three times with CHCl$_3$ and concentrated under reduced pressure to afford diKrytox-peg-azide surfactants 23a and 23b as yellowish oils.

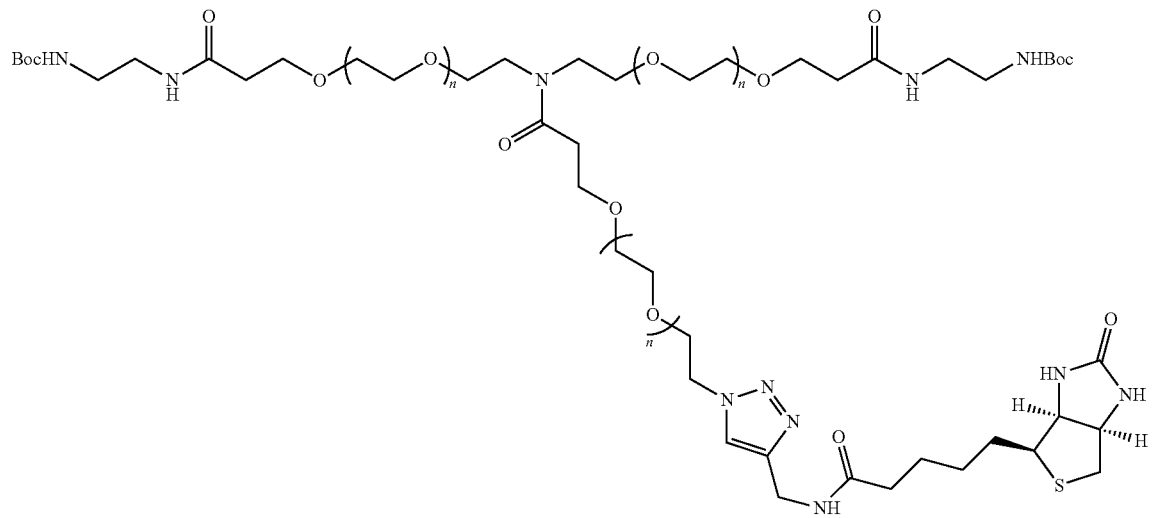

n = 5, 24a 24a, di-tert-Butyl (4,46-dioxo-25-(1-(4-((5-((3aS,4S,6aR)-2-oxohexahydro-1H-thieno[3,4-d]imidazol-4-yl)pentanamido)methyl)-1H-1,2,3-triazol-1-yl)-3,6,9,12,15,18-hexaoxahenicosan-21-oyl)-7,10,13,16,19,22,28,31,34,37,40,43-dodecaoxa-3,25,47-triazanonatetracontane-1,49-diyl)dicarbamate, $C_{72}H_{133}N_{11}O_{27}S$, MW=1616.9 g/mol In a shlenk flask under argon were added biotin-alkyne (1.5 eq., 158 mg, 0.56 mmol), tripeg$_6$-N$_3$ 22a (1 eq., 500 mg, 0.37 mmol), THF (3 mL) and water (3 mL). The flask was evacuated and back flushed with argon. The process of evacuation and flushing was repeated three times. Sodium ascorbate (0.8 eq., 59.3 mg, 0.30 mmol) and CuSO$_4$.5H$_2$O (30%, 28 mg, 0.11 mmol) were added to the mixture and the flask was evacuated and back flushed with argon. The resulting mixture was stirred at room temperature for 4 hours. TLC monitoring: DCM/MeOH 15%, revelator KMnO$_4$. The resulting solution was diluted with water (50 mL), extracted with DCM (4×50 mL), dried over MgSO$_4$ and concentrated under reduced pressure. Purification by flash chromatography (RP-C18 16 g; H$_2$O to H$_2$O/ACN 6/4 in 30 minutes) afforded tripeg$_6$-biotin 24a as a yellowish oil.

24a, $^1$H NMR (400 MHz, CDCl$_3$) δ 7.73 (s, 1H), 7.51 (d, J=9.5 Hz, 1H), 6.94 (s, 2H), 6.62 (s, 1H), 6.06 (s, 1H), 5.30 (d, J=4.0 Hz, 2H), 4.58-4.47 (m, 4H), 4.43-4.32 (m, 2H), 3.85 (t, J=5.2 Hz, 2H), 3.79-3.51 (m, 74H), 3.34 (dd, J=5.5 and 11.2 Hz, 4H), 3.23 (d, J=5.4 Hz, 4H), 3.14 (dd, J=7.3 and 11.8 Hz, 1H), 2.93 (dd, J=5.0 and 12.8 Hz, 1H), 2.77 (d, J=12.6 Hz, 1H), 2.68 (t, J=6.9 Hz, 2H), 2.45 (t, J=5.8 Hz, 4H), 2.31-2.14 (m, 2H), 1.81-1.61 (m, 4H), 1.43 (s, 18H), 1.41-1.18 (m, 2H). $^{13}$C NMR (100 MHz, CDCl$_3$) δ 173.2, 171.9, 171.2, 164.3, 156.3, 144.9, 123.3, 78.8, 77.7, 77.6, 77.4, 77.1, 70.6-70.1, 69.2, 69.2, 67.3, 67.1, 61.7, 60.1, 55.7, 50.1, 48.6, 46.1, 40.4, 39.6, 36.8, 35.6, 34.4, 33.4, 28.4, 28.2, 28.0, 25.3.

MS (ESI) m/z: 809.1 [(M+2H)/2]$^{2+}$.

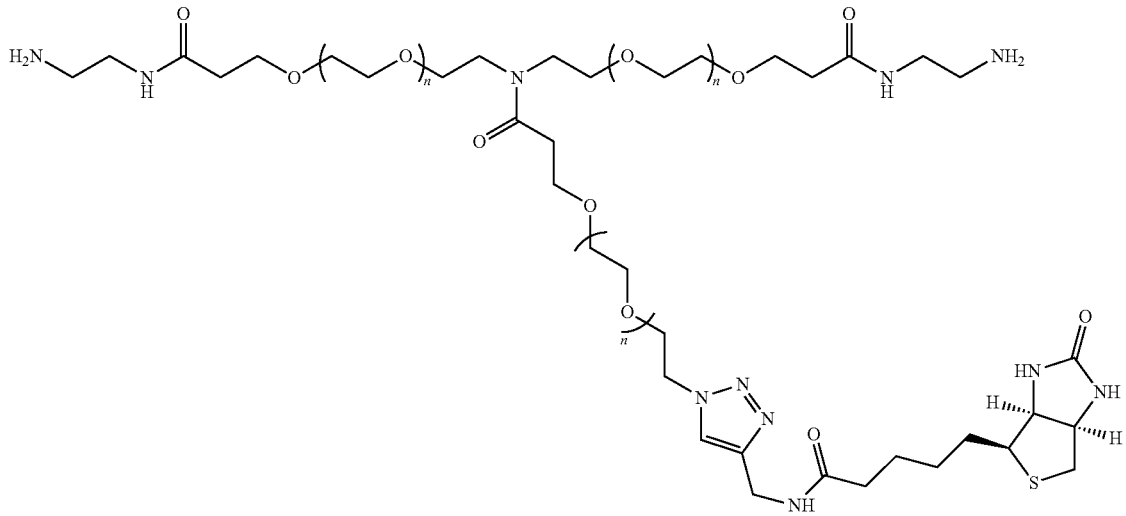

n = 5, 25a

25a, N,N-bis(24-Amino-21-oxo-3,6,9,12,15,18-hexaoxa-22-azatetracosyl)-1-(4-((5-((3aS,4S,6aR)-2-oxohexahydro-1H-thieno[3,4-d]imidazol-4-yl)pentanamido)methyl)-1H-1,2,3-triazol-1-yl)-3,6,9,12,15,18-hexaoxahenicosan-21-amide, $C_{62}H_{117}N_{11}O_{23}S$, MW=1416.7 g/mol To a solution of tripeg$_6$-biotin (1 eq., 360 mg, 0.223 mmol) in DCM (6 mL) was added a 4M solution of HCl in dioxane (30 eq., 1.67 mL, 6.68 mmol) and the reaction mixture was stirred for 4 hours. After concentration the crude was dissolved in MeOH (5 mL) and diethylamine-polystyrene was added (5 eq., 3 mmol/g, 372 mg). The resin was filtered off and washed with MeOH. After evaporation of the filtrate the free diamine derivative 25a was obtained as a yellowish oil (290 mg, 0.21 mmol, 92%).

25a, $^1$H NMR (400 MHz, CD$_3$OD) δ 7.93 (s, 1H), 4.60-4.53 (m, 2H), 4.50 (dd, J=4.3 and 7.9 Hz, 1H), 4.44 (s, 2H), 4.30 (dd, J=3.9 and 7.3 Hz, 1H), 3.91-3.86 (m, 2H), 3.83-3.72 (m, 6H), 3.70-3.53 (m, 68H), 3.48 (td, J=3.5 and 5.8 Hz, 4H), 3.25-3.16 (m, 1H), 3.11-3.02 (m, 4H), 2.93 (dd, J=5.0 and 12.7 Hz, 1H), 2.75 (t, J=6.5 Hz, 2H), 2.71 (d, J=12.9 Hz, 1H), 2.49 (t, J=5.9 Hz, 4H), 2.25 (t, J=7.4 Hz, 2H), 1.81-1.52 (m, 4H), 1.50-1.38 (m, 2H). NH$_2$ and NH signals are missing.

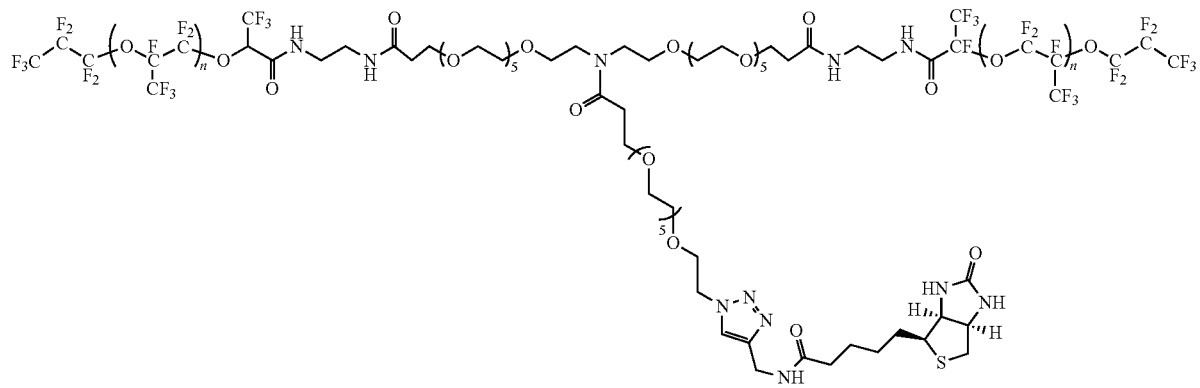

26a, diKrytox-peg$_{18}$-biotin

Tripeg$_6$-biotin-NH$_2$ 25a (1 eq., 100 mg, 0.071 mmol) and TEA (6 eq., 0.059 mL, 0.424 mmol) were dissolved in a mixture of DMF (0.5 mL) and CHCl$_3$ (9.5 mL) under argon. A solution of Krytox157FSH-COCl 5 (2 eq., 917 mg, 0.141 mmol) in Novec 7100 (10 mL) was added and the mixture was stirred for 48 hours at room temperature. The crude material obtained after evaporation of the solvent was dissolved in FC3283 (80 mL). The resulting solution was transferred in a separatory funnel and CHCl$_3$ (80 mL) was added forming an emulsion. After the separation of the two layers the desired compound was extracted in the FC 3283 layer. The latter was concentrated under reduced pressure to afford diKrytox-peg$_{18}$-biotin as a sticky yellowish oil.

4. Fluorescent Strained Cycloalkyne Derivative Synthesis

Figure 4:
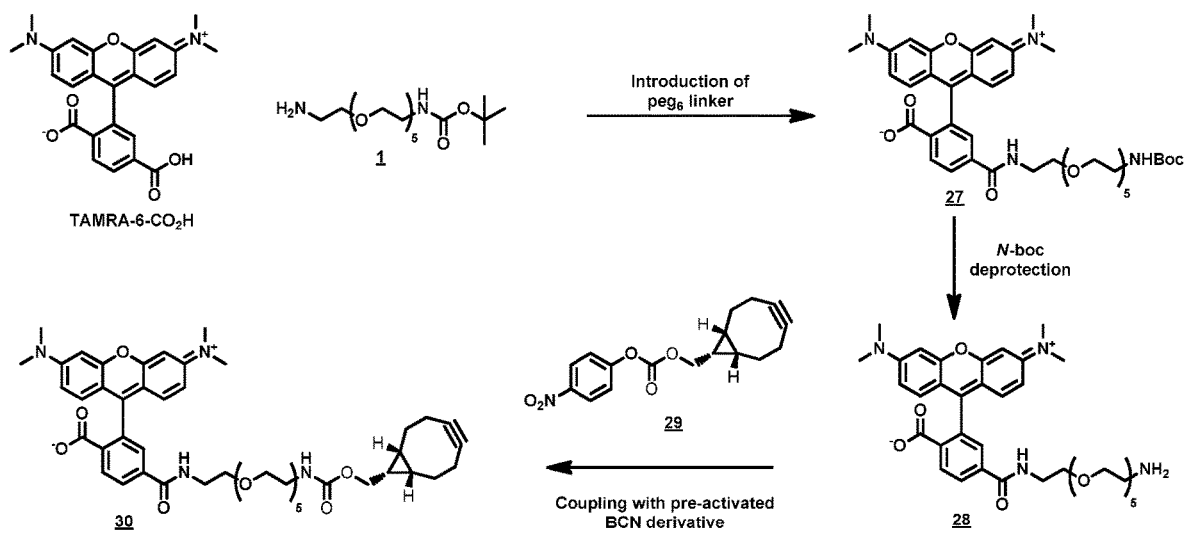
FIG. 4: Synthesis of TAMRA-peg$_6$-BCN derivative.
Figure 5:
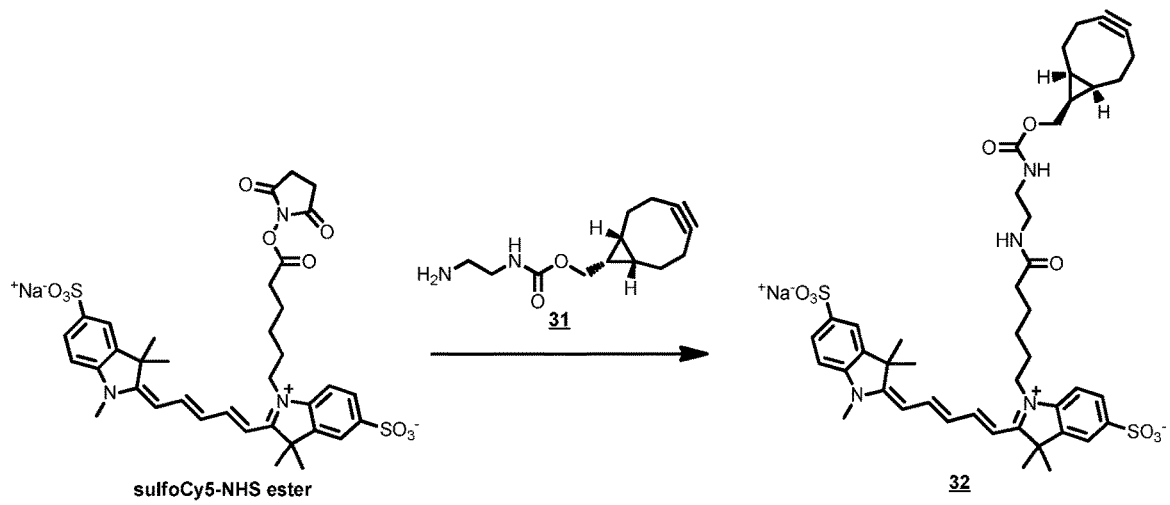
FIG. 5: Synthesis of sulfoCy5-BCN derivative.

To establish a proof of concept of the capture at the inner surface of the microdroplet by copper-free click chemistry two fluorescent strained cycloalkyne derivatives have been synthesized. BCN ((1R,8S,9s)-bicyclo[6.1.0]non-4-yn-9-yl-methyl) was chosen for its readily availability and conjugated with TAMRA and sulfo-Cy5 fluorophores. For TAMRA derivative a pseudo-peptidic coupling reaction was first performed between TAMRA-6-CO$_2$H and mono N-boc peg$_6$ diamine derivative 1. After N-boc deprotection the fluorophore was coupled to BCN in its nitro-phenyl carbonate activated form 21 (FIG. 4). SulfoCy5 NHS ester was directly coupled to BCN—NH$_2$ 31 via an amide bond (FIG. 5).

(1R,8S,9s)-Bicyclo[6.1.0]non-4-yn-9-ylmethyl (4-nitrophenyl) carbonate 29 (Dommerholt, J.; Schmidt, S.; Temming, R.; Hendriks, L. J. A; Rutjes, F. P. J. T.; van Hest, J. C. M.; Lefeber, D. J.; Friedl, P.; van Delft, F. L. Angew. Chem. Int. Ed., 2010, 49, 9422-9425) and (1R,8S,9S)-bicyclo[6.1.0]non-4-yn-9-ylmethyl (2-aminoethyl)carbamate 31 (Wang, K., Sachdeva, A., Cox, D. J., Wilf, N. M., Lang, K., Wallace, S., Mehl, R. A., Chin J. W. Nature Chemistry, 2014, 6, 393) was synthesized according to procedures described in the literature.

TAMRA-peg₆-NHBoc (TFA Salt), 27

(N-(9-(2-Carboxy-5-((2,2-dimethyl-4-oxo-3,8,11,14,17,20-hexaoxa-5-azadocosan-22-yl)carbamoyl)phenyl)-6-(dimethylamino)-3H-xanthen-3-ylidene)-N-methylmethanaminium 2,2,2-trifluoroacetate)

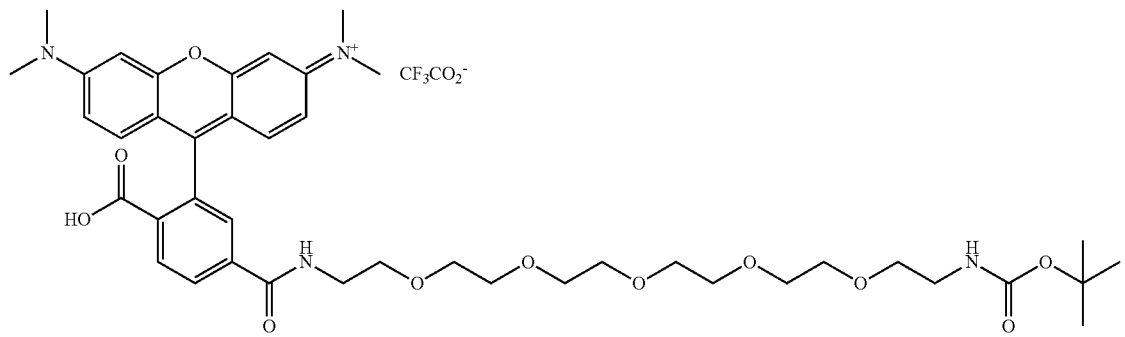

$C_{44}H_{57}F_3N_4O_{13}$ MW=906.94 g/mol

To a solution of TAMRA-6-COOH (1 eq., 60.0 mg, 0.14 mmol) and TEA (3.3 eq., 0.06 mL, 0.46 mmol) in DMF (1 mL) cooled to 0° C. was added HBTU (1.5 eq., 79.3 mg, 0.21 mmol). After 5 minutes a solution of tert-butyl N-(17-amino-3,6,9,12,15-pentaoxaheptadecan-1-yl)carbamate 1 (1.5 eq., 79.6 mg, 0.209 mmol) in DMF (1 mL) was added and the mixture was stirred for 2 hours at room temperature. Water was added (5 mL) and the mixture was concentrated under reduced pressure. The residue was dissolved in a minimum of MeOH and purified by flash chromatography (RP 16 g, H₂O (0.05% TFA) to ACN, 30 minutes) to afford TAMRA-peg₆-NHBoc 19 (67.9 mg, 0.0856 mmol, 61%) as a pink solid. CO₂H and NH signals are missing.

¹H NMR (400 MHz, CD₃OD) 3 8.39 (d, J=8.2 Hz, 1H), 8.21 (d, J=7.0 Hz, 1H), 7.83 (brs, 1H), 7.12 (d, J=9.5 Hz, 2H), 7.01 (dd, J=2.0 and 9.4 Hz, 2H), 6.92 (d, J=1.9 Hz, 2H), 3.78-3.49 (m, 20H), 3.47-3.42 (m, 2H), 3.27 (s, 12H), 3.16 (t, J=5.5 Hz, 2H), 1.40 (s, 9H).

MS (ESI) m/z: 793.4 [M]⁺.

TAMRA-peg₆-NH₂ (TFA Salt), 28

(1-(4-Carboxy-3-(6-(dimethylamino)-3-(dimethyliminio)-3H-xanthen-9-yl)phenyl)-1-oxo-5,8,11,14,17-pentaoxa-2-azanonadecan-19-aminium 2,2,2-trifluoroacetate)

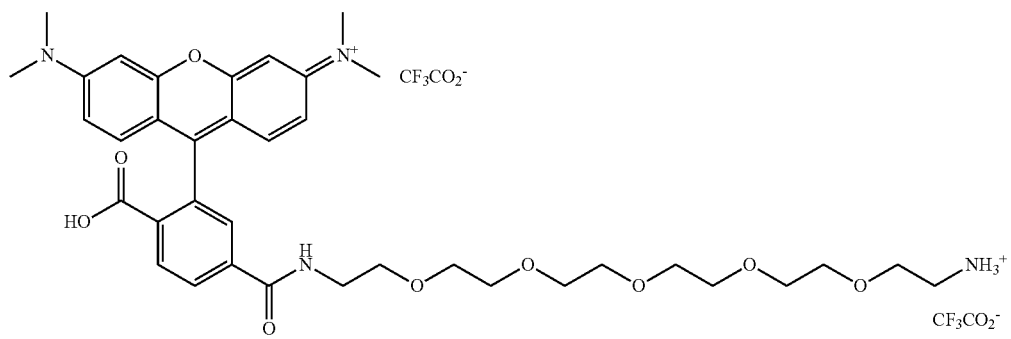

$C_{41}H_{50}F_6N_4O_{13}$ MW=920.84 g/mol

To a solution of TAMRA-peg$_6$-NHBoc 27 (1 eq., 60 mg, 0.076 mmol) in MeOH (3 mL) was added a 4M solution of HCl in dioxane (15 eq., 0.28 mL, 1.14 mmol) and the reaction was stirred at room temperature for 3 hours. After concentration under reduced pressure the mixture was dissolved in a minimum of MeOH and purified by flash chromatography (RP 16 g, H$_2$O (0.05% TFA) to ACN, 30 minutes) to afford TAMRA-peg$_6$-NH$_2$ (TFA salt) 28 (59.2 mg, 0.0643 mmol, 85%) as a pink solid.

$^1$H NMR (400 MHz, CD$_3$OD) δ 8.40 (d, J=8.2 Hz, 1H), 8.21 (dd, J=1.8, 8.2 Hz, 1H), 7.88 (dd, J=33.9, 10.5 Hz, 1H), 7.16 (d, J=9.5 Hz, 2H), 7.06 (dd, J=2.4, 9.5 Hz, 2H), 6.99 (d, J=2.4 Hz, 2H), 3.75-3.70 (m, 2H), 3.69-3.55 (m, 20H), 3.31 (s, 12H), 3.15-3.11 (m, 2H). CO$_2$H, NH and NH$_2$ signals are missing.

MS (ESI) m/z: 693.2 [M]$^+$.

TAMRA-peg$_6$-BCN (TFA Salt), 30

(N-(9-(5-((1-(((1R,8S,9s)-Bicyclo[6.1.0]non-4-yn-9-yl)-3-oxo-2,7,10,13,16,19-hexaoxa-4-azahenicosan-21-yl)carbamoyl)-2-carboxyphenyl)-6-(dimethylamino)-3H-xanthen-3-ylidene)-N-methylmethanaminium 2,2,2-trifluoroacetate)

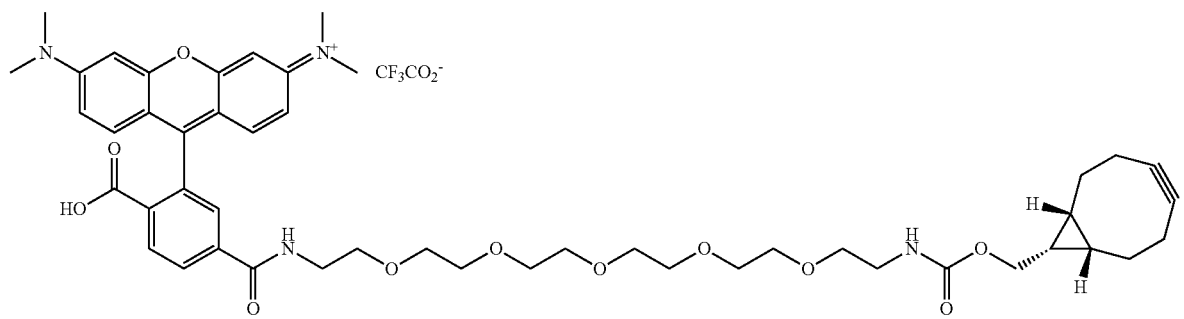

$C_{50}H_{61}F_3N_4O_{13}$ MW=983.03 g/mol

To a solution of TAMRA-peg$_6$-NH$_2$ 28 (TFA salt) (1 eq., 17 mg, 0.018 mmol) and TEA (5 eq., 0.013 mL, 0.092 mmol) in DMF (2 mL) was added (1R,8S,9s)-bicyclo[6.1.0] non-4-yn-9-ylmethyl (4-nitrophenyl) carbonate 29 (1.1 eq., 6.4 mg, 0.020 mmol). The reaction was stirred at room temperature for 3 hours. After evaporation under reduced pressure the crude material was purified by preparative HPLC to afford TAMRA-peg$_6$-BCN (TFA salt) 30 (12.2 mg, 0.012 mmol, 67%) as a pink solid.

$^1$H NMR (400 MHz, d$_6$-DMSO) δ 8.82 (t, J=5.5 Hz, 1H), 8.29 (d, J=8.2 Hz, 1H), 8.24 (dd, J=1.7 and 8.2 Hz, 1H), 7.88 (d, J=1.3 Hz, 1H), 7.12-7.00 (m, 5H), 6.97 (s, 2H), 4.01 (d, J=8.0 Hz, 2H), 3.63-3.33 (m, 22H), 3.26 (s, 12H), 3.09 (q, J=6.0 Hz, 2H), 2.30-2.01 (m, 6H), 1.64-1.40 (m, J=9.6 Hz, 2H), 1.33-1.13 (m, 1H), 0.83 (t, J=9.6 Hz, 2H). CO$_2$H signal is missing.

MS (ESI) m/z: 869.4 [M]$^+$.

sulfoCy5-BCN 32

1-(6-((2-((((1R,8S,9s)-Bicyclo[6.1.0]non-4-yn-9-ylmethoxy)carbonyl)amino)ethyl)amino)-6-oxo-hexyl)-3,3-dimethyl-2-((1E,3E,5E)-5-(1,3,3-trim-ethyl-5-sulfoindolin-2-ylidene)penta-1,3-dien-1-yl)-3H-indol-1-ium-5-sulfonate

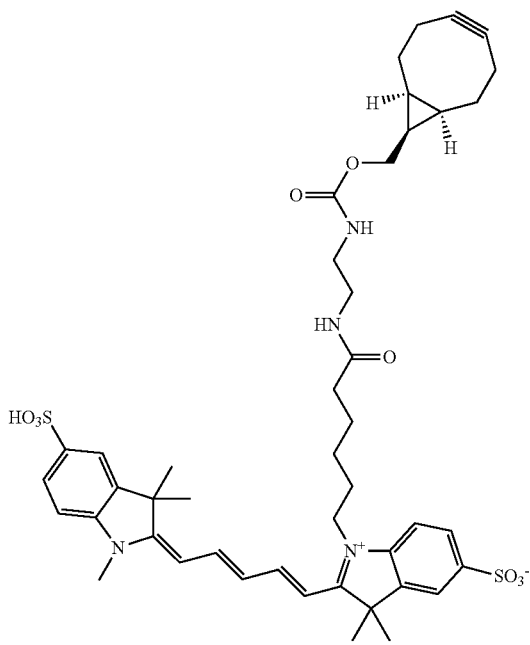

$C_{45}H_{56}N_4O_9S_2$ MW=861.08 g/mol

To a solution of sulfoCy5-NHS (1 eq., 8.60 mg, 0.0113 mmol) and DIEA (3 eq., 0.0056 mL, 0.0339 mmol) in DMF (2 mL) was added (1R,8S,9S)-bicyclo[6.1.0]non-4-yn-9-ylmethyl (2-aminoethyl)carbamate 31 (1.2 eq., 3.2 mg, 0.0135 mmol). The reaction was stirred 3 hours at room temperature. After concentration under reduced pressure the crude material was purified by flash chromatography (RP 5 g, H$_2$O to ACN, 30 minutes) to afford sulfoCy5-BCN 32 (7.70 mg, 0.0087 mmol, 77%) as a dark solid.

MS (ESI) m/z: 859.3 [M–H]$^-$.

Example 2: Microdroplet Surface Engineering by SPAAC (Strain-Promoted Azide-Alkyne Cycloaddition)

1. Materials and Methods

Microchip Fabrication:

A mold of SU-8 resist (MicroChem Corp.) was prepared on a silicon wafer (Siltronix) by UV exposure (MJB3 contact mask aligner; SUSS MicroTec) through a photolithography mask (Selba SA) and subsequent development (SU-8 developer; MicroChem Corp.). A curing agent was added to the PDMS base (Sylgard 184 silicone elastomer kit; Dow Corning Corporation) to a final concentration of 10% (w/w), mixed and poured over the mold to a depth of 5 mm. Following degassing for several minutes and cross-linking at 70° C. overnight, the PDMS was peeled off the mold and the input and output ports were punched with a 0.75 mm-diameter Harris Uni-Core biopsy punch (Electron Microscopy Sciences). The PDMS was activated by incubation for 3 minutes in an oxygen plasma (Diener Zepto) and was bound to a 50 mm×75 mm glass slide (Fisher Bioblock). Channels were made fluorophilic using a commercial surface coating agent (ABCR, AB111155). Height of the channel was 40 m and size of the nozzle was m with a channel width of 40 m. A second chip was used to reinject collected emulsion with a channel width of 50 m.

Microfluidic Station:

If not mentioned, all optical materials were purchased from Thorlab. The optical setup comprises an Eclipse Ti inverted microscope (Nikon) mounted on an optical table and includes 4 lasers (Strasus-375 nm 16 mW, Stradus-488 nm 50 mW, Stradus-532 nm 40 mW and Stradus-642 nm 110 mW). Emitted fluorescence was detected by photomultiplier tubes (PMT, Hamamatsu Photosensor H10722-20). The output signal from the PMTs was analyzed using a PCI-7852R Virtex-5 LX50R FPGA card (National Instruments Corporation) executing a program written in LabView 2013 (FPGA module, National Instruments Corporation). The optical table includes also a camera (Guppy F-080, Allied Vision Technologies).

Experimental Setup and Materials:

Flow rates were controlled by syringe pumps (Harvard Apparatus PHD 2000).

Flow rates of 500 μL/h for aqueous phase and of 500 μL/h for fluorinated oil phase (3M Novec 7500) were used to create droplets of 40-50 pL. Emulsion was collected in an Eppendorf filled with oil and closed with a PDMS plug to prevent coalescence due to contact with air. For control and surfactant dilution experiments 2.5% w/w of non-functionalized surfactant (008-FluoroSurfactant, RAN Biotechnologies) was used in oil phase. For SPAAC reaction the azide diblock surfactant Krytox-peg$_{12}$-azide 14 and the azide triblock surfactant diKrytox-peg$_{12}$-azide 23b were used at 2.5% w/w in oil phase. For the aqueous phase TAMRA-peg$_6$-BCN 30, sulfoCy5-BCN 32 and control fluorophores (TAMRA-6-CO$_2$H and Cy5-alkyne) were dissolved in Pluronic F-127 (0.01% in PBS 1×).

W/O emulsions were reinjected in the second chip and spaced by fluorous oil (3M Novec 7500). Flow rates of 200 μL/h for Novec 7500 and of 100 μL/h for emulsion sample were used.

ACMS used as fluorophore control was synthesized according to the literature (Woronoff, G., El Harrak, A., Mayot, E., Schicke, O., Miller, O. J., Soumillion, P., Griffiths, A. D., Ryckelynck M. Anal. Chem., 2011, 83, 2852-2857).

Confocal Microscopy:

W/O emulsions were analyzed using a Leica SPE confocal microscope (lasers used: 405 nm (ACMS), 561 nm (TAMRA derivatives) and 635 nm (sulfoCy5 derivatives), objective 20×, Leica 11506513).

Fluorescence Polarization.

W/O emulsions (15-30 µL) were put on Corning® 96 Well Half Area Microplates 3686. Fluorescence polarization analyses were performed in triplicates using Wallac® Victor 3 Multilabel Reader (Excitation/emission wavelengths 620/665 nm).

2. Results 2.1 SPAAC Reaction at the Inner Surface Droplet Using Krytox-Peg$_{12}$-Azide 14

Figure 6:
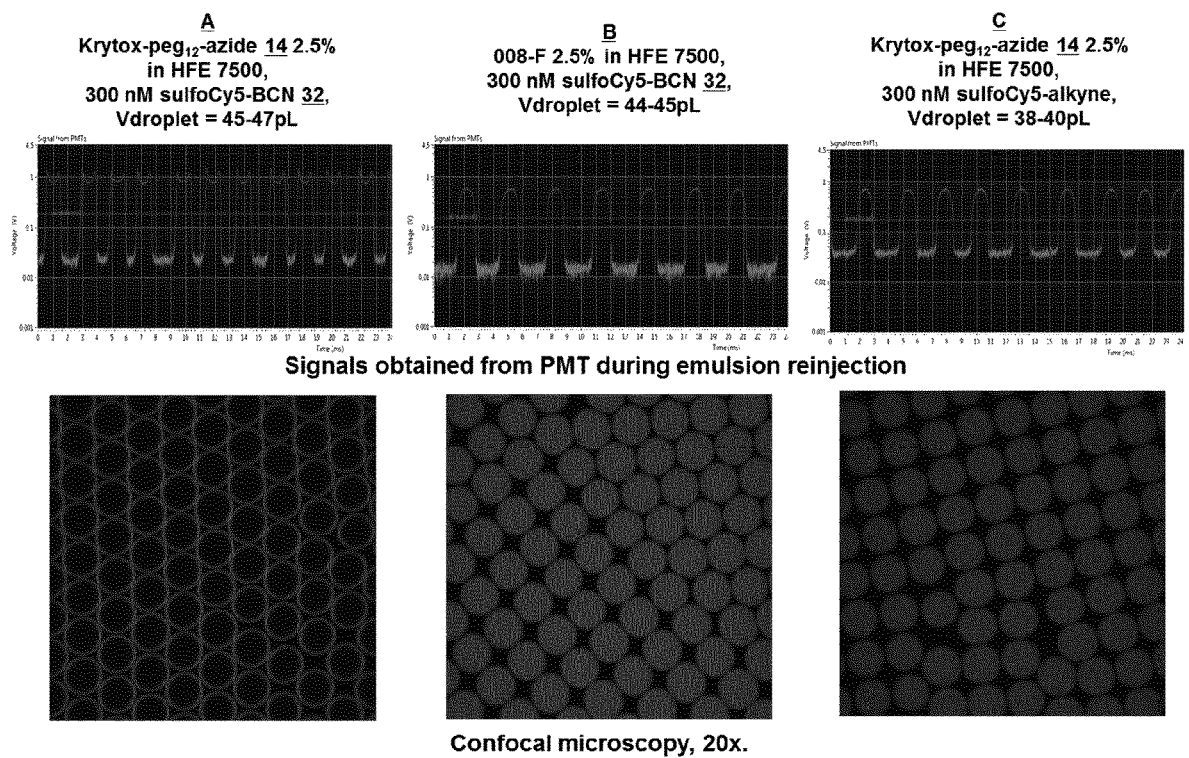
FIG. 6: SPAAC reaction at the inner surface using sulfoCy5 derivatives. A: Krytox-peg$_{12}$-azide 2.5%/sulfoCy5-BCN 300 nM, B: 008-F 2.5%/sulfoCy5-BCN 300 nM, C: Krytox-peg$_{12}$-azide 2.5%/sulfoCy5-alkyne 300 nM.
Figure 7:
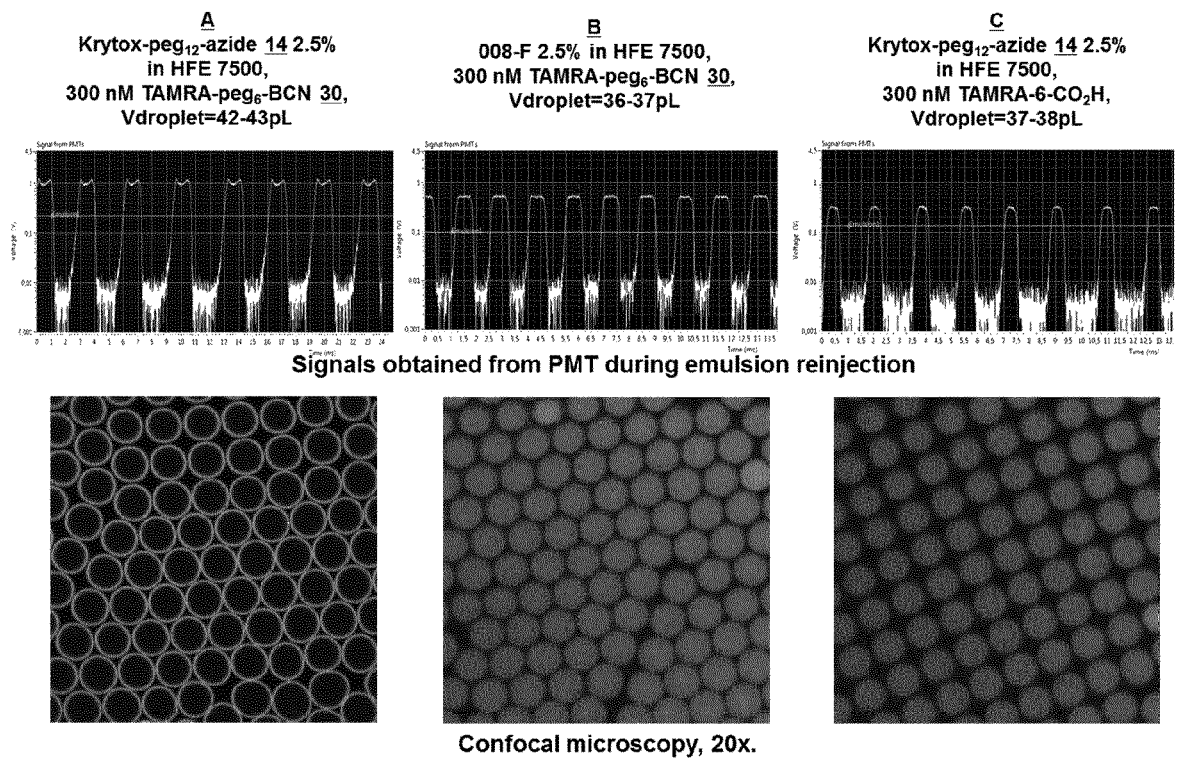
FIG. 7: SPAAC reaction at the inner surface using Krytox-peg$_{12}$-azide 14 and TAMRA-peg$_6$-BCN 30. A: Krytox-peg$_{12}$-azide 2.5%/TAMRA-peg$_6$-BCN 300 nM, B: 008-F 2.5%/TAMRA-peg$_6$-BCN 300 nM, C: Krytox-peg$_{12}$-azide 2.5%/TAMRA-6-$CO_2$H 300 nM.

The SPAAC reaction at the inner surface droplet was evaluated using Krytox-peg$_{12}$-azide 14 and the two fluorescent BCN derivatives (sulfoCy5-BCN 32 FIG. 6 and TAMRA peg$_6$-BCN 30 FIG. 7).

A first emulsion was prepared using azide diblock surfactant (Krytox-peg$_{12}$-azide 14) at 2.5% in Novec 7500 and sulfoCy5-BCN 32 at 300 nM in Pluronic 0.01% for aqueous phase (FIG. 6A). Signals obtained during emulsion reinjection showed that sulfoCy5 fluorescence was higher in front and in the back of the droplets indicated that the probe was located preferably at the inner surface of the water droplet. This result was confirmed by confocal microscopy which clearly demonstrated that fluorescence was concentrated at the inner surface of microdroplets as a result of the click reaction between azide fluorosurfactant 14 and the fluorescent strained cycloalkyne 32. To demonstrate the specificity of the reaction two negative controls were also performed. First non-functionalized commercial fluorosurfactant (008-F, Ran Biotechnologies) and fluorescent BCN derivative 32 were used to prepare the second emulsion (FIG. 6B). Finally microdroplets were generated with azide diblock surfactant 14 in the presence of sulfoCy5-alkyne fluorophore (FIG. 6C). This fluorophore control is not functionalized with a strained alkyne and the click reaction cannot occur without copper catalyst. In both cases signals from PMT and confocal microscopy showed that fluorescence was uniform across the droplets confirming that the click reaction did not occur under these conditions.

Similar results were obtained with the second fluorescent BCN derivative TAMRA-peg$_6$-BCN 30. SPAAC reaction occurred only when Krytox-peg$_{12}$-azide 14 was used in the presence of TAMRA-peg$_6$-BCN 30 as shown by the fluorescence concentration at the inner surface droplet (FIG. 7A). Using a non-functionalized surfactant (008-F, FIG. 7B) or a non-functionalized fluorophore (TAMRA-6-CO$_2$H, FIG. 7C) led to microdroplets with uniform fluorescence concentration confirming that the SPAAC reaction did not occur.

Microdroplet surface multifunctionalization was evaluated by co-encapsulating both fluorescent probes in microdroplets stabilized with diblock-azide 14 as fluorosurfactant. sulfoCy5-BCN 32 and TAMRA-peg$_6$-BCN 30 were diluted at 200 nM in Pluronic 0.01% (in PBS 1×) and Krytox-peg$_{12}$-azide 14 was used at 2.5% in Novec 7500 for the oil phase. Signals from PMT during emulsion reinjection and confocal microscopy showed that the fluorescence of both probes was preferably located at the microdroplets inner surface (FIG. 8).

2.2 Dilution of Diblock-Azide in Commercial Non-Functionalized Surfactant 008-F

To modulate the surface density of azide group diblock-azide 14 was diluted in commercial non-functionalized fluorosurfactant (008-F, Ran Biotechnologies). SPAAC reaction was evaluated at three concentrations of Krytox-peg$_{12}$-azide 14 (A: 20%, B: 10% and C: 5%) in commercial fluorosurfactant (008-F). Aqueous phase was charged with sulfoCy5-BCN 32 at 300 nM and a control fluorophore ACMS at 1 pM in Pluronic 0.01%. Characteristic PMT signals for surface located fluorescence were obtained for concentrations A (14 20%) and B (14 10%) but not for concentration C (14 5%). For all conditions confocal microscopy revealed that SPAAC reaction occurred after diblock-azide dilution in commercial non-functionalized surfactant (FIG. 9). In all conditions control fluorophore was distributed in the droplets confirmed by PMT signals during emulsion reinjection and confocal microscopy.

2.3 Surface Functionalization Characterization by Fluorescence Polarization

Figure 10:
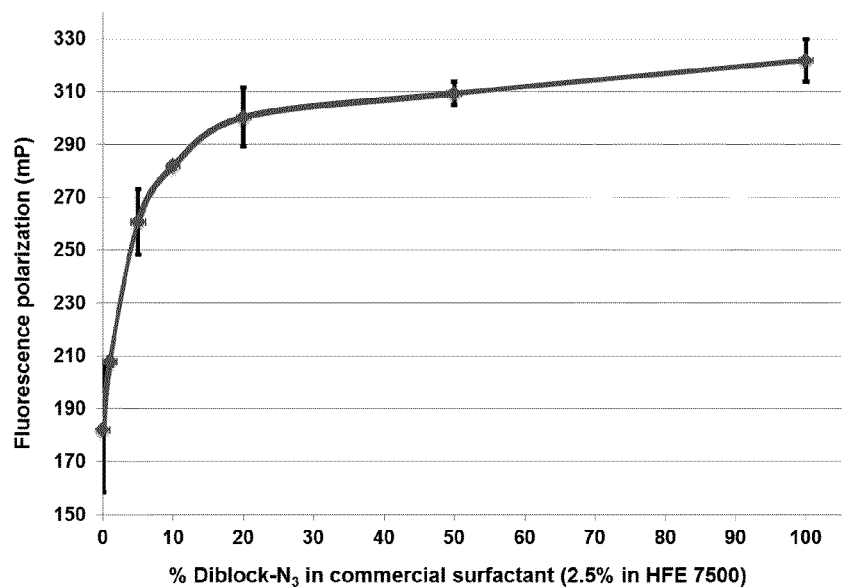
FIG. 10: Fluorescence polarization for a concentration range of diblock-azide 14 in commercial fluorosurfactant (008-).

To characterize the modulation of azide surface density at the interface, fluorescence polarization analyses were performed on collected emulsion after reaction with a fluorescent strained alkyne derivative. First experiments were performed using a concentration range of diblock-azide 14 in commercial non-functionalized surfactant maintaining the concentration of fluorescent sulfoCy5-BCN probe constant. Seven emulsions were prepared with increasing concentration of Krytox-peg$_{12}$-azide 14 (0, 1, 5, 10, 20, 50 and 100%) in non-functionalized surfactant (008-F) for the oil phase and sulfoCy5-BCN 32 at 250 nM in Pluronic 0.01% for the aqueous phase. Results are depicted in FIG. 10. Increasing concentration of diblock-azide 14 led to a polarization fluorescence increase indicating that higher concentration of fluorescent probe was captured at the inner surface droplet. In addition results showed that fluorescence polarization reached a plateau at around 20% of diblock-azide 14. From this concentration surface microdroplet does not seem to be saturated and the fluorescent strained alkyne probe can react completely with the azide moieties at the inner surface. A rough calculation considering a microdroplets volume of 44 pL and the concentration of 32 of 250 nM indicate that one droplet contains about 11 attomol of probe 32. Thus, microdroplets stabilized with a mixture of 14/008-F 20/80 contains 11 attomol of azide at their inner surface corresponding to a surface density of 1.8 nmol/m$^2$.

Figure 11:
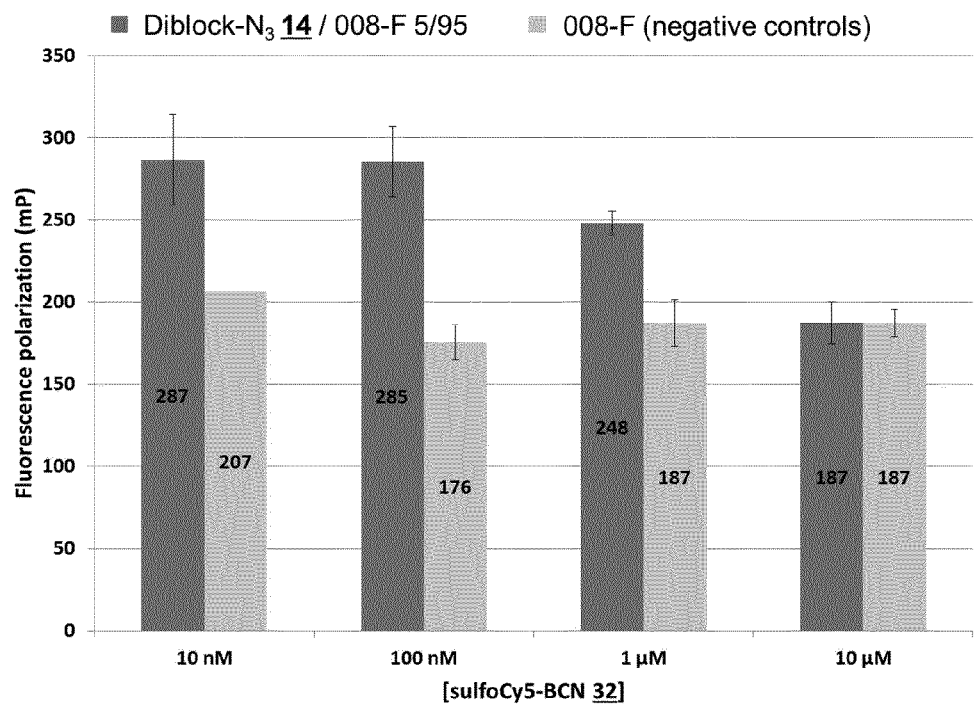
FIG. 11: Fluorescence polarization for a concentration range of sulfoCy5-BCN 32 probe.

A second fluorescence polarization experiment was performed with a concentration range of sulfoCy5-BCN probe 32. A 5% concentration of Krytox-peg$_{12}$-azide 14 in commercial surfactant (008-F) was maintained constant and the aqueous phase was charged with increasing concentration of sulfoCy5-BCN 32 (0.01, 0.1, 1 and 10 µM in Pluronic 0.01%). Results are depicted in FIG. 11. Negative controls using only non-functionalized surfactant 008-F as stabilizer were also performed and fluorescence polarization remained constant (186±15 mP) for each probe concentration. No modification of fluorescence polarization was observed between 10 and 100 nM indicating that microdroplets surface was not saturated at this concentration range. Increasing the fluorescent probe concentration to 1 µM led to a decrease of fluorescence polarization. Microdroplets interface thus appear to be saturated between 100 nM and 1 µM of free probe. This corresponds to a quantity of azide group per droplet between 4.4 to 44 attomol. Satisfactorily, this number 4.4-44 attomol of azide/droplet for 5% of azide surfactant is coherent with the result obtained above about 11 attomol of azide/droplet for 20% azide surfactant. Finally at 10 µM negative and positive controls exhibited the same fluorescence polarization values showing that the quantity of fluorophore probe located at the inner microdroplet surface is negligible compared to free fluorophore probe inside the droplet.

2.4 SPAAC Reaction Using Triblock-Azide (diKrytox-Peg$_{12}$-Azide 23b)

Figure 12:
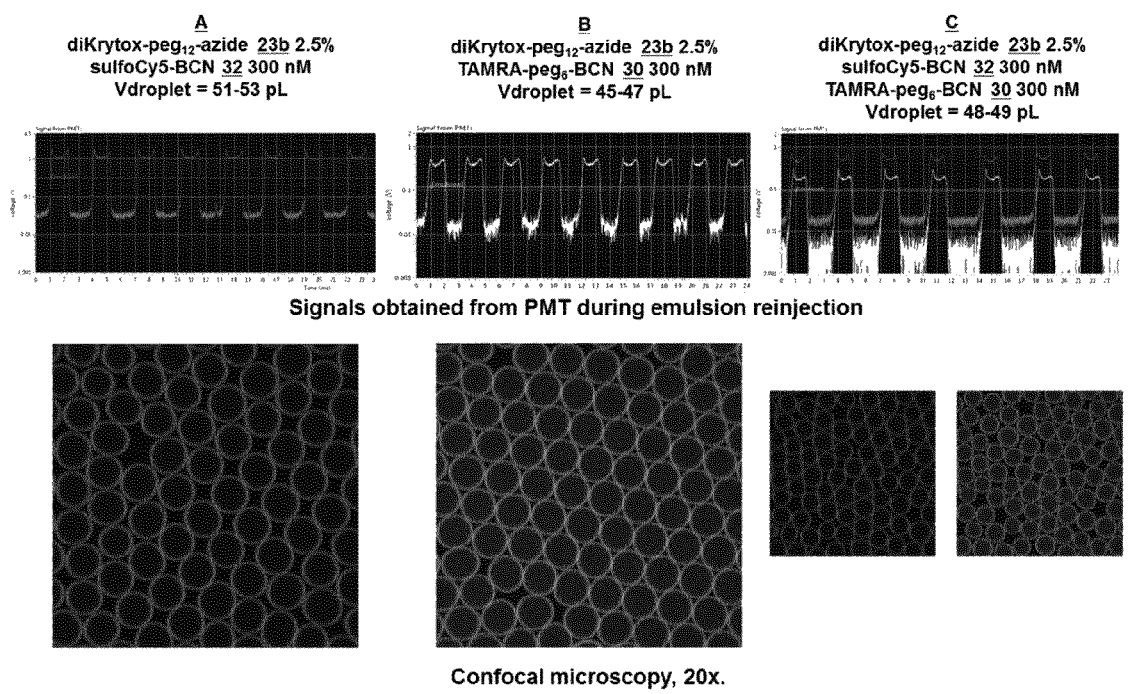
FIG. 12: SPAAC reaction using diKrytox-peg$_{12}$-azide 23b. Oil phase: A, B, C=diKrytox-peg$_{12}$-azide 23b 2.5% in Novec 7500. Aqueous phase: A=sulfoCy5-BCN 32 300 nM in Pluronic 0.01%, B=TAMRA-peg$_6$-BCN 30 300 nM in Pluronic 0.01%, C=sulfoCy5-BCN 32 200 nM+TAMRA-peg$_6$-BCN 30 200 nM in Pluronic 0.01%.

SPAAC reaction at the inner microdroplet surface was evaluated for triblock-azide fluorosurfactant according the same condition applied for diblock-azide 14. For this diKrytox-peg$_{12}$-azide was used at 2.5% in Novec 7500 to encapsulate the two fluorescent probes first separately then together. The two fluorescent probes were successfully react with triblock-azide surfactant 23b (sulfoCy5-BCN 32 FIG. 12A and TAMRA-peg$_6$-BCN 30 FIG. 12B) and surface microdroplet di-functionalization was also validated by co-encapsulating the two fluorescent probes (FIG. 12C).

Example 3

Materials and Methods

1. Emulsion Inversion

Figure 13:
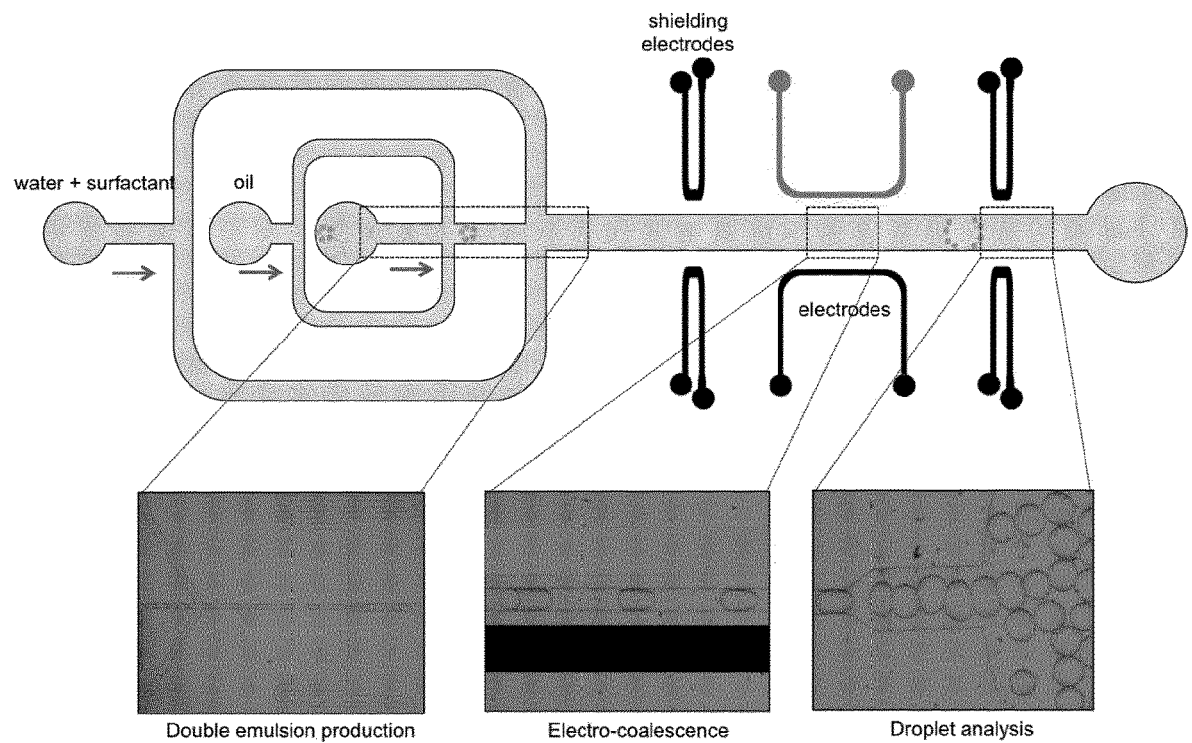
FIG. 13: Principle of phase inversion by electrical destabilisation.

To invert water-in-oil emulsion (w/o), double emulsion was used to create an oil capsule around the aqueous droplets and electric field was used to break this capsule. Basically, electro-coalescence of inner aqueous droplets with external aqueous phase lead to the destabilization of the oil capsule, generating an oil droplet in water (o/w), which outer surface corresponds to the inner surface of the water droplet it comes from. Flow focusing junction was used to generate w/o emulsion in a first microchip. Double emulsion generation using flow focusing and electrical destabilization were done on a second microchip (FIG. 13).

2. Microchip Fabrication

Microfluidic channels of second microchip were designed with Autocad (Autodesk 2014) to generate a double emulsion with electrodes to destabilize it. Shielding electrodes prevent the electric field to spread everywhere (FIG. 13). $L_1$ (3 mm) and $L_2$ (4 mm) in FIG. 2 has to be long enough respectively to prevent w/o emulsion from electro-coalescence in the reinjector and to perturb double emulsion generation due to electric field.

A mold of SU-8 resist (MicroChem Corp.) was fabricated on a silicon wafer (Siltronix) by UV exposure (MJB3 contact mask aligner; SUSS MicroTec) through a photolithography mask (Selba SA) and subsequent development (SU-8 developer; MicroChem Corp.). A curing agent was added to the PDMS base (Sylgard 184 silicone elastomer kit; Dow Corning Corporation) to a final concentration of 10% (w/w), mixed and poured over the mold to a depth of 5 mm. Following degassing for several minutes and cross-linking at 70° C. overnight, the PDMS was peeled off the mold and the input and output ports were punched with a 0.75 mm-diameter Harris Uni-Core biopsy punch (Electron Microscopy Sciences). The PDMS was activated by incubation for 3 min in an oxygen plasma (Diener Zepto) and was bound to a 50 mm×75 mm glass slide (Fisher Bioblock).

The first microchip was used to create water-in-oil emulsion (w/o) of 30 pL droplets. Channels were made fluorophilic using a commercial surface coating agent (ABCR, AB111155). High of the channel was 20 µm, and size of the nozzle was 25 µm with a channel width of 40 µm.

The second microchip was used to create double emulsion and destabilize it with electric field. Chip was used just after binding of PDMS to a glass slide using oxygen plasma so that PDMS remain hydrophilic.

High of the channels, reinjection channel width and double emulsion generation channel width were respectively 20 µm, 30 µm and 50 µm. Electrodes were made of salt solution (NaCl 180 g/L in deionized water, Sigma S3014) and were mold around the channel in a parallel channel with the same high. Sinusoidal voltage wave was applied to the electrodes at 400V and 10 kHz with a function generator (Agilent, 33220A) and a voltage amplifier (TREK Model 623D).

3. Microfluidic Station Setup

Figure 16:
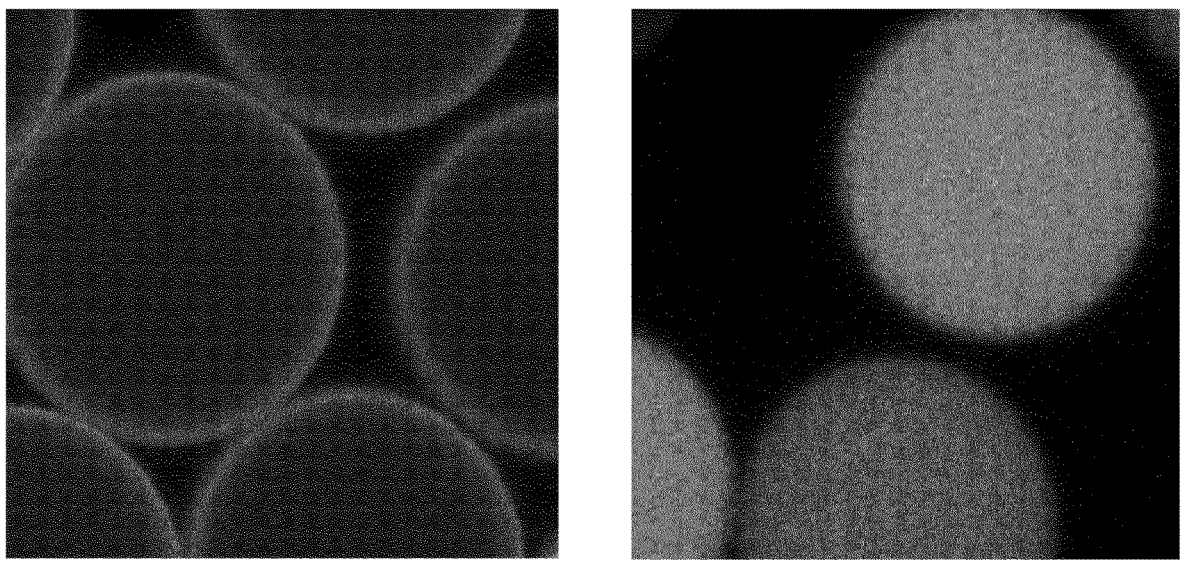
FIG. 16: Streptavidin fluorescence in oil-in-water droplets with biotinilated surfactant (left) and non-functionalized surfactant (right).

If not mentioned, all optical materials were purchased at Thorlab. The optical setup comprised an Eclipse Ti inverted microscope (Nikon) mounted on an optical table. A 640 nm laser (Obis, Coherent) and a 532 nm laser (MXL-III-532) beams were combined using a dichroic mirror "D3" and the resulting beam was combined with a 488 nm laser (Picarro) using a dichroic mirror "D2". The resulting beam was combined with a 375 nm laser (LAS, Newport-Spectraphysics) using a dichroic mirror "D1" and directed in the microscope objective using a mirror "M" and a dichroic mirror "D5" focused in the middle of the channel of the device at the detection point. The emitted fluorescence was collected by the microscope objective and separated from the laser beams by a first dichroic mirror "D5". Blue light, green light, orange light and red light was resolved from others with dichroic mirrors respectively "D6", "D7", "D8" and "D9". Emitted fluorescence was detected by photomultiplier tubes (PMT, Hamamatsu Photonics KK) equipped with band pass filters "F1" for blue light, "F2" for green light, "F3" for orange light, "F4" for red light and "F5" for infrared light. The output signal from the PMTs was analyzed using a PCI-7831R RIO Multifunction FPGA card (National Instruments Corporation) executing a program written in LabView 2013 (FPGA module, National Instruments Corporation). The data acquisition rate for the system was 166 kHz. The full process was monitored by redirecting part of the emitted light using a dichroic mirror "D0" towards a CCD camera (Guppy, Allied Vision Technologies) equipped with a long pass filter "F0" eliminated potentially damaging reflections of the lasers (FIG. 16).

4. Experimental Setup and Materials

Flow rates were controlled by syringe pumps (Harvard Apparatus PHD 2000). W/O emulsion was produced with an aqueous phase containing 500 nM Fluorescent Streptavidin (Lifetechnologies, S11223) in Phosphate Buffer Saline (PBS) (Sigma P-3619). Flow rates of 400 µL/h for aqueous phase and 400 µL/h for fluorinated oil phase (3M Novec 7500) were used to create droplets of 30 pL. Emulsion was collected in an eppendorf filled with oil and closed with a PDMS plug to prevent from coalescence due to contact with air. For control experiment, 5% w/w of non-functionalized surfactant (008-FluoroSurfactant, RAN Biotechnologies) was used in oil phase. For protein capture, a special surfactant (Krytox-PEG-Biotin) was functionalized with biotin to bind specifically to streptavidin and used at 5% w/w in oil phase.

Figure 14:
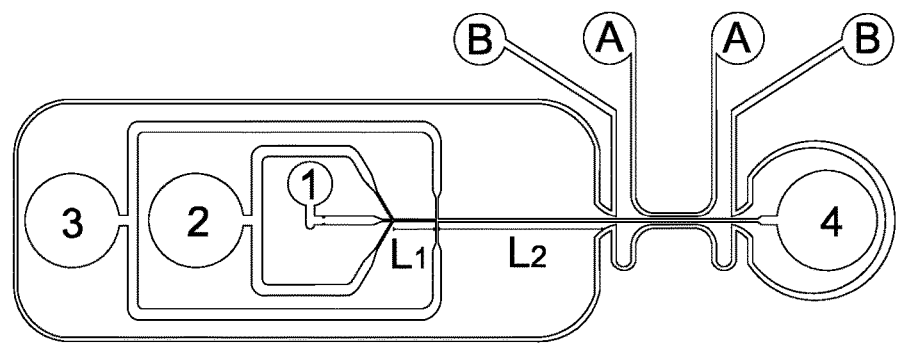
FIG. 14: Microchip for double emulsion generation and phase inversion. (1) W/O emulsion inlet. (2) Spacing oil inlet. (3) External aqueous phase inlet. (4) Outlet. (A) Electrode (300 Vpp, 10 kHz). (B) Electrode 0V.
Figure 15:
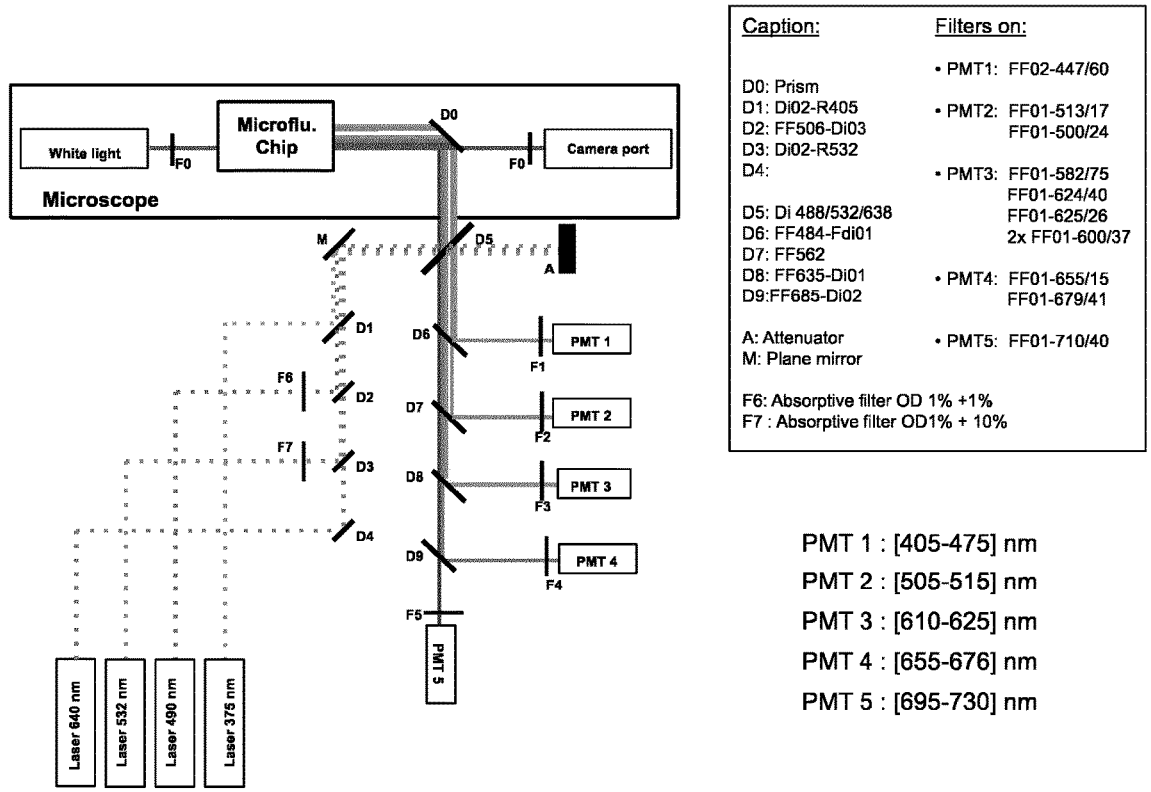
FIG. 15: Spectral setup for fluorescence.

W/O emulsion was reinjected (inlet 1, FIG. 14) in the second microchip in a packed manner (due to difference of density between oil and water). Water droplets (50 µL/h) were spaced by oil (50 µL/h) (inlet 2, FIG. 14). Double emulsion was created with an outer aqueous stream made of 2.5 µM Dye647 (Dyomics 647-00) and Triton X-100 1% w/w (Sigma X-100) in PBS at a flow rate of 200 µL/h (inlet 3, FIG. 14). An AC electric field was applied across the electrodes through connectors plugged in A (300 Vpp, 10 kHz) and B (0V) inlets in FIG. 14.

Results

1. Protein Capture

In control experiment with a non-functionalized surfactant, fluorescence from streptavidin was uniform across the droplets (FIG. 16). In the presence of biotinilated surfactant, streptavidin fluorescence was located at the inner surface of the droplets, indicated that streptavidin was located preferably at the inner surface of the water droplet (FIG. 16).

2. Phase Inversion

Figure 17:
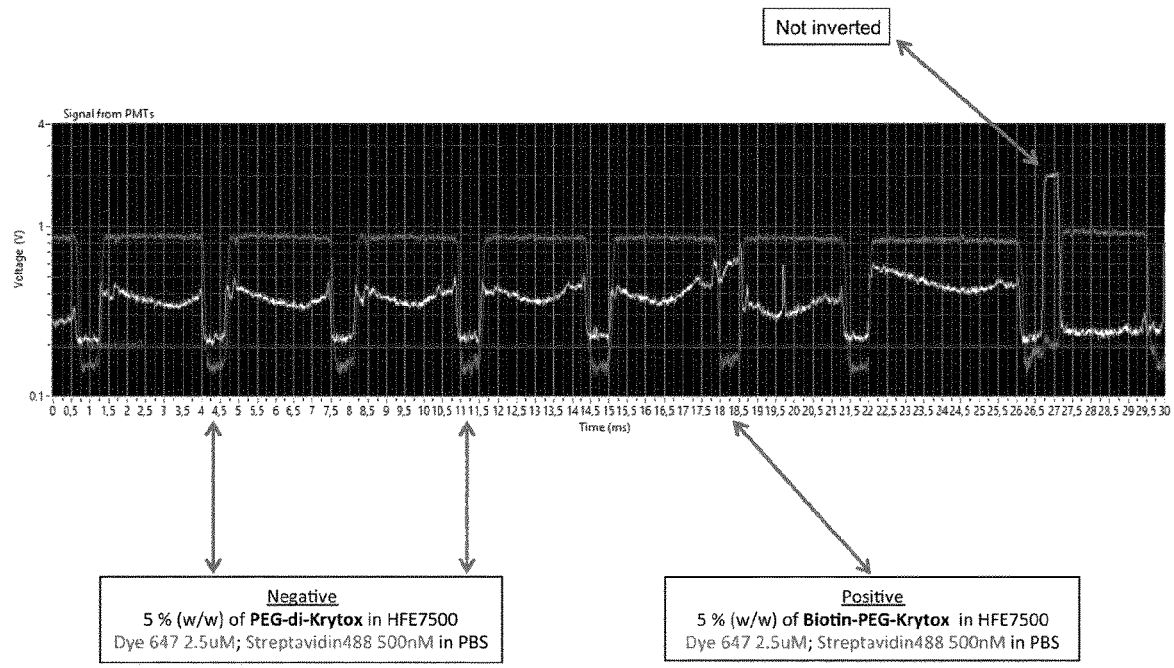
FIG. 17: Streptavidin fluorescence in oil-in-water droplets after phase inversion.

In control experiment with a non-functionalized surfactant, streptavidin fluorescence was higher between the oil droplets than on the oil droplets with a mean value of 0.2V on the droplets, indicating that streptavidin was not localized in the outer surface of the oil droplets (FIG. 17). In experiment with functionalized surfactant, streptavidin fluorescence was higher on the oil droplet (with a mean value of 0.55V) than between them (FIG. 17), indicating that streptavidin remained bound to biotinilated surfactant after phase inversion. For data analysis, not inverted droplets were eliminated by size as they were bigger than inverted ones.

Figure 18:
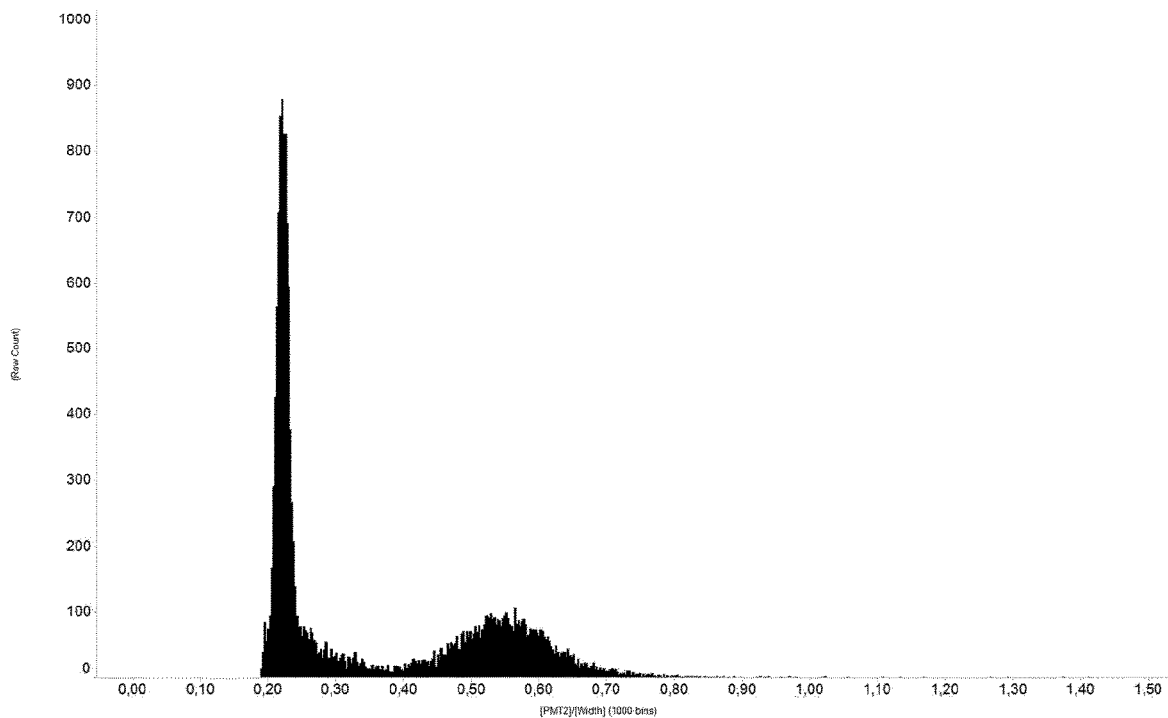
FIG. 18: Histogram plotting the mean value of the streptavidin fluorescence on the oil droplets.

The negative and positive populations can be distinguished on a histogram by plotting the mean value of the streptavidin fluorescence on the oil droplets (FIG. 18). The first population, centered around 0.22V, is the negative control while the population centered around 0.55V is the positive one. This method of inversion allows a quick and clear separation between positive and negative droplets.

Example 4

Materials and Methods
1. Emulsion Inversion

To invert water-in-oil emulsion (w/o), double emulsion was used to create an oil capsule around the aqueous droplets and voltage applied on the outer aqueous phase was used to break this oil capsule. Basically, electro-coalescence of inner aqueous droplets with external aqueous phase lead to the destabilization of the oil capsule, generating an oil droplet in water (o/w), which outer surface corresponds to the inner surface of the water droplet it comes from. Flow focusing junction was used to generate w/o emulsion in a first microchip. Double emulsion generation using flow focusing was done on a second microchip and electrical destabilization was done on an electroporation cuvette on which a voltage was applied.

2. Microchip Fabrication

Microfluidic channels of second microchip were designed with Autocad (Autodesk 2014) to generate a double emulsion and to incubate it on chip with a delay-line to destabilize it.

A mold of SU-8 resist (MicroChem Corp.) was fabricated on a silicon wafer (Siltronix) by UV exposure (MJB3 contact mask aligner; SUSS MicroTec) through a photolithography mask (Selba SA) and subsequent development (SU-8 developer; MicroChem Corp.). A curing agent was added to the PDMS base (Sylgard 184 silicone elastomer kit; Dow Corning Corporation) to a final concentration of 10% (w/w), mixed and poured over the mold to a depth of 5 mm. Following degassing for several minutes and cross-linking at 70° C. overnight, the PDMS was peeled off the mold and the input and output ports were punched with a 0.75 mm-diameter Harris Uni-Core biopsy punch (Electron Microscopy Sciences). The PDMS was activated by incubation for 3 min in an oxygen plasma (Diener Zepto) and was bound to a 50 mm×75 mm glass slide (Fisher Bioblock).

The first microchip was used to create water-in-oil emulsion (w/o) of 30 pL droplets. Channels were made fluorophilic using a commercial surface coating agent (ABCR, AB111155). High of the channel was 20 µm, and size of the nozzle was 25 m with a channel width of 40 µm.

The second microchip was used to create double emulsion and destabilize it. Chip was used just after binding of PDMS to a glass slide using oxygen plasma so that PDMS remain hydrophilic.

High of the channels, reinjection channel width and double emulsion generation channel width were respectively 40 µm, 30 µm and 50 µm.

3. Microfluidic Station Setup

See example 3

4. Experimental Setup and Materials

Flow rates were controlled by syringe pumps (Harvard Apparatus PHD 2000). W/O emulsion was produced with an aqueous phase consisted in PBS buffer (Sigma P-3619). Flow rates of 400 µL/h for aqueous phase and 400 µL/h for fluorinated oil phase (3M Novec 7500) were used to create droplets of 30 pL. Emulsion was collected in an eppendorf filled with oil and closed with a PDMS plug to prevent from coalescence due to contact with air. 5% w/w of non-functionalized surfactant (008-FluoroSurfactant, RAN Biotechnologies) was used in oil phase.

Figure 19:
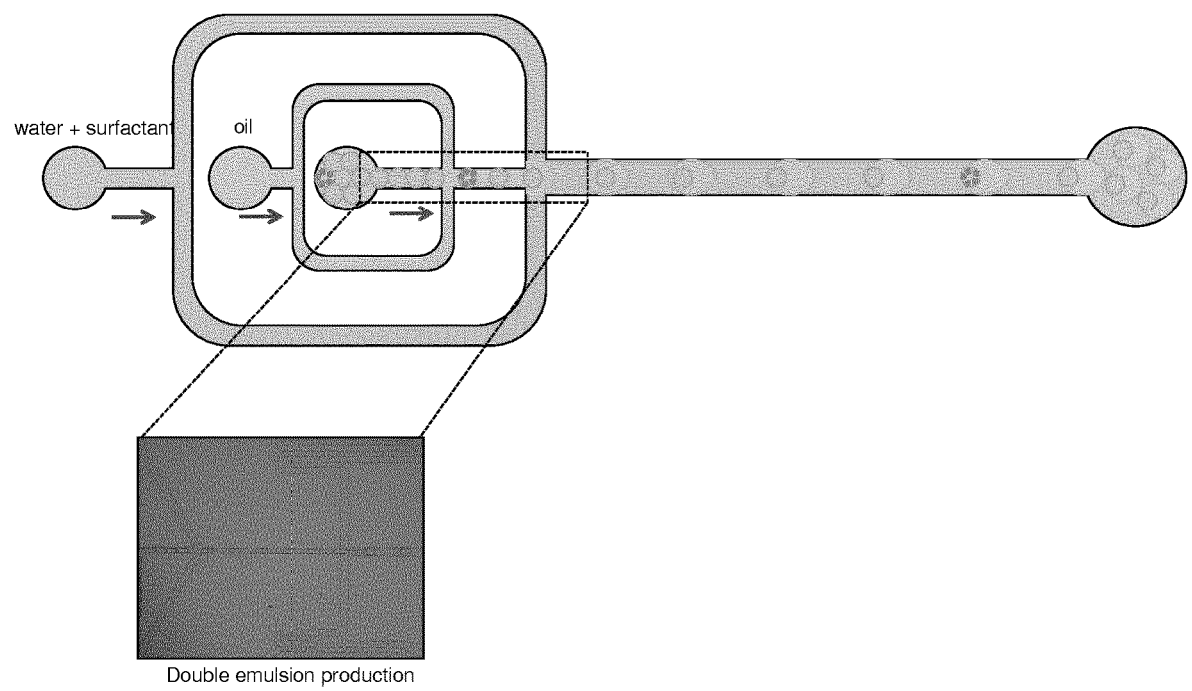
FIG. 19: Principle of phase inversion by electroporation.
Figure 20:
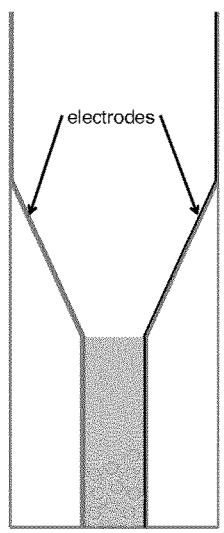
FIG. 20: Schematic representation of the electroporation cuvette.

W/O emulsion was re-injected in the second microchip in a packed manner (due to difference of density between oil and water). Water droplets (50 µL/h) were spaced by oil (50 µL/h) (FIG. 19). Double emulsion was created with an outer aqueous stream made of Triton X-100 1% w/w (Sigma X-100) in water at a flow rate of 200 µL/h. Double emulsion was transferred in a 1 mm electroporation cuvette (FIG. 20) on which a 10V, 25V, and 50V voltage was applied during 100 ms.

Results

Figure 21:
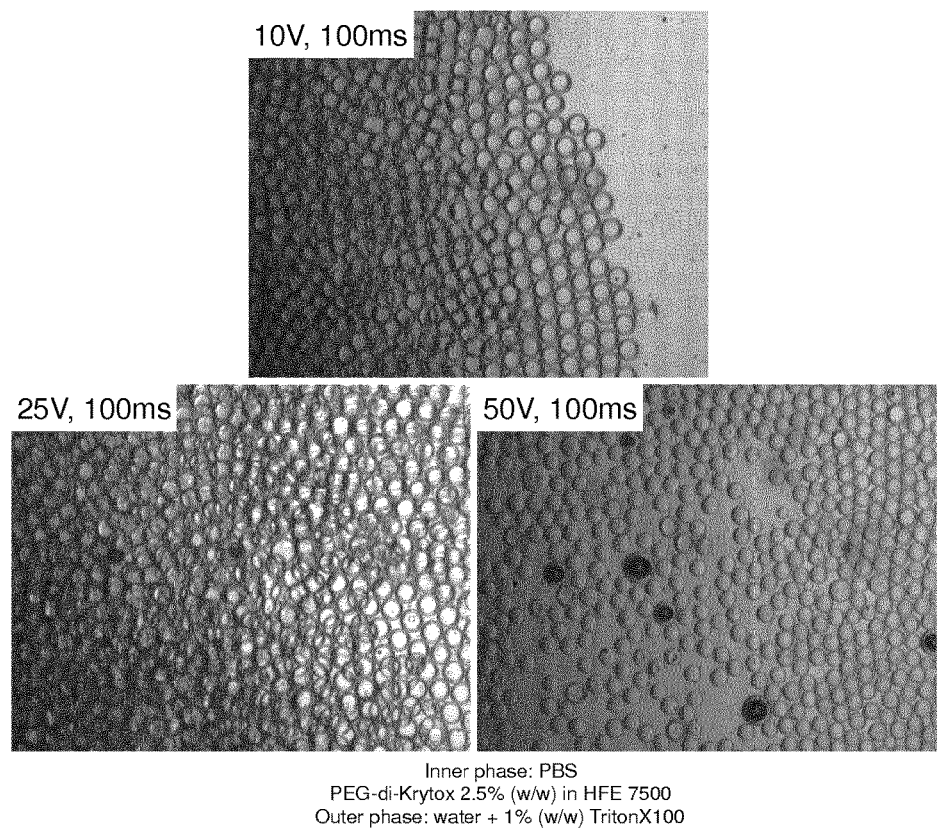
FIG. 21: Droplet population after applying 10, 25 or 50V during 100 ms.

For an applied voltage of less than 25V during 100 ms, the double emulsion remains intact, no inversion was observed. For an applied voltage of 50V during 100 ms, inversion was observed and a simple o/w emulsion was obtained (FIG. 21).

Example 5

Materials and Methods
1. Emulsion Inversion

To invert water-in-oil emulsion (w/o), double emulsion was used to create an oil capsule around the aqueous droplets and we observe that this capsule break by itself when incubated on chip at room temperature. Basically, coalescence of inner aqueous droplets with external aqueous phase lead to the destabilization of the oil capsule, generating an oil droplet in water (o/w), which outer surface corresponds to the inner surface of the water droplet it comes from. Flow focusing junction was used to generate w/o emulsion in a first microchip. Double emulsion generation using flow focusing and spontaneous destabilization were done on a second microchip.

2. Microchip Fabrication

Microfluidic channels of second microchip were designed with Autocad (Autodesk 2014) to generate a double emulsion and to incubate it on chip with a delay-line to destabilize it.

A mold of SU-8 resist (MicroChem Corp.) was fabricated on a silicon wafer (Siltronix) by UV exposure (MJB3 contact mask aligner; SUSS MicroTec) through a photolithography mask (Selba SA) and subsequent development (SU-8 developer; MicroChem Corp.). A curing agent was added to the PDMS base (Sylgard 184 silicone elastomer kit; Dow Corning Corporation) to a final concentration of 10% (w/w), mixed and poured over the mold to a depth of 5 mm. Following degassing for several minutes and cross-linking at 70° C. overnight, the PDMS was peeled off the mold and the input and output ports were punched with a 0.75 mm-diameter Harris Uni-Core biopsy punch (Electron Microscopy Sciences). The PDMS was activated by incubation for 3 min in an oxygen plasma (Diener Zepto) and was bound to a 50 mm×75 mm glass slide (Fisher Bioblock).

The first microchip was used to create water-in-oil emulsion (w/o) of 30 pL droplets. Channels were made fluorophilic using a commercial surface coating agent (ABCR, AB111155). High of the channel was 20 µm, and size of the nozzle was 25 µm with a channel width of 40 µm.

The second microchip was used to create double emulsion and destabilize it. Chip was used just after binding of PDMS to a glass slide using oxygen plasma so that PDMS remain hydrophilic.

High of the channels, reinjection channel width and double emulsion generation channel width were respectively 40 µm, 30 µm and 50 µm. A 10 minutes delay-line was used to observe spontaneous destabilization on chip.

3. Microfluidic Station Setup

See example 3.

4. Experimental Setup and Materials a. Phase Inversion

Flow rates were controlled by syringe pumps (Harvard Apparatus PHD 2000). W/O emulsion was produced with an aqueous phase consisted in PBS buffer (Sigma P-3619). Flow rates of 400 µL/h for aqueous phase and 400 µL/h for fluorinated oil phase (3M Novec 7500) were used to create droplets of 30 pL. Emulsion was collected in an eppendorf filled with oil and closed with a PDMS plug to prevent from coalescence due to contact with air. 5% w/w of non-functionalized surfactant (008-FluoroSurfactant, RAN Biotechnologies) was used in oil phase.

Figure 22:
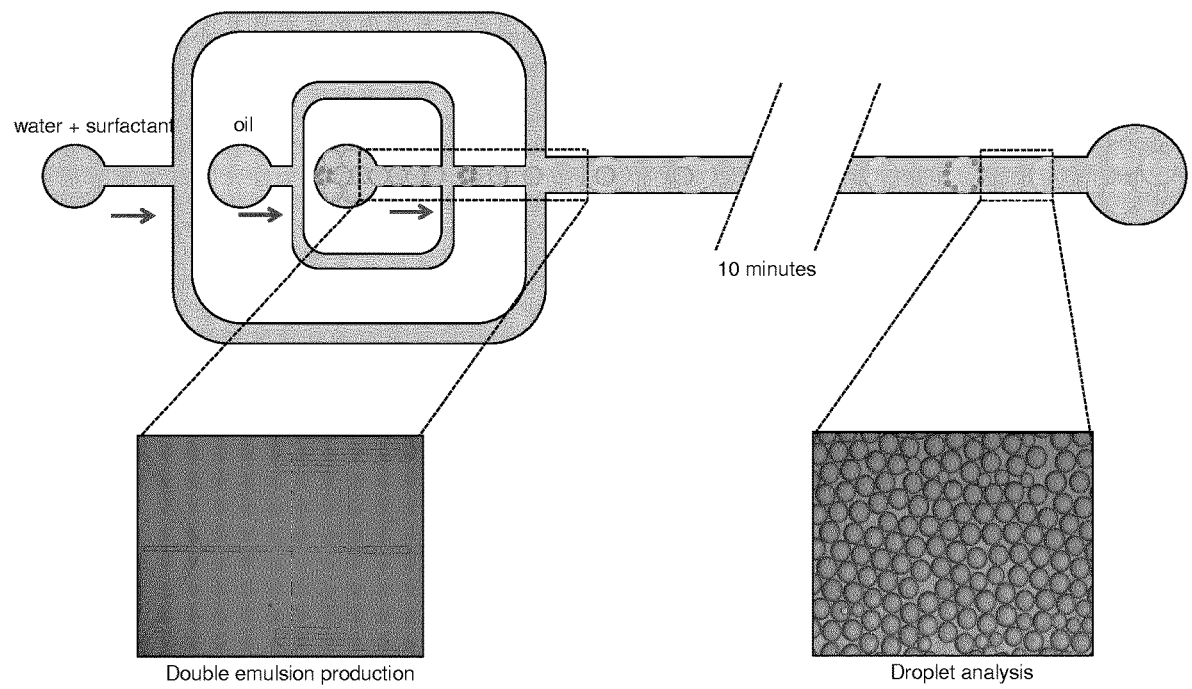
FIG. 22: Principle of phase inversion by spontaneous destabilisation.
Figure 23:
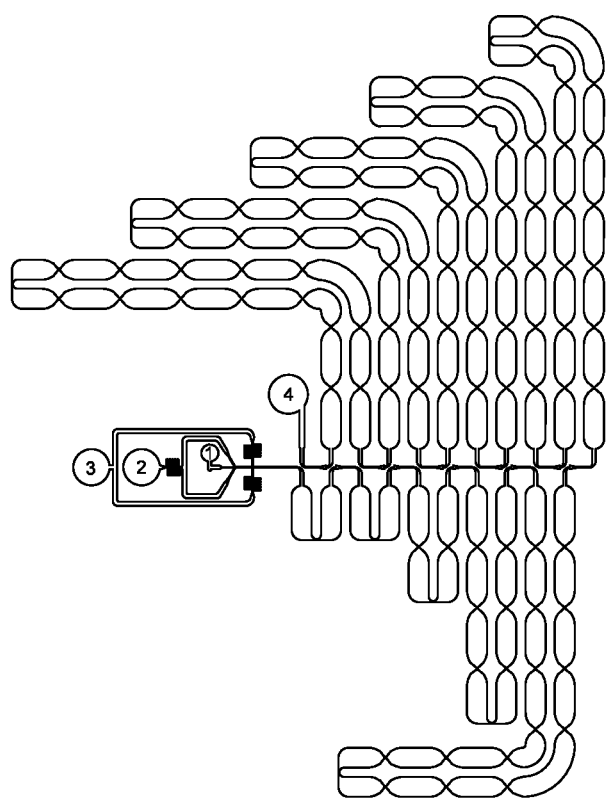
FIG. 23: Microchip for double emulsion generation and phase inversion by spontaneous destabilisation. (1) W/O emulsion inlet. (2) Spacing oil inlet. (3) External aqueous phase inlet. (4) Outlet.

W/O emulsion was re-injected (inlet 1, FIG. 23) in the second microchip in a packed manner (due to difference of density between oil and water). Water droplets (50 µL/h) were spaced by oil (50 µL/h) (inlet 2, FIG. 23). Double emulsion was created with an outer aqueous stream made of Triton X-100 1% w/w (Sigma X-100) in water at a flow rate of 200 µL/h (inlet 3, FIG. 23) and incubated on chip in a delay-line for 10 minutes (FIGS. 22 and 23).

b. Protein Capture

Goat anti-Mouse IgG FITC (Lifetechnologies, 62-6511) conjugated was bionitilated using One-step Antibody Biotinylation Kit (Miltenyi Biotec, 130-093-385). This antibody was premix at 100 nM with AlexaFluor532 Streptavidin (Lifetechnologies, S11223) at 1 uM in Phosphate Buffer Saline (Sigma P-3619) for 45 min at room temperature. W/O emulsion was produced with this premixed aqueous phase. Flow rates of 400 µL/h for aqueous phase and 400 µL/h for fluorinated oil phase (3M Novec 7500) were used to create droplets of 30 pL.

For control experiment, 2.5% w/w of non-functionalized surfactant (008-FluoroSurfactant, RAN Biotechnologies) was used in oil phase. For protein capture, a special surfactant (Krytox-PEG-Biotin) was functionalized with biotin to bind specifically to streptavidin and used at 2.5% w/w in oil phase.

Results

1. Phase Inversion

Figure 24:
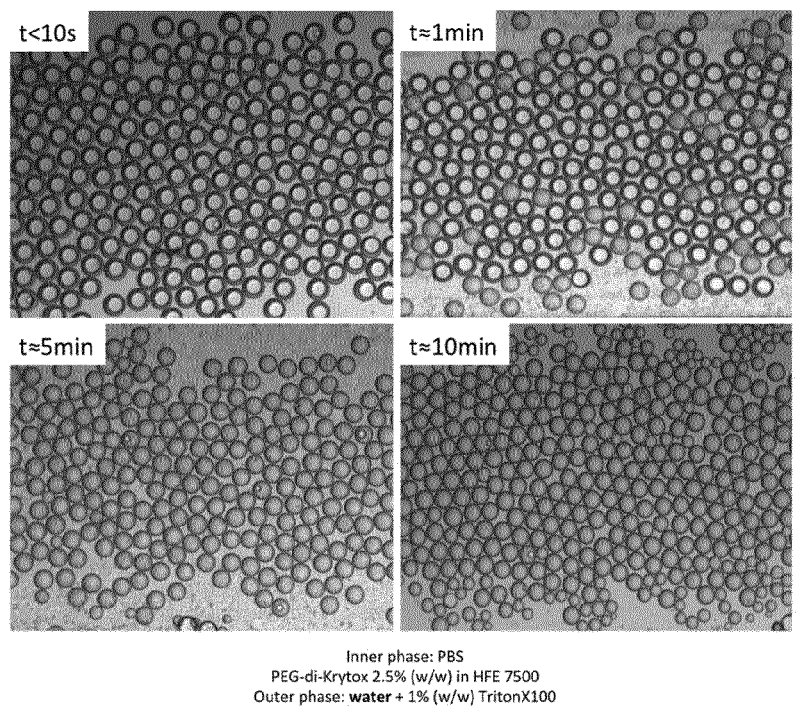
FIG. 24: Droplet population after incubation for 10 sec, 1, 5 or 10 min in the delay-line.

After double emulsion generation, phase inversion was observed to happen spontaneously (FIG. 24). In the presence of surfactant, the interfaces between inner aqueous phase, oil phase and outer aqueous phase happened to be instable. However, inversion was not done in the same time for all droplets due to surfactant migration time. For data analysis, not inverted droplets were eliminated by size as they were bigger than inverted ones.

2. Protein Capture

In the presence of non-functionalized surfactant, green fluorescence from IgG was located in the volume of the droplets in confocal images. On the contrary, in the presence of biotin-surfactant, green fluorescence from IgG is located on the surface of the droplets, indicating that the surfactant captured the IgG with the Streptavidin (FIG. 25).

After phase inversion in the presence of biotin-surfactant with spontaneous inversion, the green fluorescence from IgG remained at the surface of the droplets, indicating that the capture remained after phase inversion (FIG. 26).

Example 6: Synthesis of Multi-Azide Surfactants

Figure 27:
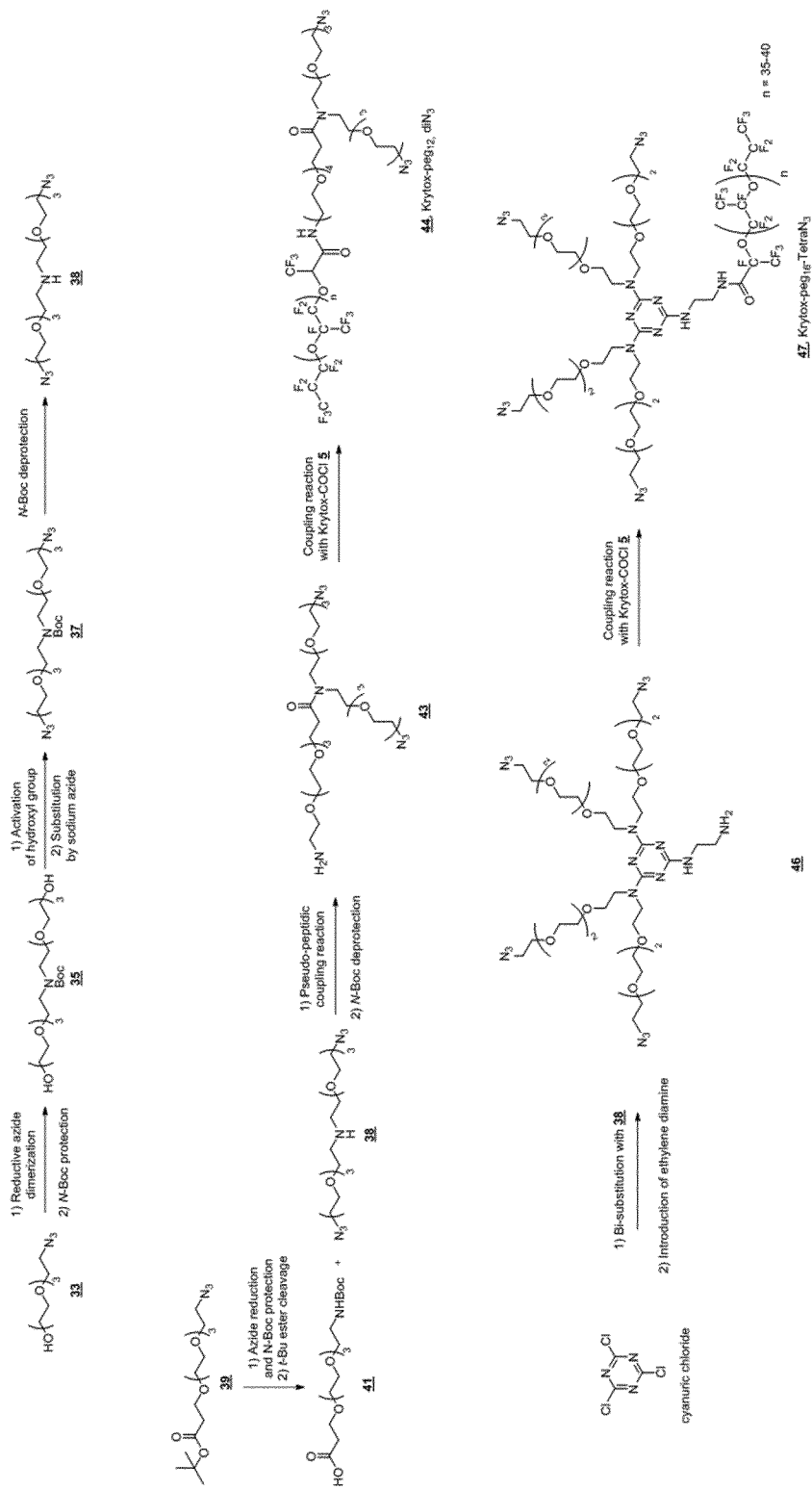
FIG. 27: Synthesis strategy of multi-azide fluorosurfactants.

Multi-azide surfactants bearing two or four azide moieties were synthesized according to the synthesis strategy reported in FIG. 27. The key intermediate of this synthesis consisted in the preparation of a dialkylamine peg linker containing two azide moieties 38 via reductive azide dimerization. For the di-azide surfactant 44, this intermediate was coupled to a third peg chain 41 comprising a carboxylic acid moiety and a N-boc protected group. After N-boc cleavage the hydroxylic head was coupled to Krytox-COCl 5 to afford the di-azide fluorosurfactant 44. The tetra-azide surfactant 47 was also obtained by substitution of cyanuric chloride with two dialkylamine 38, followed by the introduction of ethylene diamine and then the coupling reaction with Krytox-COCl 5.

2-(2-(2-(2-azidoethoxy)ethoxy)ethoxy)ethan-1-ol 33 (Sayyadi, N.; Connallyc, R. E.; Try, A. Chem. Commun., 2016, 52, 1154-1157) and tert-butyl 1-azido-3,6,9,12-tetraoxapentadecan-15-oate 39 (Garofalo, A.; Parat, A.; Bordeianu, C.; Ghobril, C.; Kueny-Stotz, M.; Walter, A.; Jouhannaud, J.; Begin-Colina, S.; Felder-Flesch, D. New J. Chem., 2014, 38, 5226-5239) were synthesized according to procedures described in the literature.

34,
3,6,9,15,18,21-hexaoxa-12-azatricosane-1,23-diol
$C_{16}H_{35}NO_8$ MW=369.46 g/mol

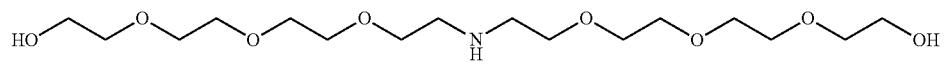 [SMILES: OCCOCCOCCOCCNCCOCCOCCOCCO]

To a solution of 33 (1 eq., 1.14 g, 5.20 mmol) in dioxane (10.4 mL) was added Pd/C (5%, 0.28 g, 0.26 mmol). The mixture was stirred under atmospheric pressure of $H_2$ for 12 hours. The reaction mixture was diluted in DCM (150 mL) and filtered through a pad of celite. The crude was used in the next step without purification.

35, tert-butyl bis(2-(2-(2-(2-hydroxyethoxy)ethoxy)ethoxy)ethyl)carbamate $C_{21}H_{43}NO_{10}$ MW=469.57 g/mol

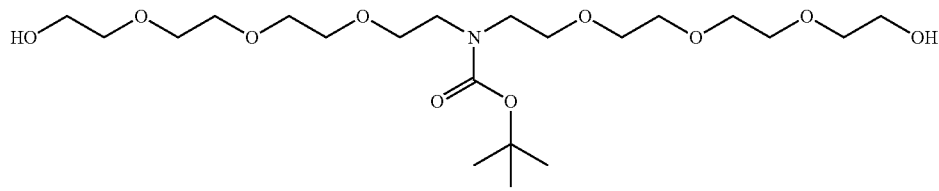 [SMILES: CC(C)(C)OC(=O)N(CCOCCOCCOCCO)CCOCCOCCOCCO]

To a solution of 34 (1 eq., 1.3 g, 3.52 mmol) and TEA (3 eq., 1.47 mL, 10.60 mmol) in DCM (23.2 mL) was added $Boc_2O$ (1.1 eq., 0.845 g, 3.87 mmol). The reaction mixture was stirred overnight at room temperature. 50 mL of an aqueous solution of $NaH_2PO_4$ (1M) were added and the mixture was extracted with DCM (3×50 mL). The crude was purified by silica gel flash chromatography (EtOAc 5 min then DCM to DCM/MeOH 9/1 in 30 minutes) to afford 35 (1.32 g, 2.82 mmol, 80%) as a yellowish oil.

$^1$H NMR ($CDCl_3$, 400 MHz) δ 3.73-3.71 (m, 4H), 3.66-3.56 (m, 24H), 3.45-3.42 (m, 4H), 1.44 (s, 9H). The OH signals are missing.

$^{13}$C NMR ($CDCl_3$, 100 MHz) δ 154.9, 79.0, 72.1, 70.1-69.8, 69.2-69.0, 60.9, 47.3-47.1, 27.9 (3C).

36, 12-(tert-butoxycarbonyl)-3,6,9,15,18,21-hexaoxa-12-azatricosane-1,23-diyl bis(4-methylbenzenesulfonate)

$C_{35}H_{55}NO_{14}S_2$ MW=777.94 g/mol

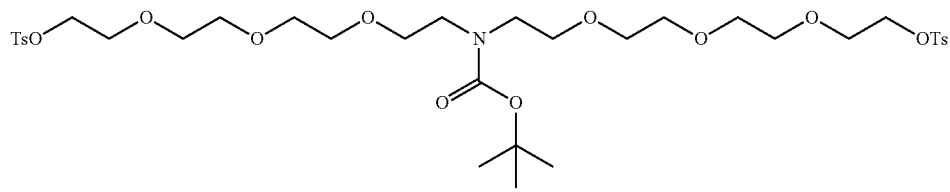 [SMILES: Cc1ccc(S(=O)(=O)OCCOCCOCCOCCN(CCOCCOCCOCCOS(=O)(=O)c2ccc(C)cc2)C(=O)OC(C)(C)C)cc1]

To a solution of dimer 35 (1 eq., 734 mg, 1.56 mmol) in DCM (14.5 mL) under argon were added TEA (10 eq., 2.19 mL, 15.60 mmol) and DMAP (0.2 eq., 38.2 mg, 0.31 mmol). The reaction mixture was stirred 5 minutes at 0° C. and tosyl chloride (4 eq., 1.19 g, 6.25 mmol) was added. The reaction mixture was stirred 2 hours at room temperature. 100 mL of DCM were added and the mixture was washed with an aqueous solution of $NaHCO_3$ (3×50 mL), dried over $MgSO_4$ and evaporated. The crude was purified by silica gel flash chromatography (Cyclohexane/EtOAc 1/1 to EtOAc in 30 minutes) to afford 36 (1.11 g, 1.42 mmol, 91%) as a yellowish oil.

$^1$H NMR ($CDCl_3$, 400 MHz) δ 7.66 (d, J=8.1 Hz, 4H), 7.22 (d, J=8.1 Hz, 4H), 4.02 (t, J=4.5 Hz, 4H), 3.55 (t, J=4.5 Hz, 4H), 3.48-3.40 (m, 20H), 3.34-3.24 (m, 4H), 2.31 (s, 6H), 1.32 (s, 9H).

$^{13}$C NMR (CDCl$_3$, 100 MHz) δ 155.1, 144.6, 132.8, 129.6 (4C), 127.7 (4C), 79.1, 70.4-70.0, 69.4, 69.1, 68.3, 47.4, 28.2 (3C), 21.3.

37, tert-butyl bis(2-(2-(2-(2-azidoethoxy)ethoxy)ethoxy)ethyl)carbamate

C$_{21}$H$_{41}$N$_7$O$_8$ MW=519.60 g/mol

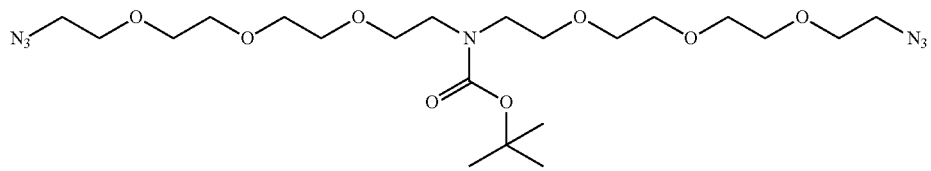 [SMILES: CC(C)(C)OC(=O)N(CCOCCOCCOCCN=[N+]=[N-])CCOCCOCCOCCN=[N+]=[N-]]

To a solution of 36 (1 eq., 973 mg, 1.25 mmol) in DMF (8 mL) was added NaN$_3$ (4 eq., 325 mg, 5.00 mmol) and the mixture was stirred overnight at 80° C. After concentration, 100 mL of DCM were added and the mixture was filtered through a pad of celite and washed with brine (3×50 mL). The organic layer was dried over MgSO$_4$ and evaporated to afford 37 (1.05 g, 2.02 mmol, 86%) as a yellow oil.

$^1$H NMR (CDCl$_3$, 400 MHz) δ 3.83-3.49 (m, 24H), 3.51-3.30 (m, 8H), 1.44 (s, 9H).

$^{13}$C NMR (CDCl$_3$, 100 MHz) δ 155.1, 79.1, 71.4-69.1, 50.5, 47.7, 47.4, 28.2.

38, bis(2-(2-(2-(2-azidoethoxy)ethoxy)ethoxy)ethyl)amine

C$_{16}$H$_{33}$N$_7$O$_6$ MW=419.48 g/mol

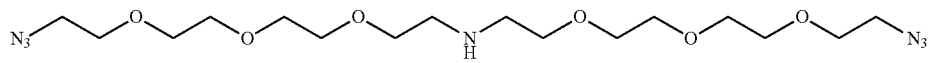 [SMILES: [N-]=[N+]=NCCOCCOCCOCCNCCOCCOCCOCCN=[N+]=[N-]]

To a solution of 37 (1 eq., 1 g, 1.92 mmol) in DCM (20 mL) under argon was added a 4 M HCl solution in dioxane (15 eq., 7.22 mL, 28.9 mmol). The reaction mixture was stirred overnight at room temperature. After concentration the crude was purified by silica gel flash chromatography (DCM to DCM/MeOH/NH$_4$OH 9/0.9/0.1 in 30 minutes) to afford 38 (605 mg, 1.44 mmol, 75%) as a yellow oil.

$^1$H NMR (CDCl$_3$, 400 MHz) δ 3.72-3.54 (m, 24H), 3.39 (t, J=4.9 Hz, 4H), 2.81 (t, J=5.3 Hz, 4H). The NH signal is missing.

$^{13}$C NMR (CDCl$_3$, 100 MHz) δ 70.1, 69.8, 65.8, 50.6, 46.8.

40, tert-butyl 2,2-dimethyl-4-oxo-3,8,11,14,17-pentaoxa-5-azaicosan-20-oate

C$_{20}$H$_{39}$NO$_8$ MW=421.53 g/mol

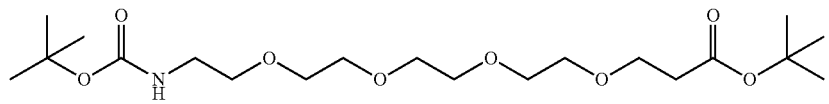 [SMILES: CC(C)(C)OC(=O)CCOCCOCCOCCOCCNC(=O)OC(C)(C)C]

To a solution of 39 (1 eq., 1.4 g, 4.03 mmol) in MeOH (70 mL) was added Pd/C (1%, 42 mg, 0.04 mmol). The reaction mixture was stirred under atmospheric pressure of $H_2$ for 12 hours at room temperature. After filtration through a pad of celite, the crude was dissolved in DCM (30 mL). $Et_3N$ (2 eq., 1.12 mL, 8.06 mmol) and $Boc_2O$ (1.2 eq., 1.06 g, 4.84 mmol) were added and the mixture was stirred at room temperature overnight. After concentration, 30 mL of water were added and the mixture was extracted with DCM (3×50 mL). The combined organic layers were dried over $MgSO_4$ and evaporated. The crude was purified by silica gel flash chromatography (Cyclohexane/EtOAc 1/1 to EtOAc in 30 minutes) to afford 40 (1.44 g, 3.42 mmol, 85%) as a yellow oil.

$^1$H NMR (CDCl$_3$, 400 MHz) δ 5.04 (bs, 1H), 3.70 (t, J=6.6 Hz, 2H), 3.66-3.56 (m, 12H), 3.53 (t, J=5.0 Hz, 2H), 3.35-3.25 (m, 2H), 2.50 (t, J=6.6 Hz, 2H), 1.44 (s, 18H).

41, 2,2-dimethyl-4-oxo-3,8,11,14,17-pentaoxa-5-azaicosan-20-oic acid $C_{16}H_{31}NO_8$ MW=365.42 g/mol

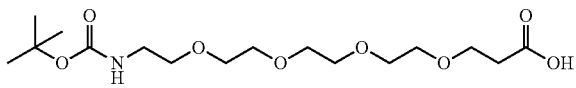 [SMILES: CC(C)(C)OC(=O)NCCOCCOCCOCCOCCC(=O)O]

To a solution of 40 (1 eq., 1.18 g, 2.80 mmol) in MeOH (10 mL) and $H_2O$ (10 mL) was added LiOH (5 eq., 0.342 g, 14.00 mmol). The reaction mixture was stirred overnight at room temperature. 50 mL of water were added and the mixture was extracted with DCM (3×50 mL). The aqueous phase was acidified with an aqueous solution of citric acid (0.1 M, 50 mL) and extracted with DCM (3×75 mL). The combined organic layers were dried over $MgSO_4$ and concentrated to afford 41 (964 mg, 2.64 mmol, 94%) as a colorless oil.

$^1$H NMR (CDCl$_3$, 400 MHz) δ 5.24 (bs, 1H), 3.78 (t, J=6.0 Hz, 2H), 3.73-3.54 (m, 14H), 3.40-3.19 (m, 2H), 2.61 (t, J=5.6 Hz, 2H), 1.44 (s, 9H). The $CO_2H$ signal is missing.

$^{13}$C NMR (CDCl$_3$, 100 MHz) δ 174.7, 156.1, 79.1, 70.4, 70.4-70.0, 66.4, 40.2, 34.7, 28.3.

42, tert-butyl (1-azido-12-(2-(2-(2-(2-azidoethoxy)ethoxy)ethyl)-13-oxo-3,6,9,16,19,22,25-heptaoxa-12-azaheptacosan-27-yl)carbamate $C_{32}H_{62}N_8O_{13}$ MW=766.89 g/mol

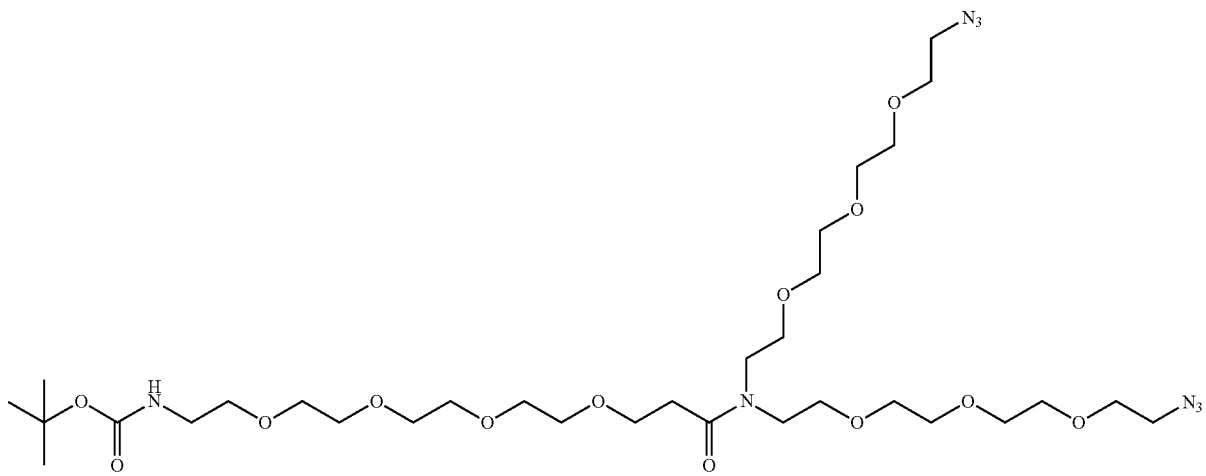 [SMILES: CC(C)(C)OC(=O)NCCOCCOCCOCCOCCC(=O)N(CCOCCOCCOCCN=[N+]=[N-])CCOCCOCCOCCN=[N+]=[N-]]

To a solution of 41 (1.05 eq., 0.875 g, 2.4 mmol) in DCM (10 mL) were added HOBt (1.1 eq., 0.339 g, 2.51 mmol) and EDC (1.1 eq., 0.39 g, 2.51 mmol). The mixture was stirred at room temperature for 15 minutes. A solution of 38 (1 eq., 1.04 g, 2.28 mmol) and TEA (3 eq., 0.951 mL, 6.84 mmol) in DCM (10 mL) was then added and the reaction mixture was stirred at room temperature overnight. After concentration, 100 mL of water were added and the mixture was extracted with DCM (3×100 mL). The combined organic layers were dried over MgSO$_4$ and evaporated. The crude was purified by silica gel flash chromatography (DCM to DCM/MeOH 9/1 in 35 minutes) to afford 42 (1.43 g, 1.87 mmol, 82%) as a yellowish oil.

$^1$H NMR (CDCl$_3$, 400 MHz) δ 5.04 (bs, 1H), 3.71 (t, J=6.9 Hz, 2H), 3.64-3.43 (m, 42H), 3.32 (t, J=4.7 Hz, 4H), 3.28-3.19 (m, 2H), 2.63 (t, J=6.9 Hz, 2H), 1.38 (s, 9H).

$^{13}$C NMR (CDCl$_3$, 100 MHz) δ 171.1, 155.8, 78.7, 70.6-70.0, 69.9, 69.3, 69.1, 67.3, 50.5, 48.6, 46.1, 40.2, 33.4, 28.3.

43, 1-amino-N,N-bis(2-(2-(2-(2-azidoethoxy)ethoxy)ethoxy)ethyl)-3,6,9,12-tetraoxapentadecan-15-amide C$_{27}$H$_{54}$N$_8$O$_{11}$ MW=666.77 g/mol

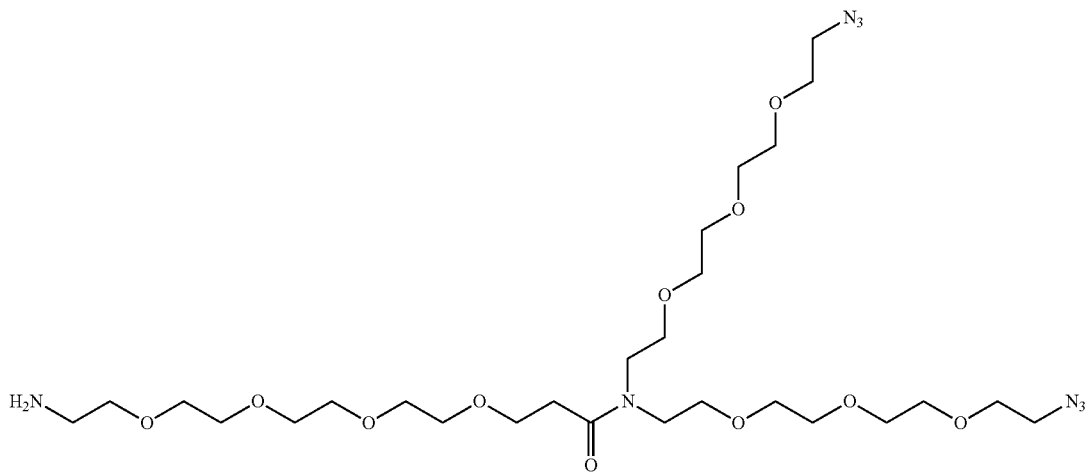 [SMILES: [N-]=[N+]=NCCOCCOCCOCCN(CCOCCOCCOCCN=[N+]=[N-])C(=O)CCOCCOCCOCCOCCN]

To a solution of 42 (1 eq., 1.10 g, 1.43 mmol) in DCM (20 mL) was added a 4 M HCl solution in dioxane (15 eq., 5.38 mL, 21.5 mmol). The reaction mixture was stirred at room temperature for 5 hours. After concentration, the crude was purified by silica gel flash chromatography (DCM to DCM/MeOH/NH$_4$OH 9/0.9/0.1 in 30 minutes) to afford 43 (853 mg, 1.28 mmol, 89%) as a yellowish oil.

$^1$H NMR (CDCl$_3$, 400 MHz) δ 3.73 (t, J=6.9 Hz, 2H), 3.68-3.49 (m, 40H), 3.47 (t, J=5.2 Hz, 2H), 3.35 (t, J=4.9 Hz, 4H), 2.89-2.76 (m, 2H), 2.66 (t, J=6.9 Hz, 2H). The NH$_2$ signal is missing.

$^{13}$C NMR (CDCl$_3$, 100 MHz) δ 171.1, 73.2, 70.5-70.0, 69.8, 69.2, 69.1, 67.3, 50.4, 48.6, 46.0, 41.6, 33.3.

44, Krytox-peg$_{12}$-diN$_3$

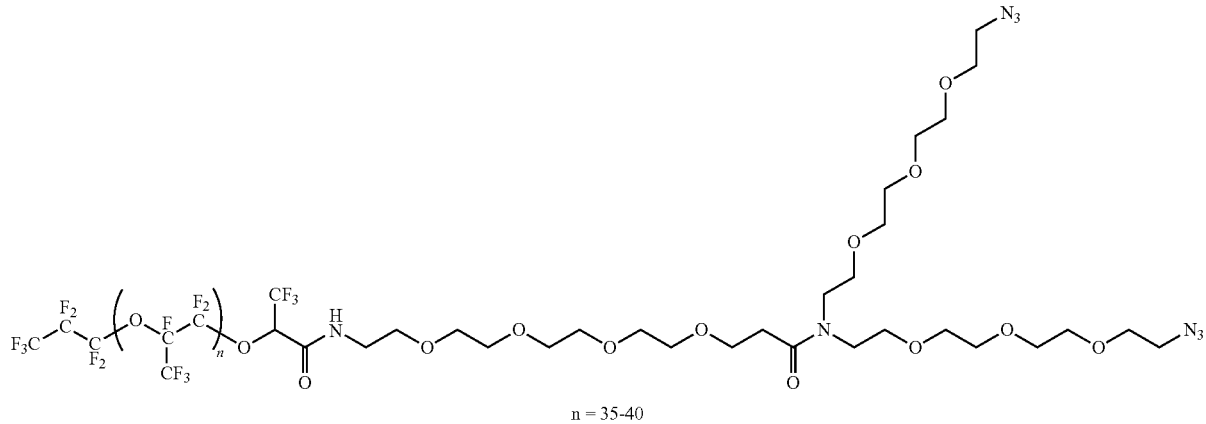

n = 35-40

Krytox157FSH-COCl 5 (1 eq., 3.00 g, 0.46 mmol) was dissolved in a mixture of Novec7100 (10 mL) and DCM (5 mL). A solution of 43 (1.2 eq., 0.37 g, 0.55 mmol) and TEA (3 eq., 0.14 g, 0.192 mL, 1.38 mmol) in DCM (5 mL) was added. The resulting mixture was stirred at room temperature for 48 hours. The crude obtained after evaporation of the solvent was dissolved in HFE7500 (75 mL). The resulting solution was transferred in a separatory funnel and washed with a mixture of DCM/$H_2O$ 1/1 (2×200 mL) then DCM (100 mL). The fluorinated phase was concentrated in vacuo affording Krytox-peg$_{12}$-diN$_3$ 44 as a sticky yellowish oil.

45, $N^2,N^2,N_4,N^4$-tetrakis(2-(2-(2-(2-azidoethoxy)ethoxy)ethoxy)ethyl)-6-chloro-1,3,5-triazine-2,4-diamine $C_{35}H_{64}ClN_{17}O_{12}$ MW=950.45 g/mol

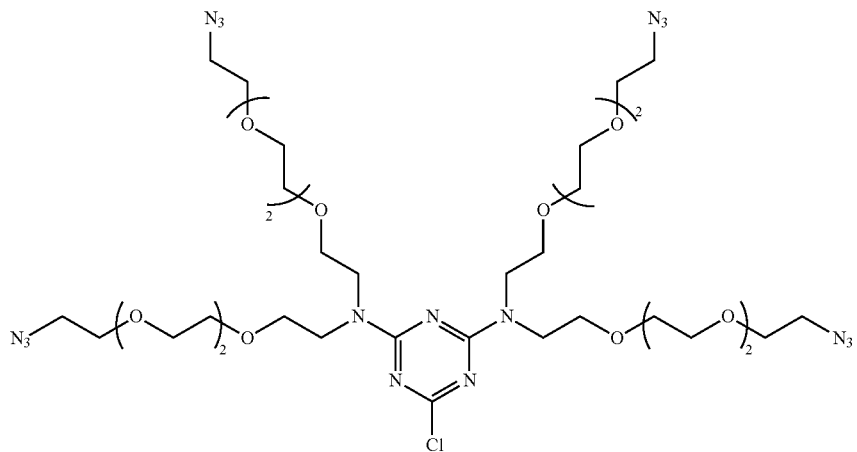

To a solution of 38 (2.1 eq., 700 mg, 1.54 mmol) in acetonitrile (5 mL) and DIEA (10 eq., 1.21 mL, 7.31 mmol) was added cyanuric chloride (1 eq., 134 mg, 0.73 mmol) and the reaction was stirred at room temperature for 5 hours. After concentration, 40 mL of a 10% HCl aqueous solution were added and the mixture was extracted with DCM. The combined organic layers were dried over MgSO$_4$ and concentrated. The crude was purified by silica gel flash chromatography (Cyclohexane to EtOAc in 35 minutes) to afford 45 (505 mg, 0.53 mmol, 73%) as a colorless oil.

$^1$H NMR (CDCl$_3$, 400 MHz) δ 3.78 (t, J=5.6 Hz, 4H), 3.74 (t, J=5.8 Hz, 4H), 3.70-3.54 (m, 48H), 3.39 (t, J=5.0 Hz, 8H).

$^{13}$C NMR (CDCl$_3$, 100 MHz) δ 168.7, 164.5, 70.5-70.4, 70.2, 69.9, 69.2, 68.7, 50.5, 48.1, 47.7, 27.2.

46, $N^2$-(2-aminoethyl)-$N^4$,$N^4$,$N^6$,$N^6$-tetrakis(2-(2-(2-(2-azidoethoxy)ethoxy)ethoxy)ethyl)-1,3,5-triazine-2,4,6-triamine $C_{37}H_{71}N_{19}O_{12}$ MW=974.10 g/mol

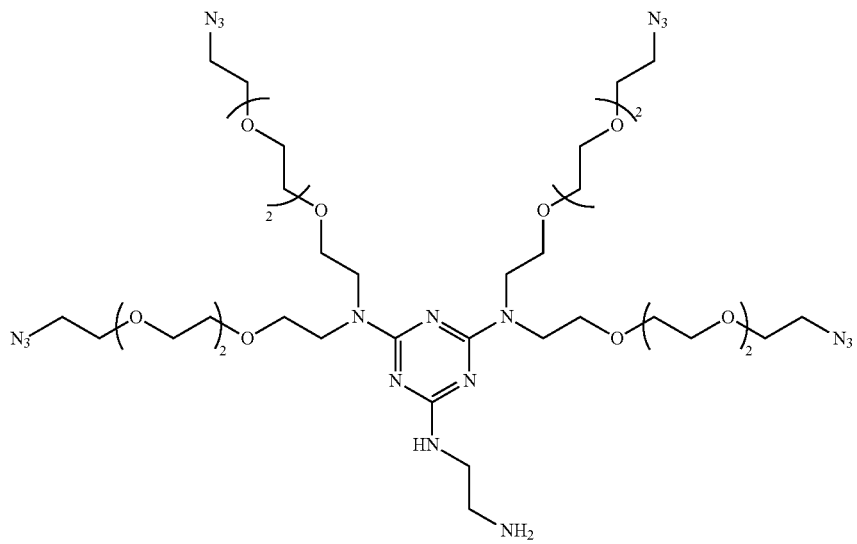

To a solution of 45 (1 eq., 500 mg, 0.53 mmol) and DIEA (20 eq., 1.74 mL, 10.50 mmol) in acetonitrile (5 mL) was added ethylene diamine (20 eq., 633 mg, 10.50 mmol). The reaction mixture was stirred at 80° C. for 15 hours. After concentration, the crude was directly purified by silica gel flash chromatography (DCM to DCM/MeOH/NH$_4$OH 9/0.9/0.1 in 35 minutes) to afford 46 (405 mg, 0.42 mmol, 79%) as a yellowish oil.

$^1$H NMR (CDCl$_3$, 400 MHz) δ 4.94 (bt, J=5.7 Hz, 1H), 3.66 (m, 56H), 3.45-3.31 (m, 10H), 2.87 (dd, J=9.4, 5.5 Hz, 2H). The NH$_2$ signal is missing.

$^{13}$C NMR (CDCl$_3$, 100 MHz) δ 166.3, 165.0, 70.6-70.3, 70.0, 69.5, 69.3, 50.6, 47.6, 47.5, 43.6, 42.1.

47, Krytox-peg$_{16}$-tetraN$_3$

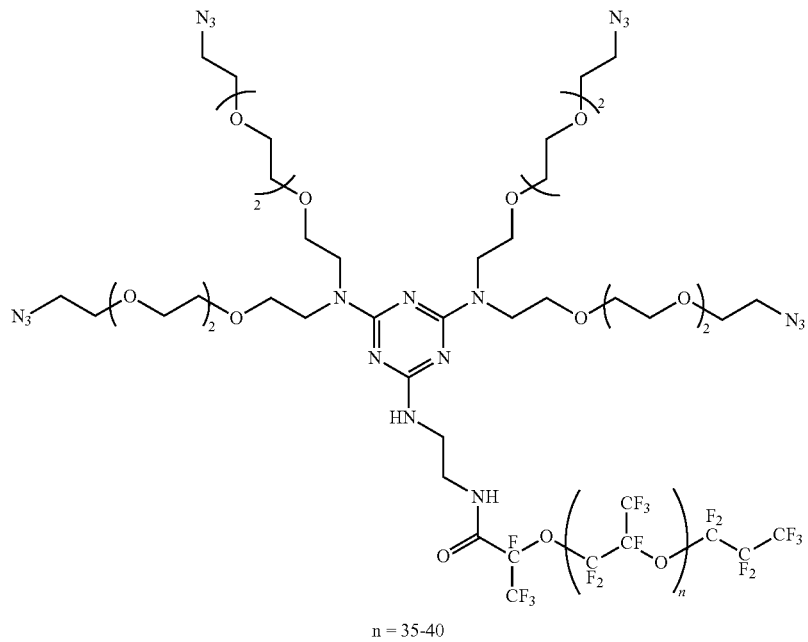

n = 35-40

Krytox157FSH-COCl 5 (1 eq., 1.75 g, 0.27 mmol) was dissolved in a mixture of Novec7100 (8 mL) and DCM (4 mL). A solution of 46 (1.5 eq., 392 mg, 0.40 mmol) and TEA (3 eq., 0.112 mL, 0.81 mmol) in DCM (4 mL) was added followed by the addition of HOBt (1 eq., 36.4 mg, 0.27 mmol). The resulting mixture was stirred at rt under argon for 48 hours. The crude obtained after evaporation of the solvent was dissolved in HFE7500 (75 mL). The resulting solution was transferred in a separatory funnel and washed with a mixture of DCM/H$_2$O 1/1 (2×200 mL) then DCM (100 mL). The fluorinated phase was concentrated in vacuo affording Krytox-peg$_{16}$-tetraN$_3$ 47 as a sticky yellowish oil.

Example 7: Synthesis of Conjugation Reagents

Figure 28:
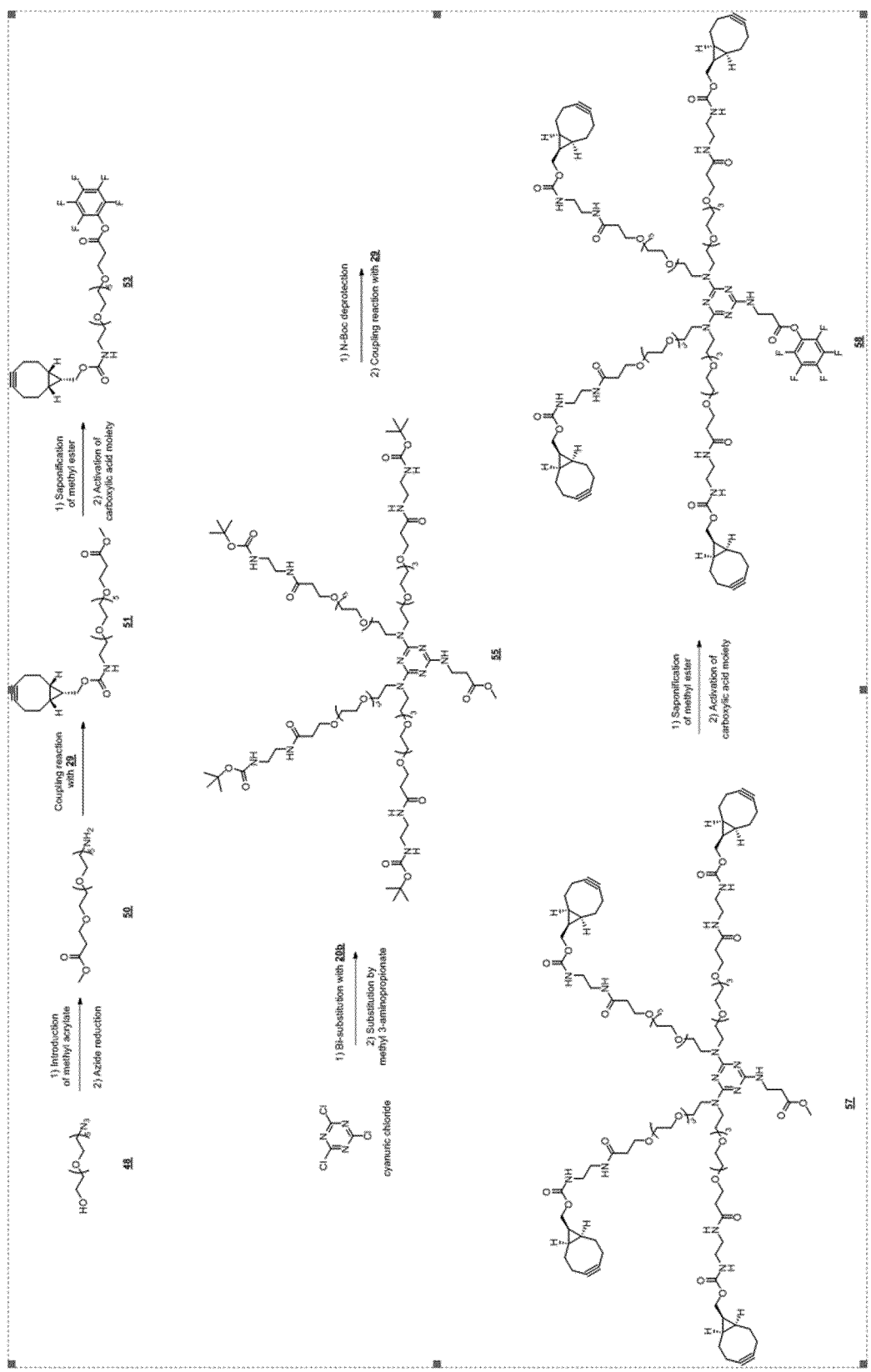
FIG. 28: Synthesis strategy of conjugation reagents.

Conjugation reagents were synthesized to ensure the introduction of a strained alkyne moiety on biomolecules (oligonucleotide and antibody) which will be graft at the microdroplet inner surface and permit the capture of corresponding targets. Conjugation reagents containing one or four BCN moieties and an activated ester able to react with amino-oligonucleotide and antibody through lysine residue have been synthesized according to the synthesis strategy described in FIG. 28. To prepare the mono-BCN conjugation reagent 53, a peg derivative 50 comprising an amine and a methyl ester was first synthesized and coupled to BCN in its nitro-phenyl carbonate activated form 29. After the saponification of the methyl ester, the carboxylic acid compound 51 was activated. A tetra-BCN conjugation reagent 58 has been also obtained by bi-substitution of cyanuric chloride with 22b followed by the introduction of a methyl propionate. Then the N-boc moieties have been deprotected and the resulting free amines have been coupled to the pre-activated BCN derivative 29. The saponification of the methyl ester 67 followed by the activation of the carboxylic acid moiety afforded the tetra-BCN conjugation reagent 58.

49, methyl 1-azido-3,6,9,12,15,18-hexaoxahenicosan-21-oate $C_{16}H_{31}N_3O_8$ MW=393.44 g/mol

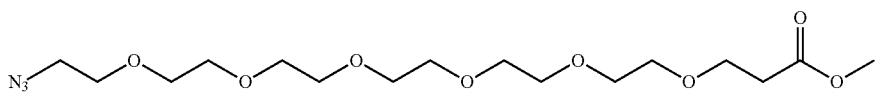

To a solution of 17-azido-3,6,9,12,15-pentaoxaheptadecan-1-ol 48 (1 eq., 3.40 g, 11.10 mmol)) and methyl acrylate (1.5 eq., 1.49 mL, 16.60 mmol) in THF (30 mL) at 0° C. was added tBuOK (0.1 eq., 135 mg, 1.20 mmol). The reaction was stirred at room temperature for 5 hours. After concentration, $H_2O$ (100 mL) was added and the mixture was extracted with EtOAc (150 mL). The combined organic layers were dried over $MgSO_4$ and evaporated. The crude was purified by silica gel flash chromatography (Cyclohexane to EtOAc in 35 minutes) to afford 49 (1.80 g, 4.58 mmol, 41%) as a yellowish oil.

$^1$H NMR (CDCl$_3$, 400 MHz) δ 3.74 (t, J=6.4 Hz, 2H), 3.70-3.58 (m, 25H), 3.38 (t, J=4.7 Hz, 2H), 2.59 (t, J=6.4 Hz, 2H).

50, methyl 1-amino-3,6,9,12,15,18-hexaoxahenicosan-21-oate $C_{16}H_{33}NO_8$ MW=393.44 g/mol

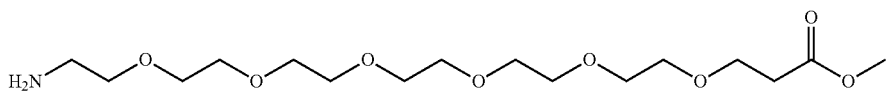 [SMILES: COC(=O)CCOCCOCCOCCOCCOCCOCCN]

To a solution of 49 (1 eq., 600 mg, 1.53 mmol) in MeOH (30 mL) was added Pd/C (1%, 16.2 mg, 0.0153 mmol) and the mixture was stirred at room temperature under atmospheric pressure of $H_2$ for 14 hours. The mixture was filtered through celite, concentrated and purified by silica gel flash chromatography (DCM to DCM/MeOH/$NH_4$OH 9/0.9/0.1 in 30 minutes) to afford 50 (455 mg, 1.24 mmol, 81%) as a yellowish oil.

$^1$H NMR (CDCl$_3$, 400 MHz) δ 3.75 (t, J=6.5 Hz, 2H), 3.68 (s, 3H), 3.67-3.59 (m, 20H), 3.50 (t, J=5.2 Hz, 2H), 2.85 (t, J=5.2 Hz, 2H), 2.60 (t, J=6.5 Hz, 2H). The $NH_2$ signal is missing.

$^{13}$C NMR (CDCl$_3$, 100 MHz) δ 171.8, 73.4, 70.5-70.2, 66.5, 51.5, 41.7, 34.8.

51, methyl 1-((1R,8S,9s)-bicyclo[6.1.0]non-4-yn-9-yl)-3-oxo-2,7,10,13,16,19,22-heptaoxa-4-azapentacosan-25-oate $C_{27}H_{45}NO_{10}$ MW=543.65 g/mol

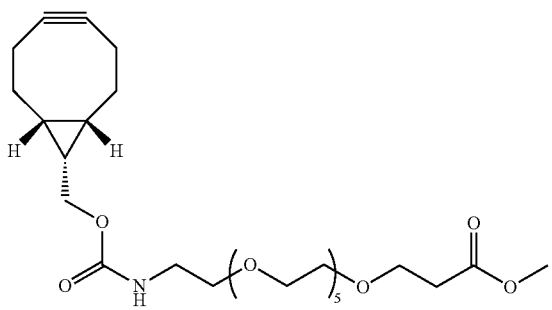

To a solution of (1R,8S,9s)-bicyclo[6.1.0]non-4-yn-9-yl-methyl (4-nitrophenyl) carbonate 29 (1 eq., 250 mg, 0.79 mmol) in 0.5 mL of DMF was added a solution of 50 (1.1 eq., 320 mg, 0.87 mmol) and TEA (3 eq., 0.331 mL, 2.38 mmol) in 0.5 mL of DMF. The reaction mixture was stirred overnight at room temperature. After evaporation, 20 mL of an aqueous solution of NaHPO$_4$ (1M) were added and the mixture was extracted with EtOAc (3×40 mL). The organic layer was dried over MgSO$_4$ and concentrated. The crude was purified by silica gel flash chromatography (DCM to DCM/MeOH 85/15 in 30 minutes) to afford 51 (360 mg, 0.66 mmol, 84%) as a colorless oil.

$^1$H NMR (CDCl$_3$, 400 MHz) δ 5.24 (bs, 1H), 4.15 (d, J=8.0 Hz, 2H), 3.75 (t, J=6.5 Hz, 2H), 3.69 (s, 3H), 3.67-3.60 (m, 20H), 3.55 (t, J=5.0 Hz, 2H), 3.42-3.30 (m, 2H), 2.60 (t, J=6.5 Hz, 2H), 2.35-2.15 (m, 6H), 1.62-1.51 (m, 2H), 1.44-1.29 (m, 1H), 0.94 (t, J=9.8 Hz, 2H).

$^{13}$C NMR (CDCl$_3$, 100 MHz) δ 171.6, 156.6, 98.5, 70.4, –70.2, 70.1, 69.9, 66.4, 62.2, 51.4, 40.6, 34.6, 28.9, 21.2, 19.9, 17.7.

52, 1-((1R,8S,9s)-bicyclo[6.1.0]non-4-yn-9-yl)-3-oxo-2,7,10,13,16,19,22-heptaoxa-4-azapentacosan-25-oic acid $C_{26}H_{43}NO_{10}$ MW=529.63 g/mol

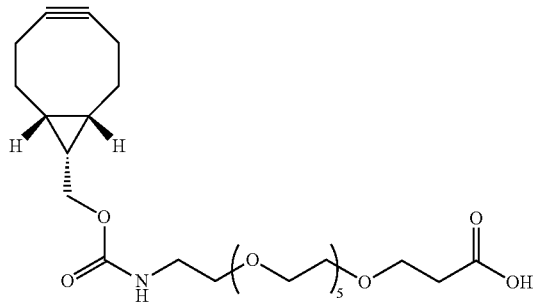

To a solution of 51 (1 eq., 915 mg, 1.68 mmol) in 10 mL of MeOH/H$_2$O 1/1 was added LiOH (5 eq., 201 mg, 8.42 mmol). The reaction mixture was stirred at room temperature overnight. After MeOH evaporation, the aqueous layer was acidified by addition of 50 mL of an aqueous solution of NaH$_2$PO$_4$ (1M) and extracted with DCM (4×50 mL). The combined organic layer was dried over MgSO$_4$ and concentrated to afford 52 (815 mg, 1.54 mmol, 91%) as a yellowish oil.

$^1$H NMR (CDCl$_3$, 400 MHz) δ 5.35 (bs, 1H), 4.14 (d, J=8.0 Hz, 2H), 3.77 (t, J=6.0 Hz, 2H), 3.71-3.58 (m, 20H), 3.56 (t, J=5.0 Hz, 2H), 3.41-3.30 (m, 2H), 2.60 (t, J=6.0 Hz, 2H), 2.38-2.13 (m, 6H), 1.66-1.50 (m, 2H), 1.41-1.28 (m, 1H), 0.94 (t, J=9.7 Hz, 2H). The CO$_2$H signal is missing.

$^{13}$C NMR (CDCl$_3$, 100 MHz) δ 173.8, 156.9, 98.8, 70.2, 70.7-70.2, 66.6, 62.7, 40.8, 35.0, 29.1, 21.4, 20.1, 17.8.

53, perfluorophenyl 1-((1R,8S,9s)-bicyclo[6.1.0]non-4-yn-9-yl)-3-oxo-2,7,10,13,16,19,22-heptaoxa-4-azapentacosan-25-oate $C_{32}H_{42}F_5NO_{10}$ MW=695.68 g/mol

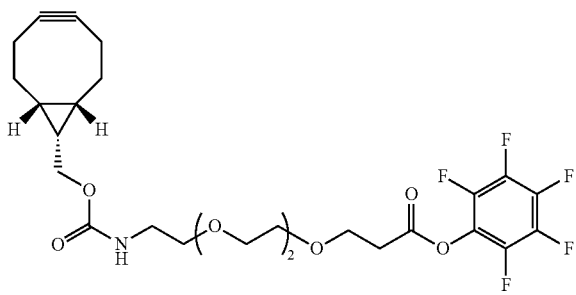

To a solution of 52 (1 eq., 800 mg, 1.51 mmol) and pentafluorophenol (1.2 eq., 333 mg, 1.81 mmol) in DCM (20 mL) was added DCC (1.1 eq., 342 mg, 1.66 mmol). The reaction mixture was stirred at room temperature for 4 hours. After concentration, the crude was dissolved in DCM (75 mL), filtered through a pad of celite and washed with an aqueous solution of NaHCO$_3$ (2×75 mL). The organic layer was dried over MgSO$_4$ and purified by silica gel flash chromatography (Cyclohexane/EtOAc 1/1 to EtOAc in 30 minutes then EtOAc/MeOH 95/5 in 10 minutes) to afford 53 (875 mg, 1.26 mmol, 83%) was obtained as a yellowish oil.

¹H NMR (CDCl₃, 400 MHz) δ 5.24 (bs, 1H), 4.14 (d, J=8.0 Hz, 2H), 3.87 (t, J=6.2 Hz, 2H), 3.69-3.57 (m, 20H), 3.55 (t, J=5.0 Hz, 2H), 3.42-3.28 (m, 2H), 2.94 (t, J=6.2 Hz, 2H), 2.35-2.11 (m, 6H), 1.67-1.50 (m, 2H), 1.41-1.29 (m, 1H), 0.93 (t, J=9.7 Hz, 2H).
¹³C NMR (CDCl₃, 100 MHz) δ 167.5, 156.8, 98.8, 70.7-70.1, 66.0, 62.7, 40.8, 34.4, 29.1, 21.4, 20.1, 17.8.
54, tetra-tert-butyl ((6-chloro-1,3,5-triazine-2,4-diyl) bis(4,34-dioxo-7,10,13,16,22,25,28,31-octaoxa-3,19, 35-triazaheptatriacontane-19,1,37-triyl))tetracarbamate
$C_{75}H_{140}N_{13}O_{28}$ MW=1707.46 g/mol
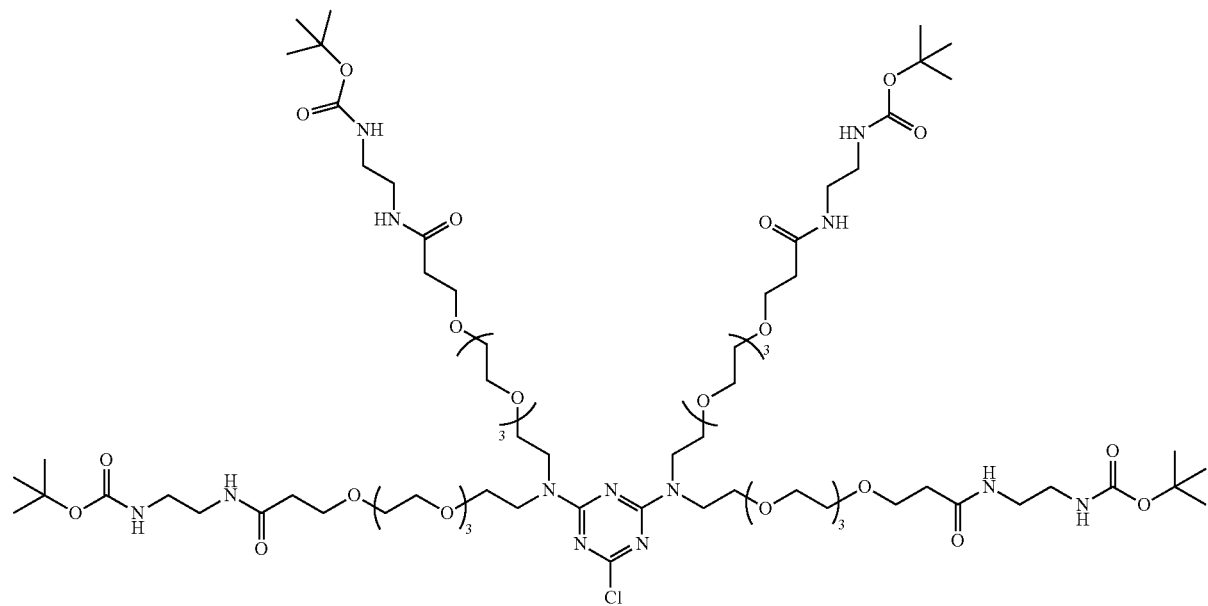

To a solution of 20b (2.3 eq., 615 mg, 0.77 mmol) in acetonitrile (3 mL) and DIEA (10 eq., 0.554 mL, 3.35 mmol) was added cyanuric chloride (1 eq., 61.8 mg, 0.33 mmol) and the reaction was stirred at room temperature for 5 hours. After concentration, 40 mL of an aqueous solution of $NaHPO_4$ 1M were added and the mixture was extracted with DCM (3×50 mL). The combined organic layers were dried over $MgSO_4$ and concentrated. The crude was purified by silica gel flash chromatography (DCM to DCM/MeOH 90/10 in 30 minutes) to afford 54 (380 mg, 0.22 mmol, 66%) as a clear yellow oil.

$^1$H NMR (CDCl$_3$, 400 MHz) δ 6.96 (bs, 4H), 5.32 (bs, 4H), 3.80-3.68 (m, 16H), 3.61 (dd, J=17.7, 9.8 Hz, 56H), 3.39-3.29 (m, J=5.1 Hz, 8H), 3.27-3.16 (m, 8H), 2.45 (t, J=5.7 Hz, 8H), 1.42 (s, 36H).

$^{13}$C NMR (CDCl$_3$, 100 MHz) δ 172.1, 168.8, 164.5, 156.3, 78.9, 70.5-70.1, 69.1, 68.8, 67.1, 48.1, 47.7, 40.3, 39.6, 36.8, 28.4 (12C).

55, methyl 3-((4,6-bis(bis(2,2-dimethyl-4,9-dioxo-3,12,15,18,21-pentaoxa-5,8-diazatricosan-23-yl)amino)-1,3,5-triazin-2-yl)amino)propanoate $C_{79}H_{148}N_{14}O_{30}$ MW=1774.12 g/mol

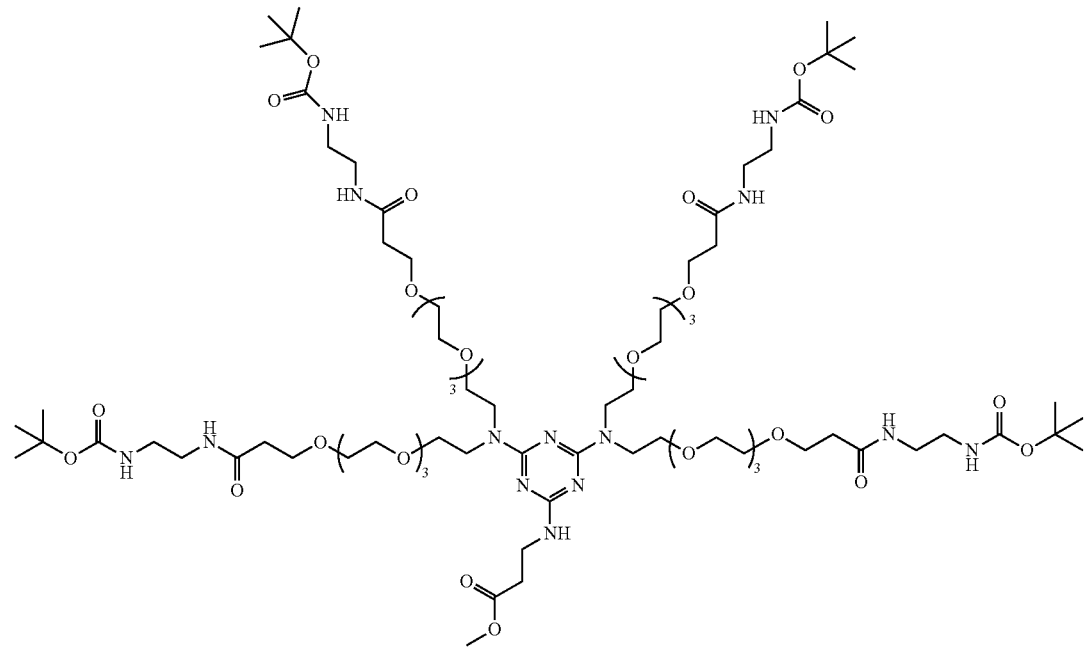

To a solution of 54 (1 eq., 375 mg, 0.22 mmol) and DIEA (10 eq., 0.363 mL, 2.20 mmol) in acetonitrile (7 mL) was added methyl 3-aminopropionate hydrochloride (8 eq., 245 mg, 1.76 mmol). The reaction mixture was stirred at 80° C. for 48 hours. After concentration, 70 mL of an aqueous solution of $NaH_2PO_4$ (1M) were added and the mixture was extracted with DCM (3×75 mL). The crude was purified by silica gel flash chromatography (DCM to DCM/MeOH 9/1 in 30 minutes) to afford 55 (330 mg, 0.19 mmol, 85%) as a yellowish oil.

$^1$H NMR ($CDCl_3$, 400 MHz) δ 6.98 (bs, 4H), 5.34 (bs, 4H), 3.85-3.47 (m, 77H), 3.39-3.27 (m, 8H), 3.28-3.14 (m, 8H), 2.60 (t, J=6.2 Hz, 2H), 2.46 (t, J=5.7 Hz, 8H), 1.43 (s, 36H). The NH signal is missing.

$^{13}$C NMR ($CDCl_3$, 100 MHz) δ 172.7, 172.0, 156.3, 78.9, 70.4-70.1, 69.4, 69.2, 67.1, 51.5, 47.6, 40.3, 39.6, 36.8, 36.3, 34.3, 28.4 (12C).

56, methyl 3-((4,6-bis(bis(1-((1R,8S,9s)-bicyclo[6.1.0]non-4-yn-9-yl)-3,8-dioxo-2,11,14,17,20-pentaoxa-4,7-diazadocosan-22-yl)amino)-1,3,5-triazin-2-yl)amino)propanoate $C_{103}H_{164}N_{14}O_{30}$ MW=2078.51 g/mol

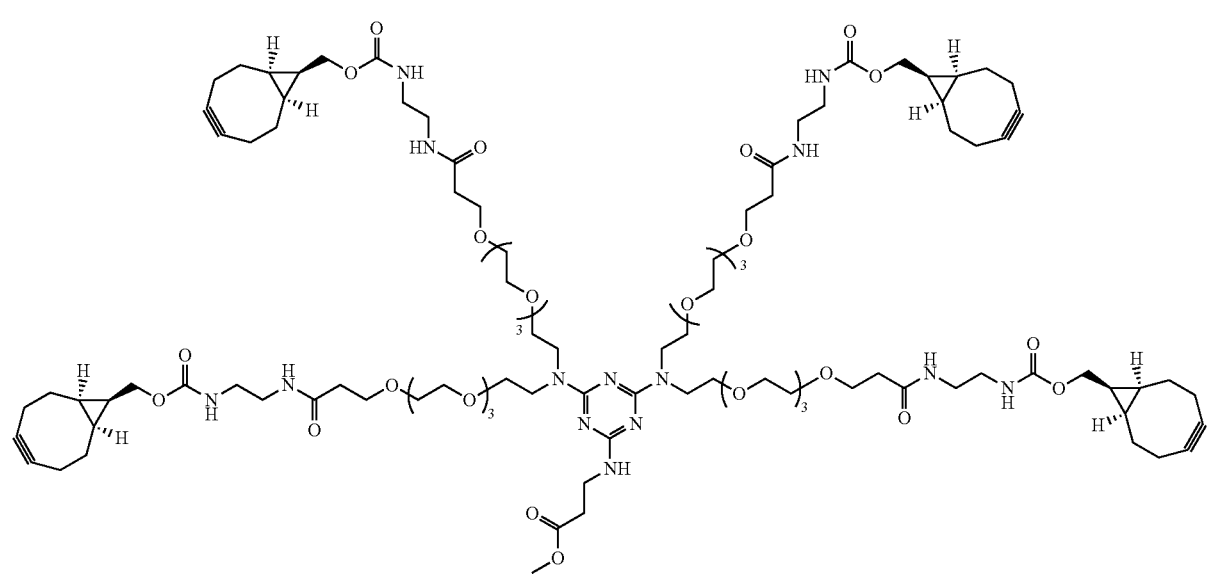

To a solution of 55 (1 eq., 280 mg, 0.16 mmol) in DCM/MeOH 1/1 (7.5 mL) was added a 4M HCl solution in dioxane (60 eq., 2.37 mL, 9.47 mmol). The reaction mixture was stirred 5 hours and concentrated. The crude was dissolved in DMF (5 mL) then TEA (10 eq., 159 mg, 0.219 mL, 1.58 mmol) and (1R,8S,9s)-bicyclo[6.1.0]non-4-yn-9-ylmethyl (4-nitrophenyl) carbonate 29 (4 eq., 199 mg, 0.63 mmol) were added. The reaction mixture was stirred at room temperature for 15 hours. After concentration, 50 mL of water were added and the mixture was extracted with DCM (3×50 mL). The combined organic layers were dried over $MgSO_4$ and concentrated. The crude was purified by silica gel flash chromatography (DCM to DCM/MeOH 9/1 in 35 min) to afford 56 (230 mg, 0.11 mmol, 70%) as a yellowish oil.

$^1$H NMR ($CDCl_3$, 400 MHz) δ 7.01 (bs, 4H), 5.60 (bs, 4H), 5.33 (bs, 1H), 4.12 (d, J=7.9 Hz, 8H), 3.78-3.47 (m, 77H), 3.42-3.31 (m, 8H), 3.33-3.20 (m, 8H), 2.60 (t, J=6.2 Hz, 2H), 2.46 (t, J=5.5 Hz, 8H), 2.36-2.13 (m, 24H), 1.56 (d, J=11.4 Hz, 8H), 1.32 (dd, J=18.6, 10.3 Hz, 4H), 0.92 (t, J=9.6 Hz, 8H).

57, 3-((4,6-bis(bis(1-((1R,8S,9s)-bicyclo[6.1.0]non-4-yn-9-yl)-3,8-dioxo-2,11,14,17,20-pentaoxa-4,7-diazadocosan-22-yl)amino)-1,3,5-triazin-2-yl)amino)propanoic acid
$C_{102}H_{162}N_{14}O_{30}$ MW=2064.49 g/mol
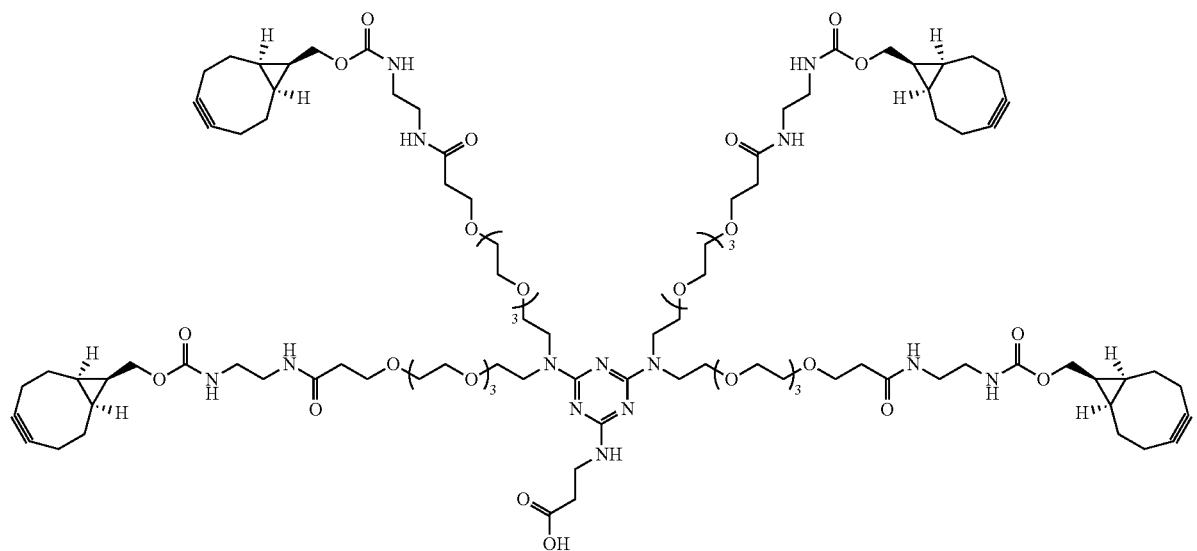

To a solution of 56 (1 eq., 230 mg, 0.11 mmol) in H$_2$O/MeOH 1/1 (2 mL) was added LiOH (5 eq., 13 mg, 0.55 mmol). The reaction mixture was stirred at room temperature for 5 hours. After MeOH evaporation, the aqueous phase was acidified by addition of 30 mL of an aqueous solution of NaHPO$_4$ 1M and extracted with DCM (3×50 mL). The combined organic layers were dried over MgSO$_4$ and concentrated. The crude was purified by silica gel flash chromatography (DCM to DCM/MeOH 85/15 in 35 minutes) to afford 57 (125 mg, 0.06 mmol, 55%) as a yellowish oil.

$^1$H NMR (400 MHz, d$_6$-DMSO) δ 7.87 (s, 4H), 7.07 (s, 4H), 6.69 (s, 1H), 4.03 (d, J=8.0 Hz, 8H), 3.54 (dt, J=11.1, 7.3 Hz, 74H), 3.12-3.04 (m, 8H), 3.04-2.94 (m, 8H), 2.49-2.41 (m, 2H), 2.30 (t, J=6.4 Hz, 8H), 2.18 (dd, J=28.0, 12.0 Hz, 24H), 1.52 (d, J=10.5 Hz, 8H), 1.33-1.25 (m, 4H), 0.87 (d, J=9.1 Hz, 8H).

58, perfluorophenyl 3-((4,6-bis(bis(1-((1R,8S,9s)-bicyclo[6.1.0]non-4-yn-9-yl)-3,8-dioxo-2,11,14,17,20-pentaoxa-4,7-diazadocosan-22-yl)amino)-1,3,5-triazin-2-yl)amino)propanoate C$_{108}$H$_{161}$F$_5$N$_{14}$O$_{30}$ MW=2230.54 g/mol

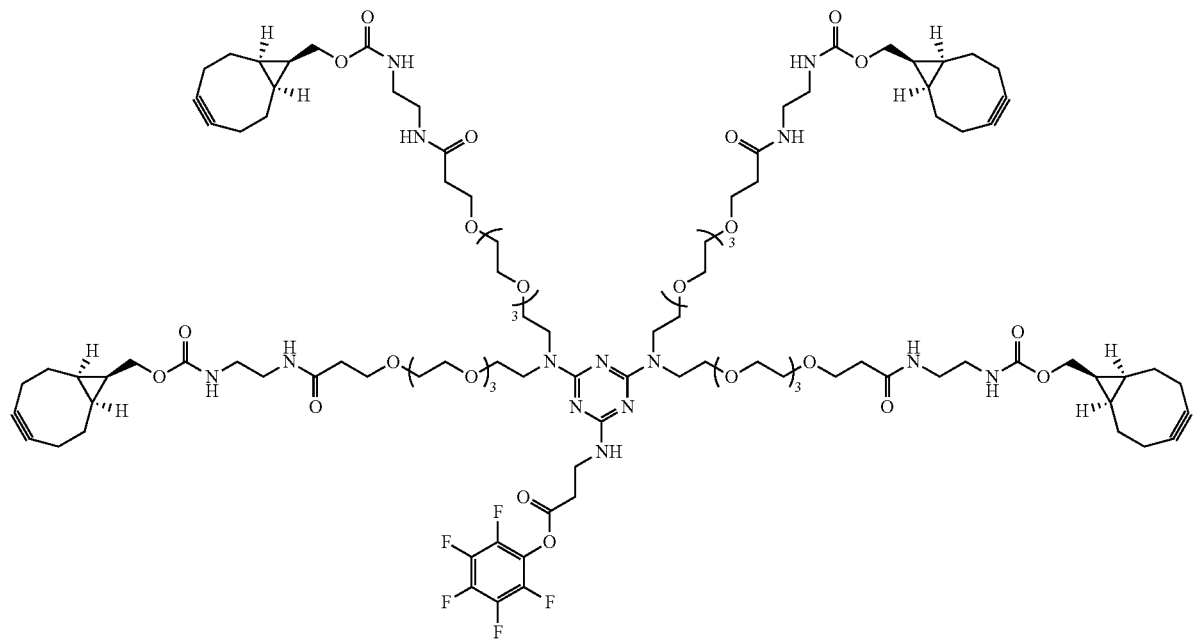

To a solution of 57 (1 eq., 125 mg, 0.06 mmol) and pentafluorophenol (1.2 eq., 13.4 mg, 0.07 mmol) in DCM (0.52 mL) was added DCC (1.1 eq., 13.7 mg, 0.07 mmol). The reaction mixture was stirred at room temperature for 4 hours. After concentration, 30 mL of DCM were added and the mixture was filtered through a pad of celite to afford 58 (111 mg, 0.05 mmol, 90%) as a yellowish oil.

$^1$H NMR (CDCl$_3$, 400 MHz) δ 7.00 (bs, 4H), 5.58 (bs, 4H), 5.49 (bs, 1H), 4.12 (d, J=7.9 Hz, 8H), 3.79-3.49 (m, 74H), 3.43-3.32 (m, 8H), 3.33-3.22 (m, 8H), 3.00 (t, J=6.3 Hz, 2H), 2.46 (t, J=5.4 Hz, 8H), 2.36-2.13 (m, 24H), 1.65-1.49 (m, 8H), 1.40-1.28 (m, 4H), 0.92 (t, J=9.6 Hz, 8H).

Example 8: Preparation of a Chemoprobe by Reaction of an Amino-Modified Oligonucleotide with a Conjugation Reagent Described in Example 7

Materials and Methods:

Amino-modified oligonucleotides were purchased from IDT. The purifications after oligonucleotide conjugation were carried out on a Shimadzu system (pump: LC 20-AD, detector: SPD 20-A, autosampler: SIL 20-A) using a SunFire™ C18 5 μM 4.6×150 mm column (Waters). HPLC parameters were as follows: flow rate 1 mL/min, mobile phase A was triethylammonium acetate (TEAA) in water (50 mM), and mobile phase B was TEAA in acetonitrile (50 mM). The detection was done at 260 nm. Gradient A: from 15 to 40% of mobile phase B from 0 to 30 min. Gradient B:

from 15 to 35% of mobile phase B from 0 to 30 min. Gradient C: from 15 to 50% of mobile phase B from 0 to 30 min.

General Procedure for Oligonucleotide Conjugations:

In a 2 mL Eppendorf tube, amino-modified oligonucleotide (1 nmol/μL in water, 1 eq.), a solution of conjugation reagent 53 or 58 in acetonitrile (10 eq.) and NaHCO$_3$ (1 M in water, 250 eq.) were introduced. The final volume was adjusted with acetonitrile to obtain a 1/1 water/acetonitrile ratio. The mixture was incubated at room temperature overnight under argon atmosphere and was then directly injected in HPLC for purification. The details of oligonucleotide conjugations as well as the sequences of amino-modified oligonucleotides and their complementary sequences used during microfluidic experiments are resumed in the below table.

Details of Oligonucleotide Conjugations and Sequences.

5AmC12: 5' Amino Modifier C12, iCy5: Internal Cy5™, 3Cy5Sp: 3' Cy5™ introduced on supported resin, 5ATTO488N: 5' Atto™ 488 (NHS ester), 3ATTO488N: 3' Atto™ 488 (NHS ester).

| Amino-modified oligonucleotide sequences | Conjugation reagent | HPLC gradient ob-tained | BCN-based conjugates | Complementary oligonucleotide sequences |
|---|---|---|---|---|
| 5'-/5AmMC12/AA/iCy5/GATACGAATTCGGGTGTTCTGCTGGTAGTGGTCGG-3' (SEQ ID NO: 1) | 53 | A | 59 | 60: 5'-/5ATTO488N/CCACTACCAGCAGAACACCCCCAGAATTCGTATC-3' (SEQ ID NO: 2) |
| 5'-/5AmMC12/TTGCTGTAGCCAAATTCG/3Cy5Sp/-3' (SEQ ID NO: 3) | 53 | B | 61 | 62: 5'-CGAATTTGGCTACAGCAA/3ATTO488N/-3' (SEQ ID NO: 4) |
| 5'-/5AmMC12/TTGCTGTAGCCAAATTCG/3Cy5Sp/-3' (SEQ ID NO: 5) | 58 | C | 63 | 62: 5'-CGAATTTGGCTACAGCAA/3ATTO488N/-3' (SEQ ID NO: 6) |
| 5'-/5AmMC12/TTGCAGTTTTTTTTTTTTTTTTTTT-3' (SEQ ID NO: 7) | 53 | B | 64 | 65: 5'-/5ATTO488N/TTGATCCAAAAAAAAAAAAAAAAAA-3' (SEQ ID NO: 8) |

Example 9: Capture of an Oligonucleotide Target by the Method of the Invention (Chemoprobe: Oligonucleotide Commentary to the Target)

1. Materials and Methods
See example 2.
Experimental Setup and Materials:

Flow rates were controlled by syringe pumps (Harvard Apparatus PHD 2000). Flow rates of 500 μL/h for aqueous phase and of 500 μL/h for fluorinated oil phase (3M Novec 7500) were used to create droplets (40-60 pL). Emulsion was collected in an Eppendorf filled with oil and closed with a PDMS plug to prevent coalescence due to contact with air. For biomolecule grafting via SPAAC reaction, the azide surfactants Krytox-peg$_{12}$-diN$_3$ 44 and Krytox-peg$_{16}$-tetraN$_3$ 47 were used at 2.5% w/w in oil phase. For negative control experiments, 2.5% w/w of non-functionalized surfactant (008-FluoroSurfactant, RAN Biotechnologies) was used in oil phase. For the aqueous phase, BCN-based oligonucleotide conjugates and their complementary targets were dissolved in CutSmart 1× (New England Biolabs, Reference: B7204S).

W/O emulsions were reinjected in the second chip and spaced by fluorinated oil (3M Novec 7500). Flow rates of 200 μL/h for Novec 7500 and of 100 μL/h for emulsion sample were used.

Confocal Microscopy:

W/O emulsions were analyzed using a Leica SPE confocal microscope (lasers used: 405 nm (ACMS), 488 nm (Atto488 derivatives) and 635 nm (sulfoCy5 derivatives), objective 20×, Leica 11506513).

Figure 30:
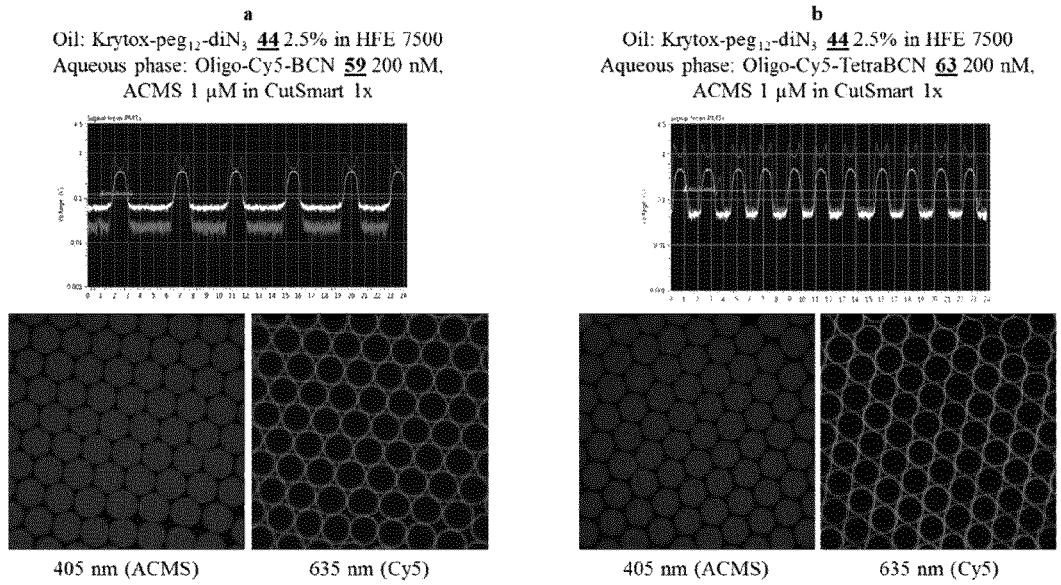
FIG. 30: Oligonucleotide grafting via SPAAC reaction. Top: Signals obtained during emulsion reinjection, Red: laser 642 nm, Blue: laser 375 nm. Bottom: Confocal microscopy, image size: 367.83 µm×367.83 µm, Blue: laser 405 nm, Red: laser 635 nm.

2. Results:

Oligonucleotide grafting at microdroplet inner surface. The grafting of Cy5-oligonucleotide after conjugation to one or four BCN moieties (59 and 63) was validated using Krytox-peg$_{12}$-diN$_3$ 44 as fluorosurfactant (FIG. 30). In both cases, signals obtained during emulsion reinjection showed that Cy5 fluorescence was higher in front and in the back of the droplets indicated that the oligonucleotides were located preferably at the inner surface of the water droplet. These results were confirmed by confocal microscopy which demonstrated that Cy5-oligonucleotides were concentrated at the microdroplets inner surface.

Oligonucleotide Grafting and Capture of Complementary Oligonucleotide.

Figure 31:
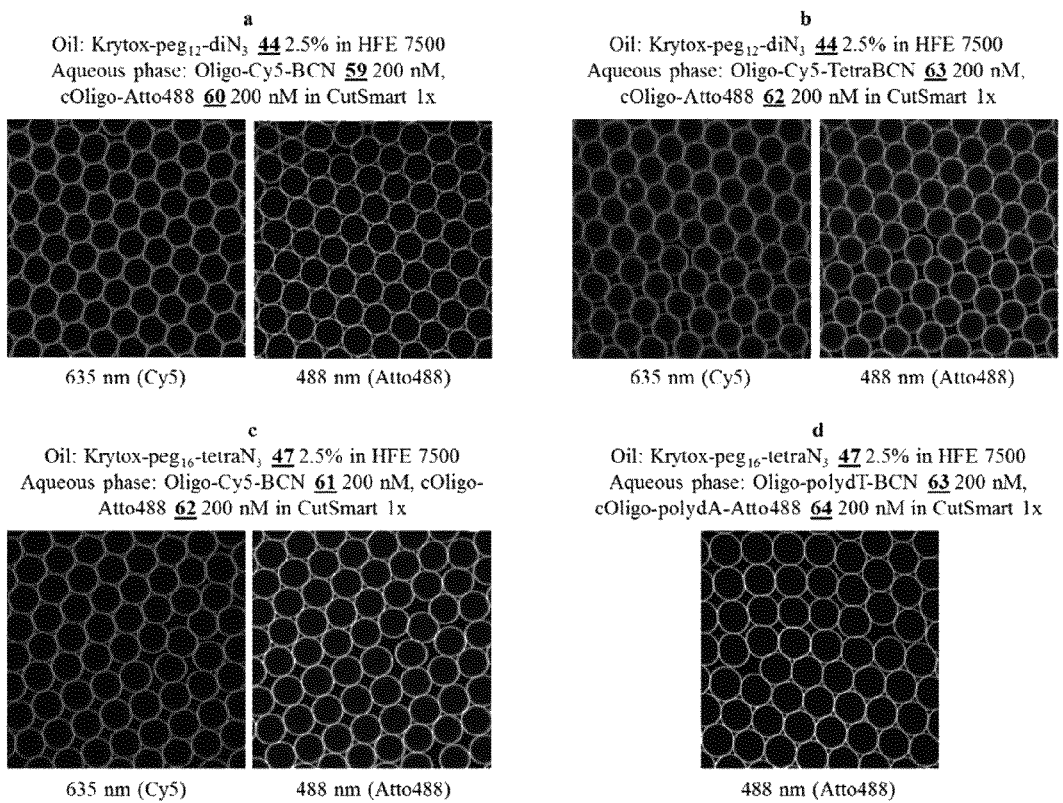
FIG. 31: Oligonucleotides grafting and capture of complementary sequences. Confocal microscopy, image size: 367.83 µm×367.83 µm, Red: laser 635 nm, Green: laser 488 nm.

To mimic the capture of a complementary DNA sequence, the experiments were repeated by co-encapsulating the grafting oligonucleotide bearing BCN moieties and a complementary oligonucleotide sequence (FIG. 31). Using the fluorosurfactant Krytox-peg$_{12}$-diN$_3$ 44, the grafting of a mono-BCN and a tetra-BCN Cy5-oligonucleotide conjugates (respectively 59 and 63) followed by the capture of a complementary oligonucleotide containing an Atto488 fluorophore was demonstrated. Confocal microscopy showed that Cy5 and Atto488 fluorescence were concentrated at the microdroplets inner surface confirming that the BCN-modified oligonucleotides were conveniently grafted at the inner surface allowing the capture of the complementary oligonucleotides (FIG. 31 a-b). A third emulsion was prepared using Krytox-peg$_{16}$-tetraN$_3$ 47 as fluorosurfactant, the mono-BCN Cy5-oligonucleotide 61 and the complementary Atto488-oligonucleotide 62. Confocal microscopy analysis confirmed again the successful grafting and capture of oligonucleotides (FIG. 31c). Finally, the oligo-polydT 63 beforehand conjugated to a BCN moiety was grafted at the microdroplets inner surface allowing the capture of the Atto488-polydA oligonucleotide 64 (FIG. 31d). This result showed the opportunity to capture total mRNA which bears polydA sequence after in-cellular maturation process.

Negative Controls.

Figure 32:
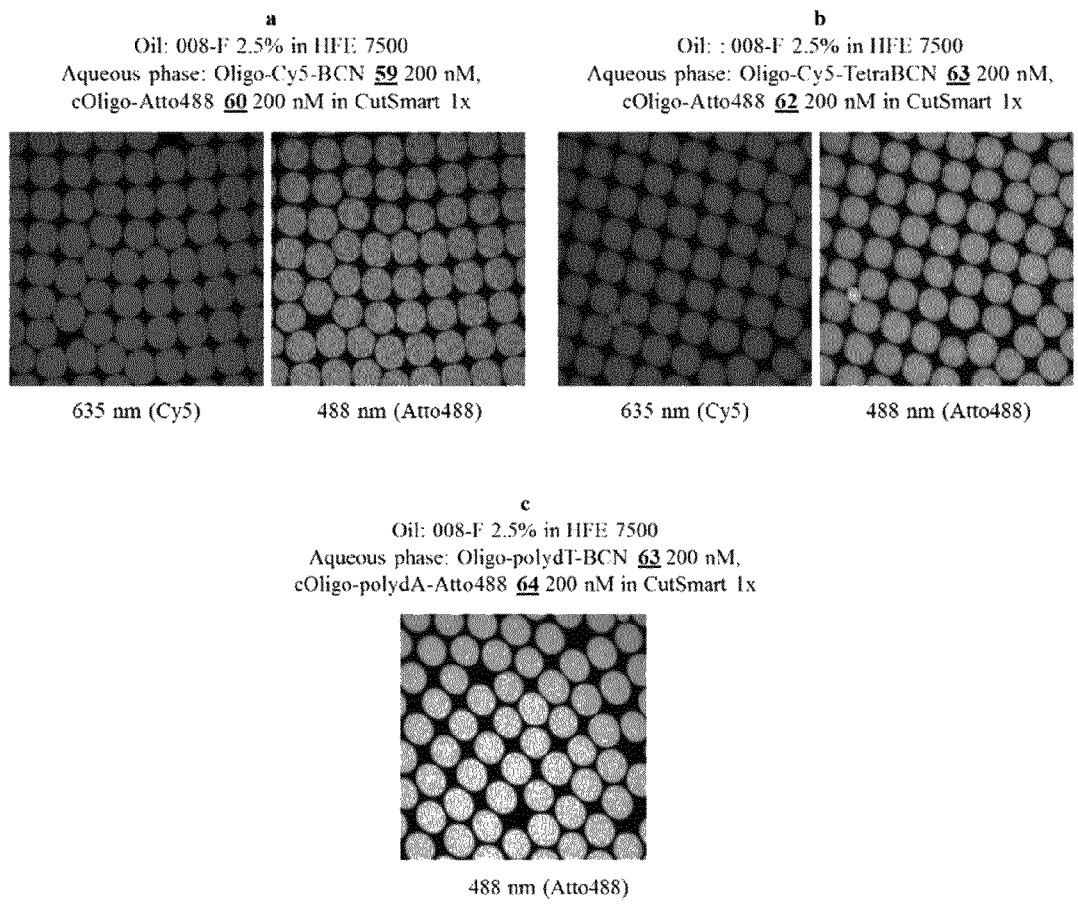
FIG. 32: Negative controls using non-functionalized fluorosurfactant 008-F. Confocal microscopy, image size: 367.83 µm×367.83 µm, Red: laser 635 nm, Green: laser 488 nm.

To demonstrate the specificity of the reaction, negative controls were performed using non-functionalized commercial fluorosurfactant (008-F, Ran Biotechnologies). Emulsions were prepared by co-encapsulating mono-BCN and tetra-BCN Cy5-oligonucleotides (respectively 59 and 63) and the corresponding complementary Atto488-oligonucleotides (respectively 60 and 62). In both cases the Cy5 and Atto488 fluorescence were homogenously distributed across the water droplets demonstrating that the SPAAC reaction cannot occur without azide fluorosurfactants (FIG. 32a-b). The same result was obtained using the BCN-oligo-polydT 63 and the complementary Atto-488 polydA 64 (FIG. 32c).

Example 10: Grafting of an Antibody (Trastuzumab) by the Method of the Invention

1. Preparation of the Chemoprobe

Trastuzumab has been conjugated to sulfoCy5 and BCN through its lysine residues. sulfoCy5CO$_2$NHS was purchased from Interchim (Ref. 992779).

General procedure: In a 2 mL Eppendorf tube, Trastuzumab (2.5 mg/mL in borate buffer 50 mM pH 8, 1 eq.), a solution of conjugation reagent 53 (1.5 mM in DMSO, 6 eq.) and a solution of sulfoCy5-CO$_2$NHS (1 mM in DMSO, 3 eq.) were introduced. The mixture was incubated at room temperature overnight. The solution was then purified by BioSpin P-30 (BioRad) according to the supplier recommendations to obtain Trastuzumab-Cy5-BCN 66.

2. Grafting of the Chemoprobe According to the Invention

Materials and Methods: See Example 2.

Experimental Setup and Materials:

Flow rates were controlled by syringe pumps (Harvard Apparatus PHD 2000). Flow rates of 500 µL/h for aqueous phase and of 500 µL/h for fluorinated oil phase (3M Novec 7500) were used to create droplets (40-60 pL). Emulsion was collected in an Eppendorf filled with oil and closed with a PDMS plug to prevent coalescence due to contact with air. For antibody grafting via SPAAC reaction, the azide surfactants Krytox-peg$_{12}$-diN$_3$ 44 was used at 2.5% w/w in oil phase. For negative control experiments, 2.5% w/w of non-functionalized surfactant (008-FluoroSurfactant, RAN Biotechnologies) was used in oil phase. For the aqueous phase, Trastuzumab-Cy5-BCN 66 and ACMS were dissolved in CutSmart 1× (New England Biolabs, Reference: B7204S).

Confocal Microscopy:

W/O emulsions were analyzed using a Leica SPE confocal microscope (lasers used: 405 nm (ACMS), and 635 nm (sulfoCy5 derivatives), objective 20×, Leica 11506513).

Figure 33:
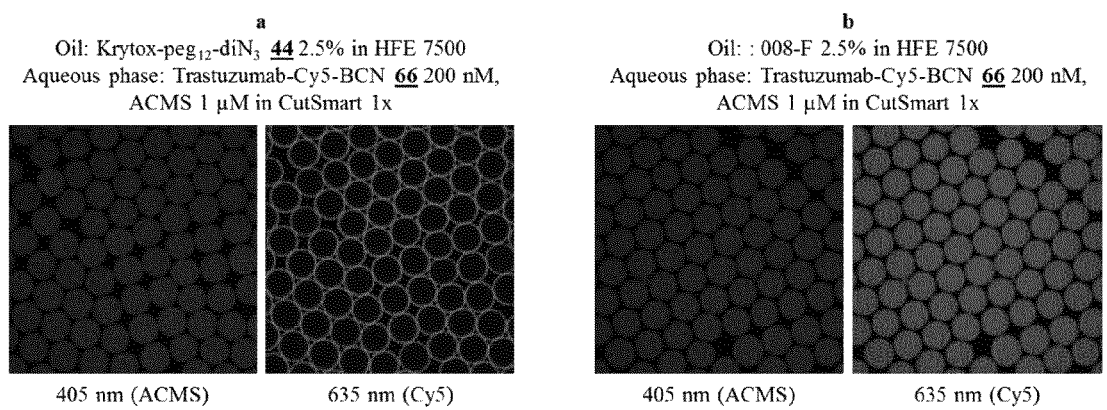
FIG. 33: Antibody (Trastuzumab) grafting via SPAAC reaction. Confocal microscopy, image size: 367.83 µm×367.83 µm, Blue: laser 405 nm, Red: laser 635 nm.

Results:

The grafting of Trastuzumab-Cy5-BCN 66 was validated using Krytox-peg$_{12}$-diN$_3$ 44 as fluorosurfactant (FIG. 33). The analysis of the emulsion by confocal microscopy showed that Trastuzumab-Cy5 was concentrated at the microdroplets inner surface while the control fluorophore (ACMS) was homogenously distributed across the droplets (FIG. 33a). This result confirms the successful grafting of the antibody at the microdroplets surface. A negative control was performed using non-functionalized commercial fluorosurfactant (008-F, Ran Biotechnologies). In this case, confocal microscopy revealed that, as control fluorophore (ACMS), Trastuzumab-Cy5-BCN 67 was not grafted at the microdroplet surface demonstrating that the reaction can occur only using an azide fluorosurfactant (FIG. 33b).

Example 11: Capture of Labelled RNAs and their Purification by Droplet Inversion In this example, a fluorescently labelled 970-nt long fragment of the GAPDH mRNA was prepared and purified prior to i) diluting it into a stabilizing buffer in the presence of a large excess of non specific RNAs, ii) dispersing the solution into water-in-oil droplets into which iii) RNA was captured at inner droplet surface and, finally, iv) target RNA was purified from the reaction mixture.

Sequences

| Molecule | ID no | Sequence | Modification |
|---|---|---|---|
| Template GAPDH DNA *, ** | 1 | <u>TAATACGACTCACTATAGGG</u>atggggaaggtgaagtcggagtcaacggatttggtcgtattgggcgcctggtcaccagggctgcttttaactctggtaaagtggatattgttgccatcaatgacccccttcattgacctcaactacatggtttacatgttccaatatgattccaccatggcaaattccatggcaccgtcaaggctgagaacggggaagcttgtcatcaatggaaatcccatcaccatcttccaggagcgagatccctccaaaatcaagtggggcgatgctggcgctgagtacgtcgtggagtccactggcgtcttcaccaccatggagaaggctggggctcatttcaggggggagccaaaagggtcatcatctctgcccctctgctgatgccccccatgttcgtcatggtgtgaaccatgagaagtatgacaacagcctcaagatcatcagcaatgcctcctgcaccaccaactgcttagcaccctggccaaggtcatccatgacaactttggtatcgtggaaggactcatgaccacagtccatgccatcactgccacccagaagactgtggatgccctccgggaaactgtggcgtgatggccgcggggctctccagaacatcatccctgcctctactggcgctgccaagctgtgggcaaggtcatccctgagctgaacgggaagctcactggcatggccttccgtgtccccactgccaacgtgtcagtggtggacctgacctgccgtctagaaaaacctgccaaatatgatgacatcaaggaaggtggtgaagcaggcgtcggagggcccctcaagggcatcctggggctacactgagcaccaggtggtctcctctgacttcaacagcgacacccactcctccacctttgacgctgggggctggcattgccctcaacgaccactttgtcagctcatttcctggtatgacaacgaatttggctacagcaaca (SEQ ID NO: 9) | none |
| GAPDH Fwd** | 2 | ggaacttgaatt<u>cTAATACGACTCACTATAGGG</u>atggggaaggtgaaggtcgg (SEQ ID NO: 10) | none |
| GAPDH Rev | 3 | Tgttgctgtagccaaattcg (SEQ ID NO: 11) | none |
| GAPDH RNA fragment | 4 | GggaugggaaggugaaggucggagucaacggauuAuggucguauugggcgccuggucaccagggcugcuuuaacucugguaaaguggauauuguugccaucaauUTPgaccccuucauugaccucaacuacaugguuuacauguuccaauauccaccauggcaaauuccaaggcaccgucaaggcugagaacgggaagcuugucaucaauggaaauccaucaccaucuuccaggagcgagaucccuccaaaaucaaguggggcgaugcuggcgcugaguacgucguggaguccacuggcgucuucaccaccauggagaaggcuggggcucaaauugcagggggggagccaaaagggucaucaucucugcccccucugcugaugcccccauguucgucauggguguguaaccaugagaaguaugacaacagccucaagaucaucagcaaugccuccugcaccaccaacugcuuagcaccccuggccaaggucauccaugacaacuuugguaucguggaaggacucaugaccacaguccaugccaucacugccacccagaagacuguggaugcccuccgggaaacuguggcguggauggccgcggggcucuccagaacaucaucccugccucuacuggcgcugccaaggcugugggcaaggucaucccugagcugaacgggaagcucacuggcauggccuuccgugucccacaugccaacgugucagugguggacugaccugccgucuagaaaaaccugccaaauaugaugacaucaaggaagguggugaaggcaggcgucggaggcgccccucaagggcaucccugggcuacacugagcaccagguggucucucugacuucaacagcgacacccacuccuccaccuuugacgcgggggcuggcauugcccucaacgaccacuuugucaagcucauuuccugguaugacaacgaauuggcuacagcaaca (SEQ ID NO: 12) | Atto488-UTP |
| Capture DNA | 5 | 5'-NH2-C12-TTGCTGTAGCCAAATTCG-3' (SEQ ID NO: 13) | BCN-peg$_6$ |

*The DNA was obtained by gene-specific reverse-transcription of GAPDH mRNA contained into the total RNA fraction extracted from mammalian HeLa cells. cDNA was cloned into pUC18 vector and its sequence verified by Sanger sequencing (GATC Biotech).
**T7 promoter is underlined and shown in capital letters DNA oligonucleotide 5 was modified with the conjugation reagent 53 via its 5' end amine function according to the procedure described in Example 8.

Microfluidic Chips Preparation and Operation

Microfluidic devices were obtained using a classic replica molding process as described previously in (Mazutis et al. 2009. Anal Chem 81: 4813-4821). Briefly, devices were designed on Autocad (Autodesk 2014), negative photomasks were printed (Selba S. A.) and used to prepare molds by standard photolithography methods. SU8-2025 photoresist (MicroChem Corp.) was used to pattern 40 m deep channels onto silicon wafers (Siltronix). Microfluidic devices were then fabricated in polydimethylsiloxane (PDMS, Silgard 184, Dow-Corning) using conventional soft lithography methods (Xia and Whitesides 1998. Annu Rev Mater Sci 28: 153-184). Patterned electrodes were filled with metal by heating the microfluidic chip to 90° C. and injecting molten 51In/32.5Bi/16.5Sn low temperature solder (Indium Corporation, Singapore) (Siegel et al. 2007. Adv Mater 19: 727-733). Finally, electrical connections with the solder were made with short pieces of electric wires (Radiospares). The main dimensions and depth of microfluidic devices are given on concerned figures and in their captions.

Aqueous phases were loaded in I.D. 0.75 mm PTFE tubings (Thermo Scientific) and oils were loaded in 2 mL Micrew Tubes (Thermo Scientific). Liquids were injected into microfluidic devices at constant and highly controlled flow-rates using a 7-bar MFCS™ pressure-driven flow controller (Fluigent) equipped with Flowells (7 μL/min flow-meters) allowing for operation in flow-rate controlled mode.

Optical Set-Up, Data Acquisition and Control System

The optical setup was based on an inverted microscope (Nikon Eclipse Ti—S) mounted on a vibration-dampening platform (Thorlabs B75150AE). The beams of a 375 nm laser (CrystaLaser DL375-020-O) and a 488 nm laser (CrystaLaser DL488-050-O) were combined using a dichroic mirror (Semrock Di02-R405-25×36), shaped as lines using a pair of lenses (Semrock LJ1878L2-A and LJ1567L1-A) and directed into the microscope objective (Nikon Super Plan Fluor 20×ELWD or Nikon Super Plan Fluor 40×ELWD) to be focused in the middle of the channel at the detection point. The emitted fluorescence was collected by the same objective and separated from the laser beams by a multi-edges dichroic mirror (Semrock Di01-R405/488/561/635-25×36). Blue (7-aminocoumarin-4-methanesulfonic acid) fluorescence was resolved from green (Atto488-RNA) and orange (TAMRA) fluorescence by a third dichroic mirror (Semrock LM01-480-25). Then green fluorescence was separated from orange fluorescence by an additional dichroic mirror (Semrock FF562-Di03-25×36). Fluorescence was finally measured by three photomultiplier tubes (Hamamatsu H10722-20) equipped with bandpass filters (Semrock FF01-445/45-25, FF01-600/37-25 and FF03-525/50-25 for blue, green and orange detection respectively). Signal acquisition from the PMTs was performed using an intelligent data acquisition (DAQ) module featuring a user-programmable FPGA chip (National Instruments PCI-7851R) driven by internally developed firmware and software. To monitor the experiment we used an additional dichroic mirror (Semrock FF665-Di02-25×36) to split light to a CCD camera (Allied Vision Technologies Guppy F-033). A long-pass filter (Semrock BLP01-664R-25) prevented potentially damaging reflections of the lasers into the camera.

Preparation of Labelled Target RNA

Template DNA 1 was PCR-amplified by mixing 10 ng of 1 in an amplification mixture (Total volume=50 μL) containing 0.2 μM of 2, 0.2 μM of 3, 0.2 mM of each dNTP (Thermo Scientific), 1 μL of Phire DNA polymerase (Thermo Scientific) and the supplied buffer. DNA 1 was then amplified using an initial denaturation of 30 sec at 98° C., followed by 25 cycles of 5 sec at 98° C., 30 sec at 55° C. and 90 sec at 72° C., before a final extension step of 120 sec at 72° C. The DNA was then purified using Wizard SV Gel and PCR Clean-Up System (Promega) following supplier instructions and eluted in DNase-free/RNase-free deionized water. Purified DNA was then quantified by measuring $OD^{260\ nm}$ of the solution (NanoDrop).

2500 ng of amplified and purified template DNA 1 were then transcribed in the presence of Atto488-UTP using the kit Atto488 RNA Labelling Kit (Jena Bioscience) as recommended by the supplier. Proper transcription was assessed by agarose gel electrophoresis (data not shown) and the RNA of expected size was gel-purified after proteins elimination by phenol extraction. To do so, 100 μL of reaction mixture were mixed with 100 μL of loading buffer (Glycerol 20%, TBE 1×, Urea 8M, Bromophenol Blue) prior to being loaded onto a 1% agarose gel in TBE and subjected to a migration in TBE buffer for 35 min at 130 V. After migration, the band containing RNA was identified under UV irradiation, cut out of the gel and placed into a length of dialysis membrane (cut-off=6000-8000, SpectraPore), filled with nuclease-free water and close was recommended clamps. Labelled RNA was then eluted from the gel by immerging the montage into a solution of TBE subjected to a 95V DC-field for 60 min. Eluted RNA contained the aqueous phase was then precipitated in 70% ethanol, 300 mM sodium acetate and in the presence of Glycoblue carrier (Invitrogen). After centrifugation, the pellet was washed by 70% ethanol prior to being resuspended in 15% DMSO. Finally, the RNA was quantified by measuring $OD^{260\ nm}$ of the solution (NanoDrop) that constituted a solution of RNA 4.

RNA Encapsulation and Capture

Experimental Procedure

Figure 34:
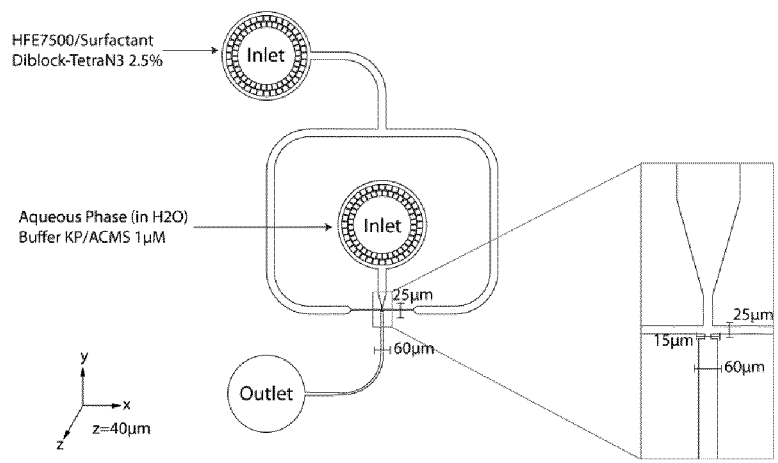
FIG. 34: 40 pL droplet generator. The main dimensions of the microfluidic device are indicated. The depth was 40 µm. The channels of the devices were passivated with a solution of 1% (v/v) 1H, 1H, 2H, 2H-perfluorodecyltrichlorosilane (97%, ABCR GmbH and Co,) in HFE7500 (3M) and subsequently flushed with compressed air.

A solution of 25 nM of labelled RNA 4 was mixed with 200 nM of BCN-containing capture DNA 5 in stabilizing buffer KP (25 mM MES pH 6, 2 mM EDTA, 100 mM NaCl and 0.4 mg/mL BSA). The mixture was further supplemented with 4 mg/mL of competing yeast total RNA (Ambion) and 5 μM 7-aminocoumarin-4-methanesulfonic acid (used as droplet tracker). The mixture was loaded into a length of PTFE tubing (I.D. 0.75 mm tubing; Thermo Scientific) and one end of the tubing was connected to the Fluigent infusion device while the other end of the tubing was connected to the droplet generator (FIG. 34). An oil phase composed of Novec 7500 supplemented with 2.5% Krytox-peg$_{16}$-tetraN$_3$ 47 surfactant was infused into the second inlet of the device and used to produce 40 pL droplets at rate of 3500 droplets per second by infusing the aqueous phase at 1500 nL/min and the oil phase at 1900 nL/min. Droplets were collected for 20 min via a length of tubing into a 0.2 mL PCR tube closed by a plug of PDMS. The emulsion was then subjected to an incubation of 5 min at 85° C. followed by 5 min at 50° C. and final step of 5 min at 25° C.

Results

Figure 35:
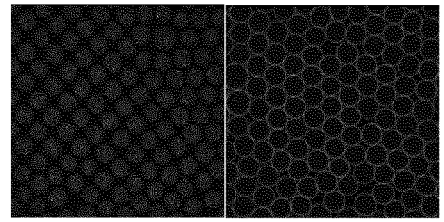
FIG. 35. Imaging captured RNA. 40 pL droplets containing labelled RNA 4, capture DNA 5 and 7-aminocoumarin-4-methanesulfonic acid were imaged by exciting the coumarin with a 408 nm laser and collecting the light emitted at 410-483 nm while green fluorescence was visualized by exciting Atto 488 with a 488 nm laser and collecting the light emitted at 499-553 nm.

Upon a short incubation of 20 min at 25° C., the emulsion was imaged on a confocal system (Zeiss LSM 780). On FIG. 35, the formation of a green ring demonstrated the capture of the RNA at the inner surface of the droplet while the coumarin dye (in blue) stayed diffuse in the droplets.

RNA Purification by Droplet Inversion

Experimental Procedure

Figure 36:
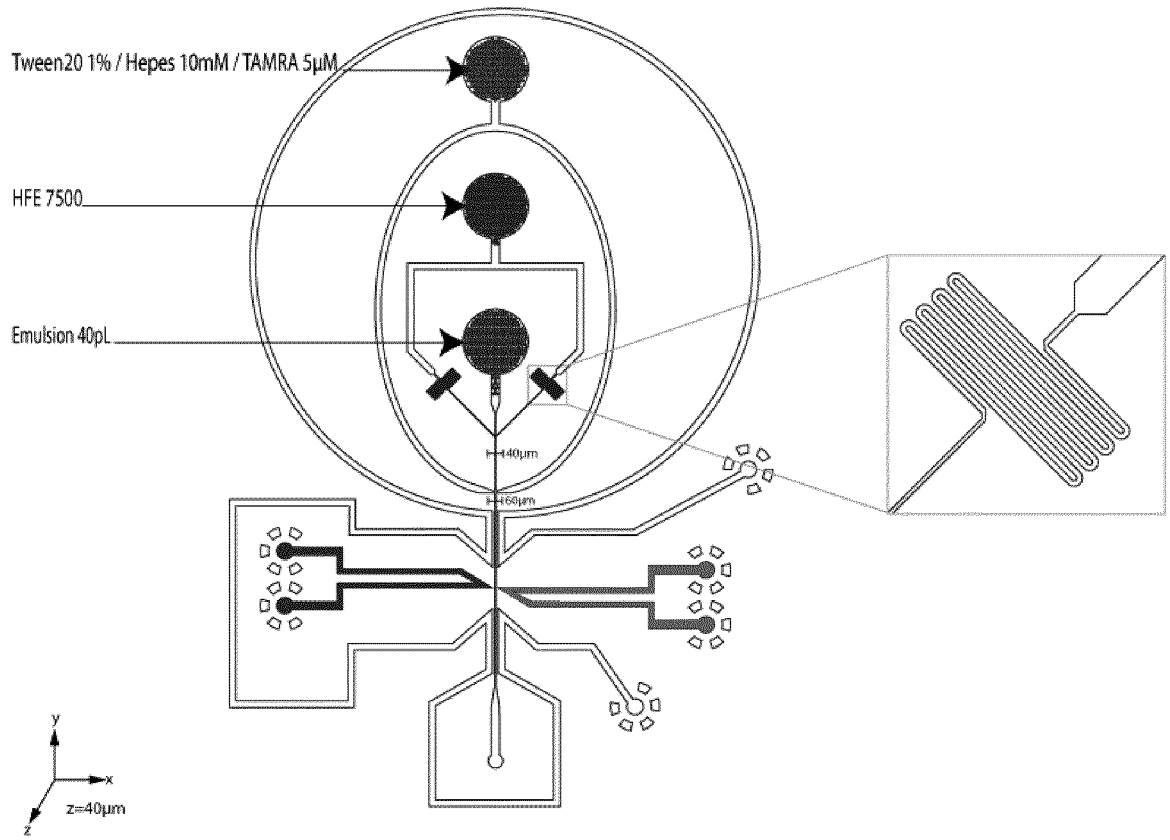
FIG. 36. Droplet inversion device. The main dimensions of the microfluidic device are indicated. The depth was 40 µm. The channels of the devices were passivated with PAH-PSS treatment (Zinchenko et al. 2014, Anal Chem 86: 2526-2533).

Water-in-oil (w/o) droplets displaying captured RNA were reinjected into an inverter device (FIG. 36) and infused of 350 nL/min to be reinjected at a rate of 165 droplets per second. w/o droplets were spaced by a stream of surfactant free Novec-7500 oil infused at 400 nL/min and a double (water-in-oil-in-water, w/o/w) emulsion was produced by pinching the resulting stream by a flow of aqueous phase (0.1% Tween 20, 10 mM Hepes pH7.4 and 5 µM TAMRA) infused at 1300 nL/min. Using these settings, each 40 pL w/o droplet was individualized into a 100 pL (40 pL w/o droplet+60 pL of oil) with no more than 1 w/o droplet per w/o/w droplet while around 90% of the o/w droplets were occupied.

w/o/w droplets were then converted (inverted) into oil-in-water (o/w) droplets when passing in between a pair of electrodes to which a squared AC field (2500V, 30 Hz) was applied using a function generator connected to an high voltage amplifier (TREK Model 623B). Droplets were collected in a 0.5 mL tube under water.

Results

Using this procedure up to 90% of the o/w droplets were occupied and up to 95% of these occupied droplets were successfully converted into o/w droplets. In addition, whereas the coumarin initially contained into the w/o was eliminated by the inversion process, the captured green fluorescent RNA stayed immobilized at the outer surface of the droplets (FIG. 37).

The invention claimed is:

1. A method for capturing a molecular target, said method comprising:
   a) providing water-in-oil emulsion droplets comprising a functionalized surfactant at the interface of droplets, said functionalized surfactant comprising at least one lipophilic tail linked to a functionalized hydrophilic head, said at least one lipophilic tail comprising a perfluoropolyether chain, a perfluorocarbon chain or a combination thereof and said functionalized hydrophilic head comprising a polyether and a functional moiety selected from an alkynyl group, an azido group, a biotin, a streptavidin and an avidin, said alkynyl and azido groups being suitable to perform click reaction;
   b) contacting said functionalized surfactant with a chemoprobe present or added in the aqueous phase of the droplets, said chemoprobe comprising at least (i) one capture moiety capable of specific binding to a molecular target and at least (ii) one binding domain capable of direct or indirect binding to the functionalized hydrophilic head of the functionalized surfactant; and
   c) contacting said functionalized surfactant with the molecular target present or added in the aqueous phase of the droplets,
   thereby capturing the molecular target at the inner interface of the emulsion droplets through (i) the direct or indirect binding of the chemoprobe to the functionalized surfactant and (ii) the specific binding of the chemoprobe to the molecular target, and
   wherein steps b) and c) are performed simultaneously or sequentially, in any order.

2. The method of claim 1, which is implemented using a microfluidic system.

3. The method of claim 1, which further comprises inverting the phase of water-in-oil emulsion droplets thereby producing oil-in-water emulsion droplets and exposing the captured molecular target at the outer surface of the emulsion droplets.

4. The method of claim 1, which further comprises a step of recovering, detecting, and/or quantifying the captured molecular target.

5. The method of claim 1, wherein the molecular target is a protein or a nucleic acid.

6. The method of claim 1, wherein the capture moiety of the chemoprobe is selected from the group consisting of an antibody, a spiegelmer, a peptide aptamer, an aptamer, a ligand or a substrate of the molecular target, a nucleic acid capable of hybridizing the molecular target, and a receptor fragment able to bind the molecular target.

7. The method of claim 1, wherein the functionalized surfactant is a diblock or triblock surfactant.

8. The method of claim 1, wherein the chemoprobe binds the functionalized surfactant through covalent interactions.

9. The method of claim 1, wherein the chemoprobe directly binds to the functionalized surfactant through covalent interactions.

10. The method of claim 9, wherein the functionalized hydrophilic head of the surfactant comprises an azido group and the binding domain of the chemoprobe comprises an alkyne group, or vice versa, said azido group and said alkyne group being able to react together through a click reaction.

11. The method of claim 1, wherein the chemoprobe binds to the functionalized surfactant via a binding intermediate.

12. The method of claim 11, wherein the functionalized hydrophilic head of the surfactant comprises an azido group and the binding intermediate comprises an alkyne group, or vice versa, said azido group and said alkyne group being able to react together through a click reaction.

13. The method of claim 12, wherein the click reaction is selected from the group consisting of copper-catalyzed azide-alkyne dipolar cycloaddition (CuAAC) and strain promoted alkyne-azide cycloaddition (SPAAC).

14. The method of claim 1, wherein the chemoprobe binds the functionalized surfactant through non-covalent interactions, directly or via a binding intermediate.

15. The method of claim 14, wherein the functionalized hydrophilic head comprises a biotin, a streptavidin or an avidin and the non-covalent interaction between the chemoprobe and the functionalized surfactant relies on an affinity system or protein tags involving said biotin, streptavidin or avidin.

16. The method of claim 1, wherein the molecular target is from a biological entity encapsulated within the droplets and wherein the method optionally comprises lysing said entity to release said molecular target.

17. The method of claim 16, wherein each emulsion droplet comprises a single genetic element or biological entity.

18. The method of claim 1, wherein the functionalized surfactant comprises or consists in a moiety of formula (Ib)

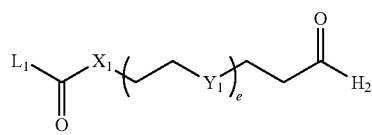

wherein:
a and b are integers independently selected from 1 to 5,
each LIPO is a perfluoropolyether chain, a perfluorocarbon chain and combinations thereof,
each HYDRO is a hydrophilic head comprising at least one polyether chain,
each FUNCT is a functional moiety of the surfactant selected from a biotin, a streptavidin, an avidin and a functional moiety being suitable to perform click reaction which is an alkynyl group or an azido group.

19. The method of claim 1, wherein the functionalized surfactant comprises:
one or two lipophilic tails comprising, or consisting of the moiety of formula (L1):

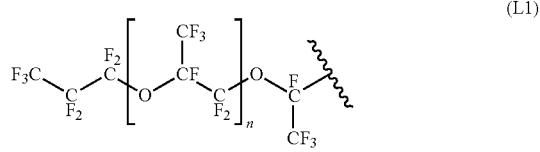

wherein n is an integer from 25 to 45;
one hydrophilic head bearing at least one moiety of formula (H2)

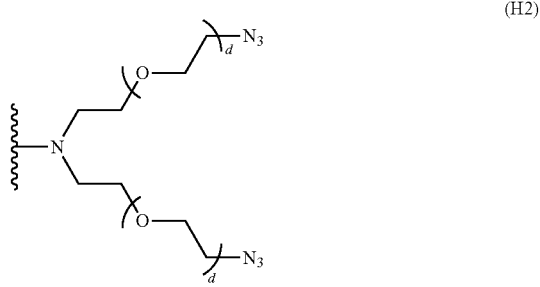

wherein d is an integer from 2 to 12.

20. The method of claim 19, wherein the functionalized surfactant has one of the following formula:

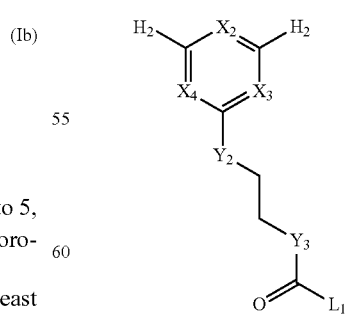

wherein e is an integer from 1 to 12 and X1 and Y1 are independently selected from NH, CH2 and O;

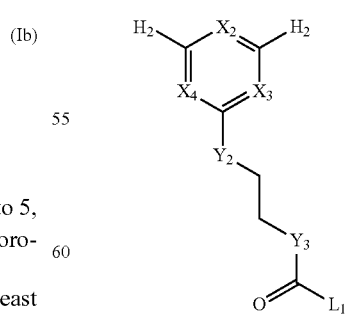

wherein Y2 and Y3 are independently selected from NH, CH2 or O and X2, X3 and X4 are independently selected from CH and N, and

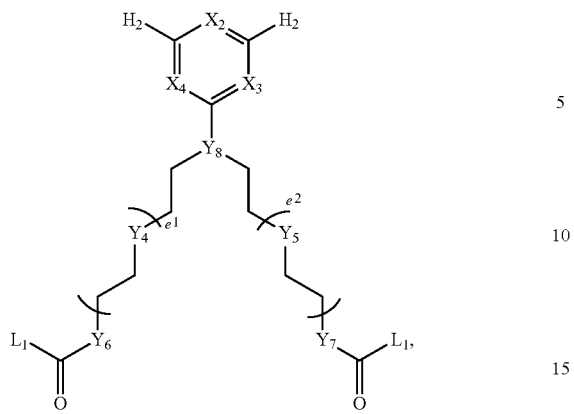
wherein
X2, X3 and X4 are independently selected from CH and N,
Y8 is CH or N,
Y4, Y5, Y6 and Y7 are independently selected from NH, O and CH2 and,
e1 and e2 are integers independently selected from 1 to 12,
wherein L1 and H2 being as defined in claim 19.
* * * * *

UNITED STATES PATENT AND TRADEMARK OFFICE
CERTIFICATE OF CORRECTION

PATENT NO. : 11,181,521 B2
APPLICATION NO. : 16/091217
DATED : November 23, 2021
INVENTOR(S) : Alain Wagner et al.

It is certified that error appears in the above-identified patent and that said Letters Patent is hereby corrected as shown below:

In the Specification

Column 4,
Line 21, "to 45" should read --to 45,--.

Column 29,
Line 54, "and (Ma) or" should read --and (IIIa) or--.

Column 30,
Lines 9-11,

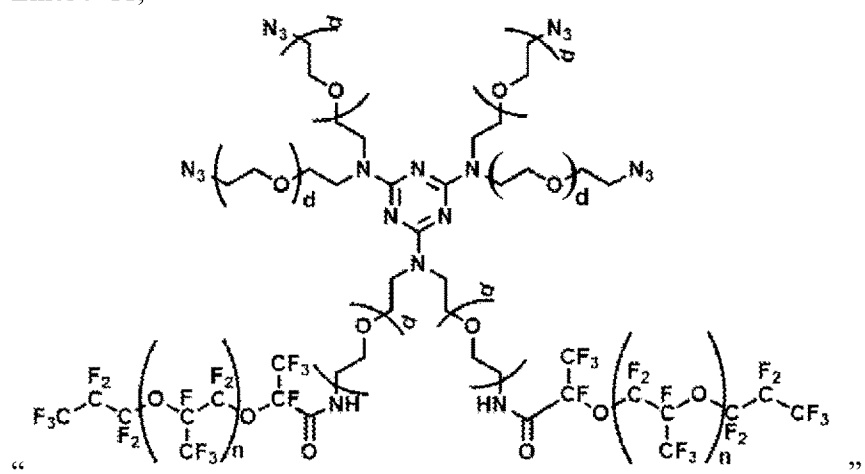

" "
should read

Signed and Sealed this
Second Day of August, 2022

Katherine Kelly Vidal
*Director of the United States Patent and Trademark Office*

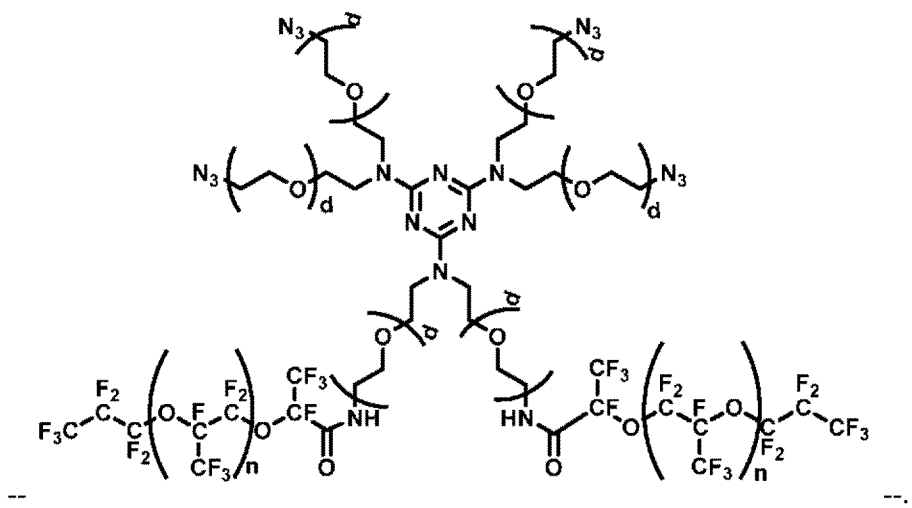
--
Column 39,
Lines 42-43, "500 m, 200 m, 150 m, 100 m or 50 am, and" should read --500 µm, 200 µm, 150 µm, 100 µm or 50 µm, and--.
Column 49,
Line 11, "and (Ma) or" should read --and (IIIa) or--.
Column 51,
Line 7, "per million (6)" should read --per million (δ)--.
Columns 73-74,
Lines 31-45,
"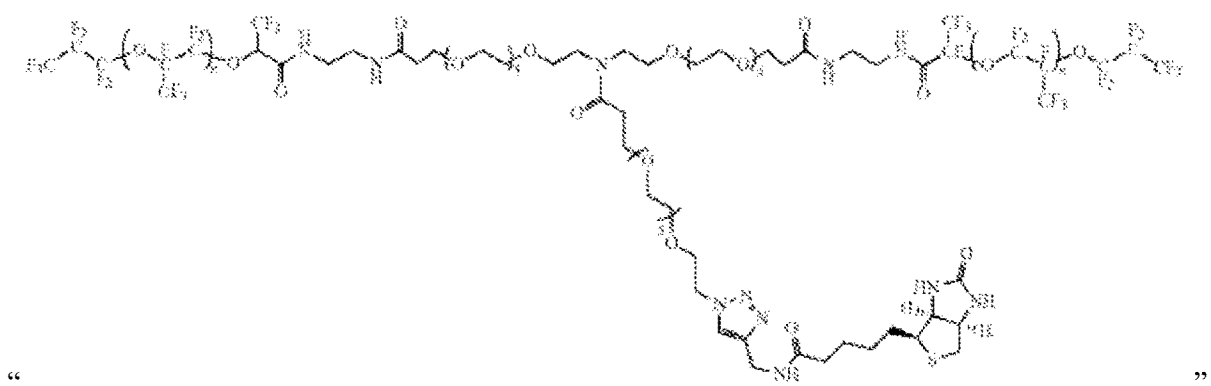"
should read

CERTIFICATE OF CORRECTION (continued)
U.S. Pat. No. 11,181,521 B2

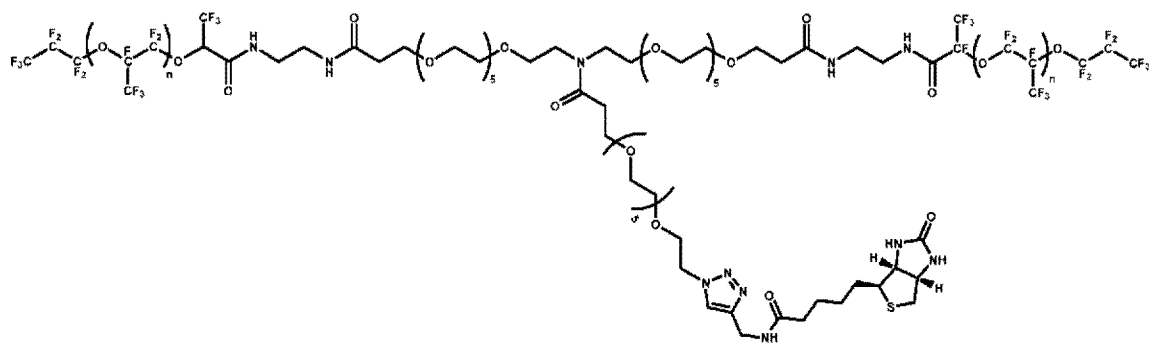

-- --.

Column 80,
Line 27, "was 40 m and size of the nozzle was m with" should read --was 40 μm and size of the nozzle was 25 μm with--.
Line 28, "of 40 m." should read --of 40 μm.--.
Line 29, "of 50 m." should read --of 50 μm.--.

Column 85,
Line 67, "was 25 m" should read --was 25 μm--.

Column 97,
Line 15, "N4," should read --$N^4$,--.

Column 121,
Line 11, "40 m deep" should read --40 μm deep--.